(12) United States Patent
Seiser et al.

(10) Patent No.: US 11,247,980 B2
(45) Date of Patent: Feb. 15, 2022

(54) HERBICIDAL URACILPYRID

(71) Applicant: BASF SE, Ludwigshafen am Rhein (DE)

(72) Inventors: Tobias Seiser, Limburgerhof (DE); Matthias Witschel, Ludwigshafen (DE); Manuel Johannes, Duesseldorf (DE); Dario Massa, Limburgerhof (DE); Liliana Parra Rapado, Limburgerhof (DE); Raphael Aponte, Research Triangle Park, NC (US); Thomas Mietzner, Ludwigshafen (DE); Trevor William Newton, Limburgerhof (DE); Thomas Seitz, Ludwigshafen (DE); Richard R. Evans, Raleigh, NC (US); Andreas Landes, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 271 days.

(21) Appl. No.: 16/303,783

(22) PCT Filed: May 22, 2017

(86) PCT No.: PCT/EP2017/062262
§ 371 (c)(1),
(2) Date: Nov. 21, 2018

(87) PCT Pub. No.: WO2017/202768
PCT Pub. Date: Nov. 30, 2017

(65) Prior Publication Data
US 2020/0317634 A1 Oct. 8, 2020

(51) Int. Cl.
| | |
|---|---|
| *A01N 43/54* | (2006.01) |
| *C07D 213/73* | (2006.01) |
| *C07D 213/75* | (2006.01) |
| *C07D 401/04* | (2006.01) |
| *C07D 401/12* | (2006.01) |
| *C07D 401/14* | (2006.01) |

(52) U.S. Cl.
CPC .......... *C07D 401/04* (2013.01); *A01N 43/54* (2013.01); *C07D 213/73* (2013.01); *C07D 213/75* (2013.01); *C07D 401/12* (2013.01); *C07D 401/14* (2013.01)

(58) Field of Classification Search
None
See application file for complete search history.

(56) References Cited

FOREIGN PATENT DOCUMENTS

| | | |
|---|---|---|
| EP | 2394993 A2 | 12/2011 |
| WO | 199952892 A2 | 10/1999 |
| WO | 2002098227 A1 | 12/2002 |
| WO | 2011137088 A1 | 11/2011 |
| WO | 2014187297 A1 | 11/2014 |
| WO | 2015197392 A1 | 12/2015 |
| WO | 2016062814 A1 | 4/2016 |
| WO | 2016087234 A1 | 6/2016 |
| WO | 2016113334 A1 | 7/2016 |
| WO | 2016116531 A1 | 7/2016 |
| WO | 2016120116 A1 | 8/2016 |
| WO | 2016120355 A2 | 8/2016 |
| WO | 2016128470 A1 | 8/2016 |
| WO | 2016169831 A1 | 10/2016 |
| WO | 2016202500 A1 | 12/2016 |
| WO | 2016202659 A1 | 12/2016 |
| WO | 2016203377 A1 | 12/2016 |
| WO | 2017009054 A1 | 1/2017 |
| WO | 2017009056 A1 | 1/2017 |
| WO | 2017009060 A1 | 1/2017 |
| WO | 2017009061 A1 | 1/2017 |
| WO | 2017009088 A1 | 1/2017 |
| WO | 2017009089 A1 | 1/2017 |
| WO | 2017009090 A1 | 1/2017 |
| WO | 2017009092 A1 | 1/2017 |
| WO | 2017009095 A1 | 1/2017 |
| WO | 2017009124 A1 | 1/2017 |

(Continued)

OTHER PUBLICATIONS

European Search Report for EP Patent Application No. 16171063.7, dated Sep. 5, 2016.

(Continued)

*Primary Examiner* — Alton N Pryor
(74) *Attorney, Agent, or Firm* — Marshall, Gerstein & Borun LLP

(57) ABSTRACT

The present invention relates to uracilpyridines of formula (I)

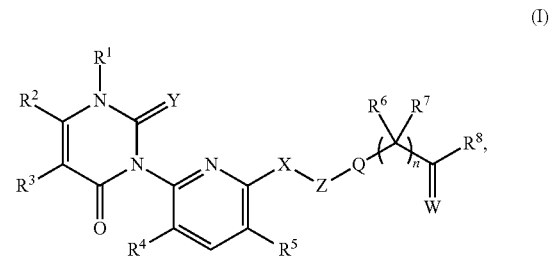

or their agriculturally acceptable salts or derivatives, wherein the variables are defined according to the description, processes and intermediates for preparing the uracilpyryidines of the formula (I), compositions comprising them and their use as herbicides, i.e. for controlling harmful plants, and also a method for controlling unwanted vegetation which comprises allowing a herbicidal effective amount of at least one urycilpyridine of the formula (I) to act on plants, their seed and/or their habitat.

22 Claims, 1 Drawing Sheet

(56) References Cited

FOREIGN PATENT DOCUMENTS

| WO | 2017009134 A1 | 1/2017 |
|---|---|---|
| WO | 2017009137 A1 | 1/2017 |
| WO | 2017009138 A1 | 1/2017 |
| WO | 2017009139 A1 | 1/2017 |
| WO | 2017009140 A1 | 1/2017 |
| WO | 2017009142 A1 | 1/2017 |
| WO | 2017009143 A1 | 1/2017 |
| WO | 2017009144 A1 | 1/2017 |
| WO | 2017009145 A1 | 1/2017 |
| WO | 2017009146 A1 | 1/2017 |
| WO | 2017009147 A1 | 1/2017 |
| WO | 2017009148 A1 | 1/2017 |
| WO | 2017027359 A1 | 2/2017 |
| WO | 2017080905 A1 | 5/2017 |
| WO | 2017102275 A1 | 6/2017 |
| WO | 2017198859 A1 | 11/2017 |
| WO | 2018095811 A1 | 5/2018 |

OTHER PUBLICATIONS

International Search Report for PCT Application No. PCT/EP2017/062262, dated Jun. 27, 2017.
International Preliminary Report on Patentability for PCT Application No. PCT/EP2017/062262, dated Jul. 10, 2018.
Wang, et al., "Synthesis and Biological Evaluation Of N-Alkyl-N-(4-Methoxyphenyl)Pyridin-2-Amines as a New Class of Tubulin Polymerization Inhibitors", Bioorganic and Medicinal Chemistry, vol. 23, Issue 3, Dec. 6, 2012, pp. 632-642.

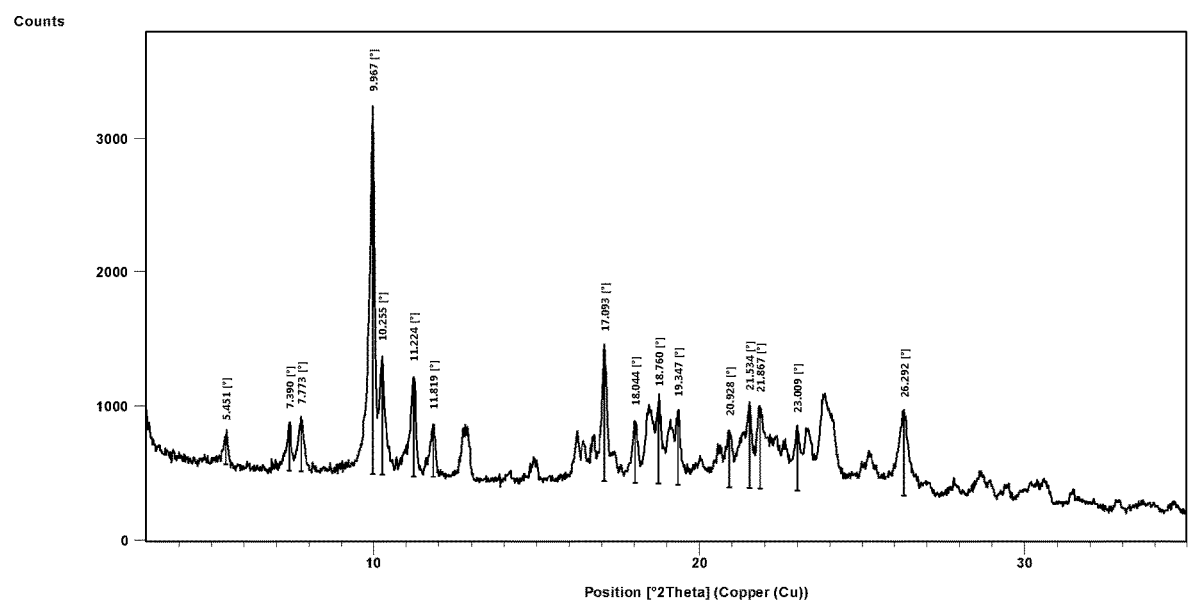

HERBICIDAL URACILPYRID

CROSS-REFERENCE TO RELATED APPLICATIONS

This application is a National Stage application of International Application No. PCT/EP2017/062262, filed May 22, 2017. This application also claims priority under 35 U.S.C. § 119 to European Patent Application No. 16171063.7, filed May 24, 2016.

The present invention relates to uracilpyridines of the general formula (I) defined below and to their use as herbicides. Moreover, the invention relates to compositions for crop protection and to a method for controlling unwanted vegetation.

WO 02/098227 and WO 11/137088 describe structurally similar compounds, which differ from the uracilpyridines (I) according to the present invention inter alia that the uracil is substituted by a phenyl, whereas the uracil according to the invention is substituted by a pyridyl.

However, the herbicidal properties of these known compounds with regard to the harmful plants are not always entirely satisfactory.

It is therefore an object of the present invention to provide uracilpyridines of formula (I) having improved herbicidal action. To be provided are in particular uracilpyridines of formula (I) which have high herbicidal activity, in particular even at low application rates, and which are sufficiently compatible with crop plants for commercial utilization.

These and further objects are achieved by the uracilpyridines of formula (I), defined below, and by their agriculturally suitable salts.

Accordingly, the present invention provides uracilpyridines of formula (I)

(I)

wherein the substituents have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$ or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9(O)_2NR^{10}R^{11}$, wherein
  $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^{12}R^{13}$, wherein $R^{12}$ and $R^{13}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
    wherein each cycloalkyl, heterocyclyl, phenyl or heteroaryl ring can be substituted by one to four substituents selected from $R^{14}$ or a 3- to 7-membered carbocyclus,
    which carbocyclus optionally has in addition to carbon atoms one or two ring members selected from the group consisting of —N($R^{12}$)—, —N=N—, —C(=O)—, —O— and —S—, and
    which carbocyclus is optionally substituted with one to four substituents selected from $R^{14}$;
    wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
  $R^{10}$, $R^{11}$ independently of one another are $R^9$, or together form a 3- to 7-membered carbocyclus,
    which carbocyclus optionally has in addition to carbon atoms one or two ring members selected from the group consisting of —N($R^{12}$)—, —N=N—, —C(=O)—, —O— and —S—, and
    which carbocyclus is optionally substituted with one to four substituents selected from $R^{14}$;
n 1 to 3;
Q $CH_2$, O, S, SO, $SO_2$, NH or ($C_1$-$C_3$-alkyl)N;
W O or S;
X NH, $NCH_3$, O or S;
Y O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
including their agriculturally acceptable salts or derivatives, provided the compounds of formula (I) have a carboxyl group.

The present invention provides also uracilpyridines of formula (I)

(I)

wherein the substituents have the following meanings:
R$^1$ hydrogen, NH$_2$, C$_1$-C$_6$-alkyl or C$_3$-C$_6$-alkynyl;
R$^2$ hydrogen, C$_1$-C$_6$-alkyl or C$_1$-C$_6$-haloalkyl;
R$^3$ hydrogen or C$_1$-C$_6$-alkyl;
R$^4$ H or halogen;
R$^5$ halogen, CN, NO$_2$, NH$_2$, CF$_3$ or C(=S)NH$_2$;
R$^6$ H, halogen, CN, C$_1$-C$_3$-alkyl, C$_1$-C$_3$-haloalkyl, C$_1$-C$_3$-alkoxy, C$_1$-C$_3$-haloalkoxy, C$_1$-C$_3$-alkylthio, (C$_1$-C$_3$-alkyl)amino, di(C$_1$-C$_3$-alkyl)amino, C$_1$-C$_3$-alkoxy-C$_1$-C$_3$-alkyl, C$_1$-C$_3$-alkoxycarbonyl;
R$^7$ H, halogen, C$_1$-C$_3$-alkyl, C$_1$-C$_3$-alkoxy;
R$^8$ OR$^9$, SR$^9$, NR$^{10}$R$^{11}$, NR$^9$OR$^9$, NR$^9$S(O)$_2$R$^{10}$ or NR$^9$S(O)$_2$NR$^{10}$R$^{11}$, wherein
  R$^9$ is hydrogen, C$_1$-C$_6$-alkyl, C$_3$-C$_6$-alkenyl, C$_3$-C$_6$-alkynyl, C$_1$-C$_6$-haloalkyl, C$_3$-C$_6$-haloalkenyl, C$_3$-C$_6$-haloalkynyl, C$_1$-C$_6$-cyanoalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, di(C$_1$-C$_6$-alkoxy)C$_1$-C$_6$-alkyl, C$_1$-C$_6$-haloalkoxy-C$_1$-C$_6$-alkyl, C$_3$-C$_6$-alkenyloxy-C$_1$-C$_6$-alkyl, C$_3$-C$_6$-haloalkenyloxy-C$_1$-C$_6$-alkyl, C$_3$-C$_6$-alkenyloxy-C$_1$-C$_6$-alkoxy-C$_1$-C$_6$-alkyl, C$_1$-C$_6$-alkylthio-C$_1$-C$_6$-alkyl, C$_1$-C$_6$-alkylsulfinyl-C$_1$-C$_6$-alkyl, C$_1$-C$_6$-alkylsulfonyl-C$_1$-C$_6$-alkyl, C$_1$-C$_6$-alkylcarbonyl-C$_1$-C$_6$-alkyl, C$_1$-C$_6$-alkoxycarbonyl-C$_1$-C$_6$-alkyl, C$_1$-C$_6$-haloalkoxycarbonyl-C$_1$-C$_6$-alkyl, C$_3$-C$_6$-alkenyloxycarbonyl-C$_1$-C$_6$-alkyl, C$_3$-C$_6$-alkynyloxycarbonyl-C$_1$-C$_6$-alkyl, amino, (C$_1$-C$_6$-alkyl)amino, di(C$_1$-C$_6$-alkyl)amino, (C$_1$-C$_6$-alkylcarbonyl)amino, amino-C$_1$-C$_6$-alkyl, (C$_1$-C$_6$-alkyl)amino-C$_1$-C$_6$-alkyl, di(C$_1$-C$_6$-alkyl)amino-C$_1$-C$_6$-alkyl, aminocarbonyl-C$_1$-C$_6$-alkyl, (C$_1$-C$_6$-alkyl)aminocarbonyl-C$_1$-C$_6$-alkyl, di(C$_1$-C$_6$-alkyl)aminocarbonyl-C$_1$-C$_6$-alkyl,
    —N=CR$^{12}$R$^{13}$, wherein R$^{12}$ and R$^{13}$ independently of one another are H, C$_1$-C$_4$-alkyl or phenyl;
  C$_3$-C$_6$-cycloalkyl, C$_3$-C$_6$-cycloalkyl-C$_1$-C$_6$-alkyl, C$_3$-C$_6$-heterocyclyl, C$_3$-C$_6$-heterocyclyl-C$_1$-C$_6$-alkyl, phenyl, phenyl-C$_1$-C$_4$-alkyl or a 5- or 6 membered heteroaryl,
    wherein each cycloalkyl, heterocyclyl, phenyl or heteroaryl ring can be substituted by one to four substituents selected from R$^{14}$ or a 3- to 7-membered carbocyclus,
      which carbocyclus optionally has in addition to carbon atoms one or two ring members selected from the group consisting of —N(R$^{12}$)—, —N=N—, —C(=O)—, —O— and —S—, and
      which carbocyclus is optionally substituted with one to four substituents selected from R$^{14}$;
      wherein R$^{14}$ is halogen, NO$_2$, CN, C$_1$-C$_4$-alkyl, C$_1$-C$_4$-haloalkyl, C$_1$-C$_4$-alkoxy or C$_1$-C$_4$-alkoxycarbonyl;
  R$^{10}$, R$^{11}$ independently of one another are R$^9$, or together form a 3- to 7-membered carbocyclus,
    which carbocyclus optionally has in addition to carbon atoms one or two ring members selected from the group consisting of —N(R$^{12}$)—, —N=N—, —C(=O)—, —O— and —S—, and
    which carbocyclus is optionally substituted with one to four substituents selected from R$^{14}$;
n 1 to 3;
Q O, S, SO, SO$_2$, NH or (C$_1$-C$_3$-alkyl)N;
W O or S;
X O or S;
Y O or S;
Z phenyl, pyridyl, pyridazinyl, pyrimidinyl or pyrazinyl, each of which is optionally substituted by 1 to 4 substituents selected from the group consisting of halogen, CN, C$_1$-C$_6$-alkyl, C$_1$-C$_6$-haloalkyl, C$_1$-C$_6$-alkoxy, C$_1$-C$_6$-haloalkoxy;
including their agriculturally acceptable salts or derivatives, provided the compounds of formula (I) have a carboxyl group.

The present invention also provides agrochemical compositions comprising at least one uracilpyridine of formula (I) and auxiliaries customary for formulating crop protection agents.

The present invention also provides herbicidal compositions comprising at least one uracilpyridine of formula (I) (component A) and at least one further compound selected from the herbicidal compounds B (component B) and safeners C (component C).

The present invention also provides the use of uracilpyridines of formula (I) as herbicides, i.e. for controlling harmful plants.

The present invention furthermore provides a method for controlling unwanted vegetation where a herbicidal effective amount of at least one uracilpyridines of the formula (I) is allowed to act on plants, their seeds and/or their habitat. Application can be done before, during and/or after, preferably during and/or after, the emergence of the undesirable plants.

Moreover, the invention relates to processes and intermediates for preparing uracilpyridines of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms. As used herein, the terms "undesirable vegetation" and "harmful plants" are synonyms.

If the uracilpyridines of formula (I), the herbicidal compounds B and/or the safeners C as described herein are capable of forming geometrical isomers, for example E/Z isomers, it is possible to use both, the pure isomers and mixtures thereof, in the compositions according to the invention.

If the uracilpyridines of formula (I), the herbicidal compounds B and/or the safeners C as described herein have one or more centres of chirality and, as a consequence, are present as enantiomers or diastereomers, it is possible to use both, the pure enantiomers and diastereomers and their mixtures, in the compositions according to the invention.

Within the substituents of the uracilpyridines of formula (I), instead of hydrogene also the corresponding isotope deuterium can be used.

If the uracilpyridines of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by C$_1$-C$_4$- alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris(isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine.

Also preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, di hydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Uracilpyridines of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$ to $R^{14}$ and $R^a$ to $R^e$, are—like the term halogen—collective terms for individual enumerations of the individual group members. The term halogen denotes in each case fluorine, chlorine, bromine or iodine. All hydrocarbon chains, e.g. all alkyl, alkenyl, alkynyl, alkoxy chains, can be straight-chain or branched, the prefix $C_n$-$C_m$ denoting in each case the possible number of carbon atoms in the group.

Examples of such meanings are:

$C_1$-$C_3$-alkyl and also the $C_1$-$C_3$-alkyl moieties of di($C_1$-$C_3$-alkyl)amino, $C_1$-$C_3$-alkoxy-$C_1$-$C_3$-alkyl: for example $CH_3$, $C_2H_5$, n-propyl and $CH(CH_3)_2$;

$C_1$-$C_4$-alkyl and also the $C_1$-$C_4$-alkyl moieties of phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cyanoalkyl, $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl, $C_3$-$C_6$-cycloalkyl-$C_1$-$C_6$-alkyl, $C_3$-$C_6$-heterocyclyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethyl propyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_3$-haloalkyl: $C_1$-$C_3$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-alkenyl and also the $C_3$-$C_6$-alkenyl moieties of $C_3$-$C_6$-alkenyloxy-$C_1$-$C_6$-alkyl, $C_3$-$C_6$-alkenyloxy-$C_1$-$C_6$-alkoxy-$C_1$-$C_6$-alkyl, $C_3$-$C_6$-alkenyloxycarbonyl-$C_1$-$C_6$-alkyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl and also the $C_3$-$C_6$-haloalkenyl moieties of $C_3$-$C_6$-haloalkenyloxy-$C_1$-$C_6$-alkyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl moieties of $C_3$-$C_6$-alkynyloxycarbonyl-$C_1$-$C_6$-alkyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_3$-alkoxy and also the $C_1$-$C_3$-alkoxy moieties of $C_1$-$C_3$-alkoxy-$C_1$-$C_3$-alkyl, $C_1$-$C_3$-alkoxycarbonyl: for example methoxy, ethoxy, propoxy;

$C_1$-$C_4$-alkoxy and also the $C_1$-$C_4$-alkoxy moieties of $C_1$-$C_4$-alkoxycarbonyl: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_3$-$C_6$-alkenyloxy-$C_1$-$C_6$-alkoxy-$C_1$-$C_6$-alkyl, $C_1$-$C_6$-alkoxycarbonyl-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_3$-haloalkoxy: a $C_1$-$C_3$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3, 3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and also the $C_1$-$C_6$-haloalkoxy moieties of $C_1$-$C_6$-haloalkoxy-$C_1$-$C_6$-alkyl, $C_1$-$C_6$-haloalkoxycarbonyl-$C_1$-$C_6$-alkyl: a $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_3$-alkylthio: for example methylthio, ethylthio, propylthio, 1-methylethylthio;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio and also the $C_1$-$C_6$-alkylthio moieties of $C_1$-$C_6$-alkylthio-$C_1$-$C_6$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—) and also the $C_1$-$C_6$-alkylsulfinyl moieties of $C_1$-$C_6$-alkylsulfinyl-$C_1$-$C_6$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_6$-alkyl: for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethyl propylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-tri methylpropylsulfonyl, 1-ethyl-1-methylpropylsulfonyl and 1-ethyl-2-methylpropylsulfonyl;

($C_1$-$C_3$-alkyl)amino: for example methylamino, ethylamino, propylamino, 1-methylethylamino;

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, Nethyl-N-(1-ethylpropyl)amino, N-ethyl-N-hexylamino, N-ethyl-N-(1,1-dimethylpropyl)amino, Nethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-

(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-heterocyclyl and also the heterocyclyl moieties of $C_3$-$C_6$-heterocyclyl-$C_1$-$C_6$-alkyl: aliphatic heterocycle having 3 to 6 ring members which, in addition to carbon atoms, contains 1 to 4 nitrogen atoms, or 1 to 3 nitrogen atoms and an oxygen or sulphur atom, or an oxygen or a sulphur atom, for example three- or four-membered heterocycles like 2-oxetanyl, 3-oxetanyl, 2-thietanyl, 3-thietanyl, 1-azetidinyl, 2-azetidinyl, 1-azetinyl, 2-azetinyl; five-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl; six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

5- or 6 membered heteroaryl: aromatic heteroaryl having 5 or 6 ring members which, in addition to carbon atoms, contains 1 to 4 nitrogen atoms, or 1 to 3 nitrogen atoms and an oxygen or sulphur atom, or an oxygen or a sulphur atom, for example 5-membered aromatic rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); 1-tetrazolyl; 6-membered aromatic rings like pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl);

3- to 7-membered carbocyclus: a three- to seven-membered monocyclic, saturated, partial unsaturated or aromatic cycle having three to seven ring members which comprises apart from carbon atoms optionally one or two ring members selected from the group consisting of —N($R^{12}$)—, —N=N—, —C(=O)—, —O— and —S—.

The preferred embodiments of the invention mentioned herein below have to be understood as being preferred either independently from each other or in combination with one another.

According to a preferred embodiment of the invention preference is also given to those uracilpyridines of formula (I), wherein the variables, either independently of one another or in combination with one another, have the following meanings:

Preferred are the uracilpyridines of formula (I) wherein
$R^1$ is hydrogen, $NH_2$ or $C_1$-$C_6$-alkyl;
preferably is $NH_2$ or $C_1$-$C_4$-alkyl;
particularly preferred is $NH_2$ or $CH_3$;
also preferably is $C_1$-$C_6$-alkyl;
particularly preferred is $C_1$-$C_4$-alkyl;
especially preferred is $CH_3$.

Also preferred are the uracilpyridines of formula (I) wherein
$R^2$ is $C_1$-$C_6$-alkyl or $C_1$-$C_6$-haloalkyl;
preferably is $C_1$-$C_4$-alkyl or $C_1$-$C_4$-haloalkyl;
more preferred is $C_1$-$C_4$-haloalkyl;
particularly preferred is $C_1$-$C_2$-haloalkyl;
especially preferred is $CF_3$.

Also preferred are the uracilpyridines of formula (I) wherein
$R^3$ is H;
also preferably is $C_1$-$C_6$-alkyl,
particularly preferred is $C_1$-$C_4$-alkyl,
especially preferred is $CH_3$.

Also preferred are the uracilpyridines of formula (I) wherein
$R^4$ is H, F or Cl;
particularly preferred is H or F;
especially preferred is H;
also particularly preferred is H or Cl;
especially preferred is Cl;
also particularly preferred is F or Cl;
especially preferred is F.

Also preferred are the uracilpyridines of formula (I) wherein
$R^5$ is halogen or CN;
preferably F, Cl, Br or CN;
particularly preferred is F, Cl or CN;
especially preferred is Cl or CN;

more preferred is Cl;
also more preferred is CN;
also especially preferred is F or Cl;
more preferred is F.

Also preferred are the uracilpyridines of formula (I) wherein
$R^6$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;
particularly preferred is H, $C_1$-$C_3$-alkyl, $C_1$-$C_3$-haloalkyl or $C_1$-$C_3$-alkoxy;
especially preferred is H, $C_1$-$C_3$-alkyl or $C_1$-$C_3$-alkoxy;
more preferred is H, $CH_3$ or $OCH_3$.

Also preferred are the uracilpyridines of formula (I) wherein
$R^7$ is H, halogen or $C_1$-$C_3$-alkyl;
particularly preferred is H, F or $CH_3$;
especially preferred is H.

Also preferred are the uracilpyridines of formula (I) wherein
$R^8$ is $OR^9$, $SR^9$, $NR^{10}R^{11}$, $NR^9S(O)_2R^{10}$ or $NR^9S(O)_2NR^{10}R^{11}$;
particularly preferred is $OR^9$, $NR^{10}R^{11}$, $NR^9S(O)_2R^{10}$ or $NR^9S(O)_2NR^{10}R^{11}$;
especially preferred $OR^9$, $NR^9S(O)_2R^{10}$ or $NR^9S(O)_2NR^{10}R^{11}$;
especially preferred is $OR^9$ or $NR^9S(O)_2R^{10}$.

Also preferred are the uracilpyridines of formula (I) wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$,
wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6-membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$,
wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
preferably is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
particularly preferred is hydrogen, $C_1$-$C_6$-alkyl, $C_3$-$C_6$-alkenyl, $C_3$-$C_6$-alkynyl or $C_1$-$C_6$-haloalkyl;
also particularly preferred is hydrogen, $C_1$-$C_6$-alkyl, $C_3$-$C_6$-alkenyl or $C_3$-$C_6$-alkynyl;
especially preferred is hydrogen, $C_1$-$C_6$-alkyl, or $C_3$-$C_6$-alkynyl;
more preferred is hydrogen, $CH_3$, $C_2H_5$, $CH_2CH=CH_2$ or $CH_2C\equiv CH$;
most preferred is hydrogen, $CH_3$, $C_2H_5$ or $CH_2C\equiv CH$.

Also preferred are the uracilpyridines of formula (I) wherein
$R^{10}$ is H, $C_1$-$C_6$-alkyl or $C_3$-$C_6$-cycloalkyl;
particularly preferred is H or $C_1$-$C_6$-alkyl;
more preferred is H;
also more preferred is $C_1$-$C_6$-alkyl.

Also preferred are the uracilpyridines of formula (I) wherein
$R^{11}$ is H, $C_1$-$C_6$-alkyl or $C_1$-$C_6$-alkoxycarbonyl-$C_1$-$C_6$-alkyl;
particularly preferred is H or $C_1$-$C_6$-alkyl;
more preferred is H;
also more preferred is $C_1$-$C_6$-alkyl.

Also preferred are the uracilpyridines of formula (I) wherein
$R^{12}$ is phenyl or $C_1$-$C_4$-alkyl;
particularly preferred is phenyl or $CH_3$;
also particularly preferred is phenyl;
also particularly preferred is $C_1$-$C_4$-alkyl.

Also preferred are the uracilpyridines of formula (I) wherein
$R^{13}$ is phenyl or $C_1$-$C_4$-alkyl;
particularly preferred is phenyl or $CH_3$;
also particularly preferred is phenyl;
also particularly preferred is $C_1$-$C_4$-alkyl.

Also preferred are the uracilpyridines of formula (I) wherein
$R^{14}$ is halogen or $C_1$-$C_6$-alkyl;
particularly preferred is F, Cl or $CH_3$;
also particularly preferred is halogen;
especially preferred is F or Cl;
also particularly preferred is $C_1$-$C_6$-alkyl;
especially preferred is $CH_3$.

Also preferred are the uracilpyridines of formula (I) wherein
n is 1 or 2;
particularly preferred is 2;
also particularly preferred is 1

Also preferred are the uracilpyridines of formula (I) wherein
Q is O, S, SO, $SO_2$, NH or ($C_1$-$C_3$-alkyl)N;
preferably is O or S;
particularly preferred is O.

Also preferred are the uracilpyridines of formula (I) wherein
W is O,
also preferably is S.

Also preferred are the uracilpyridines of formula (I) wherein
X is O,
also preferably is S.

Also preferred are the uracilpyridines of formula (I) wherein
Y is O,
also preferably is S.

Also preferred are the uracilpyridines of formula (I) wherein

Z is phenyl or pyridyl,
  each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
  preferably is phenyl,
  which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
  also preferably is pyridyl,
  which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy.

Also preferred are the uracilpyridines of formula (I) wherein

Z is phenyl or pyridyl,
  each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
  preferably is phenyl or pyridyl,
  each of which is optionally substituted by 1 to 4 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
  particularly preferred is phenyl or pyridyl,
  each of which is optionally substituted by 1 to 4 substituents selected from the group consisting of halogen or $C_1$-$C_6$-alkyl;
  especially preferred is phenyl or pyridyl,
  each of which is optionally substituted by 1 to 4 substituents selected from the group consisting of F, Cl or $CH_3$;
  more preferred is phenyl or pyridyl,
  each of which is unsubstituted.

Also preferred are the uracilpyridines of formula (I) wherein

Z is phenyl,
  which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
  preferably is phenyl,
  which is optionally substituted by 1 to 4 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
  particularly preferred is phenyl,
  which is optionally substituted by 1 to 4 substituents selected from the group consisting of halogen or $C_1$-$C_6$-alkyl;
  especially preferred is phenyl
  which is optionally substituted by 1 to 4 substituents selected from the group consisting of F, Cl or $CH_3$;
  more preferred is unsubstituted phenyl.

Also preferred are the uracilpyridines of formula (I) wherein

Z is pyridyl,
  which is optionally substituted by 1 to 3 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy;
  preferably is pyridyl,
  which is optionally substituted by 1 to 3 substituents selected from the group consisting of halogen, $C_1$-$C_6$-alkyl, $C_1$-$C_6$-haloalkyl, $C_1$-$C_6$-alkoxy or $C_1$-$C_6$-haloalkoxy;
  particularly preferred is pyridyl,
  which is optionally substituted by 1 to 3 substituents selected from the group consisting of halogen or $C_1$-$C_6$-alkyl;
  especially preferred is pyridyl,
  which is optionally substituted by 1 to 3 substituents selected from the group consisting of F, Cl or $CH_3$;
  more preferred is unsubstituted pyridyl.

Also preferred are the uracilpyridines of formula (I) wherein

Z is selected from the group consisting of $Z^1$ to $Z^{29}$

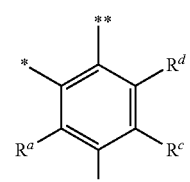

Z-1

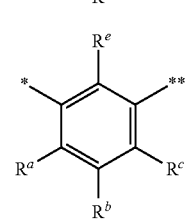

Z-2

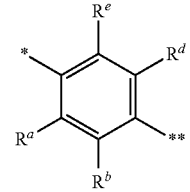

Z-3

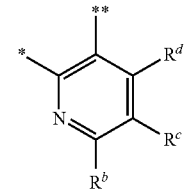

Z-4

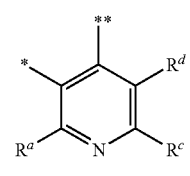

Z-5

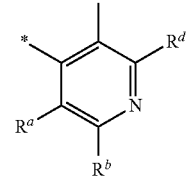

Z-6

-continued
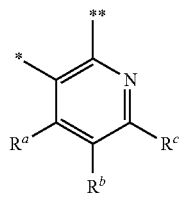 Z-7
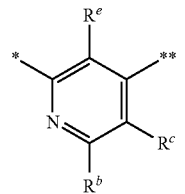 Z-8
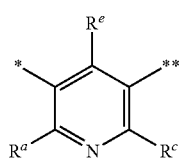 Z-9
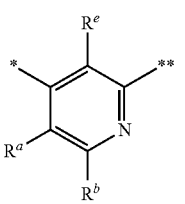 Z-10
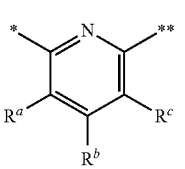 Z-11
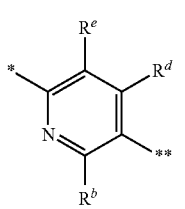 Z-12
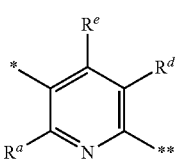 Z-13
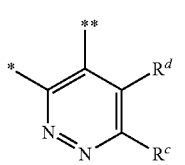 Z-14
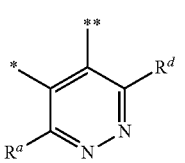 Z-15
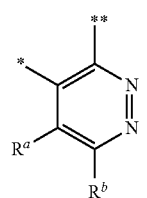 Z-16
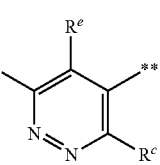 Z-17
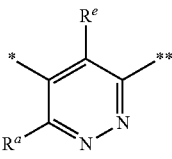 Z-18
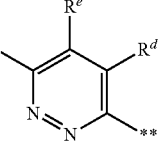 Z-19
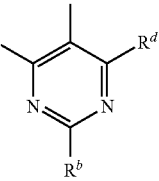 Z-20
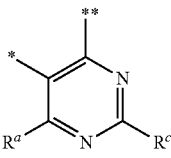 Z-21
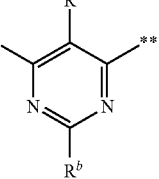 Z-22
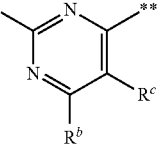 Z-23
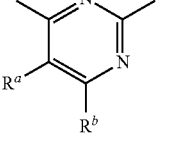 Z-24

-continued

Z-25

Z-26

Z-27

Z-28

Z-29 wherein
* denotes the point of attachment of Z to X;
* denotes the point of attachment of Z to Q; and
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H.

Also preferred are the uracilpyridines of formula (I) wherein
Z is selected from the group consisting of $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above;
particularly preferred is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above;
more particularly preferred is selected from the group consisting of $Z^1$, $Z^4$, $Z^5$, $Z^6$, $Z^7$ and $Z^{21}$ as defined above;
especially preferred is selected from the group consisting of $Z^1$, $Z^4$, $Z^5$, $Z^6$ and $Z^7$ as defined above;
more preferred is selected from the group consisting of $Z^1$ and $Z^7$ as defined above.

Also preferred are the uracilpyridines of formula (I) wherein
Z is selected from the group consisting of $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above;
wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy; preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
particularly preferred is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
more particularly preferred is selected from the group consisting of $Z^1$, $Z^4$, $Z^5$, $Z^6$, $Z^7$, and $Z^{21}$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
especially preferred is selected from the group consisting of $Z^1$, $Z^4$, $Z^5$, $Z^6$ and $Z^7$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy; preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
more preferred is selected from the group consisting of $Z^1$ and $Z^7$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H.

Also preferred are the uracilpyridines of formula (I) wherein
$R^1$ is $C_1$-$C_6$-alkyl,
$R^2$ is $C_1$-$C_4$-haloalkyl,
$R^3$ is H, and
Y is O.

Also preferred are the uracilpyridines of formula (I) wherein
$R^4$ is H or F, and
$R^5$ is F, Cl, Br or CN.

Also preferred are the uracilpyridines of formula (I) wherein
$R^4$ is H or F, and
$R^5$ is F, Cl or CN.

Also preferred are the uracilpyridines of formula (I) wherein
$R^6$ is H, $C_1$-$C_3$-alkyl or $C_1$-$C_3$-alkoxy, and
$R^7$ is H.

Also preferred are the uracilpyridines of formula (I) wherein
$R^8$ is $OR^9$, $NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl; and
$R^{10}$, $R^{11}$ are $C_1$-$C_6$-alkyl.

Also preferred are the uracilpyridines of formula (I) wherein
n is 1.

Also preferred are the uracilpyridines of formula (I) wherein
Q, W and X are O.

Also preferred are the uracilpyridines of formula (I) wherein
$R^1$ is hydrogen, $NH_2$ or $C_1$-$C_6$-alkyl;
$R^2$ is $C_1$-$C_6$-alkyl or $C_1$-$C_6$-haloalkyl;
$R^3$ is H;
$R^4$ is H or halogen;
$R^5$ is halogen or CN;
$R^6$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;
$R^7$ is H,
$R^8$ is $OR^9$, $SR^9$, $NR^{10}R^{11}$, $NR^9S(O)_2R^{10}$ or $NR^9S(O)_2NR^{10}R^{11}$; wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$,
wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6 membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$;

$R^{10}$ is $C_1$-$C_6$-alkyl;
$R^{11}$ is H or $C_1$-$C_6$-alkyl;
$R^{12}$ is phenyl or $CH_3$;
$R^{13}$ is phenyl or $CH_3$;
$R^{14}$ is halogen or $C_1$-$C_6$-alkyl;
n is 1 or 2;
Q is O, S, SO, $SO_2$, NH or ($C_1$-$C_3$-alkyl)N;
W is O;
X is O;
Y is O;
Z $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above, wherein
$R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
particularly preferred are the uracilpyridines of formula (I) wherein
$R^1$ is $NH_2$ or $C_1$-$C_4$-alkyl;
$R^2$ is $C_1$-$C_4$-alkyl or $C_1$-$C_4$-haloalkyl;
$R^3$ is H;
$R^4$ is H or halogen;
$R^5$ is halogen or CN;
$R^6$ is H, $C_1$-$C_3$-alkyl, $C_1$-$C_3$-haloalkyl or $C_1$-$C_3$-alkoxy;
$R^7$ is H;
$R^8$ $OR^9$, $NR^{10}R^{11}$, $NR^9S(O)_2R^{10}$ or $NR^9S(O)_2NR^{10}R^{11}$;
wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
$R^{10}$ is $C_1$-$C_6$-alkyl;
$R^{11}$ is H or $C_1$-$C_6$-alkyl;
n is 1;
Q is O, S, SO, $SO_2$, NH or ($C_1$-$C_3$-alkyl)N;
W is O;
X is O;
Y is O;
Z is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
especially preferred are the uracilpyridines of formula (I) wherein
$R^1$ is $NH_2$ or $CH_3$;
$R^2$ is $C_1$-$C_4$-haloalkyl;
$R^3$ is H;
$R^4$ is H, F or Cl;
$R^5$ is F, Cl, Br or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein
$R^9$ is hydrogen, $C_1$-$C_6$-alkyl, $C_3$-$C_6$-alkenyl, $C_3$-$C_6$-alkynyl or $C_1$-$C_6$-haloalkyl, and
$R^{10}$ is $C_1$-$C_6$-alkyl;
n is 1;
Q is O or S;
W is O;
X is O;
Y is O;
Z is selected from the group consisting of $Z^1$, $Z^4$, $Z^5$, $Z^6$, $Z^7$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;

also especially preferred are the uracilpyridines of formula (I) wherein
$R^1$ is $NH_2$ or $CH_3$;
$R^2$ is $C_1$-$C_4$-haloalkyl;
$R^3$ is H;
$R^4$ is H, F or Cl;
$R^5$ is F, Cl or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein
  $R^9$ is hydrogen, $C_1$-$C_6$-alkyl, $C_3$-$C_6$-alkenyl, $C_3$-$C_6$-alkynyl or $C_1$-$C_6$-haloalkyl, and
  $R^{10}$ is $C_1$-$C_6$-alkyl;
n is 1;
Q is O or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
more preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl, Br or CN;
$R^6$ is H, $CH_3$ or $OCH_3$;
$R^7$ is H;
$R^8$ is $OR^9$ or $NR^9S(O)_2R^{10}$; wherein
  $R^9$ is hydrogen, $C_1$-$C_6$-alkyl, $C_3$-$C_6$-alkenyl, or $C_3$-$C_6$-alkynyl, and
  $R^{10}$ is $C_1$-$C_6$-alkyl;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.
also more preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl or CN;
$R^6$ is H, $CH_3$ or $OCH_3$;
$R^7$ is H;
$R^8$ is $OR^9$ or $NR^9S(O)_2R^{10}$; wherein
  $R^9$ is hydrogen, $C_1$-$C_6$-alkyl, or $C_3$-$C_6$-alkynyl, and
  $R^{10}$ is $C_1$-$C_6$-alkyl;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

Also preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl, Br or CN;
$R^6$ is H, $CH_3$ or $OCH_3$;
$R^7$ is H;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
  $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^{12}R^{13}$, wherein $R^{12}$ and $R^{13}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6-membered heteroaryl,
    wherein each cycloalkyl, heterocyclyl, phenyl or heteroaryl ring can be substituted by one to four substituents selected from $R^{14}$ or a 3- to 7-membered carbocyclus,
      which carbocyclus optionally has in addition to carbon atoms one or two ring members selected from the group consisting of
      —N($R^{12}$)—, —N=N—, —C(=O)—, —O— and —S—, and
      which carbocyclus is optionally substituted with one to four substituents selected from $R^{14}$;
      wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
  $R^{10}$, $R^{11}$ independently of one another are $R^9$, or together form a 3- to 7-membered carbocyclus,
    which carbocyclus optionally has in addition to carbon atoms one or two ring members selected from the group consisting of —N($R^{12}$)—, —N=N—, —C(=O)—, —O— and —S—, and
    which carbocyclus is optionally substituted with one to four substituents selected from $R^{14}$;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

Also preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl or CN;
$R^6$ is H, $CH_3$ or $OCH_3$;
$R^7$ is H;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
  $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^{12}R^{13}$, wherein $R^{12}$ and $R^{13}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
    wherein each cycloalkyl, heterocyclyl, phenyl or heteroaryl ring can be substituted by one to four substituents selected from $R^{14}$ or a 3- to 7-membered carbocyclus,
      which carbocyclus optionally has in addition to carbon atoms one or two ring members selected from the group consisting of —N($R^{12}$)—, —N=N—, —C(=O)—, —O— and —S—, and
      which carbocyclus is optionally substituted with one to four substituents selected from $R^{14}$;
        wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
$R^{10}$, $R^{11}$ independently of one another are $R^9$, or together form a 3- to 7-membered carbocyclus,
  which carbocyclus optionally has in addition to carbon atoms one or two ring members selected from the group consisting of —N($R^{12}$)—, —N=N—, —C(=O)—, —O— and —S—, and
  which carbocyclus is optionally substituted with one to four substituents selected from $R^{14}$;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

Particular preference is given to uracilpyrimidines of formula (I.a) (corresponds to formula (I) wherein $R^1$ is $CH_3$, $R^2$ is $CF_3$, $R^3$ is H, $R^7$ is H, n is 1, Q, W, X and Y are O, and Z is Z-1 as defined, wherein $R^a$, $R^b$, $R^c$ and $R^d$ are H:

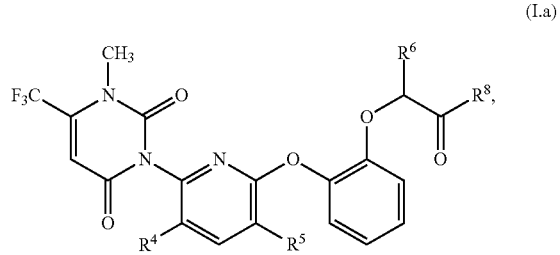

(I.a)

wherein the variables $R^4$, $R^5$, $R^6$ and $R^8$ have the meanings, in particular the preferred meanings, as defined above.

Special preference is given to the compounds of the formulae (I.a.1) to (I.a.672), preferably (I.a.1) to (I.a.504), of Table A, where the definitions of the variables $R^4$, $R^5$, $R^6$ and $R^8$ are of particular importance for the compounds according to the invention not only in combination with one another but in each case also on their own:

TABLE A

| No. | $R^4$ | $R^5$ | $R^6$ | $R^8$ |
|---|---|---|---|---|
| I.a.1. | H | F | H | OH |
| I.a.2. | H | F | H | $OCH_3$ |
| I.a.3. | H | F | H | $OC_2H_5$ |
| I.a.4. | H | F | H | $OCH(CH_3)_2$ |
| I.a.5. | H | F | H | $OCH_2CH_2CH_3$ |
| I.a.6. | H | F | H | $OCH_2CH(CH_3)_2$ |
| I.a.7. | H | F | H | $OCH_2CH=CH_2$ |
| I.a.8. | H | F | H | $OCH_2C\equiv CH$ |
| I.a.9. | H | F | H | $OCH_2CF_3$ |
| I.a.10. | H | F | H | $OCH_2CHF_2$ |
| I.a.11. | H | F | H | $OC_6H_5$ |
| I.a.12. | H | F | H | $OCH_2(C_6H_5)$ |
| I.a.13. | H | F | H | $OCH_2OCH_3$ |
| I.a.14. | H | F | H | $OCH_2OCH_2CH_3$ |
| I.a.15. | H | F | H | $OCH_2CH_2OCH_3$ |
| I.a.16. | H | F | H | $OCH_2CH_2OCH_2CH_3$ |
| I.a.17. | H | F | H | $OCH_2(CO)OCH_3$ |
| I.a.18. | H | F | H | $OCH_2(CO)OCH_2CH_3$ |
| I.a.19. | H | F | H | $OCH(CH_3)(CO)OCH_3$ |
| I.a.20. | H | F | H | $OCH(CH_3)(CO)OCH_2CH_3$ |
| I.a.21. | H | F | H | $OCH_2$-cyclopropyl |
| I.a.22. | H | F | H | $OCH_2$-cyclobutyl |
| I.a.23. | H | F | H | $SCH_3$ |
| I.a.24. | H | F | H | $SC_2H_5$ |
| I.a.25. | H | F | H | $NHSO_2CH_3$ |
| I.a.26. | H | F | H | $NHSO_2CH(CH_3)_2$ |
| I.a.27. | H | F | H | $NHSO_2N(CH_3)_2$ |
| I.a.28. | H | F | H | $NHSO_2N(CH_3)[CH(CH_3)_2]$ |
| I.a.29. | H | F | $CH_3$ | OH |
| I.a.30. | H | F | $CH_3$ | $OCH_3$ |
| I.a.31. | H | F | $CH_3$ | $OC_2H_5$ |
| I.a.32. | H | F | $CH_3$ | $OCH(CH_3)_2$ |
| I.a.33. | H | F | $CH_3$ | $OCH_2CH_2CH_3$ |
| I.a.34. | H | F | $CH_3$ | $OCH_2CH(CH_3)_2$ |
| I.a.35. | H | F | $CH_3$ | $OCH_2CH=CH_2$ |
| I.a.36. | H | F | $CH_3$ | $OCH_2C\equiv CH$ |
| I.a.37. | H | F | $CH_3$ | $OCH_2CF_3$ |
| I.a.38. | H | F | $CH_3$ | $OCH_2CHF_2$ |
| I.a.39. | H | F | $CH_3$ | $OC_6H_5$ |
| I.a.40. | H | F | $CH_3$ | $OCH_2(C_6H_5)$ |
| I.a.41. | H | F | $CH_3$ | $OCH_2OCH_3$ |
| I.a.42. | H | F | $CH_3$ | $OCH_2OCH_2CH_3$ |
| I.a.43. | H | F | $CH_3$ | $OCH_2CH_2OCH_3$ |
| I.a.44. | H | F | $CH_3$ | $OCH_2CH_2OCH_2CH_3$ |

TABLE A-continued

| No. | R⁴ | R⁵ | R⁶ | R⁸ |
|---|---|---|---|---|
| I.a.45. | H | F | CH₃ | OCH₂(CO)OCH₃ |
| I.a.46. | H | F | CH₃ | OCH₂(CO)OCH₂CH₃ |
| I.a.47. | H | F | CH₃ | OCH(CH₃)(CO)OCH₃ |
| I.a.48. | H | F | CH₃ | OCH(CH₃)(CO)OCH₂CH₃ |
| I.a.49. | H | F | CH₃ | OCH₂-cyclopropyl |
| I.a.50. | H | F | CH₃ | OCH₂-cyclobutyl |
| I.a.51. | H | F | CH₃ | SCH₃ |
| I.a.52. | H | F | CH₃ | SC₂H₅ |
| I.a.53. | H | F | CH₃ | NHSO₂CH₃ |
| I.a.54. | H | F | CH₃ | NHSO₂CH(CH₃)₂ |
| I.a.55. | H | F | CH₃ | NHSO₂N(CH₃)₂ |
| I.a.56. | H | F | CH₃ | NHSO₂N(CH₃)[CH(CH₃)₂] |
| I.a.57. | H | F | OCH₃ | OH |
| I.a.58. | H | F | OCH₃ | OCH₃ |
| I.a.59. | H | F | OCH₃ | OC₂H₅ |
| I.a.60. | H | F | OCH₃ | OCH(CH₃)₂ |
| I.a.61. | H | F | OCH₃ | OCH₂CH₂CH₃ |
| I.a.62. | H | F | OCH₃ | OCH₂CH(CH₃)₂ |
| I.a.63. | H | F | OCH₃ | OCH₂CH=CH₂ |
| I.a.64. | H | F | OCH₃ | OCH₂C≡CH |
| I.a.65. | H | F | OCH₃ | OCH₂CF₃ |
| I.a.66. | H | F | OCH₃ | OCH₂CHF₂ |
| I.a.67. | H | F | OCH₃ | OC₆H₅ |
| I.a.68. | H | F | OCH₃ | OCH₂(C₆H₅) |
| I.a.69. | H | F | OCH₃ | OCH₂OCH₃ |
| I.a.70. | H | F | OCH₃ | OCH₂OCH₂CH₃ |
| I.a.71. | H | F | OCH₃ | OCH₂CH₂OCH₃ |
| I.a.72. | H | F | OCH₃ | OCH₂CH₂OCH₂CH₃ |
| I.a.73. | H | F | OCH₃ | OCH₂(CO)OCH₃ |
| I.a.74. | H | F | OCH₃ | OCH₂(CO)OCH₂CH₃ |
| I.a.75. | H | F | OCH₃ | OCH(CH₃)(CO)OCH₃ |
| I.a.76. | H | F | OCH₃ | OCH(CH₃)(CO)OCH₂CH₃ |
| I.a.77. | H | F | OCH₃ | OCH₂-cyclopropyl |
| I.a.78. | H | F | OCH₃ | OCH₂-cyclobutyl |
| I.a.79. | H | F | OCH₃ | SCH₃ |
| I.a.80. | H | F | OCH₃ | SC₂H₅ |
| I.a.81. | H | F | OCH₃ | NHSO₂CH₃ |
| I.a.82. | H | F | OCH₃ | NHSO₂CH(CH₃)₂ |
| I.a.83. | H | F | OCH₃ | NHSO₂N(CH₃)₂ |
| I.a.84. | H | F | OCH₃ | NHSO₂N(CH₃)[CH(CH₃)₂] |
| I.a.85. | H | Cl | H | OH |
| I.a.86. | H | Cl | H | OCH₃ |
| I.a.87. | H | Cl | H | OC₂H₅ |
| I.a.88. | H | Cl | H | OCH(CH₃)₂ |
| I.a.89. | H | Cl | H | OCH₂CH₂CH₃ |
| I.a.90. | H | Cl | H | OCH₂CH(CH₃)₂ |
| I.a.91. | H | Cl | H | OCH₂CH=CH₂ |
| I.a.92. | H | Cl | H | OCH₂C≡CH |
| I.a.93. | H | Cl | H | OCH₂CF₃ |
| I.a.94. | H | Cl | H | OCH₂CHF₂ |
| I.a.95. | H | Cl | H | OC₆H₅ |
| I.a.96. | H | Cl | H | OCH₂(C₆H₅) |
| I.a.97. | H | Cl | H | OCH₂OCH₃ |
| I.a.98. | H | Cl | H | OCH₂OCH₂CH₃ |
| I.a.99. | H | Cl | H | OCH₂CH₂OCH₃ |
| I.a.100. | H | Cl | H | OCH₂CH₂OCH₂CH₃ |
| I.a.101. | H | Cl | H | OCH₂(CO)OCH₃ |
| I.a.102. | H | Cl | H | OCH₂(CO)OCH₂CH₃ |
| I.a.103. | H | Cl | H | OCH(CH₃)(CO)OCH₃ |
| I.a.104. | H | Cl | H | OCH(CH₃)(CO)OCH₂CH₃ |
| I.a.105. | H | Cl | H | OCH₂-cyclopropyl |
| I.a.106. | H | Cl | H | OCH₂-cyclobutyl |
| I.a.107. | H | Cl | H | SCH₃ |
| I.a.108. | H | Cl | H | SC₂H₅ |
| I.a.109. | H | Cl | H | NHSO₂CH₃ |
| I.a.110. | H | Cl | H | NHSO₂CH(CH₃)₂ |
| I.a.111. | H | Cl | H | NHSO₂N(CH₃)₂ |
| I.a.112. | H | Cl | H | NHSO₂N(CH₃)[CH(CH₃)₂] |
| I.a.113. | H | Cl | CH₃ | OH |
| I.a.114. | H | Cl | CH₃ | OCH₃ |
| I.a.115. | H | Cl | CH₃ | OC₂H₅ |
| I.a.116. | H | Cl | CH₃ | OCH(CH₃)₂ |
| I.a.117. | H | Cl | CH₃ | OCH₂CH₂CH₃ |
| I.a.118. | H | Cl | CH₃ | OCH₂CH(CH₃)₂ |
| I.a.119. | H | Cl | CH₃ | OCH₂CH=CH₂ |
| I.a.120. | H | Cl | CH₃ | OCH₂C≡CH |
| I.a.121. | H | Cl | CH₃ | OCH₂CF₃ |
| I.a.122. | H | Cl | CH₃ | OCH₂CHF₂ |
| I.a.123. | H | Cl | CH₃ | OC₆H₅ |
| I.a.124. | H | Cl | CH₃ | OCH₂(C₆H₅) |
| I.a.125. | H | Cl | CH₃ | OCH₂OCH₃ |
| I.a.126. | H | Cl | CH₃ | OCH₂OCH₂CH₃ |
| I.a.127. | H | Cl | CH₃ | OCH₂CH₂OCH₃ |
| I.a.128. | H | Cl | CH₃ | OCH₂CH₂OCH₂CH₃ |
| I.a.129. | H | Cl | CH₃ | OCH₂(CO)OCH₃ |
| I.a.130. | H | Cl | CH₃ | OCH₂(CO)OCH₂CH₃ |
| I.a.131. | H | Cl | CH₃ | OCH(CH₃)(CO)OCH₃ |
| I.a.132. | H | Cl | CH₃ | OCH(CH₃)(CO)OCH₂CH₃ |
| I.a.133. | H | Cl | CH₃ | OCH₂-cyclopropyl |
| I.a.134. | H | Cl | CH₃ | OCH₂-cyclobutyl |
| I.a.135. | H | Cl | CH₃ | SCH₃ |
| I.a.136. | H | Cl | CH₃ | SC₂H₅ |
| I.a.137. | H | Cl | CH₃ | NHSO₂CH₃ |
| I.a.138. | H | Cl | CH₃ | NHSO₂CH(CH₃)₂ |
| I.a.139. | H | Cl | CH₃ | NHSO₂N(CH₃)₂ |
| I.a.140. | H | Cl | CH₃ | NHSO₂N(CH₃)[CH(CH₃)₂] |
| I.a.141. | H | Cl | OCH₃ | OH |
| I.a.142. | H | Cl | OCH₃ | OCH₃ |
| I.a.143. | H | Cl | OCH₃ | OC₂H₅ |
| I.a.144. | H | Cl | OCH₃ | OCH(CH₃)₂ |
| I.a.145. | H | Cl | OCH₃ | OCH₂CH₂CH₃ |
| I.a.146. | H | Cl | OCH₃ | OCH₂CH(CH₃)₂ |
| I.a.147. | H | Cl | OCH₃ | OCH₂CH=CH₂ |
| I.a.148. | H | Cl | OCH₃ | OCH₂C≡CH |
| I.a.149. | H | Cl | OCH₃ | OCH₂CF₃ |
| I.a.150. | H | Cl | OCH₃ | OCH₂CHF₂ |
| I.a.151. | H | Cl | OCH₃ | OC₆H₅ |
| I.a.152. | H | Cl | OCH₃ | OCH₂(C₆H₅) |
| I.a.153. | H | Cl | OCH₃ | OCH₂OCH₃ |
| I.a.154. | H | Cl | OCH₃ | OCH₂OCH₂CH₃ |
| I.a.155. | H | Cl | OCH₃ | OCH₂CH₂OCH₃ |
| I.a.156. | H | Cl | OCH₃ | OCH₂CH₂OCH₂CH₃ |
| I.a.157. | H | Cl | OCH₃ | OCH₂(CO)OCH₃ |
| I.a.158. | H | Cl | OCH₃ | OCH₂(CO)OCH₂CH₃ |
| I.a.159. | H | Cl | OCH₃ | OCH(CH₃)(CO)OCH₃ |
| I.a.160. | H | Cl | OCH₃ | OCH(CH₃)(CO)OCH₂CH₃ |
| I.a.161. | H | Cl | OCH₃ | OCH₂-cyclopropyl |
| I.a.162. | H | Cl | OCH₃ | OCH₂-cyclobutyl |
| I.a.163. | H | Cl | OCH₃ | SCH₃ |
| I.a.164. | H | Cl | OCH₃ | SC₂H₅ |
| I.a.165. | H | Cl | OCH₃ | NHSO₂CH₃ |
| I.a.166. | H | Cl | OCH₃ | NHSO₂CH(CH₃)₂ |
| I.a.167. | H | Cl | OCH₃ | NHSO₂N(CH₃)₂ |
| I.a.168. | H | Cl | OCH₃ | NHSO₂N(CH₃)[CH(CH₃)₂] |
| I.a.169. | H | CN | H | OH |
| I.a.170. | H | CN | H | OCH₃ |
| I.a.171. | H | CN | H | OC₂H₅ |
| I.a.172. | H | CN | H | OCH(CH₃)₂ |
| I.a.173. | H | CN | H | OCH₂CH₂CH₃ |
| I.a.174. | H | CN | H | OCH₂CH(CH₃)₂ |
| I.a.175. | H | CN | H | OCH₂CH=CH₂ |
| I.a.176. | H | CN | H | OCH₂C≡CH |
| I.a.177. | H | CN | H | OCH₂CF₃ |
| I.a.178. | H | CN | H | OCH₂CHF₂ |
| I.a.179. | H | CN | H | OC₆H₅ |
| I.a.180. | H | CN | H | OCH₂(C₆H₅) |
| I.a.181. | H | CN | H | OCH₂OCH₃ |
| I.a.182. | H | CN | H | OCH₂OCH₂CH₃ |
| I.a.183. | H | CN | H | OCH₂CH₂OCH₃ |
| I.a.184. | H | CN | H | OCH₂CH₂OCH₂CH₃ |
| I.a.185. | H | CN | H | OCH₂(CO)OCH₃ |
| I.a.186. | H | CN | H | OCH₂(CO)OCH₂CH₃ |
| I.a.187. | H | CN | H | OCH(CH₃)(CO)OCH₃ |
| I.a.188. | H | CN | H | OCH(CH₃)(CO)OCH₂CH₃ |
| I.a.189. | H | CN | H | OCH₂-cyclopropyl |
| I.a.190. | H | CN | H | OCH₂-cyclobutyl |
| I.a.191. | H | CN | H | SCH₃ |
| I.a.192. | H | CN | H | SC₂H₅ |
| I.a.193. | H | CN | H | NHSO₂CH₃ |
| I.a.194. | H | CN | H | NHSO₂CH(CH₃)₂ |
| I.a.195. | H | CN | H | NHSO₂N(CH₃)₂ |
| I.a.196. | H | CN | H | NHSO₂N(CH₃)[CH(CH₃)₂] |
| I.a.197. | H | CN | CH₃ | OH |
| I.a.198. | H | CN | CH₃ | OCH₃ |
| I.a.199. | H | CN | CH₃ | OC₂H₅ |
| I.a.200. | H | CN | CH₃ | OCH(CH₃)₂ |

TABLE A-continued

| No. | R⁴ | R⁵ | R⁶ | R⁸ |
|---|---|---|---|---|
| I.a.201. | H | CN | $CH_3$ | $OCH_2CH_2CH_3$ |
| I.a.202. | H | CN | $CH_3$ | $OCH_2CH(CH_3)_2$ |
| I.a.203. | H | CN | $CH_3$ | $OCH_2CH=CH_2$ |
| I.a.204. | H | CN | $CH_3$ | $OCH_2C\equiv CH$ |
| I.a.205. | H | CN | $CH_3$ | $OCH_2CF_3$ |
| I.a.206. | H | CN | $CH_3$ | $OCH_2CHF_2$ |
| I.a.207. | H | CN | $CH_3$ | $OC_6H_5$ |
| I.a.208. | H | CN | $CH_3$ | $OCH_2(C_6H_5)$ |
| I.a.209. | H | CN | $CH_3$ | $OCH_2OCH_3$ |
| I.a.210. | H | CN | $CH_3$ | $OCH_2OCH_2CH_3$ |
| I.a.211. | H | CN | $CH_3$ | $OCH_2CH_2OCH_3$ |
| I.a.212. | H | CN | $CH_3$ | $OCH_2CH_2OCH_2CH_3$ |
| I.a.213. | H | CN | $CH_3$ | $OCH_2(CO)OCH_3$ |
| I.a.214. | H | CN | $CH_3$ | $OCH_2(CO)OCH_2CH_3$ |
| I.a.215. | H | CN | $CH_3$ | $OCH(CH_3)(CO)OCH_3$ |
| I.a.216. | H | CN | $CH_3$ | $OCH(CH_3)(CO)OCH_2CH_3$ |
| I.a.217. | H | CN | $CH_3$ | $OCH_2$-cyclopropyl |
| I.a.218. | H | CN | $CH_3$ | $OCH_2$-cyclobutyl |
| I.a.219. | H | CN | $CH_3$ | $SCH_3$ |
| I.a.220. | H | CN | $CH_3$ | $SC_2H_5$ |
| I.a.221. | H | CN | $CH_3$ | $NHSO_2CH_3$ |
| I.a.222. | H | CN | $CH_3$ | $NHSO_2CH(CH_3)_2$ |
| I.a.223. | H | CN | $CH_3$ | $NHSO_2N(CH_3)_2$ |
| I.a.224. | H | CN | $CH_3$ | $NHSO_2N(CH_3)[CH(CH_3)_2]$ |
| I.a.225. | H | CN | $OCH_3$ | OH |
| I.a.226. | H | CN | $OCH_3$ | $OCH_3$ |
| I.a.227. | H | CN | $OCH_3$ | $OC_2H_5$ |
| I.a.228. | H | CN | $OCH_3$ | $OCH(CH_3)_2$ |
| I.a.229. | H | CN | $OCH_3$ | $OCH_2CH_2CH_3$ |
| I.a.230. | H | CN | $OCH_3$ | $OCH_2CH(CH_3)_2$ |
| I.a.231. | H | CN | $OCH_3$ | $OCH_2CH=CH_2$ |
| I.a.232. | H | CN | $OCH_3$ | $OCH_2C\equiv CH$ |
| I.a.233. | H | CN | $OCH_3$ | $OCH_2CF_3$ |
| I.a.234. | H | CN | $OCH_3$ | $OCH_2CHF_2$ |
| I.a.235. | H | CN | $OCH_3$ | $OC_6H_5$ |
| I.a.236. | H | CN | $OCH_3$ | $OCH_2(C_6H_5)$ |
| I.a.237. | H | CN | $OCH_3$ | $OCH_2OCH_3$ |
| I.a.238. | H | CN | $OCH_3$ | $OCH_2OCH_2CH_3$ |
| I.a.239. | H | CN | $OCH_3$ | $OCH_2CH_2OCH_3$ |
| I.a.240. | H | CN | $OCH_3$ | $OCH_2CH_2OCH_2CH_3$ |
| I.a.241. | H | CN | $OCH_3$ | $OCH_2(CO)OCH_3$ |
| I.a.242. | H | CN | $OCH_3$ | $OCH_2(CO)OCH_2CH_3$ |
| I.a.243. | H | CN | $OCH_3$ | $OCH(CH_3)(CO)OCH_3$ |
| I.a.244. | H | CN | $OCH_3$ | $OCH(CH_3)(CO)OCH_2CH_3$ |
| I.a.245. | H | CN | $OCH_3$ | $OCH_2$-cyclopropyl |
| I.a.246. | H | CN | $OCH_3$ | $OCH_2$-cyclobutyl |
| I.a.247. | H | CN | $OCH_3$ | $SCH_3$ |
| I.a.248. | H | CN | $OCH_3$ | $SC_2H_5$ |
| I.a.249. | H | CN | $OCH_3$ | $NHSO_2CH_3$ |
| I.a.250. | H | CN | $OCH_3$ | $NHSO_2CH(CH_3)_2$ |
| I.a.251. | H | CN | $OCH_3$ | $NHSO_2N(CH_3)_2$ |
| I.a.252. | H | CN | $OCH_3$ | $NHSO_2N(CH_3)[CH(CH_3)_2]$ |
| I.a.253. | F | F | H | OH |
| I.a.254. | F | F | H | $OCH_3$ |
| I.a.255. | F | F | H | $OC_2H_5$ |
| I.a.256. | F | F | H | $OCH(CH_3)_2$ |
| I.a.257. | F | F | H | $OCH_2CH_2CH_3$ |
| I.a.258. | F | F | H | $OCH_2CH(CH_3)_2$ |
| I.a.259. | F | F | H | $OCH_2CH=CH_2$ |
| I.a.260. | F | F | H | $OCH_2C\equiv CH$ |
| I.a.261. | F | F | H | $OCH_2CF_3$ |
| I.a.262. | F | F | H | $OCH_2CHF_2$ |
| I.a.263. | F | F | H | $OC_6H_5$ |
| I.a.264. | F | F | H | $OCH_2(C_6H_5)$ |
| I.a.265. | F | F | H | $OCH_2OCH_3$ |
| I.a.266. | F | F | H | $OCH_2OCH_2CH_3$ |
| I.a.267. | F | F | H | $OCH_2CH_2OCH_3$ |
| I.a.268. | F | F | H | $OCH_2CH_2OCH_2CH_3$ |
| I.a.269. | F | F | H | $OCH_2(CO)OCH_3$ |
| I.a.270. | F | F | H | $OCH_2(CO)OCH_2CH_3$ |
| I.a.271. | F | F | H | $OCH(CH_3)(CO)OCH_3$ |
| I.a.272. | F | F | H | $OCH(CH_3)(C0)OCH_2CH_3$ |
| I.a.273. | F | F | H | $OCH_2$-cyclopropyl |
| I.a.274. | F | F | H | $OCH_2$-cyclobutyl |
| I.a.275. | F | F | H | $SCH_3$ |
| I.a.276. | F | F | H | $SC_2H_5$ |
| I.a.277. | F | F | H | $NHSO_2CH_3$ |
| I.a.278. | F | F | H | $NHSO_2CH(CH_3)_2$ |
| I.a.279. | F | F | H | $NHSO_2N(CH_3)_2$ |
| I.a.280. | F | F | H | $NHSO_2N(CH_3)[CH(CH_3)_2]$ |
| I.a.281. | F | F | $CH_3$ | OH |
| I.a.282. | F | F | $CH_3$ | $OCH_3$ |
| I.a.283. | F | F | $CH_3$ | $OC_2H_5$ |
| I.a.284. | F | F | $CH_3$ | $OCH(CH_3)_2$ |
| I.a.285. | F | F | $CH_3$ | $OCH_2CH_2CH_3$ |
| I.a.286. | F | F | $CH_3$ | $OCH_2CH(CH_3)_2$ |
| I.a.287. | F | F | $CH_3$ | $OCH_2CH=CH_2$ |
| I.a.288. | F | F | $CH_3$ | $OCH_2C\equiv CH$ |
| I.a.289. | F | F | $CH_3$ | $OCH_2CF_3$ |
| I.a.290. | F | F | $CH_3$ | $OCH_2CHF_2$ |
| I.a.291. | F | F | $CH_3$ | $OC_6H_5$ |
| I.a.292. | F | F | $CH_3$ | $OCH_2(C_6H_5)$ |
| I.a.293. | F | F | $CH_3$ | $OCH_2OCH_3$ |
| I.a.294. | F | F | $CH_3$ | $OCH_2OCH_2CH_3$ |
| I.a.295. | F | F | $CH_3$ | $OCH_2CH_2OCH_3$ |
| I.a.296. | F | F | $CH_3$ | $OCH_2CH_2OCH_2CH_3$ |
| I.a.297. | F | F | $CH_3$ | $OCH_2(CO)OCH_3$ |
| I.a.298. | F | F | $CH_3$ | $OCH_2(CO)OCH_2CH_3$ |
| I.a.299. | F | F | $CH_3$ | $OCH(CH_3)(CO)OCH_3$ |
| I.a.300. | F | F | $CH_3$ | $OCH(CH_3)(CO)OCH_2CH_3$ |
| I.a.301. | F | F | $CH_3$ | $OCH_2$-cyclopropyl |
| I.a.302. | F | F | $CH_3$ | $OCH_2$-cyclobutyl |
| I.a.303. | F | F | $CH_3$ | $SCH_3$ |
| I.a.304. | F | F | $CH_3$ | $SC_2H_5$ |
| I.a.305. | F | F | $CH_3$ | $NHSO_2CH_3$ |
| I.a.306. | F | F | $CH_3$ | $NHSO_2CH(CH_3)_2$ |
| I.a.307. | F | F | $CH_3$ | $NHSO_2N(CH_3)_2$ |
| I.a.308. | F | F | $CH_3$ | $NHSO_2N(CH_3)[CH(CH_3)_2]$ |
| I.a.309. | F | F | $OCH_3$ | OH |
| I.a.310. | F | F | $OCH_3$ | $OCH_3$ |
| I.a.311. | F | F | $OCH_3$ | $OC_2H_5$ |
| I.a.312. | F | F | $OCH_3$ | $OCH(CH_3)_2$ |
| I.a.313. | F | F | $OCH_3$ | $OCH_2CH_2CH_3$ |
| I.a.314. | F | F | $OCH_3$ | $OCH_2CH(CH_3)_2$ |
| I.a.315. | F | F | $OCH_3$ | $OCH_2CH=CH_2$ |
| I.a.316. | F | F | $OCH_3$ | $OCH_2C\equiv CH$ |
| I.a.317. | F | F | $OCH_3$ | $OCH_2CF_3$ |
| I.a.318. | F | F | $OCH_3$ | $OCH_2CHF_2$ |
| I.a.319. | F | F | $OCH_3$ | $OC_6H_5$ |
| I.a.320. | F | F | $OCH_3$ | $OCH_2(C_6H_5)$ |
| I.a.321. | F | F | $OCH_3$ | $OCH_2OCH_3$ |
| I.a.322. | F | F | $OCH_3$ | $OCH_2OCH_2CH_3$ |
| I.a.323. | F | F | $OCH_3$ | $OCH_2CH_2OCH_3$ |
| I.a.324. | F | F | $OCH_3$ | $OCH_2CH_2OCH_2CH_3$ |
| I.a.325. | F | F | $OCH_3$ | $OCH_2(CO)OCH_3$ |
| I.a.326. | F | F | $OCH_3$ | $OCH_2(CO)OCH_2CH_3$ |
| I.a.327. | F | F | $OCH_3$ | $OCH(CH_3)(CO)OCH_3$ |
| I.a.328. | F | F | $OCH_3$ | $OCH(CH_3)(CO)OCH_2CH_3$ |
| I.a.329. | F | F | $OCH_3$ | $OCH_2$-cyclopropyl |
| I.a.330. | F | F | $OCH_3$ | $OCH_2$-cyclobutyl |
| I.a.331. | F | F | $OCH_3$ | $SCH_3$ |
| I.a.332. | F | F | $OCH_3$ | $SC_2H_5$ |
| I.a.333. | F | F | $OCH_3$ | $NHSO_2CH_3$ |
| I.a.334. | F | F | $OCH_3$ | $NHSO_2CH(CH_3)_2$ |
| I.a.335. | F | F | $OCH_3$ | $NHSO_2N(CH_3)_2$ |
| I.a.336. | F | F | $OCH_3$ | $NHSO_2N(CH_3)[CH(CH_3)_2]$ |
| I.a.337. | F | Cl | H | OH |
| I.a.338. | F | Cl | H | $OCH_3$ |
| I.a.339. | F | Cl | H | $OC_2H_5$ |
| I.a.340. | F | Cl | H | $OCH(CH_3)_2$ |
| I.a.341. | F | Cl | H | $OCH_2CH_2CH_3$ |
| I.a.342. | F | Cl | H | $OCH_2CH(CH_3)_2$ |
| I.a.343. | F | Cl | H | $OCH_2CH=CH_2$ |
| I.a.344. | F | Cl | H | $OCH_2C\equiv CH$ |
| I.a.345. | F | Cl | H | $OCH_2CF_3$ |
| I.a.346. | F | Cl | H | $OCH_2CHF_2$ |
| I.a.347. | F | Cl | H | $OC_6H_5$ |
| I.a.348. | F | Cl | H | $OCH_2(C_6H_5)$ |
| I.a.349. | F | Cl | H | $OCH_2OCH_3$ |
| I.a.350. | F | Cl | H | $OCH_2OCH_2CH_3$ |
| I.a.351. | F | Cl | H | $OCH_2CH_2OCH_3$ |
| I.a.352. | F | Cl | H | $OCH_2CH_2OCH_2CH_3$ |
| I.a.353. | F | Cl | H | $OCH_2(CO)OCH_3$ |
| I.a.354. | F | Cl | H | $OCH_2(CO)OCH_2CH_3$ |
| I.a.355. | F | Cl | H | $OCH(CH_3)(CO)OCH_3$ |
| I.a.356. | F | Cl | H | $OCH(CH_3)(CO)OCH_2CH_3$ |

TABLE A-continued

| No. | $R^4$ | $R^5$ | $R^6$ | $R^8$ |
|---|---|---|---|---|
| I.a.357. | F | Cl | H | $OCH_2$-cyclopropyl |
| I.a.358. | F | Cl | H | $OCH_2$-cyclobutyl |
| I.a.359. | F | Cl | H | $SCH_3$ |
| I.a.360. | F | Cl | H | $SC_2H_5$ |
| I.a.361. | F | Cl | H | $NHSO_2CH_3$ |
| I.a.362. | F | Cl | H | $NHSO_2CH(CH_3)_2$ |
| I.a.363. | F | Cl | H | $NHSO_2N(CH_3)_2$ |
| I.a.364. | F | Cl | H | $NHSO_2N(CH_3)[CH(CH_3)_2]$ |
| I.a.365. | F | Cl | $CH_3$ | OH |
| I.a.366. | F | Cl | $CH_3$ | $OCH_3$ |
| I.a.367. | F | Cl | $CH_3$ | $OC_2H_5$ |
| I.a.368. | F | Cl | $CH_3$ | $OCH(CH_3)_2$ |
| I.a.369. | F | Cl | $CH_3$ | $OCH_2CH_2CH_3$ |
| I.a.370. | F | Cl | $CH_3$ | $OCH_2CH(CH_3)_2$ |
| I.a.371. | F | Cl | $CH_3$ | $OCH_2CH=CH_2$ |
| I.a.372. | F | Cl | $CH_3$ | $OCH_2C\equiv CH$ |
| I.a.373. | F | Cl | $CH_3$ | $OCH_2CF_3$ |
| I.a.374. | F | Cl | $CH_3$ | $OCH_2CHF_2$ |
| I.a.375. | F | Cl | $CH_3$ | $OC_6H_5$ |
| I.a.376. | F | Cl | $CH_3$ | $OCH_2(C_6H_5)$ |
| I.a.377. | F | Cl | $CH_3$ | $OCH_2OCH_3$ |
| I.a.378. | F | Cl | $CH_3$ | $OCH_2OCH_2CH_3$ |
| I.a.379. | F | Cl | $CH_3$ | $OCH_2CH_2OCH_3$ |
| I.a.380. | F | Cl | $CH_3$ | $OCH_2CH_2OCH_2CH_3$ |
| I.a.381. | F | Cl | $CH_3$ | $OCH_2(CO)OCH_3$ |
| I.a.382. | F | Cl | $CH_3$ | $OCH_2(CO)OCH_2CH_3$ |
| I.a.383. | F | Cl | $CH_3$ | $OCH(CH_3)(CO)OCH_3$ |
| I.a.384. | F | Cl | $CH_3$ | $OCH(CH_3)(CO)OCH_2CH_3$ |
| I.a.385. | F | Cl | $CH_3$ | $OCH_2$-cyclopropyl |
| I.a.386. | F | Cl | $CH_3$ | $OCH_2$-cyclobutyl |
| I.a.387. | F | Cl | $CH_3$ | $SCH_3$ |
| I.a.388. | F | Cl | $CH_3$ | $SC_2H_5$ |
| I.a.389. | F | Cl | $CH_3$ | $NHSO_2CH_3$ |
| I.a.390. | F | Cl | $CH_3$ | $NHSO_2CH(CH_3)_2$ |
| I.a.391. | F | Cl | $CH_3$ | $NHSO_2N(CH_3)_2$ |
| I.a.392. | F | Cl | $CH_3$ | $NHSO_2N(CH_3)[CH(CH_3)_2]$ |
| I.a.393. | F | Cl | $OCH_3$ | OH |
| I.a.394. | F | Cl | $OCH_3$ | $OCH_3$ |
| I.a.395. | F | Cl | $OCH_3$ | $OC_2H_5$ |
| I.a.396. | F | Cl | $OCH_3$ | $OCH(CH_3)_2$ |
| I.a.397. | F | Cl | $OCH_3$ | $OCH_2CH_2CH_3$ |
| I.a.398. | F | Cl | $OCH_3$ | $OCH_2CH(CH_3)_2$ |
| I.a.399. | F | Cl | $OCH_3$ | $OCH_2CH=CH_2$ |
| I.a.400. | F | Cl | $OCH_3$ | $OCH_2C\equiv CH$ |
| I.a.401. | F | Cl | $OCH_3$ | $OCH_2CF_3$ |
| I.a.402. | F | Cl | $OCH_3$ | $OCH_2CHF_2$ |
| I.a.403. | F | Cl | $OCH_3$ | $OC_6H_5$ |
| I.a.404. | F | Cl | $OCH_3$ | $OCH_2(C_6H_5)$ |
| I.a.405. | F | Cl | $OCH_3$ | $OCH_2OCH_3$ |
| I.a.406. | F | Cl | $OCH_3$ | $OCH_2OCH_2CH_3$ |
| I.a.407. | F | Cl | $OCH_3$ | $OCH_2CH_2OCH_3$ |
| I.a.408. | F | Cl | $OCH_3$ | $OCH_2CH_2OCH_2CH_3$ |
| I.a.409. | F | Cl | $OCH_3$ | $OCH_2(CO)OCH_3$ |
| I.a.410. | F | Cl | $OCH_3$ | $OCH_2(CO)OCH_2CH_3$ |
| I.a.411. | F | Cl | $OCH_3$ | $OCH(CH_3)(CO)OCH_3$ |
| I.a.412. | F | Cl | $OCH_3$ | $OCH(CH_3)(CO)OCH_2CH_3$ |
| I.a.413. | F | Cl | $OCH_3$ | $OCH_2$-cyclopropyl |
| I.a.414. | F | Cl | $OCH_3$ | $OCH_2$-cyclobutyl |
| I.a.415. | F | Cl | $OCH_3$ | $SCH_3$ |
| I.a.416. | F | Cl | $OCH_3$ | $SC_2H_5$ |
| I.a.417. | F | Cl | $OCH_3$ | $NHSO_2CH_3$ |
| I.a.418. | F | Cl | $OCH_3$ | $NHSO_2CH(CH_3)_2$ |
| I.a.419. | F | Cl | $OCH_3$ | $NHSO_2N(CH_3)_2$ |
| I.a.420. | F | Cl | $OCH_3$ | $NHSO_2N(CH_3)[CH(CH_3)_2]$ |
| I.a.421. | F | CN | H | OH |
| I.a.422. | F | CN | H | $OCH_3$ |
| I.a.423. | F | CN | H | $CC_2H_5$ |
| I.a.424. | F | CN | H | $OCH(CH_3)_2$ |
| I.a.425. | F | CN | H | $OCH_2CH_2CH_3$ |
| I.a.426. | F | CN | H | $OCH_2CH(CH_3)_2$ |
| I.a.427. | F | CN | H | $OCH_2CH=CH_2$ |
| I.a.428. | F | CN | H | $OCH_2C\equiv CH$ |
| I.a.429. | F | CN | H | $OCH_2CF_3$ |
| I.a.430. | F | CN | H | $OCH_2CHF_2$ |
| I.a.431. | F | CN | H | $OC_6H_5$ |
| I.a.432. | F | CN | H | $OCH_2(C_6H_5)$ |
| I.a.433. | F | CN | H | $OCH_2OCH_3$ |
| I.a.434. | F | CN | H | $OCH_2OCH_2CH_3$ |
| I.a.435. | F | CN | H | $OCH_2CH_2OCH_3$ |
| I.a.436. | F | CN | H | $OCH_2CH_2OCH_2CH_3$ |
| I.a.437. | F | CN | H | $OCH_2(CO)OCH_3$ |
| I.a.438. | F | CN | H | $OCH_2(CO)OCH_2CH_3$ |
| I.a.439. | F | CN | H | $OCH(CH_3)(CO)OCH_3$ |
| I.a.440. | F | CN | H | $OCH(CH_3)(CO)OCH_2CH_3$ |
| I.a.441. | F | CN | H | $OCH_2$-cyclopropyl |
| I.a.442. | F | CN | H | $OCH_2$-cyclobutyl |
| I.a.443. | F | CN | H | $SCH_3$ |
| I.a.444. | F | CN | H | $SC_2H_5$ |
| I.a.445. | F | CN | H | $NHSO_2CH_3$ |
| I.a.446. | F | CN | H | $NHSO_2CH(CH_3)_2$ |
| I.a.447. | F | CN | H | $NHSO_2N(CH_3)_2$ |
| I.a.448. | F | CN | H | $NHSO_2N(CH_3)[CH(CH_3)_2]$ |
| I.a.449. | F | CN | $CH_3$ | OH |
| I.a.450. | F | CN | $CH_3$ | $OCH_3$ |
| I.a.451. | F | CN | $CH_3$ | $OC_2H_5$ |
| I.a.452. | F | CN | $CH_3$ | $OCH(CH_3)_2$ |
| I.a.453. | F | CN | $CH_3$ | $OCH_2CH_2CH_3$ |
| I.a.454. | F | CN | $CH_3$ | $OCH_2CH(CH_3)_2$ |
| I.a.455. | F | CN | $CH_3$ | $OCH_2CH=CH_2$ |
| I.a.456. | F | CN | $CH_3$ | $OCH_2C\equiv CH$ |
| I.a.457. | F | CN | $CH_3$ | $OCH_2CF_3$ |
| I.a.458. | F | CN | $CH_3$ | $OCH_2CHF_2$ |
| I.a.459. | F | CN | $CH_3$ | $OC_6H_5$ |
| I.a.460. | F | CN | $CH_3$ | $OCH_2(C_6H_5)$ |
| I.a.461. | F | CN | $CH_3$ | $OCH_2OCH_3$ |
| I.a.462. | F | CN | $CH_3$ | $OCH_2OCH_2CH_3$ |
| I.a.463. | F | CN | $CH_3$ | $OCH_2CH_2OCH_3$ |
| I.a.464. | F | CN | $CH_3$ | $OCH_2CH_2OCH_2CH_3$ |
| I.a.465. | F | CN | $CH_3$ | $OCH_2(CO)OCH_3$ |
| I.a.466. | F | CN | $CH_3$ | $OCH_2(CO)OCH_2CH_3$ |
| I.a.467. | F | CN | $CH_3$ | $OCH(CH_3)(CO)OCH_3$ |
| I.a.468. | F | CN | $CH_3$ | $OCH(CH_3)(CO)OCH_2CH_3$ |
| I.a.469. | F | CN | $CH_3$ | $OCH_2$-cyclopropyl |
| I.a.470. | F | CN | $CH_3$ | $OCH_2$-cyclobutyl |
| I.a.471. | F | CN | $CH_3$ | $SCH_3$ |
| I.a.472. | F | CN | $CH_3$ | $SC_2H_5$ |
| I.a.473. | F | CN | $CH_3$ | $NHSO_2CH_3$ |
| I.a.474. | F | CN | $CH_3$ | $NHSO_2CH(CH_3)_2$ |
| I.a.475. | F | CN | $CH_3$ | $NHSO_2N(CH_3)_2$ |
| I.a.476. | F | CN | $CH_3$ | $NHSO_2N(CH_3)[CH(CH_3)_2]$ |
| I.a.477. | F | CN | $OCH_3$ | OH |
| I.a.478. | F | CN | $OCH_3$ | $OCH_3$ |
| I.a.479. | F | CN | $OCH_3$ | $OC_2H_5$ |
| I.a.480. | F | CN | $OCH_3$ | $OCH(CH_3)_2$ |
| I.a.481. | F | CN | $OCH_3$ | $OCH_2CH_2CH_3$ |
| I.a.482. | F | CN | $OCH_3$ | $OCH_2CH(CH_3)_2$ |
| I.a.483. | F | CN | $OCH_3$ | $OCH_2CH=CH_2$ |
| I.a.484. | F | CN | $OCH_3$ | $OCH_2C\equiv CH$ |
| I.a.485. | F | CN | $OCH_3$ | $OCH_2CF_3$ |
| I.a.486. | F | CN | $OCH_3$ | $OCH_2CHF_2$ |
| I.a.487. | F | CN | $OCH_3$ | $OC_6H_5$ |
| I.a.488. | F | CN | $OCH_3$ | $OCH_2(C_6H_5)$ |
| I.a.489. | F | CN | $OCH_3$ | $OCH_2OCH_3$ |
| I.a.490. | F | CN | $OCH_3$ | $OCH_2OCH_2CH_3$ |
| I.a.491. | F | CN | $OCH_3$ | $OCH_2CH_2OCH_3$ |
| I.a.492. | F | CN | $OCH_3$ | $OCH_2CH_2OCH_2CH_3$ |
| I.a.493. | F | CN | $OCH_3$ | $OCH_2(CO)OCH_3$ |
| I.a.494. | F | CN | $OCH_3$ | $OCH_2(CO)OCH_2CH_3$ |
| I.a.495. | F | CN | $OCH_3$ | $OCH(CH_3)(CO)OCH_3$ |
| I.a.496. | F | CN | $OCH_3$ | $OCH(CH_3)(CO)OCH_2CH_3$ |
| I.a.497. | F | CN | $OCH_3$ | $OCH_2$-cyclopropyl |
| I.a.498. | F | CN | $OCH_3$ | $OCH_2$-cyclobutyl |
| I.a.499. | F | CN | $OCH_3$ | $SCH_3$ |
| I.a.500. | F | CN | $OCH_3$ | $SC_2H_5$ |
| I.a.501. | F | CN | $OCH_3$ | $NHSO_2CH_3$ |
| I.a.502. | F | CN | $OCH_3$ | $NHSO_2CH(CH_3)_2$ |
| I.a.503. | F | CN | $OCH_3$ | $NHSO_2N(CH_3)_2$ |
| I.a.504. | F | CN | $OCH_3$ | $NHSO_2N(CH_3)[CH(CH_3)_2]$ |
| I.a.505. | H | Br | H | OH |
| I.a.506. | H | Br | H | $OCH_3$ |
| I.a.507. | H | Br | H | $OC_2H_5$ |
| I.a.508. | H | Br | H | $OCH(CH_3)_2$ |
| I.a.509. | H | Br | H | $OCH_2CH_2CH_3$ |
| I.a.510. | H | Br | H | $OCH_2CH(CH_3)_2$ |
| I.a.511. | H | Br | H | $OCH_2CH=CH_2$ |
| I.a.512. | H | Br | H | $OCH_2C\equiv CH$ |

TABLE A-continued

| No. | R⁴ | R⁵ | R⁶ | R⁸ |
|---|---|---|---|---|
| I.a.513. | H | Br | H | OCH₂CF₃ |
| I.a.514. | H | Br | H | OCH₂CHF₂ |
| I.a.515. | H | Br | H | OC₆H₅ |
| I.a.516. | H | Br | H | OCH₂(C₆H₅) |
| I.a.517. | H | Br | H | OCH₂OCH₃ |
| I.a.518. | H | Br | H | OCH₂OCH₂CH₃ |
| I.a.519. | H | Br | H | OCH₂CH₂OCH₃ |
| I.a.520. | H | Br | H | OCH₂CH₂OCH₂CH₃ |
| I.a.521. | H | Br | H | OCH₂(CO)OCH₃ |
| I.a.522. | H | Br | H | OCH₂(CO)OCH₂CH₃ |
| I.a.523. | H | Br | H | OCH(CH₃)(CO)OCH₃ |
| I.a.524. | H | Br | H | OCH(CH₃)(CO)OCH₂CH₃ |
| I.a.525. | H | Br | H | OCH₂-cyclopropyl |
| I.a.526. | H | Br | H | OCH₂-cyclobutyl |
| I.a.527. | H | Br | H | SCH₃ |
| I.a.528. | H | Br | H | SC₂H₅ |
| I.a.529. | H | Br | H | NHSO₂CH₃ |
| I.a.530. | H | Br | H | NHSO₂CH(CH₃)₂ |
| I.a.531. | H | Br | H | NHSO₂N(CH₃)₂ |
| I.a.532. | H | Br | H | NHSO₂N(CH₃)[CH(CH₃)₂] |
| I.a.533. | H | Br | CH₃ | OH |
| I.a.534. | H | Br | CH₃ | OCH₃ |
| I.a.535. | H | Br | CH₃ | OC₂H₅ |
| I.a.536. | H | Br | CH₃ | OCH(CH₃)₂ |
| I.a.537. | H | Br | CH₃ | OCH₂CH₂CH₃ |
| I.a.538. | H | Br | CH₃ | OCH₂CH(CH₃)₂ |
| I.a.539. | H | Br | CH₃ | OCH₂CH=CH₂ |
| I.a.540. | H | Br | CH₃ | OCH₂C≡CH |
| I.a.541. | H | Br | CH₃ | OCH₂CF₃ |
| I.a.542. | H | Br | CH₃ | OCH₂CHF₂ |
| I.a.543. | H | Br | CH₃ | OC₆H₅ |
| I.a.544. | H | Br | CH₃ | OCH₂(C₆H₅) |
| I.a.545. | H | Br | CH₃ | OCH₂OCH₃ |
| I.a.546. | H | Br | CH₃ | OCH₂OCH₂CH₃ |
| I.a.547. | H | Br | CH₃ | OCH₂CH₂OCH₃ |
| I.a.548. | H | Br | CH₃ | OCH₂CH₂OCH₂CH₃ |
| I.a.549. | H | Br | CH₃ | OCH₂(CO)OCH₃ |
| I.a.550. | H | Br | CH₃ | OCH₂(CO)OCH₂CH₃ |
| I.a.551. | H | Br | CH₃ | OCH(CH₃)(CO)OCH₃ |
| I.a.552. | H | Br | CH₃ | OCH(CH₃)(CO)OCH₂CH₃ |
| I.a.553. | H | Br | CH₃ | OCH₂-cyclopropyl |
| I.a.554. | H | Br | CH₃ | OCH₂-cyclobutyl |
| I.a.555. | H | Br | CH₃ | SCH₃ |
| I.a.556. | H | Br | CH₃ | SC₂H₅ |
| I.a.557. | H | Br | CH₃ | NHSO₂CH₃ |
| I.a.558. | H | Br | CH₃ | NHSO₂CH(CH₃)₂ |
| I.a.559. | H | Br | CH₃ | NHSO₂N(CH₃)₂ |
| I.a.560. | H | Br | CH₃ | NHSO₂N(CH₃)[CH(CH₃)₂] |
| I.a.561. | H | Br | OCH₃ | OH |
| I.a.562. | H | Br | OCH₃ | OCH₃ |
| I.a.563. | H | Br | OCH₃ | OC₂H₅ |
| I.a.564. | H | Br | OCH₃ | OCH(CH₃)₂ |
| I.a.565. | H | Br | OCH₃ | OCH₂CH₂CH₃ |
| I.a.566. | H | Br | OCH₃ | OCH₂CH(CH₃)₂ |
| I.a.567. | H | Br | OCH₃ | OCH₂CH=CH₂ |
| I.a.568. | H | Br | OCH₃ | OCH₂C≡CH |
| I.a.569. | H | Br | OCH₃ | OCH₂CF₃ |
| I.a.570. | H | Br | OCH₃ | OCH₂CHF₂ |
| I.a.571. | H | Br | OCH₃ | OC₆H₅ |
| I.a.572. | H | Br | OCH₃ | OCH₂(C₆H₅) |
| I.a.573. | H | Br | OCH₃ | OCH₂OCH₃ |
| I.a.574. | H | Br | OCH₃ | OCH₂OCH₂CH₃ |
| I.a.575. | H | Br | OCH₃ | OCH₂CH₂OCH₃ |
| I.a.576. | H | Br | OCH₃ | OCH₂CH₂OCH₂CH₃ |
| I.a.577. | H | Br | OCH₃ | OCH₂(CO)OCH₃ |
| I.a.578. | H | Br | OCH₃ | OCH₂(CO)OCH₂CH₃ |
| I.a.579. | H | Br | OCH₃ | OCH(CH₃)(CO)OCH₃ |
| I.a.580. | H | Br | OCH₃ | OCH(CH₃)(CO)OCH₂CH₃ |
| I.a.581. | H | Br | OCH₃ | OCH₂-cyclopropyl |
| I.a.582. | H | Br | OCH₃ | OCH₂-cyclobutyl |
| I.a.583. | H | Br | OCH₃ | SCH₃ |
| I.a.584. | H | Br | OCH₃ | SC₂H₅ |
| I.a.585. | H | Br | OCH₃ | NHSO₂CH₃ |
| I.a.586. | H | Br | OCH₃ | NHSO₂CH(CH₃)₂ |
| I.a.587. | H | Br | OCH₃ | NHSO₂N(CH₃)₂ |
| I.a.588. | H | Br | OCH₃ | NHSO₂N(CH₃)[CH(CH₃)₂] |
| I.a.589. | F | Br | H | OH |
| I.a.590. | F | Br | H | OCH₃ |
| I.a.591. | F | Br | H | OC₂H₅ |
| I.a.592. | F | Br | H | OCH(CH₃)₂ |
| I.a.593. | F | Br | H | OCH₂CH₂CH₃ |
| I.a.594. | F | Br | H | OCH₂CH(CH₃)₂ |
| I.a.595. | F | Br | H | OCH₂CH=CH₂ |
| I.a.596. | F | Br | H | OCH₂C≡CH |
| I.a.597. | F | Br | H | OCH₂CF₃ |
| I.a.598. | F | Br | H | OCH₂CHF₂ |
| I.a.599. | F | Br | H | OC₆H₅ |
| I.a.600. | F | Br | H | OCH₂(C₆H₅) |
| I.a.601. | F | Br | H | OCH₂OCH₃ |
| I.a.602. | F | Br | H | OCH₂OCH₂CH₃ |
| I.a.603. | F | Br | H | OCH₂CH₂OCH₃ |
| I.a.604. | F | Br | H | OCH₂CH₂OCH₂CH₃ |
| I.a.605. | F | Br | H | OCH₂(CO)OCH₃ |
| I.a.606. | F | Br | H | OCH₂(CO)OCH₂CH₃ |
| I.a.607. | F | Br | H | OCH(CH₃)(CO)OCH₃ |
| I.a.608. | F | Br | H | OCH(CH₃)(CO)OCH₂CH₃ |
| I.a.609. | F | Br | H | OCH₂-cyclopropyl |
| I.a.610. | F | Br | H | OCH₂-cyclobutyl |
| I.a.611. | F | Br | H | SCH₃ |
| I.a.612. | F | Br | H | SC₂H₅ |
| I.a.613. | F | Br | H | NHSO₂CH₃ |
| I.a.614. | F | Br | H | NHSO₂CH(CH₃)₂ |
| I.a.615. | F | Br | H | NHSO₂N(CH₃)₂ |
| I.a.616. | F | Br | H | NHSO₂N(CH₃)[CH(CH₃)₂] |
| I.a.617. | F | Br | CH₃ | OH |
| I.a.618. | F | Br | CH₃ | OCH₃ |
| I.a.619. | F | Br | CH₃ | OC₂H₅ |
| I.a.620. | F | Br | CH₃ | OCH(CH₃)₂ |
| I.a.621. | F | Br | CH₃ | OCH₂CH₂CH₃ |
| I.a.622. | F | Br | CH₃ | OCH₂CH(CH₃)₂ |
| I.a.623. | F | Br | CH₃ | OCH₂CH=CH₂ |
| I.a.624. | F | Br | CH₃ | OCH₂C≡CH |
| I.a.625. | F | Br | CH₃ | OCH₂CF₃ |
| I.a.626. | F | Br | CH₃ | OCH₂CHF₂ |
| I.a.627. | F | Br | CH₃ | OC₆H₅ |
| I.a.628. | F | Br | CH₃ | OCH₂(C₆H₅) |
| I.a.629. | F | Br | CH₃ | OCH₂OCH₃ |
| I.a.630. | F | Br | CH₃ | OCH₂OCH₂CH₃ |
| I.a.631. | F | Br | CH₃ | OCH₂CH₂OCH₃ |
| I.a.632. | F | Br | CH₃ | OCH₂CH₂OCH₂CH₃ |
| I.a.633. | F | Br | CH₃ | OCH₂(CO)OCH₃ |
| I.a.634. | F | Br | CH₃ | OCH₂(CO)OCH₂CH₃ |
| I.a.635. | F | Br | CH₃ | OCH(CH₃)(CO)OCH₃ |
| I.a.636. | F | Br | CH₃ | OCH(CH₃)(CO)OCH₂CH₃ |
| I.a.637. | F | Br | CH₃ | OCH₂-cyclopropyl |
| I.a.638. | F | Br | CH₃ | OCH₂-cyclobutyl |
| I.a.639. | F | Br | CH₃ | SCH₃ |
| I.a.640. | F | Br | CH₃ | SC₂H₅ |
| I.a.641. | F | Br | CH₃ | NHSO₂CH₃ |
| I.a.642. | F | Br | CH₃ | NHSO₂CH(CH₃)₂ |
| I.a.643. | F | Br | CH₃ | NHSO₂N(CH₃)₂ |
| I.a.644. | F | Br | CH₃ | NHSO₂N(CH₃)[CH(CH₃)₂] |
| I.a.645. | F | Br | OCH₃ | OH |
| I.a.646. | F | Br | OCH₃ | OCH₃ |
| I.a.647. | F | Br | OCH₃ | OC₂H₅ |
| I.a.648. | F | Br | OCH₃ | OCH(CH₃)₂ |
| I.a.649. | F | Br | OCH₃ | OCH₂CH₂CH₃ |
| I.a.650. | F | Br | OCH₃ | OCH₂CH(CH₃)₂ |
| I.a.651. | F | Br | OCH₃ | OCH₂CH=CH₂ |
| I.a.652. | F | Br | OCH₃ | OCH₂C≡CH |
| I.a.653. | F | Br | OCH₃ | OCH₂CF₃ |
| I.a.654. | F | Br | OCH₃ | OCH₂CHF₂ |
| I.a.655. | F | Br | OCH₃ | OC₆H₅ |
| I.a.656. | F | Br | OCH₃ | OCH₂(C₆H₅) |
| I.a.657. | F | Br | OCH₃ | OCH₂OCH₃ |
| I.a.658. | F | Br | OCH₃ | OCH₂OCH₂CH₃ |
| I.a.659. | F | Br | OCH₃ | OCH₂CH₂OCH₃ |
| I.a.660. | F | Br | OCH₃ | OCH₂CH₂OCH₂CH₃ |
| I.a.661. | F | Br | OCH₃ | OCH₂(CO)OCH₃ |
| I.a.662. | F | Br | OCH₃ | OCH₂(CO)OCH₂CH₃ |
| I.a.663. | F | Br | OCH₃ | OCH(CH₃)(CO)OCH₃ |
| I.a.664. | F | Br | OCH₃ | OCH(CH₃)(CO)OCH₂CH₃ |
| I.a.665. | F | Br | OCH₃ | OCH₂-cyclopropyl |
| I.a.666. | F | Br | OCH₃ | OCH₂-cyclobutyl |
| I.a.667. | F | Br | OCH₃ | SCH₃ |
| I.a.668. | F | Br | OCH₃ | SC₂H₅ |

TABLE A-continued

| No. | R⁴ | R⁵ | R⁶ | R⁸ |
|---|---|---|---|---|
| I.a.669. | F | Br | OCH₃ | NHSO₂CH₃ |
| I.a.670. | F | Br | OCH₃ | NHSO₂CH(CH₃)₂ |
| I.a.671. | F | Br | OCH₃ | NHSO₂N(CH₃)₂ |
| I.a.672. | F | Br | OCH₃ | NHSO₂N(CH₃)[CH(CH₃)₂] |

Also preferred are the uracilpyridines of formula (I.b), preferably the uracilpyridines of formulae (I.b.1) to (I.b.672), particularly preferred the uracilpyridines of formulae (I.b.1) to (I.b.504), which differ from the corresponding uracilpyridines of formulae (I.a.1) to (I.a.672) only in that Q is S:

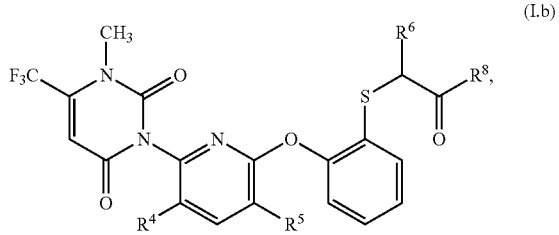
(I.b)

Also preferred are the uracilpyridines of formula (I.c), preferably the uracilpyridines of formulae (I.c.1) to (I.c.672), particularly preferred the uracilpyridines of formulae (I.c.1) to (I.c.504), which differ from the corresponding uracilpyridines of formulae (I.a.1) to (I.a.672) only in that Z is Z-2, wherein $R^a$, $R^b$, $R^c$ and $R^e$ are H:

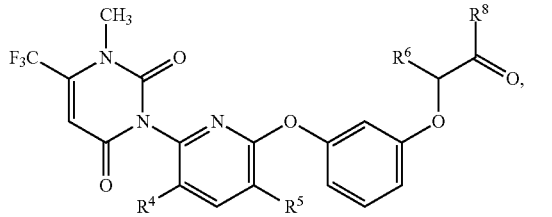
(I.c)

Also preferred are the uracilpyridines of formula (I.d), preferably the uracilpyridines of formulae (I.d.1) to (I.d.672), particularly preferred the uracilpyridines of formulae (I.d.1) to (I.d.504), which differ from the corresponding uracilpyridines of formulae (I.a.1) to (I.a.672) only in that Z is Z-3, wherein $R^a$, $R^b$, $R^d$ and $R^e$ are H:

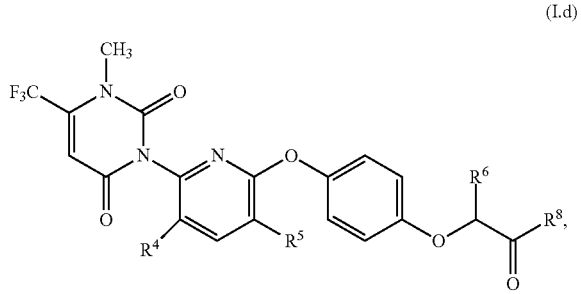
(I.d)

Also preferred are the uracilpyridines of formula (I.e), preferably the uracilpyridines of formulae (I.e.1) to (I.e.672), particularly preferred the uracilpyridines of formulae (I.e.1) to (I.e.504), which differ from the corresponding uracilpyridines of formulae (I.a.1) to (I.a.672) only in that Z is Z-4, wherein $R^b$, $R^c$ and $R^d$ are H:

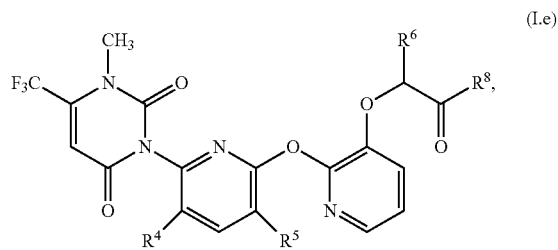
(I.e)

Also preferred are the uracilpyridines of formula (I.f), preferably the uracilpyridines of formulae (I.f.1) to (I.f.672), particularly preferred the uracilpyridines of formulae (I.f.1) to (I.f.504), which differ from the corresponding uracilpyridines of formulae (I.a.1) to (I.a.672) only in that Z is Z-5, wherein $R^a$, $R^c$ and $R^d$ are H:

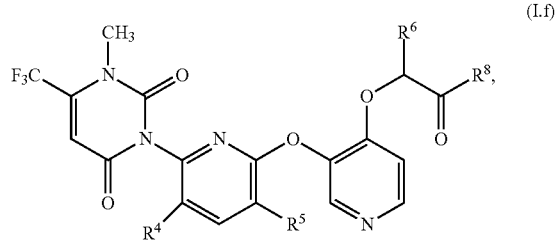
(I.f)

Also preferred are the uracilpyridines of formula (I.g), preferably the uracilpyridines of formulae (I.g.1) to (I.g.672), particularly preferred the uracilpyridines of formulae (I.g.1) to (I.g.504), which differ from the corresponding uracilpyridines of formulae (I.a.1) to (I.a.672) only in that Z is Z-6, wherein $R^a$, $R^b$ and $R^d$ are H:

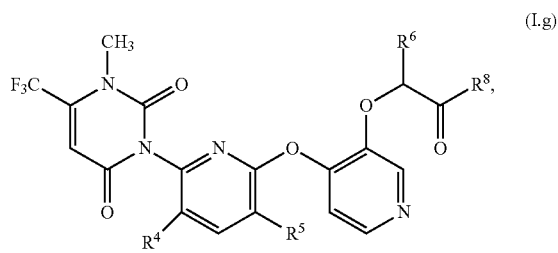
(I.g)

Also preferred are the uracilpyridines of formula (I.h), preferably the uracilpyridines of formulae (I.h.1) to (I.h.672), particularly preferred the uracilpyridines of formulae (I.h.1) to (I.h.504), which differ from the corresponding uracilpyridines of formulae (I.a.1) to (I.a.672) only in that Z is Z-7, wherein $R^a$, $R^b$ and $R^c$ are H:

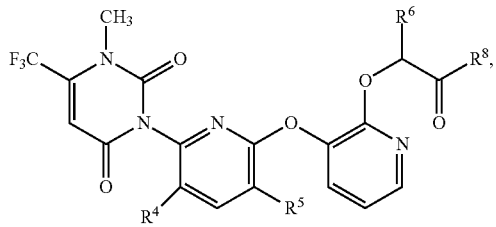
(I.h)

Also preferred are the uracilpyridines of formula (I.i), preferably the uracilpyridines of formulae (I.i.1) to (I.i.672), particularly preferred the uracilpyridines of formulae (I.i.1) to (I.i.504), which differ from the corresponding uracilpyridines of formulae (I.a.1) to (I.a.672) only in that Z is Z-7, wherein $R^a$, $R^b$ and $R^c$ are H, and Q is S:

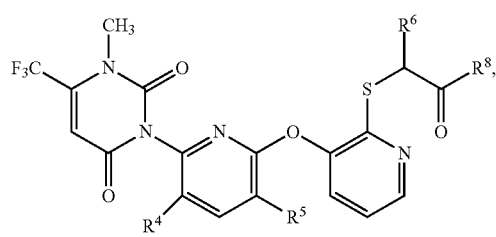
(I.i)

Also preferred are the uracilpyridines of formula (I.k), preferably the uracilpyridines of formulae (I.k.1) to (I.k.672), particularly preferred the uracilpyridines of formulae (I.k.1) to (I.k.504), which differ from the corresponding uracilpyridines of formulae (I.a.1) to (I.a.672) only in that Z is Z-8, wherein $R^b$, $R^c$ and $R^e$ are H:

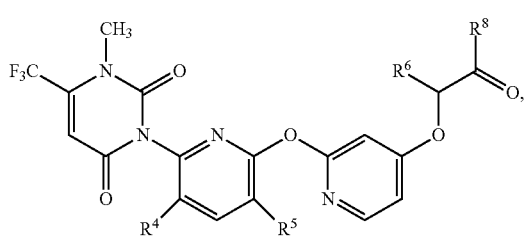
(I.k)

Also preferred are the uracilpyridines of formula (I.l), preferably the uracilpyridines of formulae (I.l.1) to (I.l.672), particularly preferred the uracilpyridines of formulae (I.l.1) to (I.l.504), which differ from the corresponding uracilpyridines of formulae (I.a.1) to (I.a.672) only in that Z is Z-9, wherein $R^a$, $R^c$ and $R^e$ are H:

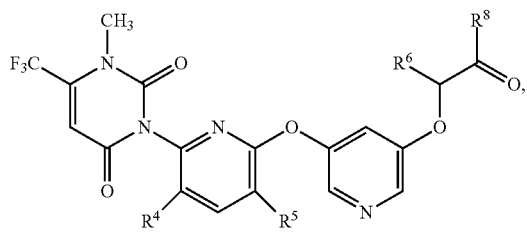
(I.l)

Also preferred are the uracilpyridines of formula (I.m), preferably the uracilpyridines of formulae (I.m.1) to (I.m.672), particularly preferred the uracilpyridines of formulae (I.m.1) to (I.m.504), which differ from the corresponding uracilpyridines of formulae (I.a.1) to (I.a.672) only in that Z is Z-10, wherein $R^a$, $R^b$ and $R^e$ are H:

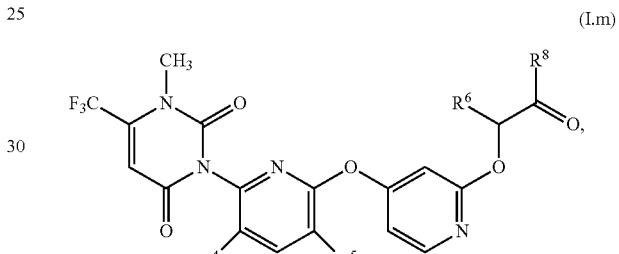
(I.m)

Also preferred are the uracilpyridines of formula (I.n), preferably the uracilpyridines of formulae (I.n.1) to (I.n.672), particularly preferred the uracilpyridines of formulae (I.n.1) to (I.n.504), which differ from the corresponding uracilpyridines of formulae (I.a.1) to (I.a.672) only in that Z is Z-11, wherein $R^a$, $R^b$ and $R^c$ are H:

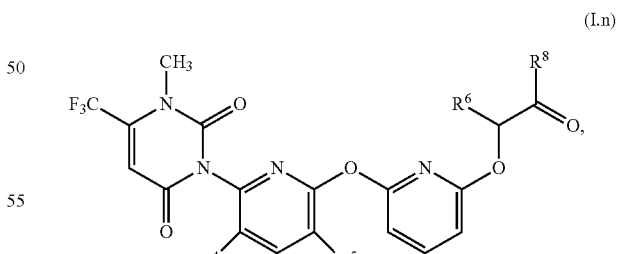
(I.n)

Also preferred are the uracilpyridines of formula (I.o), preferably the uracilpyridines of formulae (I.o.1) to (I.o.672), particularly preferred the uracilpyridines of formulae (I.o.1) to (I.o.504), which differ from the corresponding uracilpyridines of formulae (I.a.1) to (I.a.672) only in that Z is Z-12, wherein $R^b$, $R^d$ and $R^e$ are H:

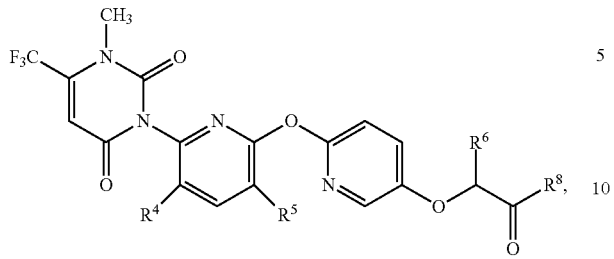

(I.o)

Also preferred are the uracilpyridines of formula (I.p), preferably the uracilpyridines of formulae (I.p.1) to (I.p.672), particularly preferred the uracilpyridines of formulae (I.p.1) to (I.p.504), which differ from the corresponding uracilpyridines of formulae (I.a.1) to (I.a.672) only in that Z is Z-13, wherein $R^a$, $R^d$ and $R^e$ are H:

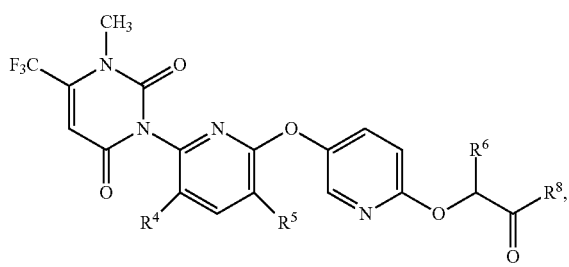

(I.p)

Also preferred are the uracilpyridines of formula (I.q), preferably the uracilpyridines of formulae (I.q.1) to (I.q.672), particularly preferred the uracilpyridines of formulae (I.q.1) to (I.q.504), which differ from the corresponding uracilpyridines of formulae (I.a.1) to (I.a.672) only in that Z is Z-21, wherein $R^a$ and $R^c$ are H:

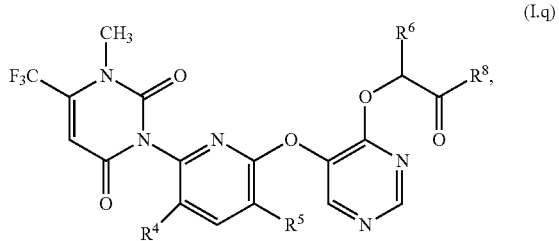

(I.q)

The uracilpyridines of formula (I) according to the invention can be prepared by standard processes of organic chemistry, for example by the following processes A to H:

Process A)

The uracilpyridines of formula (I) are obtained from the acid halides of formula (II) by reaction with compounds of formula (III) in the presence of a base:

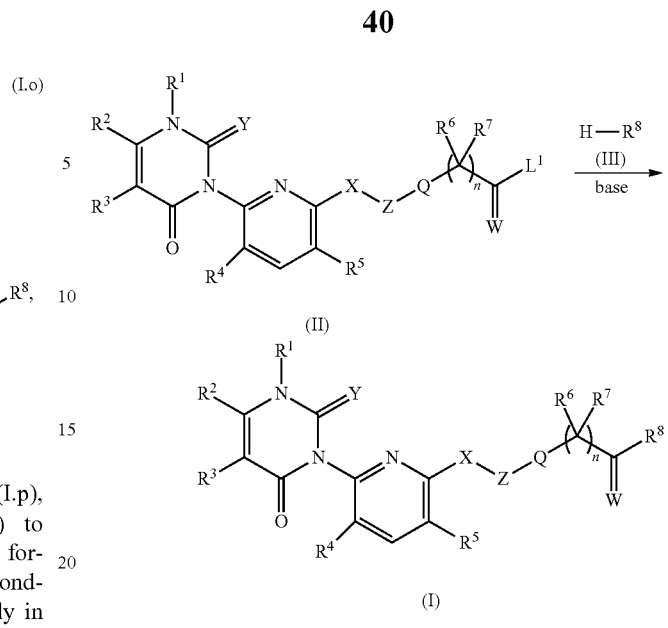

Within the acid halides of formula (II), $L^1$ is halogen; prefereably is F, Cl or Br; especially preferred is F or Cl, more preferred is Cl.

Instead of the acid halides of formula (II), also the corresponding acid (e.g. acid halide of formula (II), wherein $L^1$ is OH) in combination with an activating reagent, like carbonyldiimidazole, N,N'-Dicyclohexylcarbodiimide (DCC), 1-ethyl-3-(3-dimethylaminopropyl)carbodiimide (EDC) or N-methyl-2-chloropyridinium chloride can be used. The reaction conditions are the same as described for the acid halides of formula (II).

The compounds (III) can also be employed in the form of their salts, in particular the sodium and potassium salts, in which case the presence of a base is not necessary.

The reaction of acid halides (II) with compounds (III) is usually carried out from 0° C. to the boiling point of the reaction mixture, preferably at from 0° C. to 100° C., particularly preferably at from 0° C. to 40° C., in an inert organic solvent in the presence of a base.

The reaction may in principle be carried out in substance. However, preference is given to reacting the acid halides (II) with the compounds (III) in an organic solvent. Suitable in principle are all solvents, which are capable of dissolving the acid halides (II) and the compounds (III) at least partly, and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, tolene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tertbutyl methyl ketone, cyclohexanone; dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as mentioned above. It is also possible to use mixtures of the solvents mentioned.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate; alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; and furthermore organic bases, such as tertiary amines such as trimethylamine, triethylamine, diisopropylethylamine, tributylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are C1-C6-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates and nitrogen-containing bases as defined above; especially preferred triethylamine, pyridine or sodium carbonate.

The term base as used herein also includes mixtures of two or more, preferably two of the above compounds. Particular preference is given to the use of one base.

The bases are generally used in excess, more preferably with from 1 to 3 equivalents based on the acid halides (II), and they may also be used as the solvent.

For the reaction, the acid halides (II), the compounds (III) and the base can be brought into contact in any way per se.

Accordingly, the reaction partners and the base may be introduced into the reaction vessel and reacted separately, simultaneously or successively.

The reactants are generally employed in equimolar amounts. It might be advantageous using one of the reactants in excess, for example with a view to complete a reaction of the other reactant.

The reaction can be carried out at atmospheric pressure, reduced pressure or under elevated pressure, if appropriate under an inert gas, continuously or batchwise.

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The compounds of formula (III) are commercially available.

Process B)

As an alternative, the uracilpyridines of formula (I) can be prepared by reacting (thio)carbamates of formula (IV) with enamines of formula (V):

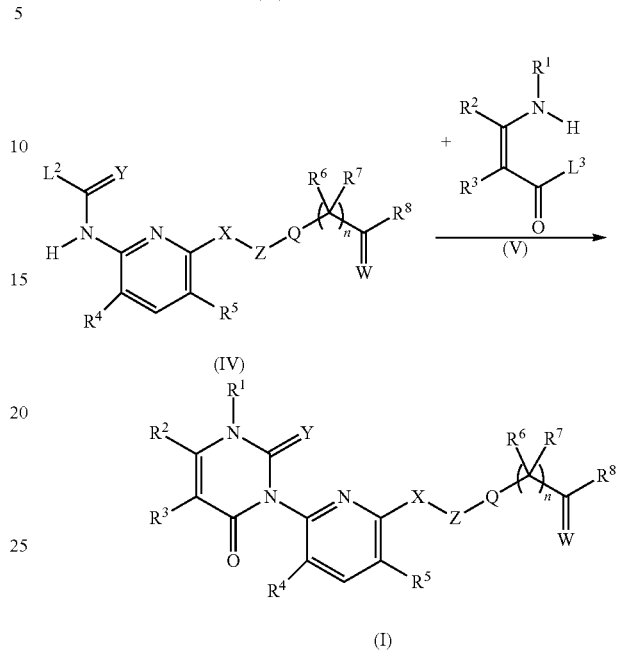

Within the (thio)carbamates of formula (IV), $L^2$ is a nucleophilically displaceable leaving group,
preferably $C_1$-$C_6$-alkoxy, $C_1$-$C_6$-alkylthio or aryloxy,
  wherein the aryl moiety may itself be partly or fully halogenated and/or may be substituted by from one to three substituents from the group of cyano, nitro, $C_1$-$C_4$-alkyl, $C_1$-$C_4$-alkoxy and $C_1$-$C_4$-alkylthio;
particularly preferably $C_1$-$C_6$-alkoxy, $C_1$-$C_6$-alkylthio or phenyloxy,
  wherein the phenyl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$-alkylthio;
more preferably $C_1$-$C_6$-alkoxy, $C_1$-$C_6$-alkylthio or phenyloxy;
most preferably $C_1$-$C_6$-alkoxy.

Within the enamines of the formula (V), $L^3$ is nucleophilically displaceable leaving group,
preferably $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyloxy, $C_3$-$C_6$-alkynyloxy, $C_3$-$C_6$-haloalkynyloxy, $C_3$-$C_6$-cycloalkyloxy, $C_1$-$C_6$-cyanoalkoxy or benzyloxy,
  which benzyl ring may itself be partly or fully halogenated and/or may be substituted by from one to three substituents selected from from the group of cyano, nitro, $C_1$-$C_4$-alkyl, $C_1$-$C_4$-alkoxy and $C_1$-$C_4$-alkylthio;
particularly preferred $C_1$-$C_6$-alkoxy, $C_1$-$C_6$-haloalkoxy, $C_1$-$C_4$-alkoxy-$C_2$-$C_4$-alkoxy, $C_2$-$C_6$-alkenyloxy, $C_2$-$C_6$-haloalkenyloxy, $C_3$-$C_6$-alkynyloxy or $C_3$-$C_6$-haloalkynyloxy;
especially preferred $C_1$-$C_6$-alkoxy, $C_1$-$C_4$-alkoxy-$C_2$-$C_4$-alkoxy, $C_2$-$C_6$-alkenyloxy or $C_3$-$C_6$-alkynyloxy;
more preferred $C_1$-$C_6$-alkoxy.

In a preferred embodiment of this reaction,
$R^1$ is hydrogen, $C_1$-$C_6$-alkyl or $C_3$-$C_6$-alkynyl;
preferably hydrogen or $C_1$-$C_6$-alkyl,
most preferably hydrogen.

The reaction of the (thio)carbamates of formula (IV) with enamines of formula (V) is typically effected at temperatures above room temperature, for example from 25° C. to 200° C., preferably from 90° C. to 190° C., more preferably from 100° C. to 140° C. in an inert organic solvent in the presence of a base (e.g. WO 99/31091; WO 11/057935).

Suitable solvents are aliphatic hydrocarbons such as pentane, hexane, cyclohexane, and mixtures of $C_5$-$C_{12}$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, diethylene glycol dimethyl ether, anisole and tetrahydrofuran, nitriles such as acetonitrile and propionitrile, alcohols such as methanol, ethanol, n-propanol, isopropanol, n-butanol and tert-butanol, carboxylic esters such as butyl acetate, and also dimethyl sulfoxide, dimethylformamide, dimethylacetamide and N-methylpyrrolidone.

Preferred solvents are dimethylformamide, dimethylacetamide and N-methylpyrrolidone.

It is also possible to use mixtures of the solvents mentioned.

Useful bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, calcium carbonate and cesium carbonate, and also alkali metal hydrogencarbonates such as sodium hydrogencarbonate, organometallic compounds, especially alkali metal alkyls such as methyllithium, butyllithium and phenyllithium, alkali metal and alkaline earth metal alkoxides such as lithium methoxide, sodium methoxide, sodium ethoxide, potassium ethoxide, potassium tert-butoxide, potassium tert-pentoxide and dimethoxymagnesium, and also organic bases, for example tertiary amines such as trimethylamine, triethylamine, diisopropylethylamine and N-methylpiperidine, pyridine, substituted pyridines such as collidine, lutidine and 4-dimethylaminopyridine, and also bicyclic amines.

Particular preference is given to alkali metal and alkaline earth metal hydroxides, alkali metal and alkaline earth metal carbonates and also alkali metal and alkaline earth metal alkoxides.

The bases are generally used in excess, based on (thio)carbamates of formula (IV), and they may also be used as the solvent. It may be advantageous to add the base offset over a period of time.

The reaction mixtures are worked up in a customary manner, for example by mixing with water, separation of the phases and, if appropriate, chromatographic purification of the crude product.

Compounds obtained in the form of viscous oils, can be purified or freed from volatile components under reduced pressure and at moderately elevated temperature.

If the end products are obtained as solid, purification can also be carried out by recrystallization or digestion.

Process C)

As an alternative, the uracilpyridines of formula (I) can also be prepared by reaction of iso(thio)cyanates of formula (VI) with enamines of formula (V):

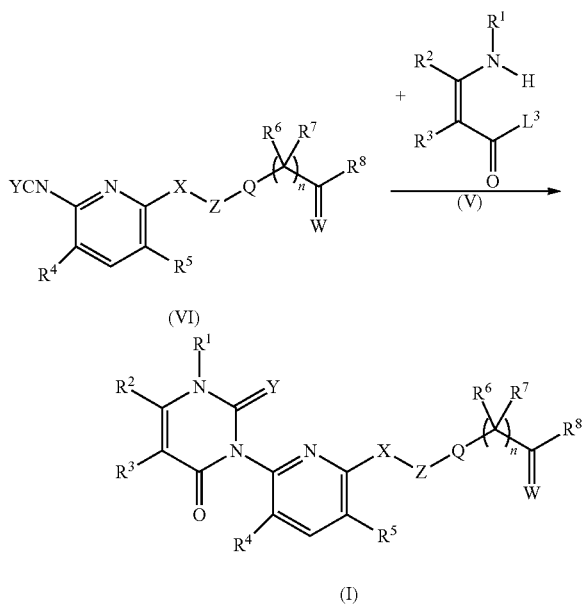

Within the enamines of the formula (V), $L^3$ is defined as above (process B).

The reaction of the iso(thio)cyanates of formula (VI) with enamines of formula (V) is usually carried out from −20° C. to 80° C. in an inert organic solvent in the presence of a base (e.g. WO 05/054208).

Suitable solvents are aliphatic hydrocarbons such as pentane, hexane, cyclohexane and mixtures of $C_5$-$C_{12}$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, diethylene glycol dimethyl ether, anisole and tetrahydrofuran, nitriles such as acetonitrile and propionitrile, alcohols such as methanol, ethanol, n-propanol, isopropanol, n-butanol and tert-butanol, carboxylic esters such as butyl acetate, and also dimethyl sulfoxide, dimethylformamide, dimethylacetamide and N-methylpyrrolidone.

Preferred solvents are dimethylformamide, dimethylacetamide and N-methylpyrrolidone.

It is also possible to use mixtures of the solvents mentioned.

Useful bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, calcium carbonate and cesium carbonate, and also alkali metal hydrogencarbonates such as sodium hydrogencarbonate, organometallic compounds, especially alkali metal alkyls such as methyllithium, butyllithium and phenyllithium, alkali metal and alkaline earth metal alkoxides such as lithium methoxide, sodium methoxide, sodium ethoxide, potassium ethoxide, potassium tert-butoxide, potassium tert-pentoxide and dimethoxymagnesium, and also organic bases, for example tertiary amines such as trimethylamine, triethylamine, diisopropylethylamine and N-methylpiperidine, pyridine, substituted pyridines such as collidine, lutidine and 4-dimethylaminopyridine, and also bicyclic amines.

Particular preference is given to alkali metal and alkaline earth metal hydroxides, alkali metal and alkaline earth metal carbonates and also alkali metal and alkaline earth metal alkoxides.

The bases are generally used in excess, based on the iso(thio)cyanate of formula (VI), and they may also be used as the solvent.

It may be advantageous to add the base offset over a period of time.

The reaction mixtures are worked up in a customary manner, for example by mixing with water, separation of the phases and, if appropriate, chromatographic purification of the crude product.

Compounds obtained in the form of viscous oils, can be purified or freed from volatile components under reduced pressure and at moderately elevated temperature.

If the end products are obtained as solid, purification can also be carried out by recrystallization or digestion.

Process D)

As an alternative, the uracilpyridines of formula (I) can also be prepared by reaction of compounds of formula (VII) with compounds of formula (VIII) in the presence of a base:

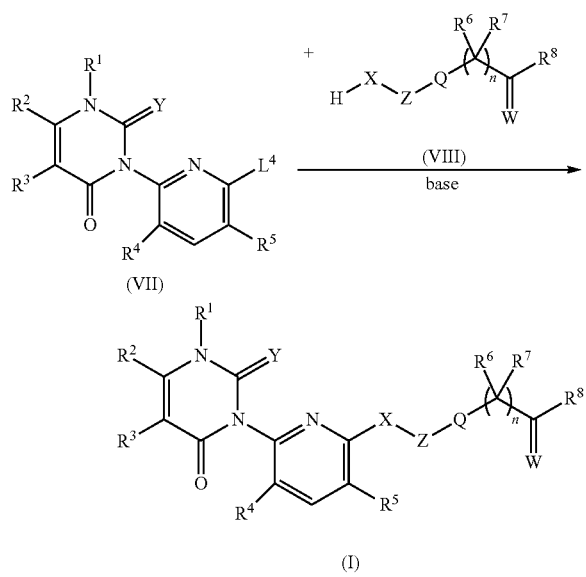

Within the compounds of formula (VII), $L^4$ is a leaving group such halogen, $C_1$-$C_6$-alkylsulfonate or arylsulfonate; preferably F, Cl, $C_1$-$C_6$-alkylsulfonate or arylsulfonate; especially preferred F, Cl, mesylate or tosylate; more preferred F or Cl.

The reaction may in principle be carried out in substance. However, preference is given to reacting the compounds of formula (VII) with the compounds of formula (VIII) in an organic solvent.

Suitable in principle are all solvents which are capable of dissolving the compounds of formula (VII) and the compounds of formula (VIII) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, tolene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles, ketones and dipolar aprotic solvents as mentioned above. More preferred solvents are ethers and dipolar aprotic solvents as mentioned above. It is also possible to use mixtures of the solvents mentioned.

Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; ammonia, pyridine, lutidine, collidine, 4-(dimethylamino) pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal hydrides, alkali metal and alkaline earth metal carbonates, as well as alkali metal hydrogen carbonates (bicarbonates); alkali metal and alkaline earth metal phosphates; metal organic compounds, alkyl magnesium halides as well as alkali metal and alkaline earth metal alkoxides; and furthermore organic bases, such as tertiary amines, pyridine, substituted pyridines and also bicyclic amines.

Especially preferred bases are alkali metal and alkaline earth metal carbonates, metal organic compounds, alkyl magnesium halides as well as alkali metal and alkaline earth metal alkoxides; and furthermore organic bases, such as tertiary amines, pyridine, substituted pyridines and also bicyclic amines.

The term base as used herein also includes mixtures of two or more, preferably two of the above compounds. Particular preference is given to the use of one base.

The bases are generally employed in equimolar amounts or in excess; however they can also be employed as solvent, or, if appropriate, in catalytic amounts.

The bases are generally used in excess, more preferably with from 1 to 20 mole equivalents based on the compound of formula (VIII), and they may also be used as the solvent. Preferably, the bases are used at from 1 to 5 mole equivalents, very preferably at from 1 to 3 mole equivalents, more preferably at 1 to 2 mole equivalents, based on the compound of formula (VIII).

It may be advantageous to add the base offset over a period of time.

Process E)

As an alternative, the uracilpyridines of formula (I) can also be prepared by reaction of compounds of formula (IX) with alkylating agents of formula (X) in the presence of a base in analogy to known processes (e.g. WO 11/137088):

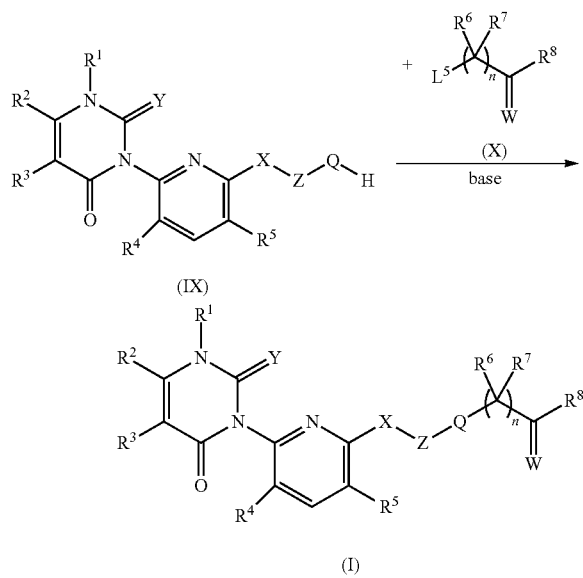

Within the alkylating agents of formula (X), $L^5$ is a leaving group such halogen, $C_1$-$C_6$-alkylsulfonate or arylsulfonate; preferably Cl, Br, I, $C_1$-$C_6$-alkylsulfonate or arylsulfonate; especially preferred Cl, Br or I; more preferred Cl or Br.

The reaction may in principle be carried out in substance. However, preference is given to reacting the compounds of formula (IX) with the alkylating agents of formula (X) in an organic solvent.

Suitable in principle are all solvents which are capable of dissolving the compounds of formula (IX) and the alkylating agents of formula (X) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, tolene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles, ketones and dipolar aprotic solvents as mentioned above.

More preferred solvents are ethers and dipolar aprotic solvents as mentioned above.

It is also possible to use mixtures of the solvents mentioned.

Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; ammonia, pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal hydrides, alkali metal and alkaline earth metal carbonates, as well as alkali metal hydrogen carbonates (bicarbonates); alkali metal and alkaline earth metal phosphates; metal organic compounds, alkyl magnesium halides as well as alkali metal and alkaline earth metal alkoxides; and furthermore organic bases, such as tertiary amines, pyridine, substituted pyridines and also bicyclic amines.

Especially preferred bases are alkali metal and alkaline earth metal carbonates, metal organic compounds, alkyl magnesium halides as well as alkali metal and alkaline earth metal alkoxides; and furthermore organic bases, such as tertiary amines, pyridine, substituted pyridines and also bicyclic amines.

The term base as used herein also includes mixtures of two or more, preferably two of the above compounds. Particular preference is given to the use of one base.

The bases are generally used in equimolar amounts or in excess, more preferably with from 1 to 20 mole equivalents based on the compounds of formula (IX), and they may also be used as solvent.

The bases are used preferably from 1 to 5 mole equivalents, very preferably from 1 to 3 mole equivalents, more preferably 1 to 2 mole equivalents, based on the compounds of formula (IX).

It may be advantageous to add the base offset over a period of time.

The alkylating agents of formula (X) are commercially available or can be prepared by known methods (e.g. Lowell, Andrew N. et al, Tetrahedron, 6(30), 5573-5582, 2010; WO 11/137088).

Process F)

As an alternative, those uracilpyridines of formula (I), wherein $R^1$ is $NH_2$, $C_1$-$C_6$-alkyl or $C_3$-$C_6$-alkynyl, can be prepared by amination or alkylation of those uracilpyridines of formula (I), wherein $R^1$ is H:

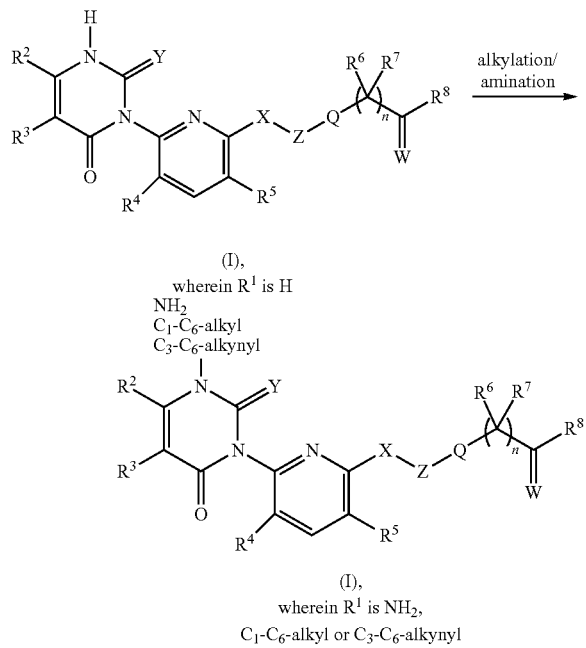

Such amination or alkylation can be conducted in analogy to known processes (e.g. WO 05/054208; WO 06/125746).

The reaction may in principle be carried out in substance. However, preference is given to reacting the uracilpyridines of formula (I), wherein $R^1$ is H, in an organic solvent. Suitable in principle are all solvents which are capable of dissolving the uracilpyridines of formula (I), wherein $R^1$ is H, at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, tolene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles, ketones and dipolar aprotic solvents as mentioned above.

More preferred solvents are ethers and dipolar aprotic solvents as mentioned above.

It is also possible to use mixtures of the solvents mentioned.

Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; ammonia, pyridine, lutidine, collidine, 4-(dimethylamino) pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal hydrides, alkali metal and alkaline earth metal carbonates, as well as alkali metal hydrogen carbonates (bicarbonates); alkali metal and alkaline earth metal phosphates; metal organic compounds, alkyl magnesium halides as well as alkali metal and alkaline earth metal alkoxides; and furthermore organic bases, such as tertiary amines, pyridine, substituted pyridines and also bicyclic amines.

Especially preferred bases are alkali metal and alkaline earth metal carbonates, metal organic compounds, alkyl magnesium halides as well as alkali metal and alkaline earth metal alkoxides; and furthermore organic bases, such as tertiary amines, pyridine, substituted pyridines and also bicyclic amines.

The term base as used herein also includes mixtures of two or more, preferably two of the above compounds. Particular preference is given to the use of one base.

The bases are generally used in equimolar amounts or in excess, more preferably with from 1 to 20 mole equivalents based on the uracilpyridines of formula (I), wherein $R^1$ is H, and they may also be used as the solvent.

The bases are used preferably from 1 to 5 mole equivalents, very preferably from 1 to 3 mole equivalents, more preferably 1 to 2 mole equivalents, based on the uracilpyridines of formula (I), wherein $R^1$ is H.

It may be advantageous to add the base offset over a period of time.

As alkylation reagents commercially available $C_1$-$C_6$-alkylhalides and alkinylhalides can be used.

Suitable amination reagents are known from literature (e.g. U.S. Pat. No. 6,333,296 or DE 10005284)

Process G)

As an alternative uracilpyridines of formula (I), wherein $R^1$ is H and Y is O, can be prepared by reaction of amines of formula (XI) with oxazinones of formula (XII) in the presence of an acid:

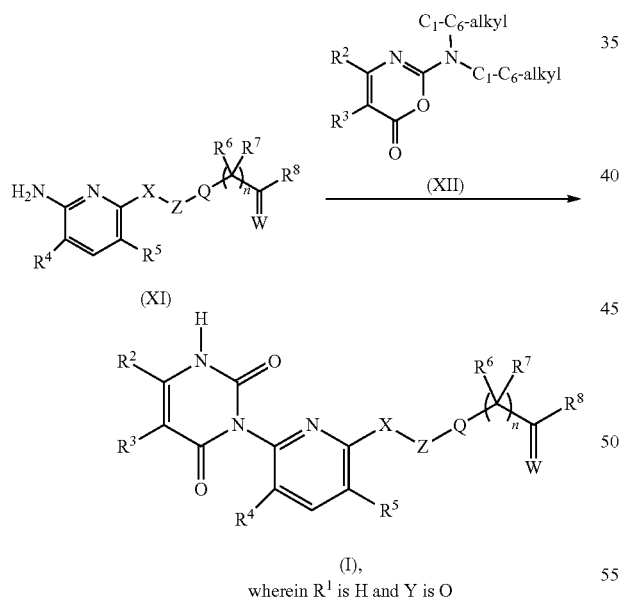

(I), wherein $R^1$ is H and Y is O

The reaction may in principle be carried out in substance. However, preference is given to reacting the amines of formula (XI) with the oxazinones of formula (XII) in an organic solvent. Suitable in principle are all solvents which are capable of dissolving the amines of formula (XI) and the oxazinones of formula (XII) at least partly, and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, tolene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are organic acids as mentioned above.

It is also possible to use mixtures of the solvents mentioned.

As acids anorganic acids like hydrochloric acid, hydrobromic acid or sulfuric acid, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in equimolar amounts, in excess or, if appropriate, be used as solvent, however they can also be employed in catalytic amounts.

Process H)

As an alternative uracilpyridines of formula (I), wherein $R^8$ is $OR^9$ with $R^9$ being H, can be prepared from the respective uracilpyridines of formula (I), wherein $R^8$ is $OR^9$ with $R^9$ being $C_1$-$C_6$-alkyl:

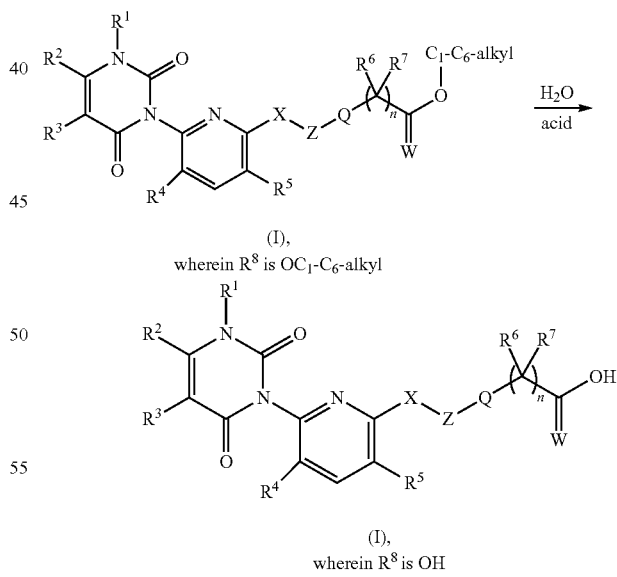

(I), wherein $R^8$ is OH

Suitable in principle are all solvents which are capable of dissolving the uracilpyridines of formula (I), wherein $R^8$ is $OR^9$ with $R^9$ being $C_1$-$C_6$-alkyl, at least partly and preferably fully under reaction conditions.

Examples of suitable solvents are $H_2O$; aliphatic hydrocarbons such as pentane, hexane, cyclohexane, nitromethane and mixtures of $C_5$-$C_8$-alkanes, aromatic hydrocarbons such as benzene, chlorobenzene, tolene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are $H_2O$, ethers, nitriles, ketones and dipolar aprotic solvents as defined above.

More preferred solvents are $H_2O$ and ethers as defined above.

It is also possible to use mixtures of the solvents mentioned.

As acids and acidic catalysist anorganic acids like hydrochloric acid, hydrobromic acid and sulfuric acid, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in catalytic amounts, however they can also be employed in equimolar amounts, in excess or, if appropriate, be used as solvent.

The intermediates necessary for preparation of the uracilpyridines of formula (I) according to the invention, and mentioned in processes A to H above, are commercially available or can be prepared by standard processes of organic chemistry, for example by the following processes:

Acid halides of formula (II) (necessary for process A mentioned above) can be prepared from uracilpyridines of formula (I), wherein $R^8$ is $OR^9$ with $R^9$ being H:

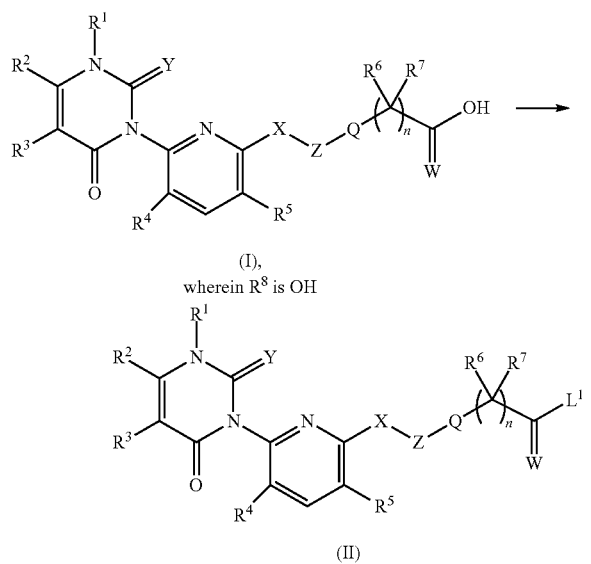

As an alternative, the respective alkali metal salts of the uracilpyridines of formula (I), wherein $R^8$ is $OR^9$ with $R^9$ being H, can be used.

Suitable halogenating agents are e.g. $POCl_3$, $POBr_3$, $PCl_3$, $PBr_3$, $PCl_3$, $PBr_5$, $SOCl_2$, $SOBr_2$, oxalyl chloride, phosgene, diphosgene, triphosgen, cyanuric chloride, cyanuric fluoride and diethylaminosulfur trifluoride (DAST).

According to a preferred embodiment of the present invention, a chlorinating agent is used as the halogenating agent. Preferably, $POCl_3$, $SOCl_2$, oxalyl chloride, phosgene, diphosgene, triphosgen are used as the chlorinating agent.

For example, acid chlorides can be prepared by chlorinating uracilpyridines of formula (I) wherein $R^8$ is $OR^9$ with $R^9$ being H.

Suitable chlorinating agents are, for example, thionyl chloride, oxalyl chloride, phosphorus trichloride, phosphorus pentachloride, phosphorus oxychloride, phosgene, diphosgene or triphosgene.

More information for carrying out such chlorination reactions are disclosed in the following references: A. J. Meyers and M. E. Flanagan, Org. Synth. 71, 107 (1992); H. J. Scheifele Jr. and D. F. DeTar, Org. Synth. Coll. Vol. IV, page 34 (1963); G. H. Coleman et al., Org. Synth. Coll. Vol. III, page 712 (1955); H. Henecka in Houben-Weyl, Methoden der Organischen Chemie [Methods in Organic Chemistry], Vol. VIII, 4th Edition, Stuttgart 1952, page 463 et seq.

(Thio)carbamates of formula (IV) (necessary for process B mentioned above) can be prepared by reacting amines of formula (XI) (necessary for process G mentioned above) with compounds of formula (XIII) in analogy to known processes (i.e. Houben-Weyl, Methoden der organischen Chemie [Methods of organic chemistry], E5, 1985, p. 972-980, and also VIII, p. 655 and XI part 2, p. 10):

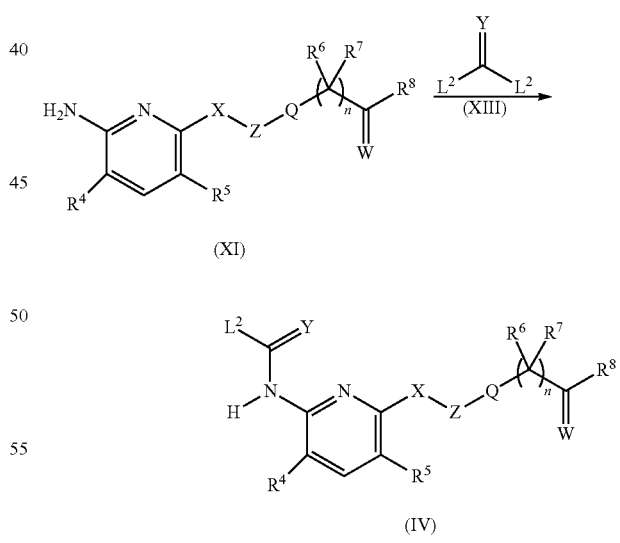

The enamines of formula (V) (necessary for process B mentioned above) are disclosed in the literature (for example A. Lutz, A. and S. Trotto, J. of Heterocyclic Chem. 1972, 9, 3, 513-522) and can be prepared in accordance.

The iso(thio)cyanates of formula (VI) (necessary for process C mentioned above) can be obtained from the corresponding amine of formula (XI):

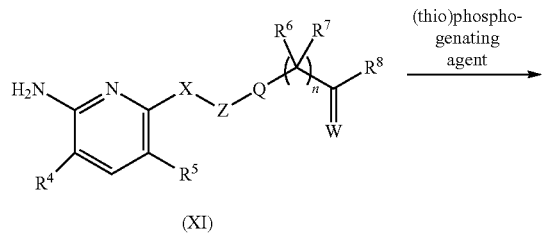

(XI)

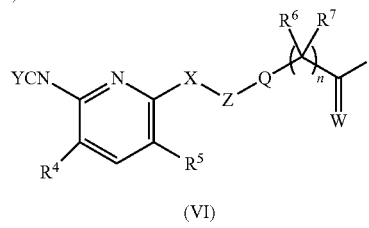

(VI)

The reaction of the amine of formula (XI) is usually carried out at from −20° C. to the boiling point of the reaction mixture, preferably at from 10° C. to 200° C., particularly preferably at from 20° C. to 150° C., in an inert organic solvent and, if appropriate, in the presence of a base (e.g. WO 04/39768).

Suitable (thio)phosgenating agents are phosgene, diphosgene or triphosgene and each of the respective thio derivatives, diphosgene being preferred.

Suitable solvents are aliphatic hydrocarbons such as pentane, hexane, cyclohexane and mixtures of C5-Ca-alkanes, aromatic hydrocarbons such as toluene, o-, m- and pxylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to aromatic hydrocarbons such as toluene, o-, m- and p-xylene.

It is also possible to use mixtures of the solvents mentioned.

Suitable bases are, in general inorganic compounds such as alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such ascoilidine, lutidine, N-methylmorpholine and 4-dimethylaminopyridine and also bicyclic amines.

Particular preference is given to tertiary amines such as triethylamine.

The bases are generally employed in catalytic amounts, however they can also be employed in equimolar amounts, in excess or, if appropriate, be used as solvent.

Work up can be carried out in a known manner.

The compounds of formula (VII) (necessary for process D mentioned above) can be prepared by reaction of compounds of formula (XVI) with enamines of formula (V) in analogy to process B mentioned above:

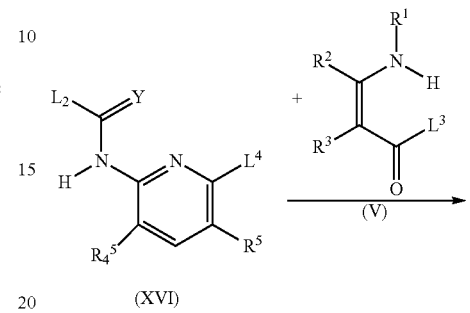

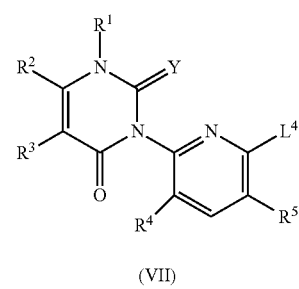

(VII)

As an alternative, the compounds of formula (VII) (necessary for process D mentioned above) can also be prepared by reaction of compounds of formula (XVII) with enamines of formula (V) in analogy to process C mentioned above:

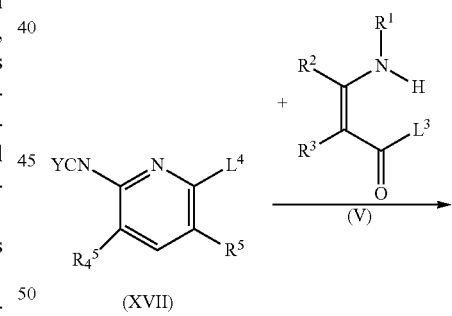

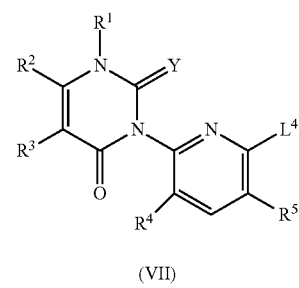

(VII)

As an alternative, compounds of formula (VII), wherein $R^1$ is H and Y is O, can be prepared by reaction of compounds of formula (XV) with oxazinones of formula (XII) in analogy to process G mentioned above:

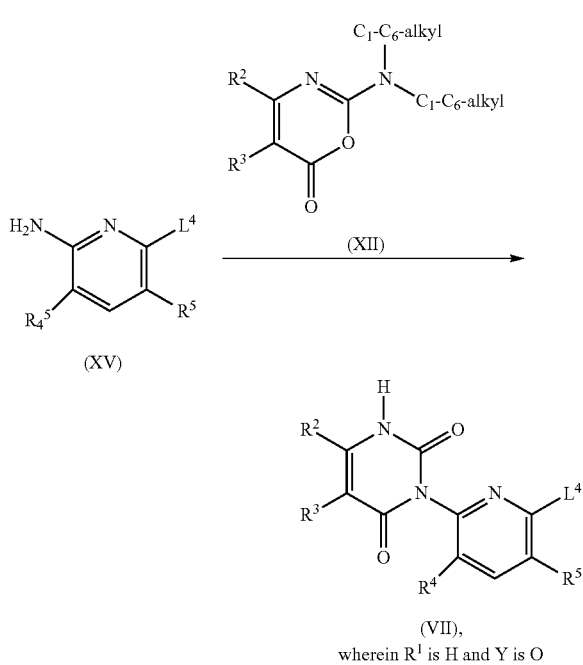

(VII),
wherein $R^1$ is H and Y is O

Those compounds of formula (VII), wherein $R^1$ is $NH_2$, $C_1$-$C_6$-alkyl or $C_3$-$C_6$-alkynyl, can be prepared by amination or alkylation of those compounds of formula (VII), wherein $R^1$ is H. Such amination or alkylation can be conducted in analogy to known processes (e.g. WO 05/054208; WO 06/125746).

The compounds of formula (VIII) (necessary for process D mentioned above) are commercially available or can be prepared by known methods (e.g. WO 02/098227 or WO 07/083090).

Compounds of formula (IX) (necessary for process E mentioned above) can be prepared by deprotection of the respective compounds of formula (XVIII):

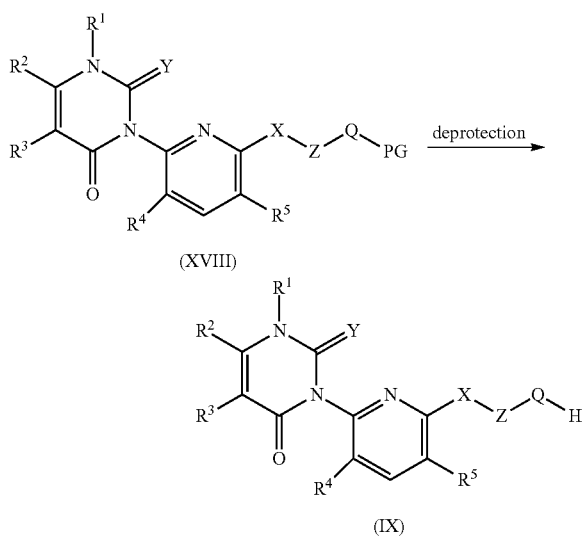

Within the compounds of formula (XVIII) "PG" is a protecting group selected from the group consisting of $C_1$-$C_6$-alkyl, $C_1$-$C_6$-cyanoalkyl, $C_1$-$C_6$-haloalkyl, $C_1$-$C_6$-alkylthio-$C_1$-$C_4$-alkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, (tri-$C_1$-$C_6$-alkyl)silyl-$C_1$-$C_4$-alkyl, (tri-$C_1$-$C_6$-alkyl)silyl-$C_1$-$C_4$-alkyoxy-$C_1$-$C_4$-alkyl, $C_2$-$C_6$-alkenyl, $C_3$-$C_6$-alkynyl, $C_3$-$C_6$-cycloalkyl, $C_3$-$C_6$-cylcloalkyl-$C_1$-$C_4$-alkyl, $C_5$-$C_6$-cycloalkenyl, tetrahydropyranyl, (tri-$C_1$-$C_6$-alkyl)silyl, [(diphenyl)($C_1$-$C_4$-alkyl)]silyl, formyl, $C_1$-$C_6$-alkyl-carbonyl, $C_1$-$C_6$-alkyl-O-carbonyl, $C_2$-$C_6$-alkenyl-O-carbonyl, [(diphenyl)($C_1$-$C_4$-alkyl)]silyl-$C_1$-$C_4$-alkyl, phenyl-$C_1$-$C_4$-alkyl, phenylthio-$C_1$-$C_6$-alkyl, phenylcarbonyl, wherein each phenyl ring can be substituted by one to three substituents selected from the group consisting of halogen, CN, $NO_2$, $C_1$-$C_4$-alkyl and $C_1$-$C_4$-alkoxy.

Preferably PG is $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, tetrahydropyranyl, (tri-$C_1$-$C_6$-alkyl)silyl, [(diphenyl)($C_1$-$C_4$-alkyl)] silyl or phenyl-$C_1$-$C_4$-alkyl.

For example, the compounds of formula (IX) can be prepared by treating the compounds of formula (XVIII), wherein "PG" is methyl, with boron tribromide in a solvent such as dichloromethane, acetonitrile or 1,4-dioxane, or without a solvent at temperatures ranging from 0° C. to 150° C.

Alternatively, compounds of formula (IX) can be prepared by deprotecting compounds of formula (XVIII), wherein "PG" is a benzyl group, by catalytic hydrogenation in a hydrogen gas atmosphere at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at ambient temperature.

The use and choice of the protecting groups will be apparent to one skilled in chemical synthesis (see, for example, Greene, T. W.; Wuts, P. G. M. Protective Groups in Organic Synthesis, 4th ed.; Wiley: New York, 2007).

Amines of formula (XI) (necessary for process G and also for preparation of (thio)carbamates of formula (IV) mentioned above) can be obtained from the corresponding pyridines of formula (XIV):

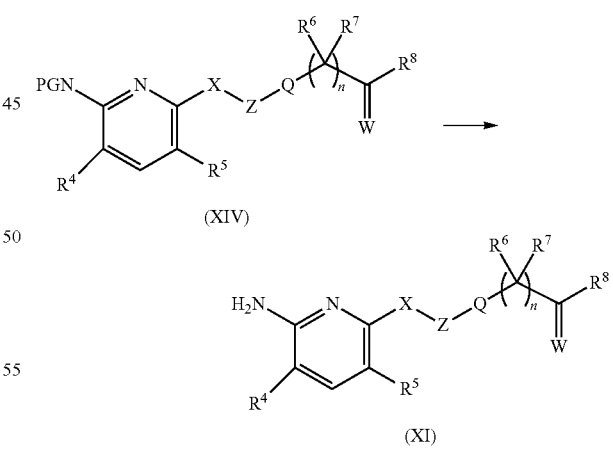

Within the pyridines of formula (XIV), the group "PGN" is a protected amine substituent selected from the group consisting of $N_3$, aliphatic or aromatic carbamates, aliphatic or aromatic amides, N—$C_1$-$C_6$-alkyl-amines, N-aryl-amines or heteroarylamides.

Preferably PGN is selected from the group consisting of $N_3$, $C_1$-$C_6$-alkyl-O(CO)NH—, $C_1$-$C_6$-haloalkyl-O(CO)—NH—, (tri-$C_1$-$C_6$-alkyl)-Si—$C_1$-$C_6$-alkyl-O(CO)NH—, $C_2$-$C_6$-alkenyl-O(CO)NH—, $C_3$-$C_6$-alkynyl-O(CO)NH—, $C_3$-$C_6$-cycloalkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH—, $C_1$-$C_6$-alkyl-NH, di($C_1$-$C_6$-alkyl)-N—, ($C_1$-$C_6$-alkyoxy-$C_1$-$C_4$-alkyl)NH—, di($C_1$-$C_6$-alkyoxy-$C_1$-$C_4$-alkyl)N—, $C_2$-$C_6$-alkenyl-NH, di($C_2$-$C_6$-alkenyl)N—, (tri-$C_1$-$C_4$-alkyl)-Si—$C_1$-$C_4$-alkoxy-$C_1$-$C_4$-alkyl-NH—, di[(tri-$C_1$-$C_4$-alkyl)-Si—$C_1$-$C_4$-alkoxy-$C_1$-$C_4$-alkyl]N—, fluorenylmethyl-NH—, di(fluorenylmethyl)N—, N-phthalimide, N-2,3-dimethylmaleimide or N-2,5-dimethylpyrrole, phenyl-O(CO)NH—, phenyl-$C_1$-$C_4$-alkyl-O(CO)NH—, phenyl-(CO)NH—, phenyl-$C_1$-$C_6$-alkyl-(CO)NH—, pyridyl-(CO)—NH—, ortho-($C_1$-$C_4$-alkoxy)-phenyl-NH, di[ortho-($C_1$-$C_4$-alkoxy)phenyl]N—, para-($C_1$-$C_4$-alkoxy)-phenyl-NH, di[para-($C_1$-$C_4$-alkoxy)-phenyl]N—, phenyl-$C_1$-$C_4$-alkyl-NH—, di(phenyl-$C_1$-$C_4$-alkyl)N—, para-($C_1$-$C_4$-alkoxy)-phenyl-$C_1$-$C_4$-alkyl-NH, di[para-($C_1$-$C_4$-alkoxy)-phenyl-$C_1$-$C_4$-alkyl]N—, wherein each phenyl or pyridyl ring can be substituted by one to three substituents selected from the group consisting of halogen, CN, $NO_2$, $C_1$-$C_4$-alkyl, $C_1$-$C_4$-alkoxy, $C_1$-$C_4$-alkylsulfinyl and $C_1$-$C_4$-alkylsulfonyl;

more preferably PGN is selected from the group consisting of $C_1$-$C_6$-alkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH, N-phthalimide, phenyl-O(CO)NH—, phenyl-$C_1$-$C_4$-alkyl-O(CO)NH—, phenyl-$C_1$-$C_4$-alkyl-NH—, di(phenyl-$C_1$-$C_4$-alkyl)N—, wherein each phenyl or pyridyl ring can be substituted by one to three $C_1$-$C_4$-alkoxy substituents.

In case "PGN" is an azide substituent, the pyridines of formula (XIV) can be converted into the amine of formula (XI) using reductive reaction conditions, such as zinc in an aqueous ammonium chloride solution.

In case "PGN" is an acylated amine substituent, the pyridines of formula (XIV) can be converted into the amines of formula (XI) using acid.

The use and choice of the "PGN" substituent and appropriate deprotection methods will be apparent to one skilled in chemical synthesis (see, for example, Greene, T. W.; Wuts, P. G. M. Protective Groups in Organic Synthesis, 4th ed.; Wiley: New York, 2007).

Oxazinones of formula (XII) (necessary for process G mentioned above) are commercially available or can be prepared by known methods (WO 2000/049002).

The compounds of the formula (XIII) required for the preparation of the (thio)carbamates of the formula (IV) are disclosed in the literature (for example Houben-Weyl, Methoden der organischen Chemie, E4, 1983, p. 6-17) and can be prepared accordingly or purchased commercially.

Pyridines of formula (XIV) (necessary for preparation of amines of formula (IX) mentioned above) can be prepared by reaction of compounds of formula (XXIII) with compounds of formula (VIII) (necessary for process D mentioned above) in the presence of a base in analogy to process D mentioned above:

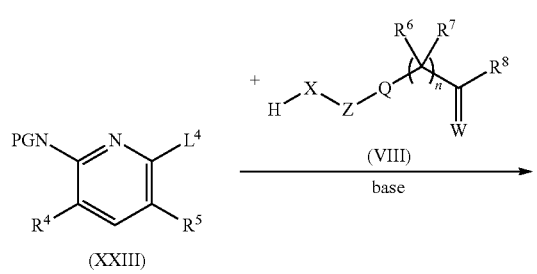

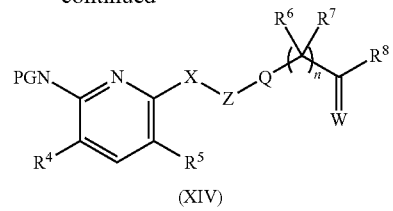

Within the compounds of formula (XXIII), $L^4$ is a leaving group such halogen, $C_1$-$C_6$-alkylsulfonate or arylsulfonate; preferably F, Cl, $C_1$-$C_6$-alkylsulfonate or arylsulfonate; especially preferred F, Cl, mesylat or tosylat; more preferred F or Cl.

Within the compounds of formulae (XIV) and (XXIII), the group "PGN" is a protected amine substituent as defined above for the amines of formula (XI).

The compounds of formula (XV) required for the preparation of the pyridines of formula (XVI), the compounds of formula (XVII) and the compounds of formula (XXIII) are commercially available.

The compounds of formula (XVI) required for the preparation of the compounds of formula (VII) can be prepared by reaction of compounds of formula (XV) with compounds of formula (XIII) in analogy to known processes (i.e. Houben-Weyl, Methoden der organischen Chemie [Methods of organic chemistry], E5, 1985, p. 972-980, and also VIII, p. 655 and XI part 2, p. 10):

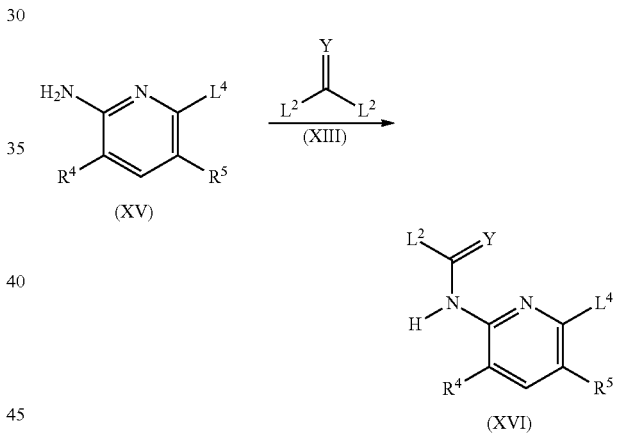

The compounds of formula (XVII) required for the alternative preparation of the compounds of formula (VII) can be prepared from compounds of formula (XV) in analogy to the preparation of iso(thio)cyanates of formula (VI) from the corresponding amine of formula (XI) as described above:

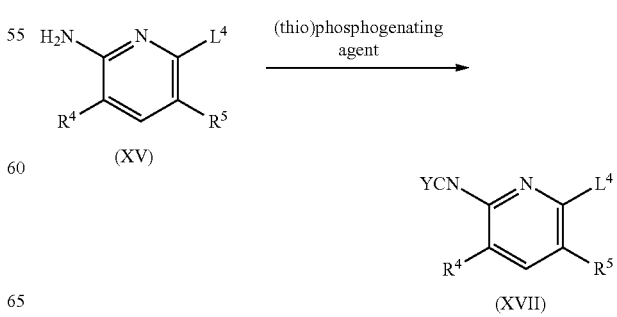

The compounds of formula (XVIII) required for the preparation of the compounds of formula (IX) can be prepared by reaction of compounds of formula (VII) with compounds of formula (XIX) in the presence of a base in analogy to process D mentioned above:

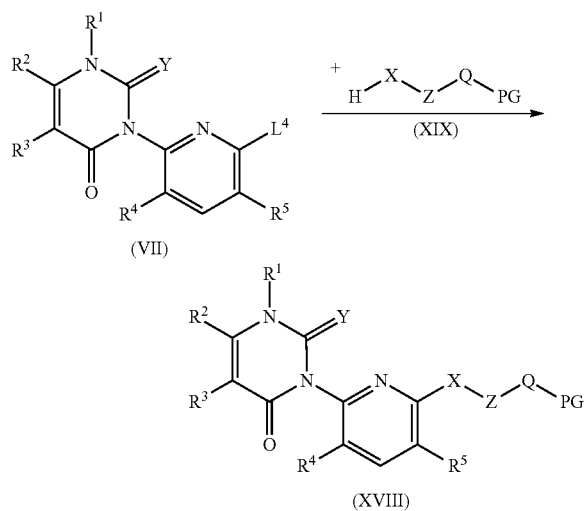

Within the compounds of formula (VII), L⁴ is a leaving group such halogen, $C_1$-$C_6$-alkylsulfonate or arylsulfonate; preferably F, Cl, $C_1$-$C_6$-alkylsulfonate or arylsulfonate; especially preferred F, Cl, mesylat or tosylat; more preferred F or Cl.

Within the compounds of formulae (XIX) and (XVIII) the group "PG" is a protecting group as defined above for the compounds of formula (IX).

As an alternative, compounds of formula (XVIII) required for the preparation of the compounds of formula (IX) can also be prepared by reaction of (thio)carbamates of formula (XX) with enamines of formula (V) in analogy to process B mentioned above:

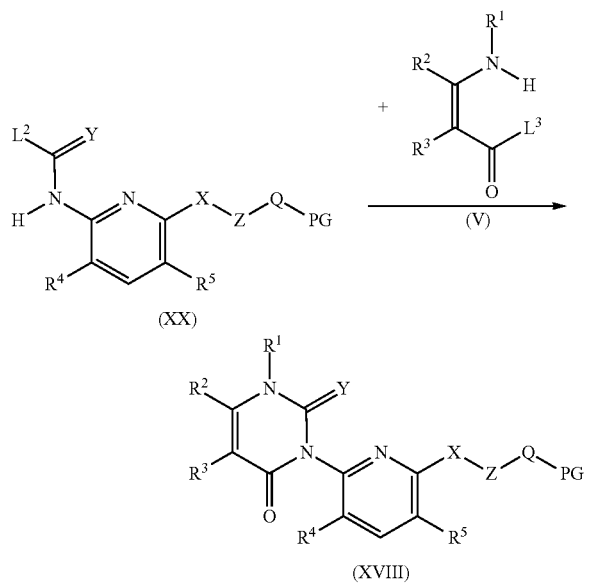

Within the (thio)carbamates of formula (XX) "PG" is a protecting group as defined above for the compounds of formula (IX).

As an alternative, compounds of formula (XVIII) required for the preparation of the compounds of formula (IX) can also be prepared by reaction of iso(thio)cyanates of formula (XXIV) with enamines of formula (V) in analogy to process C mentioned above:

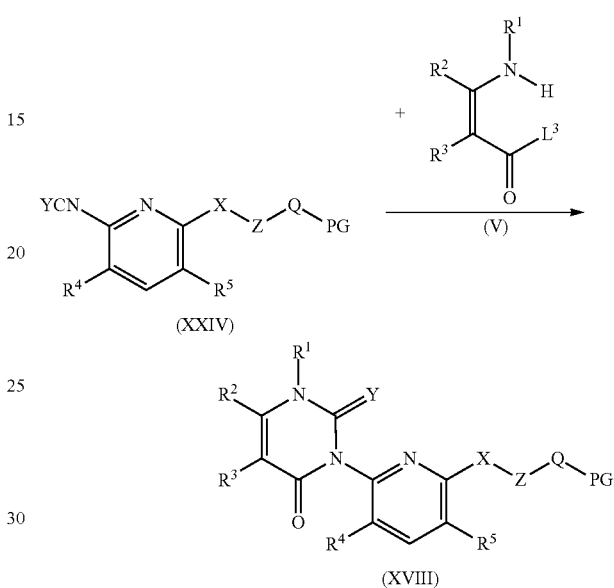

Within the compounds of formulae (XXIV) and (XVIII) the group "PG" is a protecting group as defined above for the compounds of formula (IX).

As an alternative, compounds of formula (XVIII), wherein R¹ is H and Y is O, can be prepared by reaction of amines of formula (XXI) with oxazinones of formula (XII) in analogy to process G mentioned above:

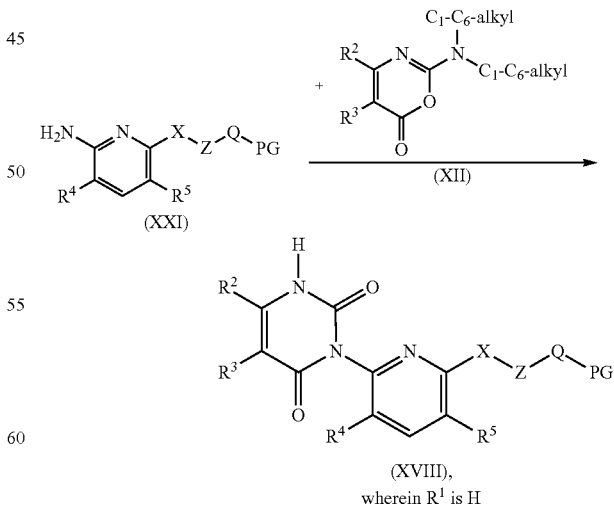

Those compounds of formula (XVIII), wherein R¹ is NH₂, $C_1$-$C_6$-alkyl or $C_3$-$C_6$-alkynyl, can be prepared by amination or alkylation of those compounds of formula (XVIII), wherein $R^1$ is H. Such amination or alkylation can be conducted in analogy to known processes (e.g. WO 05/054208; WO 06/125746).

The compounds of formula (XIX) required for the preparation of compounds of formula (XVIII) are commercially available.

The (thio)carbamates of formula (XX) required for the preparation of compounds of formula (XVIII) can be prepared by reaction of amines of formula (XXI) with compounds of formula (XIII) in analogy to known processes (i.e. Houben-Weyl, Methoden der organischen Chemie [Methods of organic chemistry], E5, 1985, p. 972-980, and also VIII, p. 655 and XI part 2, p. 10):

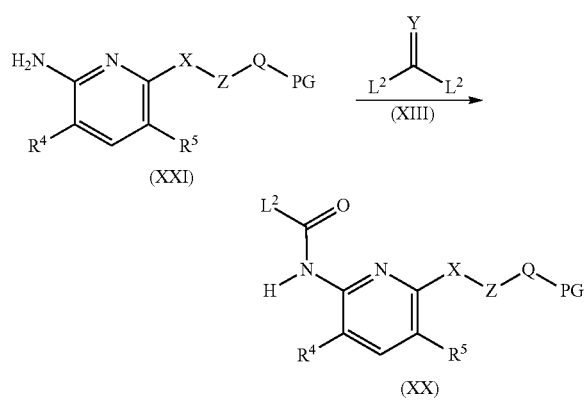

Within the (thio)carabamtes of formula (XX) and the amines of formula (XXI), the group "PG" is a protecting group as defined above for the compounds of formula (IX).

The amines of formula (XXI) required for the preparation of (thio)carbamates of formula (XX) can be prepared from the corresponding pyridines of formula (XXII):

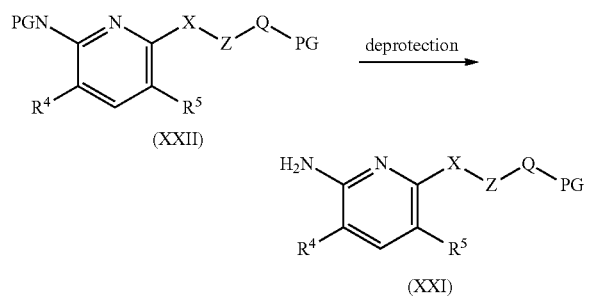

Within the pyridines of formula (XXII) the group "PG" is a protecting group as defined above for the compounds of formula (IX).

Within the pyridines of formula (XXII), the group "PGN" is a protected amine substituent as defined above for the amines of formula (XI).

The pyridines of formula (XXII) required for the preparation of amines of formula (XXI) can be prepared from compounds of formula (XXIII) with compounds of formula (XIX) in the presence of a base in analogy to process D mentioned above:

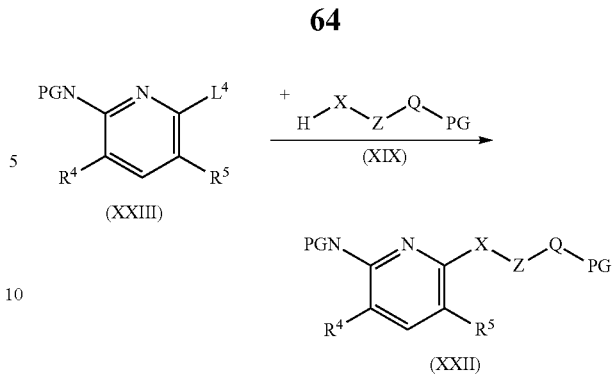

Within the compounds of formula (XXIII), $L^4$ is a leaving group such halogen, $C_1$-$C_6$-alkylsulfonate or arylsulfonate; preferably F, Cl, $C_1$-$C_6$-alkylsulfonate or arylsulfonate; especially preferred F, Cl, mesylat or tosylat; more preferred F or Cl.

Within the pyridines of formula (XXII) and the compounds of formula (XIX), the group "PG" is a protecting group as defined above for the compounds of formula (IX).

Within the pyridines of formula (XXII) and the compounds of formula (XXIII), the group "PGN" is a protected amine substituent as defined above for the amines of formula (XI).

The compounds of formula (XXIII) required for the preparation of pyridines of formula (XXII) are commercially available or can be prepared by known methods from the corresponding amine XV (e.g. Greene, T. W.; Wuts, P. G. M. Protective Groups in Organic Synthesis, 4th ed.; Wiley: New York, 2007).

The iso(thio)cyanates of formula (XXIV) required for the alternative preparation of compounds of formula (XVIII) can be obtained from amines of formula (XXI) in analogy to the preparation of iso(thio)cyanates of formula (VI) from the corresponding amine of formula (XI) as described above:

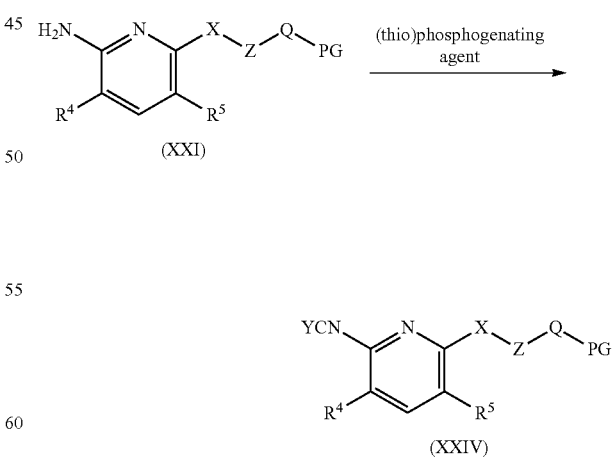

The acid halides of formula (II) are novel compounds and as shown above suitable intermediates for the preparation of the uracilpyridines of formula (I) according to the present invention.

Therefore the present invention also provides acid halides of formula (II)

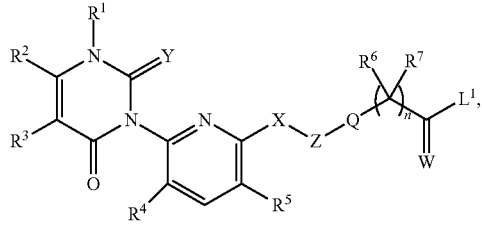

wherein the substituents have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$ or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
n 1 to 3;
Q O, S, SO, $SO_2$, NH or ($C_1$-$C_3$-alkyl)N;
W O or S;
X O or S;
Y O or S
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy; and
$L^1$ is halogen.
Preferred are those acid halides of formula (II), wherein $L^1$ is F, Cl or Br;
especially preferred is F or Cl;
more preferred is Cl.
With respect to the variables, the particularly preferred embodiments of the acid halides of formula (II) correspond, either independently of one another or in combination with one another, to those of the variables of $R^1$, $R^2$, $R^3$, $R^4$, $R^5$, $R^6$, $R^7$, n, Q, W, X, Y, Z of the uracilpyridines formula (I), or have, either independently of one another or in combination with one another, the following meanings:
$R^1$ is $NH_2$ or $CH_3$;
$R^2$ is $C_1$-$C_4$-haloalkyl;
$R^3$ is H;
$R^4$ is H, F or Cl;
$R^5$ is F, Cl, Br or CN;
$R^6$ is H, $C_1$-$C_3$-alkyl or $C_1$-$C_3$-alkoxy;
$R^7$ is H;
n is 1;
Q is O or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy; and
$L^1$ is Cl;
preferably
$R^1$ is $NH_2$ or $CH_3$;
$R^2$ is $C_1$-$C_4$-haloalkyl;
$R^3$ is H;
$R^4$ is H, F or Cl;
$R^5$ is F, Cl or CN;
$R^6$ is H, $C_1$-$C_3$-alkyl or $C_1$-$C_3$-alkoxy;
$R^7$ is H;
n is 1;
Q is O or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy; and
$L^1$ is Cl.

Particular preference is given to acid halides of formula (II.a) (corresponds to formula (II) wherein $R^1$ is $CH_3$, $R^2$ is $CF_3$, $R^3$ is H, $R^7$ is H, n is 1, Q, W, X and Y are O, Z is Z-1 as defined, wherein $R^a$, $R^b$, $R^c$ and $R^d$ are H, and $L^1$ is Cl:

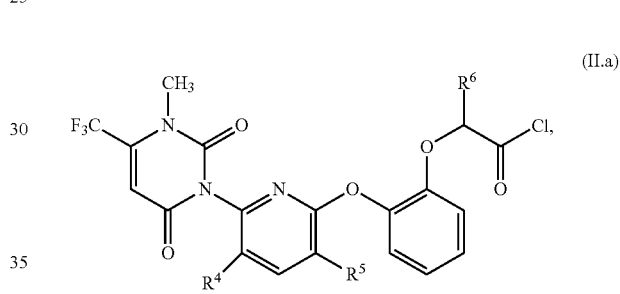

wherein the variables $R^4$, $R^5$, $R^6$ and $L^1$ have the meanings, in particular the preferred meanings, as defined above.

Special preference is given to the acid halides of the formulae (II.a.1) to (II.a.24), preferably the acid halides of the formulae (II.a.1) to (II.a.18), of table I-1, where the definitions of the variables $R^4$, $R^5$ and $R^6$ are of particular importance for the compounds according to the invention not only in combination with one another but in each case also on their own:

TABLE I-1

| No. | $R^4$ | $R^5$ | $R^6$ |
|---|---|---|---|
| II.a.1. | H | F | H |
| II.a.2. | H | F | $CH_3$ |
| II.a.3. | H | F | $OCH_3$ |
| II.a.4. | H | Cl | H |
| II.a.5. | H | Cl | $CH_3$ |
| II.a.6. | H | Cl | $OCH_3$ |
| II.a.7. | H | CN | H |
| II.a.8. | H | CN | $CH_3$ |
| II.a.9. | H | CN | $OCH_3$ |
| II.a.10. | F | F | H |
| II.a.11. | F | F | $CH_3$ |
| II.a.12. | F | F | $OCH_3$ |
| II.a.13. | F | Cl | H |
| II.a.14. | F | Cl | $CH_3$ |
| II.a.15. | F | Cl | $OCH_3$ |
| II.a.16. | F | CN | H |
| II.a.17. | F | CN | $CH_3$ |
| II.a.18. | F | CN | $OCH_3$ |

TABLE I-1-continued

| No. | $R^4$ | $R^5$ | $R^6$ |
|---|---|---|---|
| II.a.19. | H | Br | H |
| II.a.20. | H | Br | $CH_3$ |
| II.a.21. | H | Br | $OCH_3$ |
| II.a.22. | F | Br | H |
| II.a.23. | F | Br | $CH_3$ |
| II.a.24. | F | Br | $OCH_3$ |

Also preferred are the acid halides of formula (II.b), preferably the acid halides of formulae (II.b.1) to (II.b.24), particularly preferred the acid halides of formulae (II.b.1) to (II.b.18), which differ from the corresponding acid halides of formulae (II.a.1) to (II.a.24) only in that Z is Z-7, wherein $R^a$, $R^b$ and $R^c$ are H:

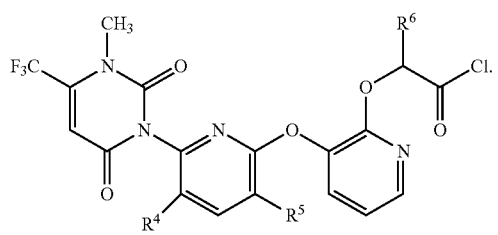

(II.b)

The intermediates of formula (int-1) combining the compounds of formulae (IX) and (XVIII) are novel compounds and as shown above suitable intermediates for the preparation of the uracilpyridines of formula (I) according to the present invention.

Therefore the present invention also provides intermediates of formula (int-1)

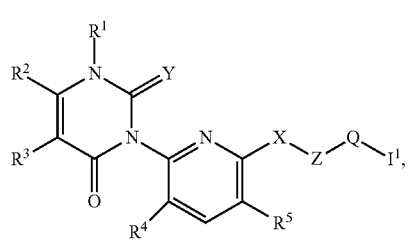

(int-1)

wherein the substituents have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$ or C(=S)$NH_2$;
Q O, S, SO, $SO_2$, NH or ($C_1$-$C_3$-alkyl)N;
X O or S;
Y O or S
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy; and
$I^1$ is H or PG, wherein PG is a protecting group selected from the group consisting of
$C_1$-$C_6$-alkyl, $C_1$-$C_6$-cyanoalkyl, $C_1$-$C_6$-haloalkyl, $C_1$-$C_6$-alkylthio-$C_1$-$C_4$-alkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, (tri-$C_1$-$C_6$-alkyl)silyl-$C_1$-$C_4$-alkyl, (tri-$C_1$-$C_6$-alkyl)silyl-$C_1$-$C_4$-alkyoxy-$C_1$-$C_4$-alkyl, $C_2$-$C_6$-alkenyl, $C_3$-$C_6$-alkynyl, $C_3$-$C_6$-cycloalkyl, $C_3$-$C_6$-cylcloalkyl-$C_1$-$C_4$-alkyl, $C_5$-$C_6$-cycloalkenyl, tetrahydropyranyl, (tri-$C_1$-$C_6$-alkyl)silyl, [(diphenyl)($C_1$-$C_4$-alkyl)]silyl, formyl, $C_1$-$C_6$-alkyl-carbonyl, $C_1$-$C_6$-alkyl-O-carbonyl, $C_2$-$C_6$-alkenyl-O-carbonyl, [(diphenyl)($C_1$-$C_4$-alkyl)]silyl-$C_1$-$C_4$-alkyl, phenyl-$C_1$-$C_4$-alkyl, phenylthio-$C_1$-$C_6$-alkyl, phenylcarbonyl,
wherein each phenyl ring can be substituted by one to three substituents selected from the group consisting of halogen, CN, $NO_2$, $C_1$-$C_4$-alkyl and $C_1$-$C_4$-alkoxy;
including their agriculturally acceptable salts or derivatives, provided the intermediates of formula (int-1) have a carboxyl group.

Preferred are those intermediates of formula (int-1), wherein
$I^1$ is H, $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, tetrahydropyranyl, (tri-$C_1$-$C_6$-alkyl)silyl, [(diphenyl)($C_1$-$C_4$-alkyl)]silyl or phenyl-$C_1$-$C_4$-alkyl; especially preferred is H.

With respect to the variables, the particularly preferred embodiments of the intermediates of formula (int-1) correspond, either independently of one another or in combination with one another, to those of the variables of $R^1$, $R^2$, $R^3$, $R^4$, Q, X, Y and Z of the uracilpyridines formula (I), or have, either independently of one another or in combination with one another, the following meanings:
$R^1$ is $NH_2$ or $CH_3$;
$R^2$ is $C_1$-$C_4$-haloalkyl;
$R^3$ is H;
$R^4$ is H, F or Cl;
$R^5$ is F, Cl, Br or CN;
n is 1;
Q is O or S;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy; and
$I^1$ is H, $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, tetrahydropyranyl, (tri-$C_1$-$C_6$-alkyl)silyl, [(diphenyl)($C_1$-$C_4$-alkyl)]silyl or phenyl-$C_1$-$C_4$-alkyl;
preferably
$R^1$ is $NH_2$ or $CH_3$;
$R^2$ is $C_1$-$C_4$-haloalkyl;
$R^3$ is H;
$R^4$ is H, F or Cl;
$R^5$ is F, Cl or CN;
n is 1,
Q is O or S;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy; and $I^1$ is H, $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, tetrahydropyranyl, (tri-$C_1$-$C_6$-alkyl)silyl, [(diphenyl)($C_1$-$C_4$-alkyl)]silyl or phenyl-$C_1$-$C_4$-alkyl.

Particular preference is given to intermediates of formula (int-1.a) (corresponds to formula (int-1) wherein $R^1$ is $CH_3$, $R^2$ is $CF_3$, $R^3$ is H, Q, X and Y are O, Z is Z-1 as defined, wherein $R^a$, $R^b$, $R^c$ and $R^d$ are H:

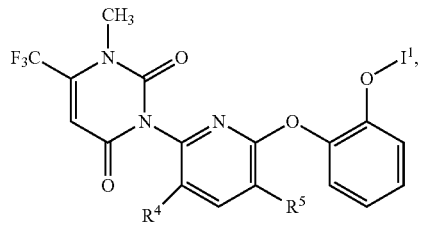

(int-1.a)

wherein the variables $R^4$, $R^5$ and $I^1$ have the meanings, in particular the preferred meanings, as defined above.

Special preference is given to the intermediates of the formulae (int-1.a.1) to (int-1.a.24), preferably the intermediates of the formulae (int-1.a.1) to (int-1.a.18), of table I-2, where the definitions of the variables $R^4$, $R^5$ and $I^1$ are of particular importance for the compounds according to the invention not only in combination with one another but in each case also on their own:

TABLE I-2

| No. | $R^4$ | $R^5$ | $I^1$ |
|---|---|---|---|
| int-1.a.1. | H | F | H |
| int-1.a.2. | H | F | $CH_3$ |
| int-1.a.3. | H | F | $CH_2$—$C_6H_5$ |
| int-1.a.4. | H | Cl | H |
| int-1.a.5. | H | Cl | $CH_3$ |
| int-1.a.6. | H | Cl | $CH_2$—$C_6H_5$ |
| int-1.a.7. | H | CN | H |
| int-1.a.8. | H | CN | $CH_3$ |
| int-1.a.9. | H | CN | $CH_2$—$C_6H_5$ |
| int-1.a.10. | F | F | H |
| int-1.a.11. | F | F | $CH_3$ |
| int-1.a.12. | F | F | $CH_2$—$C_6H_5$ |
| int-1.a.13. | F | Cl | H |
| int-1.a.14. | F | Cl | $CH_3$ |
| int-1.a.15. | F | Cl | $CH_2$—$C_6H_5$ |
| int-1.a.16. | F | CN | H |
| int-1.a.17. | F | CN | $CH_3$ |
| int-1.a.18. | F | CN | $CH_2$—$C_6H_5$ |
| int-1.a.19. | H | Br | H |
| int-1.a.20. | H | Br | $CH_3$ |
| int-1.a.21. | H | Br | $CH_2$—$C_6H_5$ |
| int-1.a.22. | F | Br | H |
| int-1.a.23. | F | Br | $CH_3$ |
| int-1.a.24. | F | Br | $CH_2$—$C_6H_5$ |

Also preferred are the intermediates of formula (int-1.b), preferably the intermediates of formulae (int-1.b.1) to (int-1.b.24), particularly preferred the intermediates of formulae (int-1.b.1) to (int-1.b.18), which differ from the corresponding intermediates of formulae (int-1.a.1) to (int-1.a.24) only in that Z is Z-7, wherein $R^a$, $R^b$ and $R^c$ are H:

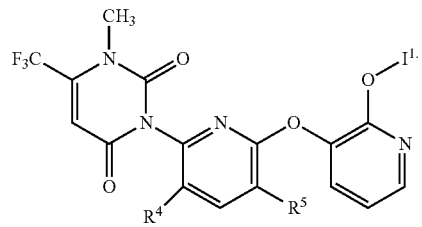

(int-1.b)

The intermediates of formula (int-2) combining the (thio)carbamates of formula (IV), the iso(thio)cyanates of formula (VI), the amines of formula (XI) and the pyridines of formula (XIV) are novel compounds and as shown above suitable intermediates for the preparation of the uracilpyridines of formula (I) according to the present invention.

Therefore the present invention also provides intermediates of formula (int-2)

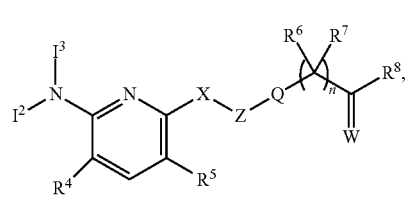

(int-2)

wherein the substituents have the following meanings:
$R^4$ H or halogen;
$R^5$ halogen, CN, $NO_2$, $NH_2$, $CF_3$ or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl, wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of $-N(R^{12})-$, $-N=N-$, $-C(=O)-$, $-O-$ and $-S-$, and
which carbocyclus is optionally substituted with one to four substituents selected from $R^{14}$;
wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxycarbonyl;
$R^{10}$, $R^{11}$ independently of one another are $R^9$, or together form a 3- to 7-membered carbocyclus,
which carbocyclus optionally has in addition to carbon atoms one or two ring members selected from the group consisting of $-N(R^{12})-$, $-N=N-$, $-C(=O)-$, $-O-$ and $-S-$, and
which carbocyclus is optionally substituted with one to four substituents selected from $R^{14}$;
n 1 to 3;
Q O, S, SO, $SO_2$, NH or ($C_1$-$C_3$-alkyl)N;
W O or S;
X O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
$I^2$ H;
$I^3$ H or $C(=Y)L^2$, wherein
Y is O or S, and
$L^2$ is is a nucleophilically displaceable leaving group, preferably $C_1$-$C_6$-alkoxy, $C_1$-$C_6$-alkylthio or aryloxy, wherein the aryl moiety may itself be partly or fully halogenated and/or may be substituted by from one to three substituents from the group of cyano, nitro, $C_1$-$C_4$-alkyl, $C_1$-$C_4$-alkoxy and $C_1$-$C_4$-alkylthio;
or $I^2$ and $I^3$ together with the N-atom, to which they are attached, form a group "YCN",
wherein Y is O or S,
or a group "PGN", which is a protected amine substituent selected from the group consisting of $N_3$, aliphatic or aromatic carbamates, aliphatic or aromatic amides, $N$—$C_1$-$C_6$-alkyl-amines, N-aryl-amines or heteroarylamides,
including their salts.

$L^2$ preferably is $C_1$-$C_6$-alkoxy, $C_1$-$C_6$-alkylthio or phenyloxy,
wherein the phenyl moiety may itself be partly or fully halogenated and/or may be substituted by from one to three radicals from the group of cyano, nitro, $C_1$-$C_4$-alkyl, $C_1$-$C_4$-alkoxy and $C_1$-$C_4$-alkylthio;
more preferably is $C_1$-$C_6$-alkoxy, $C_1$-$C_6$-alkylthio or phenyloxy;
most preferably is $C_1$-$C_6$-alkoxy.

Preferably PGN is selected from the group consisting of $N_3$, $C_1$-$C_6$-alkyl-O(CO)NH—, $C_1$-$C_6$-haloalkyl-O(CO)—NH—, (tri-$C_1$-$C_6$-alkyl)-Si—$C_1$-$C_6$-alkyl-O(CO)NH—, $C_2$-$C_6$-alkenyl-O(CO)NH—, $C_3$-$C_6$-alkynyl-O(CO)NH—, $C_3$-$C_6$-cycloalkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH—, $C_1$-$C_6$-alkyl-NH, di($C_1$-$C_6$-alkyl)-N—, ($C_1$-$C_6$-alkyoxy-$C_1$-$C_4$-alkyl)NH—, di($C_1$-$C_6$-alkyoxy-$C_1$-$C_4$-alkyl)N—, $C_2$-$C_6$-alkenyl-NH, di($C_2$-$C_6$-alkenyl)N—, (tri-$C_1$-$C_4$-alkyl)-Si—$C_1$-$C_4$-alkoxy-$C_1$-$C_4$-alkyl-NH—, di[(tri-$C_1$-$C_4$-alkyl)-Si—$C_1$-$C_4$-alkoxy-$C_1$-$C_4$-alkyl]N—, fluorenylmethyl-NH—, di(fluorenylmethyl)N—, N-phthalimide, N-2,3-dimethylmaleimide or N-2,5-dimethylpyrrole, phenyl-O(CO)NH—, phenyl-$C_1$-$C_4$-alkyl-O(CO)NH—, phenyl-(CO)NH—, phenyl-$C_1$-$C_6$-alkyl-(CO)NH—, pyridyl-(CO)—NH—, ortho-($C_1$-$C_4$-alkoxy)-phenyl-NH, di[ortho-($C_1$-$C_4$-alkoxy)phenyl]N—, para-($C_1$-$C_4$-alkoxy)-phenyl-NH, di[para-($C_1$-$C_4$-alkoxy)-phenyl]N—, phenyl-$C_1$-$C_4$-alkyl-NH—, di(phenyl-$C_1$-$C_4$-alkyl)N—, para-($C_1$-$C_4$-alkoxy)-phenyl-$C_1$-$C_4$-alkyl-NH, di[para-($C_1$-$C_4$-alkoxy)-phenyl-$C_1$-$C_4$-alkyl]N—,
wherein each phenyl or pyridyl ring can be substituted by one to three substituents selected from the group consisting of halogen, CN, $NO_2$, $C_1$-$C_4$-alkyl, $C_1$-$C_4$-alkoxy, $C_1$-$C_4$-alkylsulfinyl and $C_1$-$C_4$-alkylsulfonyl;
more preferably PGN is selected from the group consisting of $C_1$-$C_6$-alkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH, N-phthalimide, phenyl-O(CO)NH—, phenyl-$C_1$-$C_4$-alkyl-O(CO)NH—, phenyl-$C_1$-$C_4$-alkyl-NH—, di(phenyl-$C_1$-$C_4$-alkyl)N—, wherein each phenyl or pyridyl ring can be substituted by one to three $C_1$-$C_4$-alkoxy substituents.

Suitable salts of the intermediates of formula (int-2) include $NH_4^+$, $Li^+$, $Na^+$, $K^+$ or $Mg^{2+}$ salts of the described amide or carbamate derivatives.

Particularly preferred are those intermediates of formula (int-2), wherein $I^2$ and $I^3$ are H.

With respect to the variables, the particularly preferred embodiments of the intermediates of formula (int-2) correspond, either independently of one another or in combination with one another, to those of the variables of $R^4$, $R^5$, $R^6$, $R^7$, $R^8$, $R^9$, $R^{10}$, $R^{11}$, $R^{12}$, $R^{13}$, $R^{14}$, n, Q, W, X, Y and Z of the uracilpyridines formula (I), or have, either independently of one another or in combination with one another, the following meanings:
$R^4$ is H, F or Cl;
$R^5$ is F, Cl, Br or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein
$R^9$ is hydrogen, $C_1$-$C_6$-alkyl, $C_3$-$C_6$-alkenyl, $C_3$-$C_6$-alkynyl or $C_1$-$C_6$-haloalkyl, and
$R^{10}$ is $C_1$-$C_6$-alkyl;
n is 1,
Q is O or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
$I^2$ is H; and
$I^3$ is H or $C(=Y)L^2$, wherein Y is O and $L^2$ is $C_1$-$C_5$-alkoxy.
or $I^2$ and $I^3$ together with the N-atom, to which they are attached, form a group selected from "YCN", wherein Y is O,
including the salts of the intermediates of formula (int-2); preferably
$R^4$ is H, F or Cl;
$R^5$ is F, Cl or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein $R^9$ is hydrogen, $C_1$-$C_6$-alkyl, $C_3$-$C_6$-alkenyl, $C_3$-$C_6$-alkynyl or $C_1$-$C_6$-haloalkyl, and
$R^{10}$ is $C_1$-$C_6$-alkyl;
n is 1;
Q is O or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
$I^2$ is H; and
$I^3$ is H or C(=Y)$L^2$, wherein Y is O and $L^2$ is $C_1$-$C_5$-alkoxy. or $I^2$ and $I^3$ together with the N-atom, to which they are attached, form a group selected from "YCN", wherein Y is O,
including the salts of the intermediates of formula (int-2).

Preference is given to intermediates of formula (int-2.a) (correspond to formula (int-2) wherein $R^7$ is H, n is 1, Q, W, X and Y are O, Z is Z-1 as defined, wherein $R^a$, $R^b$, $R^c$ and $R^d$ are H, and $I^2$ and $I^3$ are H):

(int-2.a)

wherein the variables $R^4$, $R^5$, $R^6$ and $R^8$ have the meanings, in particular the preferred meanings, as defined above;
particularly preferred are the intermediates of the formulae (int-2.a.1) to (int-2.a.672), preferably the intermediates of the formulae (int-2.a.1) to (int-2.a.504), where the definitions of the variables $R^4$, $R^5$, $R^6$ and $R^8$ are as defined in table A above.

Also preferred are the intermediates of formula (int-2.b), preferably the intermediates of formulae (int-2.b.1) to (int-2.b.672), particularly preferred the intermediates of formulae (int-2.b.1) to (int-2.b.504), which differ from the corresponding intermediates of formulae (int-2.a.1) to (int-2.a.672) only in that Z is Z-7, wherein $R^a$, $R^b$ and $R^c$ are H:

(int-2.b)

Also preferred are the intermediates of formula (int-2.c), preferably the intermediates of formulae (int-2.c.1) to (int-2.c.672), particularly preferred the intermediates of formulae (int-2.c.1) to (int-2.c.504), which differ from the corresponding intermediates of formulae (int-2.a.1) to (int-2.a.672) only in that $I^2$ and $I^3$ together with the N-atom, to which they are attached, form the group "OCN":

(int-2.c)

Also preferred are the intermediates of formula (int-2.d), preferably the intermediates of formulae (int-2.d.1) to (int-2.d.672), particularly preferred the intermediates of formulae (int-2.d.1) to (int-2.d.504), which differ from the corresponding intermediates of formulae (int-2.a.1) to (int-2.a.672) only in that Z is Z-7, wherein $R^a$, $R^b$ and $R^c$ are H, and $I^2$ and $I^3$ together with the N-atom, to which they are attached, form the group "OCN":

(int-2.d)

Also preferred are the intermediates of formula (int-2.e), preferably the intermediates of formulae (int-2.e.1) to (int-2.e.672), particularly preferred the intermediates of formulae (int-2.e.1) to (int-2.e.672), which differ from the corresponding intermediates of formulae (int-2.a.1) to (int-2.a.504) only in that $I^3$ is (CO)OC$_2$H$_5$:

(int-2.e)

Also preferred are the intermediates of formula (int-2.f), preferably the intermediates of formulae (int-2.f.1) to (int-2.f.672), particularly preferred the intermediates of formulae (int-2.f.1) to (int-2.f.504), which differ from the corresponding intermediates of formulae (int-2.a.1) to (int-2.a.672) only in that Z is Z-7, wherein $R^a$, $R^b$ and $R^c$ are H, and $I^3$ is (CO)OC$_2$H$_5$:

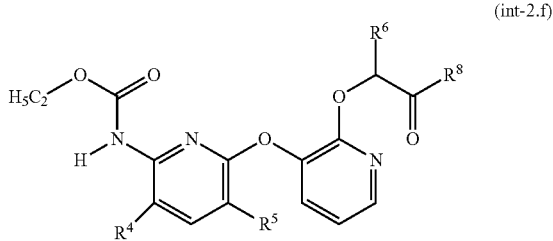
(int-2.f)

The intermediates of formula (int-3) combining the (thio)carbamates of formula (XX), the iso(thio)cyanates of formula (XXIV), the amines of formula (XXI) and the pyridines of formula (XXII) are novel compounds and as shown above suitable intermediates for the preparation of the uracilpyridines of formula (I) according to the present invention.

Therefore the present invention also provides intermediates of formula (int-3)

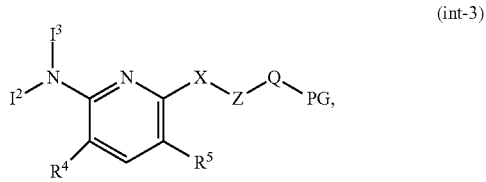
(int-3)

wherein the substituents have the following meanings:
$R^4$ H or halogen;
$R^5$ halogen, CN, $NO_2$, $NH_2$, $CF_3$ or $C(=S)NH_2$;
Q O, S, SO, $SO_2$, NH or $(C_1$-$C_3$-alkyl)N;
X O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
PG is a protecting group selected from the group consisting of
$C_1$-$C_6$-alkyl, $C_1$-$C_6$-cyanoalkyl, $C_1$-$C_6$-haloalkyl, $C_1$-$C_6$-alkylthio-$C_1$-$C_4$-alkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, (tri-$C_1$-$C_6$-alkyl)silyl-$C_1$-$C_4$-alkyl, (tri-$C_1$-$C_6$-alkyl)silyl-$C_1$-$C_4$-alkyoxy-$C_1$-$C_4$-alkyl, $C_2$-$C_6$-alkenyl, $C_3$-$C_6$-alkynyl, $C_3$-$C_6$-cycloalkyl, $C_3$-$C_6$-cylcloalkyl-$C_1$-$C_4$-alkyl, $C_5$-$C_6$-cycloalkenyl, tetrahydropyranyl, (tri-$C_1$-$C_6$-alkyl)silyl, [(diphenyl)($C_1$-$C_4$-alkyl)]silyl, formyl, $C_1$-$C_6$-alkyl-carbonyl, $C_1$-$C_6$-alkyl-O-carbonyl, $C_2$-$C_6$-alkenyl-O-carbonyl, [(diphenyl)($C_1$-$C_4$-alkyl)]silyl-$C_1$-$C_4$-alkyl, phenyl-$C_1$-$C_4$-alkyl, phenylthio-$C_1$-$C_6$-alkyl, phenylcarbonyl,
wherein each phenyl ring can be substituted by one to three substituents selected from the group consisting of halogen, CN, $NO_2$, $C_1$-$C_4$-alkyl and $C_1$-$C_4$-alkoxy;
$I^2$ H;
$I^3$ H or $C(=Y)L^2$, wherein
Y is O or S, and
$L^2$ is a nucleophilically displaceable leaving group, preferably $C_1$-$C_6$-alkoxy, $C_1$-$C_6$-alkylthio or aryloxy, wherein the aryl moiety may itself be partly or fully halogenated and/or may be substituted by from one to three substituents from the group of cyano, nitro, $C_1$-$C_4$-alkyl, $C_1$-$C_4$-alkoxy and $C_1$-$C_4$-alkylthio;
or $I^2$ and $I^3$ together with the N-atom, to which they are attached, form a group "YCN", wherein Y is O or S,
or a group "PGN", which is a protected amine substituent selected from the group consisting of $N_3$, aliphatic or aromatic carbamates, aliphatic or aromatic amides, N—$C_1$-$C_6$-alkyl-amines, N-aryl-amines or heteroarylamides,
including their salts.

Preferred are those intermediates of formula (int-3), wherein
PG $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, tetrahydropyranyl, (tri-$C_1$-$C_6$-alkyl)silyl, [(diphenyl)($C_1$-$C_4$-alkyl)]silyl or phenyl-$C_1$-$C_4$-alkyl.

Preferred are those intermediates of formula (int-3), wherein
PGN is selected from the group consisting of $N_3$, $C_1$-$C_6$-alkyl-O(CO)NH—, $C_1$-$C_6$-haloalkyl-O(CO)—NH—, (tri-$C_1$-$C_6$-alkyl)-Si—$C_1$-$C_6$-alkyl-O(CO)NH—, $C_2$-$C_6$-alkenyl-O(CO)NH—, $C_3$-$C_6$-alkynyl-O(CO)NH—, $C_3$-$C_6$-cycloalkyl-O(CO)NH—, fluorenylmethyl-O(CO)NH—, H(CO)N—, $C_1$-$C_6$-alkyl-(CO)NH—, $C_1$-$C_6$-haloalkyl-(CO)—NH—, $C_1$-$C_6$-alkyl-NH, di($C_1$-$C_6$-alkyl)-N—, ($C_1$-$C_6$-alkyoxy-$C_1$-$C_4$-alkyl)NH—, di($C_1$-$C_6$-alkyoxy-$C_1$-$C_4$-alkyl)N—, $C_2$-$C_6$-alkenyl-NH, di($C_2$-$C_6$-alkenyl)N—, (tri-$C_1$-$C_4$-alkyl)-Si—$C_1$-$C_4$-alkoxy-$C_1$-$C_4$-alkyl-NH—, di[(tri-$C_1$-$C_4$-alkyl)-Si—$C_1$-$C_4$-alkoxy-$C_1$-$C_4$-alkyl]N—, fluorenylmethyl-NH—, di(fluorenylmethyl)N—, N-phthalimide, N-2,3-dimethylmaleimide or N-2,5-dimethylpyrrole, phenyl-O(CO)NH—, phenyl-$C_1$-$C_4$-alkyl-O(CO)NH—, phenyl-(CO)NH—, phenyl-$C_1$-$C_6$-alkyl-(CO)NH—, pyridyl-(CO)—NH—, ortho-($C_1$-$C_4$-alkoxy)-phenyl-NH, di[ortho-($C_1$-$C_4$-alkoxy)phenyl]N—, para-($C_1$-$C_4$-alkoxy)-phenyl-NH, di[para-($C_1$-$C_4$-alkoxy)-phenyl]N—, phenyl-$C_1$-$C_4$-alkyl-NH—, di(phenyl-$C_1$-$C_4$-alkyl)N—, para-($C_1$-$C_4$-alkoxy)-phenyl-$C_1$-$C_4$-alkyl-NH, di[para-($C_1$-$C_4$-alkoxy)-phenyl-$C_1$-$C_4$-alkyl]N—,
wherein each phenyl or pyridyl ring can be substituted by one to three substituents selected from the group consisting of halogen, CN, $NO_2$, $C_1$-$C_4$-alkyl, $C_1$-$C_4$-alkoxy, $C_1$-$C_4$-alkylsulfinyl and $C_1$-$C_4$-alkylsulfonyl;
more preferably PGN is selected from the group consisting of $C_1$-$C_6$-alkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH, N-phthalimide, phenyl-O(CO)NH—, phenyl-$C_1$-$C_4$-alkyl-O(CO)NH—, phenyl-$C_1$-$C_4$-alkyl-NH—, di(phenyl-$C_1$-$C_4$-alkyl)N—,
wherein each phenyl or pyridyl ring can be substituted by one to three $C_1$-$C_4$-alkoxy substituents.

Suitable salts of the intermediates of formula (int-3) include $NH_{4+}$, $Li^+$, $Na^+$, $K^+$ or $Mg^{2+}$ salts of the described amide or carbamate derivatives.

Particularly preferred are those intermediates of formula (int-3), wherein $I^2$ and $I^3$ are H.

With respect to the variables, the particularly preferred embodiments of the intermediates of formula (int-3) correspond, either independently of one another or in combination with one another, to those of the variables of $R^4$, $R^5$, Q, X, Y and Z of the uracilpyridines formula (I), or have, either independently of one another or in combination with one another, the following meanings:

$R^4$ is H, F or Cl;
$R^5$ is F, Cl, Br or CN;
Q is O or S;
X is O;
Y is O;
Z is selected from the group consisting of $Z^1$, $Z^4$, $Z^5$, $Z^6$, $Z^7$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
PG is $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, or tetrahydropyranyl;
$I^2$ is H; and
$I^3$ is H or C(=Y)$L^2$, wherein Y is O and $L^2$ is $C_1$-$C_5$-alkoxy, or $I^2$ and $I^3$ together with the N-atom, to which they are attached, form a group selected from "YCN", wherein Y is O,
including salts of the intermediates of formula (int-3);
preferably
$R^4$ is H, F or Cl;
$R^5$ is F, Cl or CN;
Q is O or S;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;
PG is $C_1$-$C_6$-alkyl, $C_1$-$C_6$-alkoxy-$C_1$-$C_4$-alkyl, (tri-$C_1$-$C_6$-alkyl)silyl-$C_1$-$C_4$-alkyl, $C_2$-$C_6$-alkenyl, or tetrahydropyranyl;
$I^2$ is H; and
$I^3$ is H or C(=Y)$L^2$, wherein Y is O and $L^2$ is $C_1$-$C_5$-alkoxy, or $I^2$ and $I^3$ together with the N-atom, to which they are attached, form a group selected from "YCN", wherein Y is O,
including salts of the intermediates of formula (int-3).

Particular preference is given to intermediates of formula (int-3.a) (corresponds to formula (int-3) wherein Q and X are O, Z is Z-1 as defined, wherein $R^a$, $R^b$, $R^c$ and $R^d$ are H, and $I^2$ and $I^3$ are H:

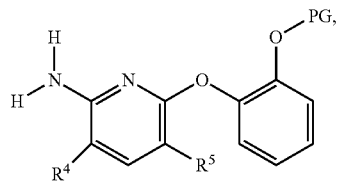
(int-3.a)

wherein the variables $R^4$, $R^5$ and PG have the meanings, in particular the preferred meanings, as defined above.

Special preference is given to the intermediates of the formulae (int-3.a.1) to (int-3.a.14), preferably the intermediates of formulae (int-3.a.1) to (int-3.a.12), of table I-3, where the definitions of the variables $R^4$, $R^5$ and PG are of particular importance for the compounds according to the invention not only in combination with one another but in each case also on their own:

TABLE I-3

| No. | $R^4$ | $R^5$ | PG |
|---|---|---|---|
| int-3.a.1. | H | F | $CH_3$ |
| int-3.a.2. | H | F | $CH_2$—$C_6H_5$ |

TABLE I-3-continued

| No. | $R^4$ | $R^5$ | PG |
|---|---|---|---|
| int-3.a.3. | H | Cl | $CH_3$ |
| int-3.a.4. | H | Cl | $CH_2$—$C_6H_5$ |
| int-3.a.5. | H | CN | $CH_3$ |
| int-3.a.6. | H | CN | $CH_2$—$C_6H_5$ |
| int-3.a.7. | F | F | $CH_3$ |
| int-3.a.8. | F | F | $CH_2$—$C_6H_5$ |
| int-3.a.9. | F | Cl | $CH_3$ |
| int-3.a.10. | F | Cl | $CH_2$—$C_6H_5$ |
| int-3.a.11. | F | CN | $CH_3$ |
| int-3.a.12. | F | CN | $CH_2$—$C_6H_5$ |
| int-3.a.13. | H | Br | $CH_3$ |
| int-3.a.14. | F | Br | $CH_2$—$C_6H_5$ |

Also preferred are the intermediates of formula (int-3.b), preferably the intermediates of formulae (int-3.b.1) to (int-3.b.14), particularly preferred the intermediates of formulae (int-3.b.1) to (int-3.b.12), which differ from the corresponding intermediates of formulae (int-3.a.1) to (int-3.a.14) only in that Z is Z-7, wherein $R^a$, $R^b$ and $R^c$ are H:

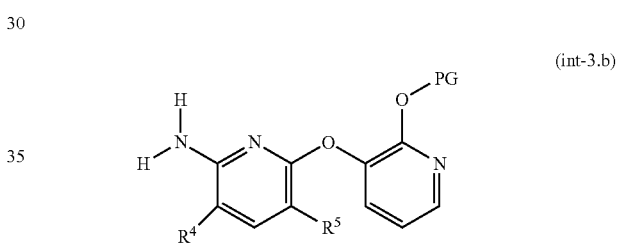
(int-3.b)

Also preferred are the intermediates of formula (int-3.c), preferably the intermediates of formulae (int-3.c.1) to (int-3.c.14), particularly preferred the intermediates of formulae (int-3.c.1) to (int-3.c.12), which differ from the corresponding intermediates of formulae (int-3.a.1) to (int-3.a.14) only in that $I^2$ and $I^3$ together with the N-atom, to which they are attached, form the group "OCN":

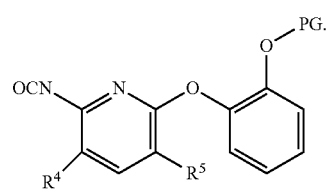
(int-3.c)

Also preferred are the intermediates of formula (int-3.d), preferably the intermediates of formulae (int-3.d.1) to (int-3.d.14), particularly preferred the intermediates of formulae (int-3.d.1) to (int-3.d.12), which differ from the corresponding intermediates of formulae (int-3.a.1) to (int-3.a.14) only in that Z is Z-7, wherein $R^a$, $R^b$ and $R^c$ are H, and $I^2$ and $I^3$ together with the N-atom, to which they are attached, form the group "OCN":

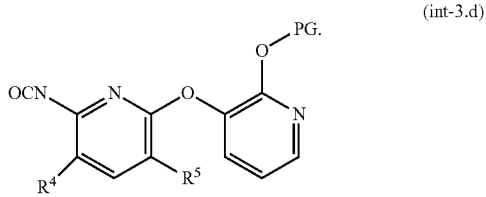

(int-3.d)

Also preferred are the intermediates of formula (int-3.e), preferably the intermediates of formulae (int-3.e.1) to (int-3.e.14), particularly preferred the intermediates of formulae (int-3.e.1) to (int-3.e.12), which differ from the corresponding intermediates of formulae (int-3.a.1) to (int-3.a.14) only in that I³ is $(CO)OC_2H_5$:

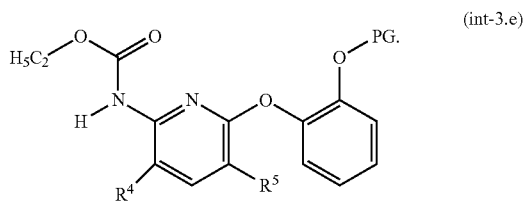

(int-3.e)

Also preferred are the intermediates of formula (int-3.f), preferably the intermediates of formulae (int-3.f.1) to (int-3.f.14), particularly preferred the intermediates of formulae (int-3.f.1) to (int-3.f.12), which differ from the corresponding intermediates of formulae (int-3.a.1) to (int-3.a.14) only in that Z is Z-7, wherein $R^a$, $R^b$ and $R^c$ are H, and I³ is $(CO)OC_2H_5$:

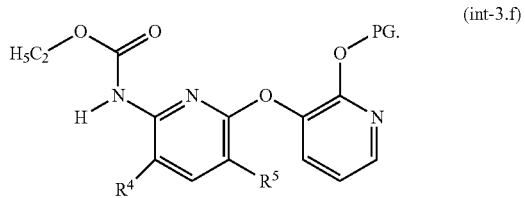

(int-3.f)

To widen the spectrum of action and to achieve synergistic effects, the uracilpyridines of formula (I) may be mixed with a large number of representatives of other herbicidal or growth-regulating active ingredient groups and then applied concomitantly. Suitable components for mixtures are, for example,
herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the uracilpyridines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one uracilpyridine of formula (I) (compound A) and at least one further active compound selected from herbicides B, preferably herbicides B of class b1) to b15), and safeners C (compound C).

In another embodiment of the present invention the compositions according to the present invention comprise at least one uracilpyridine of formula (I) and at least one further active compound B (herbicide B).

The further herbicidal compound B (component B) is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamineammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Preference is given to those compositions according to the present invention comprising at least one herbicide B selected from herbicides of class b2, b3, b4, b5, b6, b7, b9, b10 and b13.

Specific preference is given to those compositions according to the present invention which comprise at least one herbicide B selected from the herbicides of class b4, b6, b7, b9, b10 and b13.

Particular preference is given to those compositions according to the present invention which comprise at least one herbicide B selected from the herbicides of class b4, b6, b10 and b13.

Examples of herbicides B which can be used in combination with the uracilpyridines of formula (I) of formula (I) according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy] benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl;

and triafamone;

among these, a preferred embodiment of the invention relates to those compositions comprising at least one imidazolinone herbicide;

b3) from the group of the photosynthesis inhibitors:
amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methylpyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, chlorphtalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydroisoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluorophenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, fluorchloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon and 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinateammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthatdimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:
chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and 11.9

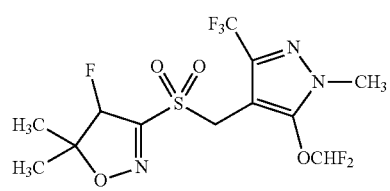

II.1

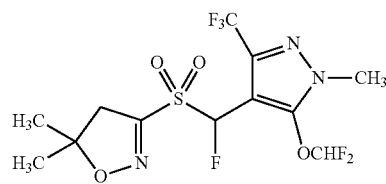

II.2

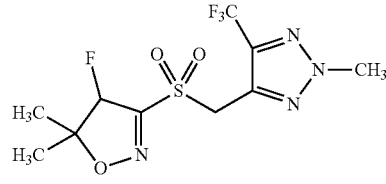

II.3

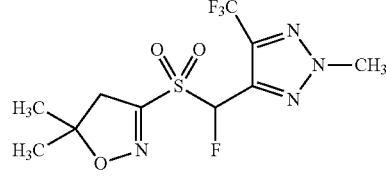

II.4

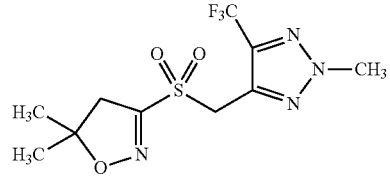

II.5

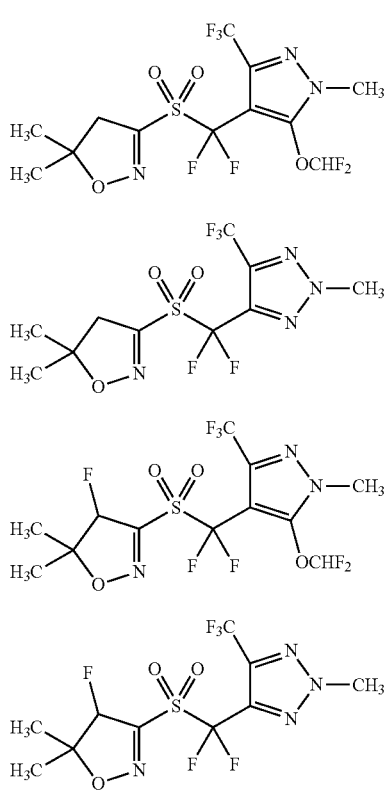

II.6
II.7
II.8
II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:
chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b12) from the group of the decoupler herbicides:
dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyraliddimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicambapotassium, dicamba-methylammonium, dicamba-dimethylammonium, dicambaisopropylammonium, dicamba-diglycolamine, dicamba-olamine, dicamba-diolamine, dicambatrolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-Disopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorpropbutotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl. Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyraliddimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecopropmethyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

A suitable salt of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicides B are the herbicides B as defined above; in particular the herbicides B.1-B.202, especially the herbicides B.1-B.201 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |

TABLE B-continued

Herbicide B

| | | |
|---|---|---|
| B.75 | hexazinone | |
| B.76 | isoproturon | |
| B.77 | linuron | |
| B.78 | metamitron | |
| B.79 | metribuzin | |
| B.80 | propanil | |
| B.81 | simazin | |
| B.82 | terbuthylazine | |
| B.83 | terbutryn | |
| B.84 | paraquat-dichloride | |
| B.85 | acifluorfen | |
| B.86 | butafenacil | |
| B.87 | carfentrazone-ethyl | |
| B88 | flumioxazin | |
| B.89 | fomesafen | |
| B.90 | oxadiargyl | |
| B.91 | oxyfluorfen | |
| B.92 | pyraflufen | |
| B.93 | pyraflufen-ethyl | |
| B.94 | saflufenacil | |
| B.95 | sulfentrazone | |
| B.96 | trifludimoxazin | |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) | |
| B.98 | benzobicyclon | |
| B.99 | bicyclopyrone | |
| B.100 | clomazone | |
| B.101 | diflufenican | |
| B.102 | flurochloridone | |
| B.103 | isoxaflutole | |
| B.104 | mesotrione | |
| B.105 | norflurazone | |
| B.106 | picolinafen | |
| B.107 | sulcotrione | |
| B.108 | tefuryltrione | |
| B.109 | tembotrione | |
| B.110 | tolpyralate | |
| B.111 | topramezone | |
| B.112 | topramezone-sodium | |
| B.113 | amitrole | |
| B.114 | fluometuron | |
| B.115 | fenquinotrione | |
| B.116 | glyphosate | |
| B.117 | glyphosate-ammonium | |
| B.118 | glyphosate-dimethylammonium | |
| B.119 | glyphosate-isopropylammonium | |
| B.120 | glyphosate-trimesium (sulfosate) | |
| B.121 | glyphosate-potassium | |
| B.122 | glufosinate | |
| B.123 | glufosinate-ammonium | |
| B.124 | glufosinate-P | |
| B.125 | glufosinate-P-ammonium | |
| B.126 | pendimethalin | |
| B.127 | trifluralin | |
| B.128 | acetochlor | |
| B.129 | butachlor | |
| B.130 | cafenstrole | |
| B.131 | dimethenamid-P | |
| B.132 | fentrazamide | |
| B.133 | flufenacet | |
| B.134 | mefenacet | |
| B.135 | metazachlor | |
| B.136 | metolachlor | |
| B.137 | S-metolachlor | |
| B.138 | pretilachlor | |
| B.139 | fenoxasulfone | |
| B.140 | indaziflam | |
| B.141 | isoxaben | |
| B.142 | triaziflam | |
| B.143 | ipfencarbazone | |
| B.144 | pyroxasulfone | |
| B.145 | 2,4-D | |
| B.146 | 2,4-D-isobutyl | |
| B.147 | 2,4-D-dimethylammonium | |
| B.148 | 2,4-D-N,N,N-trimethylethanolammonium | |
| B.149 | aminopyralid | |
| B.150 | aminopyralid-methyl | |
| B.151 | aminopyralid-dimethyl-ammonium | |
| B.152 | aminopyralid-tris(2-hydroxypropyl)ammonium | |
| B.153 | clopyralid | |
| B.154 | clopyralid-methyl | |
| B.155 | clopyralid-olamine | |
| B.156 | dicamba | |
| B.157 | dicamba-butotyl | |
| B.158 | dicamba-diglycolamine | |
| B.159 | dicamba-dimethylammonium | |
| B.160 | dicamba-diolamine | |
| B.161 | dicamba-isopropylammonium | |
| B.162 | dicamba-potassium | |
| B.163 | dicamba-sodium | |
| B.164 | dicamba-trolamine | |
| B.165 | dicamba-N,N-bis-(3-aminopropyl)methylamine | |
| B.166 | dicamba-diethylenetriamine | |
| B.167 | fluroxypyr | |
| B.168 | fluroxypyr-meptyl | |
| B.169 | halauxifen | |
| B.170 | halauxifen-methyl | |
| B.171 | MCPA | |
| B.172 | MCPA-2-ethylhexyl | |
| B.173 | MCPA-dimethylammonium | |
| B.174 | quinclorac | |
| B.175 | quinclorac-dimethylammonium | |
| B.176 | quinmerac | |
| B.177 | quinmerac-dimethylammonium | |
| B.178 | florpyrauxifen | |
| B.179 | florpyrauxifen-benzyl (CAS 1390661-72-9) | |
| B.180 | aminocyclopyrachlor | |
| B.181 | aminocyclopyrachlor-potassium | |
| B.182 | aminocyclopyrachlor-methyl | |
| B.183 | diflufenzopyr | |
| B.184 | diflufenzopyr-sodium | |
| B.185 | dymron | |
| B.186 | indanofan | |
| B.187 | oxaziclomefone | |
| B.188 | II.1 | |
| B.189 | II.2 | |
| B.190 | II.3 | |
| B.191 | II.4 | |
| B.192 | II.5 | |
| B.193 | II.6 | |
| B.194 | II.7 | |
| B.195 | II.8 | |
| B.196 | II.9 | |
| B.197 | 4-amino-3-chloro-5-fluoro-6-(7-fluoro-1H-indol-6-yl)picolinic acid (CAS 1629965-65-6) | |
| B.198 | flopyrauxifen | |
| B.199 | oxotrione (CAS 1486617-21-3) | |
| B.200 | cinmethylin | |
| B.201 | 2-chloro-3-methylsulfanyl-N-(1-methyltetrazol-5-yl)-4-(trifluoromethyl)benzamide (CAS 1361139-71-0) | |

TABLE B-continued

| | Herbicide B |
|---|---|
| B.202 | 2-(2,4-dichlorophenyl)-methyl-4,4-dimethyl-3-isoxazolidone (CAS 81777-95-9) |

Moreover, it may be useful to apply the uracilpyridines of formula (I) in combination with safeners. Safeners are chemical compounds which prevent or reduce damage on useful plants without having a major impact on the herbicidal action of the uracilpyridines of formula (I) towards unwanted plants. They can be applied either before sowings (e.g. on seed treatments, shoots or seedlings) or in the pre-emergence application or post-emergence application of the useful plant. The safeners and the uracilpyridines of formula (I) and optionally the herbicides B can be applied simultaneously or in succession.

In another embodiment of the present invention the compositions according to the present invention comprise at least one uracilpyridine of formula (I) and at least one safener C (component C).

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen and BPCMS (CAS 54091-06-4); especially preferred benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen.

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |

TABLE C-continued

| | Safener C |
|---|---|
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (CAS 71526-07-3) |
| C.16 | 2,2,5-trimethyl-3-(dichloroacetyl)-1,3-oxazolidine (CAS 52836-31-4) |
| C.17 | metcamifen |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as herbicidal active compounds B or component B at least four, preferably exactly four herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.a) or (I.h), and as component B at least one, preferably exactly one, herbicide B.

According to another preferred embodiment of the invention, the composition comprises as component A at least one, preferably exactly one compound of formula (I), preferably of formula (I.a) or (I.h), and at least two, preferably exactly two, herbicides B different from each other.

According to another preferred embodiment of the invention, the composition comprises as component A at least one, preferably exactly one compound of formula (I), preferably of formula (I.a) or (I.h), and at least three, preferably exactly three, herbicides B different from each other.

According to another preferred embodiment of the invention, the composition comprises as component A at least one, preferably exactly one compound of formula (I), preferably of formula (I.a) or (I.h), and at least four, preferably exactly four, herbicides B different from each other.

According to another preferred embodiment of the invention, the composition comprises as component A at least one, preferably exactly one compound of formula (I), preferably of formula (I.a) or (I.h), and as component C at least one, preferably exactly one, safener C.

According to another preferred embodiment of the invention, the composition comprises as component A at least one, preferably exactly one compound of formula (I), preferably of formula (I.a) or (I.h), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.a) or (I.h), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.a) or (I.h), at least three, preferably exactly three herbicides B different from each other, and as component C at least one, preferably exactly one, safener C.

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367),at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6).

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyraliddimethyl-ammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid.

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one compound of the formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:125 to 125:1.

In binary compositions comprising at least one compound of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one uracilpyridine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:125 to 125:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits.

Particularly preferred are the compositions mentioned below comprising the uracilpyridines of formula (I) as defined and the substance(s) as defined in the respective row of table 1;
especially preferred comprising as only herbicidal active compounds the uracilpyridines of formula (I) as defined and the substance(s) as defined in the respective row of table 1; most preferably comprising as only active compounds the uracilpyridines of formula (I) as defined and the substance(s) as defined in the respective row of table 1.

Particularly preferred are compositions 1.1 to 1.3653, especially compositions 1.1 to 1.3635, comprising the uracilpyridine (1a.339) and the substance(s) as defined in the respective row of table 1:

TABLE 1 compositions 1.1 to 1.3635

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |

TABLE 1-continued compositions 1.1 to 1.3635

| comp. no. | herbicide B | safener C |
|---|---|---|
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.1 | C.1 |
| 1.203 | B.2 | C.1 |
| 1.204 | B.3 | C.1 |
| 1.205 | B.4 | C.1 |
| 1.206 | B.5 | C.1 |
| 1.207 | B.6 | C.1 |
| 1.208 | B.7 | C.1 |
| 1.209 | B.8 | C.1 |
| 1.210 | B.9 | C.1 |
| 1.211 | B.10 | C.1 |
| 1.212 | B.11 | C.1 |
| 1.213 | B.12 | C.1 |
| 1.214 | B.13 | C.1 |
| 1.215 | B.14 | C.1 |
| 1.216 | B.15 | C.1 |
| 1.217 | B.16 | C.1 |
| 1.218 | B.17 | C.1 |
| 1.219 | B.18 | C.1 |
| 1.220 | B.19 | C.1 |
| 1.221 | B.20 | C.1 |
| 1.222 | B.21 | C.1 |
| 1.223 | B.22 | C.1 |
| 1.224 | B.23 | C.1 |
| 1.225 | B.24 | C.1 |
| 1.226 | B.25 | C.1 |
| 1.227 | B.26 | C.1 |
| 1.228 | B.27 | C.1 |
| 1.229 | B.28 | C.1 |
| 1.230 | B.29 | C.1 |
| 1.231 | B.30 | C.1 |
| 1.232 | B.31 | C.1 |
| 1.233 | B.32 | C.1 |
| 1.234 | B.33 | C.1 |
| 1.235 | B.34 | C.1 |
| 1.236 | B.35 | C.1 |
| 1.237 | B.36 | C.1 |
| 1.238 | B.37 | C.1 |
| 1.239 | B.38 | C.1 |
| 1.240 | B.39 | C.1 |

TABLE 1-continued compositions 1.1 to 1.3635

| comp. no. | herbicide B | safener C |
|---|---|---|
| 1.241 | B.40 | C.1 |
| 1.242 | B.41 | C.1 |
| 1.243 | B.42 | C.1 |
| 1.244 | B.43 | C.1 |
| 1.245 | B.44 | C.1 |
| 1.246 | B.45 | C.1 |
| 1.247 | B.46 | C.1 |
| 1.248 | B.47 | C.1 |
| 1.249 | B.48 | C.1 |
| 1.250 | B.49 | C.1 |
| 1.251 | B.50 | C.1 |
| 1.252 | B.51 | C.1 |
| 1.253 | B.52 | C.1 |
| 1.254 | B.53 | C.1 |
| 1.255 | B.54 | C.1 |
| 1.256 | B.55 | C.1 |
| 1.257 | B.56 | C.1 |
| 1.258 | B.57 | C.1 |
| 1.259 | B.58. | C.1 |
| 1.260 | B.59 | C.1 |
| 1.261 | B.60 | C.1 |
| 1.262 | B.61 | C.1 |
| 1.263 | B.62 | C.1 |
| 1.264 | B.63 | C.1 |
| 1.265 | B.64 | C.1 |
| 1.266 | B.65 | C.1 |
| 1.267 | B.66 | C.1 |
| 1.268 | B.67 | C.1 |
| 1.269 | B.68 | C.1 |
| 1.270 | B.69 | C.1 |
| 1.271 | B.70 | C.1 |
| 1.272 | B.71 | C.1 |
| 1.273 | B.72 | C.1 |
| 1.274 | B.73 | C.1 |
| 1.275 | B.74 | C.1 |
| 1.276 | B.75 | C.1 |
| 1.277 | B.76 | C.1 |
| 1.278 | B.77 | C.1 |
| 1.279 | B.78 | C.1 |
| 1.280 | B.79 | C.1 |
| 1.281 | B.80 | C.1 |
| 1.282 | B.81 | C.1 |
| 1.283 | B.82 | C.1 |
| 1.284 | B.83 | C.1 |
| 1.285 | B.84 | C.1 |
| 1.286 | B.85 | C.1 |
| 1.287 | B.86 | C.1 |
| 1.288 | B.87 | C.1 |
| 1.289 | B.88 | C.1 |
| 1.290 | B.89 | C.1 |
| 1.291 | B.90 | C.1 |
| 1.292 | B.91 | C.1 |
| 1.293 | B.92 | C.1 |
| 1.294 | B.93 | C.1 |
| 1.295 | B.94 | C.1 |
| 1.296 | B.95 | C.1 |
| 1.297 | B.96 | C.1 |
| 1.298 | B.97 | C.1 |
| 1.299 | B.98 | C.1 |
| 1.300 | B.99 | C.1 |
| 1.301 | B.100 | C.1 |
| 1.302 | B.101 | C.1 |
| 1.303 | B.102 | C.1 |
| 1.304 | B.103 | C.1 |
| 1.305 | B.104 | C.1 |
| 1.306 | B.105 | C.1 |
| 1.307 | B.106 | C.1 |
| 1.308 | B.107 | C.1 |
| 1.309 | B.108 | C.1 |
| 1.310 | B.109 | C.1 |
| 1.311 | B.110 | C.1 |
| 1.312 | B.111 | C.1 |
| 1.313 | B.112 | C.1 |
| 1.314 | B.113 | C.1 |
| 1.315 | B.114 | C.1 |
| 1.316 | B.115 | C.1 |
| 1.317 | B.116 | C.1 |
| 1.318 | B.117 | C.1 |
| 1.319 | B.118 | C.1 |
| 1.320 | B.119 | C.1 |
| 1.321 | B.120 | C.1 |
| 1.322 | B.121 | C.1 |
| 1.323 | B.122 | C.1 |
| 1.324 | B.123 | C.1 |
| 1.325 | B.124 | C.1 |
| 1.326 | B.125 | C.1 |
| 1.327 | B.126 | C.1 |
| 1.328 | B.127 | C.1 |
| 1.329 | B.128 | C.1 |
| 1.330 | B.129 | C.1 |
| 1.331 | B.130 | C.1 |
| 1.332 | B.131 | C.1 |
| 1.333 | B.132 | C.1 |
| 1.334 | B.133 | C.1 |
| 1.335 | B.134 | C.1 |
| 1.336 | B.135 | C.1 |
| 1.337 | B.136 | C.1 |
| 1.338 | B.137 | C.1 |
| 1.339 | B.138 | C.1 |
| 1.340 | B.139 | C.1 |
| 1.341 | B.140 | C.1 |
| 1.342 | B.141 | C.1 |
| 1.343 | B.142 | C.1 |
| 1.344 | B.143 | C.1 |
| 1.345 | B.144 | C.1 |
| 1.346 | B.145 | C.1 |
| 1.347 | B.146 | C.1 |
| 1.348 | B.147 | C.1 |
| 1.349 | B.148 | C.1 |
| 1.350 | B.149 | C.1 |
| 1.351 | B.150 | C.1 |
| 1.352 | B.151 | C.1 |
| 1.353 | B.152 | C.1 |
| 1.354 | B.153 | C.1 |
| 1.355 | B.154 | C.1 |
| 1.356 | B.155 | C.1 |
| 1.357 | B.156 | C.1 |
| 1.358 | B.157 | C.1 |
| 1.359 | B.158 | C.1 |
| 1.360 | B.159 | C.1 |
| 1.361 | B.160 | C.1 |
| 1.362 | B.161 | C.1 |
| 1.363 | B.162 | C.1 |
| 1.364 | B.163 | C.1 |
| 1.365 | B.164 | C.1 |
| 1.366 | B.165 | C.1 |
| 1.367 | B.166 | C.1 |
| 1.368 | B.167 | C.1 |
| 1.369 | B.168 | C.1 |
| 1.370 | B.169 | C.1 |
| 1.371 | B.170 | C.1 |
| 1.372 | B.171 | C.1 |
| 1.373 | B.172 | C.1 |
| 1.374 | B.173 | C.1 |
| 1.375 | B.174 | C.1 |
| 1.376 | B.175 | C.1 |
| 1.377 | B.176 | C.1 |
| 1.378 | B.177 | C.1 |
| 1.379 | B.178 | C.1 |
| 1.380 | B.179 | C.1 |
| 1.381 | B.180 | C.1 |
| 1.382 | B.181 | C.1 |
| 1.383 | B.182 | C.1 |
| 1.384 | B.183 | C.1 |
| 1.385 | B.184 | C.1 |
| 1.386 | B.185 | C.1 |
| 1.387 | B.186 | C.1 |
| 1.388 | B.187 | C.1 |
| 1.389 | B.188 | C.1 |
| 1.390 | B.189 | C.1 |

TABLE 1-continued compositions 1.1 to 1.3635

| comp. no. | herbicide B | safener C |
|---|---|---|
| 1.391 | B.190 | C.1 |
| 1.392 | B.191 | C.1 |
| 1.393 | B.192 | C.1 |
| 1.394 | B.193 | C.1 |
| 1.395 | B.194 | C.1 |
| 1.396 | B.195 | C.1 |
| 1.397 | B.196 | C.1 |
| 1.398 | B.197 | C.1 |
| 1.399 | B.198 | C.1 |
| 1.400 | B.199 | C.1 |
| 1.401 | B.200 | C.1 |
| 1.402 | B.201 | C.1 |
| 1.403 | B.1 | C.2 |
| 1.404 | B.2 | C.2 |
| 1.405 | B.3 | C.2 |
| 1.406 | B.4 | C.2 |
| 1.407 | B.5 | C.2 |
| 1.408 | B.6 | C.2 |
| 1.409 | B.7 | C.2 |
| 1.410 | B.8 | C.2 |
| 1.411 | B.9 | C.2 |
| 1.412 | B.10 | C.2 |
| 1.413 | B.11 | C.2 |
| 1.414 | B.12 | C.2 |
| 1.415 | B.13 | C.2 |
| 1.416 | B.14 | C.2 |
| 1.417 | B.15 | C.2 |
| 1.418 | B.16 | C.2 |
| 1.419 | B.17 | C.2 |
| 1.420 | B.18 | C.2 |
| 1.421 | B.19 | C.2 |
| 1.422 | B.20 | C.2 |
| 1.423 | B.21 | C.2 |
| 1.424 | B.22 | C.2 |
| 1.425 | B.23 | C.2 |
| 1.426 | B.24 | C.2 |
| 1.427 | B.25 | C.2 |
| 1.428 | B.26 | C.2 |
| 1.429 | B.27 | C.2 |
| 1.430 | B.28 | C.2 |
| 1.431 | B.29 | C.2 |
| 1.432 | B.30 | C.2 |
| 1.433 | B.31 | C.2 |
| 1.434 | B.32 | C.2 |
| 1.435 | B.33 | C.2 |
| 1.436 | B.34 | C.2 |
| 1.437 | B.35 | C.2 |
| 1.438 | B.36 | C.2 |
| 1.439 | B.37 | C.2 |
| 1.440 | B.38 | C.2 |
| 1.441 | B.39 | C.2 |
| 1.442 | B.40 | C.2 |
| 1.443 | B.41 | C.2 |
| 1.444 | B.42 | C.2 |
| 1.445 | B.43 | C.2 |
| 1.446 | B.44 | C.2 |
| 1.447 | B.45 | C.2 |
| 1.448 | B.46 | C.2 |
| 1.449 | B.47 | C.2 |
| 1.450 | B.48 | C.2 |
| 1.451 | B.49 | C.2 |
| 1.452 | B.50 | C.2 |
| 1.453 | B.51 | C.2 |
| 1.454 | B.52 | C.2 |
| 1.455 | B.53 | C.2 |
| 1.456 | B.54 | C.2 |
| 1.457 | B.55 | C.2 |
| 1.458 | B.56 | C.2 |
| 1.459 | B.57 | C.2 |
| 1.460 | B.58. | C.2 |
| 1.461 | B.59 | C.2 |
| 1.462 | B.60 | C.2 |
| 1.463 | B.61 | C.2 |
| 1.464 | B.62 | C.2 |
| 1.465 | B.63 | C.2 |
| 1.466 | B.64 | C.2 |
| 1.467 | B.65 | C.2 |
| 1.468 | B.66 | C.2 |
| 1.469 | B.67 | C.2 |
| 1.470 | B.68 | C.2 |
| 1.471 | B.69 | C.2 |
| 1.472 | B.70 | C.2 |
| 1.473 | B.71 | C.2 |
| 1.474 | B.72 | C.2 |
| 1.475 | B.73 | C.2 |
| 1.476 | B.74 | C.2 |
| 1.477 | B.75 | C.2 |
| 1.478 | B.76 | C.2 |
| 1.479 | B.77 | C.2 |
| 1.480 | B.78 | C.2 |
| 1.481 | B.79 | C.2 |
| 1.482 | B.80 | C.2 |
| 1.483 | B.81 | C.2 |
| 1.484 | B.82 | C.2 |
| 1.485 | B.83 | C.2 |
| 1.486 | B.84 | C.2 |
| 1.487 | B.85 | C.2 |
| 1.488 | B.86 | C.2 |
| 1.489 | B.87 | C.2 |
| 1.490 | B.88 | C.2 |
| 1.491 | B.89 | C.2 |
| 1.492 | B.90 | C.2 |
| 1.493 | B.91 | C.2 |
| 1.494 | B.92 | C.2 |
| 1.495 | B.93 | C.2 |
| 1.496 | B.94 | C.2 |
| 1.497 | B.95 | C.2 |
| 1.498 | B.96 | C.2 |
| 1.499 | B.97 | C.2 |
| 1.500 | B.98 | C.2 |
| 1.501 | B.99 | C.2 |
| 1.502 | B.100 | C.2 |
| 1.503 | B.101 | C.2 |
| 1.504 | B.102 | C.2 |
| 1.505 | B.103 | C.2 |
| 1.506 | B.104 | C.2 |
| 1.507 | B.105 | C.2 |
| 1.508 | B.106 | C.2 |
| 1.509 | B.107 | C.2 |
| 1.510 | B.108 | C.2 |
| 1.511 | B.109 | C.2 |
| 1.512 | B.110 | C.2 |
| 1.513 | B.111 | C.2 |
| 1.514 | B.112 | C.2 |
| 1.515 | B.113 | C.2 |
| 1.516 | B.114 | C.2 |
| 1.517 | B.115 | C.2 |
| 1.518 | B.116 | C.2 |
| 1.519 | B.117 | C.2 |
| 1.520 | B.118 | C.2 |
| 1.521 | B.119 | C.2 |
| 1.522 | B.120 | C.2 |
| 1.523 | B.121 | C.2 |
| 1.524 | B.122 | C.2 |
| 1.525 | B.123 | C.2 |
| 1.526 | B.124 | C.2 |
| 1.527 | B.125 | C.2 |
| 1.528 | B.126 | C.2 |
| 1.529 | B.127 | C.2 |
| 1.530 | B.128 | C.2 |
| 1.531 | B.129 | C.2 |
| 1.532 | B.130 | C.2 |
| 1.533 | B.131 | C.2 |
| 1.534 | B.132 | C.2 |
| 1.535 | B.133 | C.2 |
| 1.536 | B.134 | C.2 |
| 1.537 | B.135 | C.2 |
| 1.538 | B.136 | C.2 |
| 1.539 | B.137 | C.2 |
| 1.540 | B.138 | C.2 |

TABLE 1-continued compositions 1.1 to 1.3635

| comp. no. | herbicide B | safener C |
|---|---|---|
| 1.541 | B.139 | C.2 |
| 1.542 | B.140 | C.2 |
| 1.543 | B.141 | C.2 |
| 1.544 | B.142 | C.2 |
| 1.545 | B.143 | C.2 |
| 1.546 | B.144 | C.2 |
| 1.547 | B.145 | C.2 |
| 1.548 | B.146 | C.2 |
| 1.549 | B.147 | C.2 |
| 1.550 | B.148 | C.2 |
| 1.551 | B.149 | C.2 |
| 1.552 | B.150 | C.2 |
| 1.553 | B.151 | C.2 |
| 1.554 | B.152 | C.2 |
| 1.555 | B.153 | C.2 |
| 1.556 | B.154 | C.2 |
| 1.557 | B.155 | C.2 |
| 1.558 | B.156 | C.2 |
| 1.559 | B.157 | C.2 |
| 1.560 | B.158 | C.2 |
| 1.561 | B.159 | C.2 |
| 1.562 | B.160 | C.2 |
| 1.563 | B.161 | C.2 |
| 1.564 | B.162 | C.2 |
| 1.565 | B.163 | C.2 |
| 1.566 | B.164 | C.2 |
| 1.567 | B.165 | C.2 |
| 1.568 | B.166 | C.2 |
| 1.569 | B.167 | C.2 |
| 1.570 | B.168 | C.2 |
| 1.571 | B.169 | C.2 |
| 1.572 | B.170 | C.2 |
| 1.573 | B.171 | C.2 |
| 1.574 | B.172 | C.2 |
| 1.575 | B.173 | C.2 |
| 1.576 | B.174 | C.2 |
| 1.577 | B.175 | C.2 |
| 1.578 | B.176 | C.2 |
| 1.579 | B.177 | C.2 |
| 1.580 | B.178 | C.2 |
| 1.581 | B.179 | C.2 |
| 1.582 | B.180 | C.2 |
| 1.583 | B.181 | C.2 |
| 1.584 | B.182 | C.2 |
| 1.585 | B.183 | C.2 |
| 1.586 | B.184 | C.2 |
| 1.587 | B.185 | C.2 |
| 1.588 | B.186 | C.2 |
| 1.589 | B.187 | C.2 |
| 1.590 | B.188 | C.2 |
| 1.591 | B.189 | C.2 |
| 1.592 | B.190 | C.2 |
| 1.593 | B.191 | C.2 |
| 1.594 | B.192 | C.2 |
| 1.595 | B.193 | C.2 |
| 1.596 | B.194 | C.2 |
| 1.597 | B.195 | C.2 |
| 1.598 | B.196 | C.2 |
| 1.599 | B.197 | C.2 |
| 1.600 | B.198 | C.2 |
| 1.601 | B.199 | C.2 |
| 1.602 | B.200 | C.2 |
| 1.603 | B.201 | C.2 |
| 1.604 | B.1 | C.3 |
| 1.605 | B.2 | C.3 |
| 1.606 | B.3 | C.3 |
| 1.607 | B.4 | C.3 |
| 1.608 | B.5 | C.3 |
| 1.609 | B.6 | C.3 |
| 1.610 | B.7 | C.3 |
| 1.611 | B.8 | C.3 |
| 1.612 | B.9 | C.3 |
| 1.613 | B.10 | C.3 |
| 1.614 | B.11 | C.3 |
| 1.615 | B.12 | C.3 |
| 1.616 | B.13 | C.3 |
| 1.617 | B.14 | C.3 |
| 1.618 | B.15 | C.3 |
| 1.619 | B.16 | C.3 |
| 1.620 | B.17 | C.3 |
| 1.621 | B.18 | C.3 |
| 1.622 | B.19 | C.3 |
| 1.623 | B.20 | C.3 |
| 1.624 | B.21 | C.3 |
| 1.625 | B.22 | C.3 |
| 1.626 | B.23 | C.3 |
| 1.627 | B.24 | C.3 |
| 1.628 | B.25 | C.3 |
| 1.629 | B.26 | C.3 |
| 1.630 | B.27 | C.3 |
| 1.631 | B.28 | C.3 |
| 1.632 | B.29 | C.3 |
| 1.633 | B.30 | C.3 |
| 1.634 | B.31 | C.3 |
| 1.635 | B.32 | C.3 |
| 1.636 | B.33 | C.3 |
| 1.637 | B.34 | C.3 |
| 1.638 | B.35 | C.3 |
| 1.639 | B.36 | C.3 |
| 1.640 | B.37 | C.3 |
| 1.641 | B.38 | C.3 |
| 1.642 | B.39 | C.3 |
| 1.643 | B.40 | C.3 |
| 1.644 | B.41 | C.3 |
| 1.645 | B.42 | C.3 |
| 1.646 | B.43 | C.3 |
| 1.647 | B.44 | C.3 |
| 1.648 | B.45 | C.3 |
| 1.649 | B.46 | C.3 |
| 1.650 | B.47 | C.3 |
| 1.651 | B.48 | C.3 |
| 1.652 | B.49 | C.3 |
| 1.653 | B.50 | C.3 |
| 1.654 | B.51 | C.3 |
| 1.655 | B.52 | C.3 |
| 1.656 | B.53 | C.3 |
| 1.657 | B.54 | C.3 |
| 1.658 | B.55 | C.3 |
| 1.659 | B.56 | C.3 |
| 1.660 | B.57 | C.3 |
| 1.661 | B.58. | C.3 |
| 1.662 | B.59 | C.3 |
| 1.663 | B.60 | C.3 |
| 1.664 | B.61 | C.3 |
| 1.665 | B.62 | C.3 |
| 1.666 | B.63 | C.3 |
| 1.667 | B.64 | C.3 |
| 1.668 | B.65 | C.3 |
| 1.669 | B.66 | C.3 |
| 1.670 | B.67 | C.3 |
| 1.671 | B.68 | C.3 |
| 1.672 | B.69 | C.3 |
| 1.673 | B.70 | C.3 |
| 1.674 | B.71 | C.3 |
| 1.675 | B.72 | C.3 |
| 1.676 | B.73 | C.3 |
| 1.677 | B.74 | C.3 |
| 1.678 | B.75 | C.3 |
| 1.679 | B.76 | C.3 |
| 1.680 | B.77 | C.3 |
| 1.681 | B.78 | C.3 |
| 1.682 | B.79 | C.3 |
| 1.683 | B.80 | C.3 |
| 1.684 | B.81 | C.3 |
| 1.685 | B.82 | C.3 |
| 1.686 | B.83 | C.3 |
| 1.687 | B.84 | C.3 |
| 1.688 | B.85 | C.3 |
| 1.689 | B.86 | C.3 |
| 1.690 | B.87 | C.3 |

TABLE 1-continued compositions 1.1 to 1.3635

| comp. no. | herbicide B | safener C |
|---|---|---|
| 1.691 | B.88 | C.3 |
| 1.692 | B.89 | C.3 |
| 1.693 | B.90 | C.3 |
| 1.694 | B.91 | C.3 |
| 1.695 | B.92 | C.3 |
| 1.696 | B.93 | C.3 |
| 1.697 | B.94 | C.3 |
| 1.698 | B.95 | C.3 |
| 1.699 | B.96 | C.3 |
| 1.700 | B.97 | C.3 |
| 1.701 | B.98 | C.3 |
| 1.702 | B.99 | C.3 |
| 1.703 | B.100 | C.3 |
| 1.704 | B.101 | C.3 |
| 1.705 | B.102 | C.3 |
| 1.706 | B.103 | C.3 |
| 1.707 | B.104 | C.3 |
| 1.708 | B.105 | C.3 |
| 1.709 | B.106 | C.3 |
| 1.710 | B.107 | C.3 |
| 1.711 | B.108 | C.3 |
| 1.712 | B.109 | C.3 |
| 1.713 | B.110 | C.3 |
| 1.714 | B.111 | C.3 |
| 1.715 | B.112 | C.3 |
| 1.716 | B.113 | C.3 |
| 1.717 | B.114 | C.3 |
| 1.718 | B.115 | C.3 |
| 1.719 | B.116 | C.3 |
| 1.720 | B.117 | C.3 |
| 1.721 | B.118 | C.3 |
| 1.722 | B.119 | C.3 |
| 1.723 | B.120 | C.3 |
| 1.724 | B.121 | C.3 |
| 1.725 | B.122 | C.3 |
| 1.726 | B.123 | C.3 |
| 1.727 | B.124 | C.3 |
| 1.728 | B.125 | C.3 |
| 1.729 | B.126 | C.3 |
| 1.730 | B.127 | C.3 |
| 1.731 | B.128 | C.3 |
| 1.732 | B.129 | C.3 |
| 1.733 | B.130 | C.3 |
| 1.734 | B.131 | C.3 |
| 1.735 | B.132 | C.3 |
| 1.736 | B.133 | C.3 |
| 1.737 | B.134 | C.3 |
| 1.738 | B.135 | C.3 |
| 1.739 | B.136 | C.3 |
| 1.740 | B.137 | C.3 |
| 1.741 | B.138 | C.3 |
| 1.742 | B.139 | C.3 |
| 1.743 | B.140 | C.3 |
| 1.744 | B.141 | C.3 |
| 1.745 | B.142 | C.3 |
| 1.746 | B.143 | C.3 |
| 1.747 | B.144 | C.3 |
| 1.748 | B.145 | C.3 |
| 1.749 | B.146 | C.3 |
| 1.750 | B.147 | C.3 |
| 1.751 | B.148 | C.3 |
| 1.752 | B.149 | C.3 |
| 1.753 | B.150 | C.3 |
| 1.754 | B.151 | C.3 |
| 1.755 | B.152 | C.3 |
| 1.756 | B.153 | C.3 |
| 1.757 | B.154 | C.3 |
| 1.758 | B.155 | C.3 |
| 1.759 | B.156 | C.3 |
| 1.760 | B.157 | C.3 |
| 1.761 | B.158 | C.3 |
| 1.762 | B.159 | C.3 |
| 1.763 | B.160 | C.3 |
| 1.764 | B.161 | C.3 |
| 1.765 | B.162 | C.3 |
| 1.766 | B.163 | C.3 |
| 1.767 | B.164 | C.3 |
| 1.768 | B.165 | C.3 |
| 1.769 | B.166 | C.3 |
| 1.770 | B.167 | C.3 |
| 1.771 | B.168 | C.3 |
| 1.772 | B.169 | C.3 |
| 1.773 | B.170 | C.3 |
| 1.774 | B.171 | C.3 |
| 1.775 | B.172 | C.3 |
| 1.776 | B.173 | C.3 |
| 1.777 | B.174 | C.3 |
| 1.778 | B.175 | C.3 |
| 1.779 | B.176 | C.3 |
| 1.780 | B.177 | C.3 |
| 1.781 | B.178 | C.3 |
| 1.782 | B.179 | C.3 |
| 1.783 | B.180 | C.3 |
| 1.784 | B.181 | C.3 |
| 1.785 | B.182 | C.3 |
| 1.786 | B.183 | C.3 |
| 1.787 | B.184 | C.3 |
| 1.788 | B.185 | C.3 |
| 1.789 | B.186 | C.3 |
| 1.790 | B.187 | C.3 |
| 1.791 | B.188 | C.3 |
| 1.792 | B.189 | C.3 |
| 1.793 | B.190 | C.3 |
| 1.794 | B.191 | C.3 |
| 1.795 | B.192 | C.3 |
| 1.796 | B.193 | C.3 |
| 1.797 | B.194 | C.3 |
| 1.798 | B.195 | C.3 |
| 1.799 | B.196 | C.3 |
| 1.800 | B.197 | C.3 |
| 1.801 | B.198 | C.3 |
| 1.802 | B.199 | C.3 |
| 1.803 | B.200 | C.3 |
| 1.804 | B.201 | C.3 |
| 1.805 | B.1 | C.4 |
| 1.806 | B.2 | C.4 |
| 1.807 | B.3 | C.4 |
| 1.808 | B.4 | C.4 |
| 1.809 | B.5 | C.4 |
| 1.810 | B.6 | C.4 |
| 1.811 | B.7 | C.4 |
| 1.812 | B.8 | C.4 |
| 1.813 | B.9 | C.4 |
| 1.814 | B.10 | C.4 |
| 1.815 | B.11 | C.4 |
| 1.816 | B.12 | C.4 |
| 1.817 | B.13 | C.4 |
| 1.818 | B.14 | C.4 |
| 1.819 | B.15 | C.4 |
| 1.820 | B.16 | C.4 |
| 1.821 | B.17 | C.4 |
| 1.822 | B.18 | C.4 |
| 1.823 | B.19 | C.4 |
| 1.824 | B.20 | C.4 |
| 1.825 | B.21 | C.4 |
| 1.826 | B.22 | C.4 |
| 1.827 | B.23 | C.4 |
| 1.828 | B.24 | C.4 |
| 1.829 | B.25 | C.4 |
| 1.830 | B.26 | C.4 |
| 1.831 | B.27 | C.4 |
| 1.832 | B.28 | C.4 |
| 1.833 | B.29 | C.4 |
| 1.834 | B.30 | C.4 |
| 1.835 | B.31 | C.4 |
| 1.836 | B.32 | C.4 |
| 1.837 | B.33 | C.4 |
| 1.838 | B.34 | C.4 |
| 1.839 | B.35 | C.4 |
| 1.840 | B.36 | C.4 |

TABLE 1-continued compositions 1.1 to 1.3635

| comp. no. | herbicide B | safener C |
|---|---|---|
| 1.841 | B.37 | C.4 |
| 1.842 | B.38 | C.4 |
| 1.843 | B.39 | C.4 |
| 1.844 | B.40 | C.4 |
| 1.845 | B.41 | C.4 |
| 1.846 | B.42 | C.4 |
| 1.847 | B.43 | C.4 |
| 1.848 | B.44 | C.4 |
| 1.849 | B.45 | C.4 |
| 1.850 | B.46 | C.4 |
| 1.851 | B.47 | C.4 |
| 1.852 | B.48 | C.4 |
| 1.853 | B.49 | C.4 |
| 1.854 | B.50 | C.4 |
| 1.855 | B.51 | C.4 |
| 1.856 | B.52 | C.4 |
| 1.857 | B.53 | C.4 |
| 1.858 | B.54 | C.4 |
| 1.859 | B.55 | C.4 |
| 1.860 | B.56 | C.4 |
| 1.861 | B.57 | C.4 |
| 1.862 | B.58. | C.4 |
| 1.863 | B.59 | C.4 |
| 1.864 | B.60 | C.4 |
| 1.865 | B.61 | C.4 |
| 1.866 | B.62 | C.4 |
| 1.867 | B.63 | C.4 |
| 1.868 | B.64 | C.4 |
| 1.869 | B.65 | C.4 |
| 1.870 | B.66 | C.4 |
| 1.871 | B.67 | C.4 |
| 1.872 | B.68 | C.4 |
| 1.873 | B.69 | C.4 |
| 1.874 | B.70 | C.4 |
| 1.875 | B.71 | C.4 |
| 1.876 | B.72 | C.4 |
| 1.877 | B.73 | C.4 |
| 1.878 | B.74 | C.4 |
| 1.879 | B.75 | C.4 |
| 1.880 | B.76 | C.4 |
| 1.881 | B.77 | C.4 |
| 1.882 | B.78 | C.4 |
| 1.883 | B.79 | C.4 |
| 1.884 | B.80 | C.4 |
| 1.885 | B.81 | C.4 |
| 1.886 | B.82 | C.4 |
| 1.887 | B.83 | C.4 |
| 1.888 | B.84 | C.4 |
| 1.889 | B.85 | C.4 |
| 1.890 | B.86 | C.4 |
| 1.891 | B.87 | C.4 |
| 1.892 | B.88 | C.4 |
| 1.893 | B.89 | C.4 |
| 1.894 | B.90 | C.4 |
| 1.895 | B.91 | C.4 |
| 1.896 | B.92 | C.4 |
| 1.897 | B.93 | C.4 |
| 1.898 | B.94 | C.4 |
| 1.899 | B.95 | C.4 |
| 1.900 | B.96 | C.4 |
| 1.901 | B.97 | C.4 |
| 1.902 | B.98 | C.4 |
| 1.903 | B.99 | C.4 |
| 1.904 | B.100 | C.4 |
| 1.905 | B.101 | C.4 |
| 1.906 | B.102 | C.4 |
| 1.907 | B.103 | C.4 |
| 1.908 | B.104 | C.4 |
| 1.909 | B.105 | C.4 |
| 1.910 | B.106 | C.4 |
| 1.911 | B.107 | C.4 |
| 1.912 | B.108 | C.4 |
| 1.913 | B.109 | C.4 |
| 1.914 | B.110 | C.4 |
| 1.915 | B.111 | C.4 |
| 1.916 | B.112 | C.4 |
| 1.917 | B.113 | C.4 |
| 1.918 | B.114 | C.4 |
| 1.919 | B.115 | C.4 |
| 1.920 | B.116 | C.4 |
| 1.921 | B.117 | C.4 |
| 1.922 | B.118 | C.4 |
| 1.923 | B.119 | C.4 |
| 1.924 | B.120 | C.4 |
| 1.925 | B.121 | C.4 |
| 1.926 | B.122 | C.4 |
| 1.927 | B.123 | C.4 |
| 1.928 | B.124 | C.4 |
| 1.929 | B.125 | C.4 |
| 1.930 | B.126 | C.4 |
| 1.931 | B.127 | C.4 |
| 1.932 | B.128 | C.4 |
| 1.933 | B.129 | C.4 |
| 1.934 | B.130 | C.4 |
| 1.935 | B.131 | C.4 |
| 1.936 | B.132 | C.4 |
| 1.937 | B.133 | C.4 |
| 1.938 | B.134 | C.4 |
| 1.939 | B.135 | C.4 |
| 1.940 | B.136 | C.4 |
| 1.941 | B.137 | C.4 |
| 1.942 | B.138 | C.4 |
| 1.943 | B.139 | C.4 |
| 1.944 | B.140 | C.4 |
| 1.945 | B.141 | C.4 |
| 1.946 | B.142 | C.4 |
| 1.947 | B.143 | C.4 |
| 1.948 | B.144 | C.4 |
| 1.949 | B.145 | C.4 |
| 1.950 | B.146 | C.4 |
| 1.951 | B.147 | C.4 |
| 1.952 | B.148 | C.4 |
| 1.953 | B.149 | C.4 |
| 1.954 | B.150 | C.4 |
| 1.955 | B.151 | C.4 |
| 1.956 | B.152 | C.4 |
| 1.957 | B.153 | C.4 |
| 1.958 | B.154 | C.4 |
| 1.959 | B.155 | C.4 |
| 1.960 | B.156 | C.4 |
| 1.961 | B.157 | C.4 |
| 1.962 | B.158 | C.4 |
| 1.963 | B.159 | C.4 |
| 1.964 | B.160 | C.4 |
| 1.965 | B.161 | C.4 |
| 1.966 | B.162 | C.4 |
| 1.967 | B.163 | C.4 |
| 1.968 | B.164 | C.4 |
| 1.969 | B.165 | C.4 |
| 1.970 | B.166 | C.4 |
| 1.971 | B.167 | C.4 |
| 1.972 | B.168 | C.4 |
| 1.973 | B.169 | C.4 |
| 1.974 | B.170 | C.4 |
| 1.975 | B.171 | C.4 |
| 1.976 | B.172 | C.4 |
| 1.977 | B.173 | C.4 |
| 1.978 | B.174 | C.4 |
| 1.979 | B.175 | C.4 |
| 1.980 | B.176 | C.4 |
| 1.981 | B.177 | C.4 |
| 1.982 | B.178 | C.4 |
| 1.983 | B.179 | C.4 |
| 1.984 | B.180 | C.4 |
| 1.985 | B.181 | C.4 |
| 1.986 | B.182 | C.4 |
| 1.987 | B.183 | C.4 |
| 1.988 | B.184 | C.4 |
| 1.989 | B.185 | C.4 |
| 1.990 | B.186 | C.4 |

TABLE 1-continued compositions 1.1 to 1.3635

| comp. no. | herbicide B | safener C |
|---|---|---|
| 1.991 | B.187 | C.4 |
| 1.992 | B.188 | C.4 |
| 1.993 | B.189 | C.4 |
| 1.994 | B.190 | C.4 |
| 1.995 | B.191 | C.4 |
| 1.996 | B.192 | C.4 |
| 1.997 | B.193 | C.4 |
| 1.998 | B.194 | C.4 |
| 1.999 | B.195 | C.4 |
| 1.1000 | B.196 | C.4 |
| 1.1001 | B.197 | C.4 |
| 1.1002 | B.198 | C.4 |
| 1.1003 | B.199 | C.4 |
| 1.1004 | B.200 | C.4 |
| 1.1005 | B.201 | C.4 |
| 1.1006 | B.1 | C.5 |
| 1.1007 | B.2 | C.5 |
| 1.1008 | B.3 | C.5 |
| 1.1009 | B.4 | C.5 |
| 1.1010 | B.5 | C.5 |
| 1.1011 | B.6 | C.5 |
| 1.1012 | B.7 | C.5 |
| 1.1013 | B.8 | C.5 |
| 1.1014 | B.9 | C.5 |
| 1.1015 | B.10 | C.5 |
| 1.1016 | B.11 | C.5 |
| 1.1017 | B.12 | C.5 |
| 1.1018 | B.13 | C.5 |
| 1.1019 | B.14 | C.5 |
| 1.1020 | B.15 | C.5 |
| 1.1021 | B.16 | C.5 |
| 1.1022 | B.17 | C.5 |
| 1.1023 | B.18 | C.5 |
| 1.1024 | B.19 | C.5 |
| 1.1025 | B.20 | C.5 |
| 1.1026 | B.21 | C.5 |
| 1.1027 | B.22 | C.5 |
| 1.1028 | B.23 | C.5 |
| 1.1029 | B.24 | C.5 |
| 1.1030 | B.25 | C.5 |
| 1.1031 | B.26 | C.5 |
| 1.1032 | B.27 | C.5 |
| 1.1033 | B.28 | C.5 |
| 1.1034 | B.29 | C.5 |
| 1.1035 | B.30 | C.5 |
| 1.1036 | B.31 | C.5 |
| 1.1037 | B.32 | C.5 |
| 1.1038 | B.33 | C.5 |
| 1.1039 | B.34 | C.5 |
| 1.1040 | B.35 | C.5 |
| 1.1041 | B.36 | C.5 |
| 1.1042 | B.37 | C.5 |
| 1.1043 | B.38 | C.5 |
| 1.1044 | B.39 | C.5 |
| 1.1045 | B.40 | C.5 |
| 1.1046 | B.41 | C.5 |
| 1.1047 | B.42 | C.5 |
| 1.1048 | B.43 | C.5 |
| 1.1049 | B.44 | C.5 |
| 1.1050 | B.45 | C.5 |
| 1.1051 | B.46 | C.5 |
| 1.1052 | B.47 | C.5 |
| 1.1053 | B.48 | C.5 |
| 1.1054 | B.49 | C.5 |
| 1.1055 | B.50 | C.5 |
| 1.1056 | B.51 | C.5 |
| 1.1057 | B.52 | C.5 |
| 1.1058 | B.53 | C.5 |
| 1.1059 | B.54 | C.5 |
| 1.1060 | B.55 | C.5 |
| 1.1061 | B.56 | C.5 |
| 1.1062 | B.57 | C.5 |
| 1.1063 | B.58. | C.5 |
| 1.1064 | B.59 | C.5 |
| 1.1065 | B.60 | C.5 |
| 1.1066 | B.61 | C.5 |
| 1.1067 | B.62 | C.5 |
| 1.1068 | B.63 | C.5 |
| 1.1069 | B.64 | C.5 |
| 1.1070 | B.65 | C.5 |
| 1.1071 | B.66 | C.5 |
| 1.1072 | B.67 | C.5 |
| 1.1073 | B.68 | C.5 |
| 1.1074 | B.69 | C.5 |
| 1.1075 | B.70 | C.5 |
| 1.1076 | B.71 | C.5 |
| 1.1077 | B.72 | C.5 |
| 1.1078 | B.73 | C.5 |
| 1.1079 | B.74 | C.5 |
| 1.1080 | B.75 | C.5 |
| 1.1081 | B.76 | C.5 |
| 1.1082 | B.77 | C.5 |
| 1.1083 | B.78 | C.5 |
| 1.1084 | B.79 | C.5 |
| 1.1085 | B.80 | C.5 |
| 1.1086 | B.81 | C.5 |
| 1.1087 | B.82 | C.5 |
| 1.1088 | B.83 | C.5 |
| 1.1089 | B.84 | C.5 |
| 1.1090 | B.85 | C.5 |
| 1.1091 | B.86 | C.5 |
| 1.1092 | B.87 | C.5 |
| 1.1093 | B.88 | C.5 |
| 1.1094 | B.89 | C.5 |
| 1.1095 | B.90 | C.5 |
| 1.1096 | B.91 | C.5 |
| 1.1097 | B.92 | C.5 |
| 1.1098 | B.93 | C.5 |
| 1.1099 | B.94 | C.5 |
| 1.1100 | B.95 | C.5 |
| 1.1101 | B.96 | C.5 |
| 1.1102 | B.97 | C.5 |
| 1.1103 | B.98 | C.5 |
| 1.1104 | B.99 | C.5 |
| 1.1105 | B.100 | C.5 |
| 1.1106 | B.101 | C.5 |
| 1.1107 | B.102 | C.5 |
| 1.1108 | B.103 | C.5 |
| 1.1109 | B.104 | C.5 |
| 1.1110 | B.105 | C.5 |
| 1.1111 | B.106 | C.5 |
| 1.1112 | B.107 | C.5 |
| 1.1113 | B.108 | C.5 |
| 1.1114 | B.109 | C.5 |
| 1.1115 | B.110 | C.5 |
| 1.1116 | B.111 | C.5 |
| 1.1117 | B.112 | C.5 |
| 1.1118 | B.113 | C.5 |
| 1.1119 | B.114 | C.5 |
| 1.1120 | B.115 | C.5 |
| 1.1121 | B.116 | C.5 |
| 1.1122 | B.117 | C.5 |
| 1.1123 | B.118 | C.5 |
| 1.1124 | B.119 | C.5 |
| 1.1125 | B.120 | C.5 |
| 1.1126 | B.121 | C.5 |
| 1.1127 | B.122 | C.5 |
| 1.1128 | B.123 | C.5 |
| 1.1129 | B.124 | C.5 |
| 1.1130 | B.125 | C.5 |
| 1.1131 | B.126 | C.5 |
| 1.1132 | B.127 | C.5 |
| 1.1133 | B.128 | C.5 |
| 1.1134 | B.129 | C.5 |
| 1.1135 | B.130 | C.5 |
| 1.1136 | B.131 | C.5 |
| 1.1137 | B.132 | C.5 |
| 1.1138 | B.133 | C.5 |
| 1.1139 | B.134 | C.5 |
| 1.1140 | B.135 | C.5 |

TABLE 1-continued compositions 1.1 to 1.3635

| comp. no. | herbicide B | safener C |
|---|---|---|
| 1.1141 | B.136 | C.5 |
| 1.1142 | B.137 | C.5 |
| 1.1143 | B.138 | C.5 |
| 1.1144 | B.139 | C.5 |
| 1.1145 | B.140 | C.5 |
| 1.1146 | B.141 | C.5 |
| 1.1147 | B.142 | C.5 |
| 1.1148 | B.143 | C.5 |
| 1.1149 | B.144 | C.5 |
| 1.1150 | B.145 | C.5 |
| 1.1151 | B.146 | C.5 |
| 1.1152 | B.147 | C.5 |
| 1.1153 | B.148 | C.5 |
| 1.1154 | B.149 | C.5 |
| 1.1155 | B.150 | C.5 |
| 1.1156 | B.151 | C.5 |
| 1.1157 | B.152 | C.5 |
| 1.1158 | B.153 | C.5 |
| 1.1159 | B.154 | C.5 |
| 1.1160 | B.155 | C.5 |
| 1.1161 | B.156 | C.5 |
| 1.1162 | B.157 | C.5 |
| 1.1163 | B.158 | C.5 |
| 1.1164 | B.159 | C.5 |
| 1.1165 | B.160 | C.5 |
| 1.1166 | B.161 | C.5 |
| 1.1167 | B.162 | C.5 |
| 1.1168 | B.163 | C.5 |
| 1.1169 | B.164 | C.5 |
| 1.1170 | B.165 | C.5 |
| 1.1171 | B.166 | C.5 |
| 1.1172 | B.167 | C.5 |
| 1.1173 | B.168 | C.5 |
| 1.1174 | B.169 | C.5 |
| 1.1175 | B.170 | C.5 |
| 1.1176 | B.171 | C.5 |
| 1.1177 | B.172 | C.5 |
| 1.1178 | B.173 | C.5 |
| 1.1179 | B.174 | C.5 |
| 1.1180 | B.175 | C.5 |
| 1.1181 | B.176 | C.5 |
| 1.1182 | B.177 | C.5 |
| 1.1183 | B.178 | C.5 |
| 1.1184 | B.179 | C.5 |
| 1.1185 | B.180 | C.5 |
| 1.1186 | B.181 | C.5 |
| 1.1187 | B.182 | C.5 |
| 1.1188 | B.183 | C.5 |
| 1.1189 | B.184 | C.5 |
| 1.1190 | B.185 | C.5 |
| 1.1191 | B.186 | C.5 |
| 1.1192 | B.187 | C.5 |
| 1.1193 | B.188 | C.5 |
| 1.1194 | B.189 | C.5 |
| 1.1195 | B.190 | C.5 |
| 1.1196 | B.191 | C.5 |
| 1.1197 | B.192 | C.5 |
| 1.1198 | B.193 | C.5 |
| 1.1199 | B.194 | C.5 |
| 1.1200 | B.195 | C.5 |
| 1.1201 | B.196 | C.5 |
| 1.1202 | B.197 | C.5 |
| 1.1203 | B.198 | C.5 |
| 1.1204 | B.199 | C.5 |
| 1.1205 | B.200 | C.5 |
| 1.1206 | B.201 | C.5 |
| 1.1207 | B.1 | C.6 |
| 1.1208 | B.2 | C.6 |
| 1.1209 | B.3 | C.6 |
| 1.1210 | B.4 | C.6 |
| 1.1211 | B.5 | C.6 |
| 1.1212 | B.6 | C.6 |
| 1.1213 | B.7 | C.6 |
| 1.1214 | B.8 | C.6 |
| 1.1215 | B.9 | C.6 |
| 1.1216 | B.10 | C.6 |
| 1.1217 | B.11 | C.6 |
| 1.1218 | B.12 | C.6 |
| 1.1219 | B.13 | C.6 |
| 1.1220 | B.14 | C.6 |
| 1.1221 | B.15 | C.6 |
| 1.1222 | B.16 | C.6 |
| 1.1223 | B.17 | C.6 |
| 1.1224 | B.18 | C.6 |
| 1.1225 | B.19 | C.6 |
| 1.1226 | B.20 | C.6 |
| 1.1227 | B.21 | C.6 |
| 1.1228 | B.22 | C.6 |
| 1.1229 | B.23 | C.6 |
| 1.1230 | B.24 | C.6 |
| 1.1231 | B.25 | C.6 |
| 1.1232 | B.26 | C.6 |
| 1.1233 | B.27 | C.6 |
| 1.1234 | B.28 | C.6 |
| 1.1235 | B.29 | C.6 |
| 1.1236 | B.30 | C.6 |
| 1.1237 | B.31 | C.6 |
| 1.1238 | B.32 | C.6 |
| 1.1239 | B.33 | C.6 |
| 1.1240 | B.34 | C.6 |
| 1.1241 | B.35 | C.6 |
| 1.1242 | B.36 | C.6 |
| 1.1243 | B.37 | C.6 |
| 1.1244 | B.38 | C.6 |
| 1.1245 | B.39 | C.6 |
| 1.1246 | B.40 | C.6 |
| 1.1247 | B.41 | C.6 |
| 1.1248 | B.42 | C.6 |
| 1.1249 | B.43 | C.6 |
| 1.1250 | B.44 | C.6 |
| 1.1251 | B.45 | C.6 |
| 1.1252 | B.46 | C.6 |
| 1.1253 | B.47 | C.6 |
| 1.1254 | B.48 | C.6 |
| 1.1255 | B.49 | C.6 |
| 1.1256 | B.50 | C.6 |
| 1.1257 | B.51 | C.6 |
| 1.1258 | B.52 | C.6 |
| 1.1259 | B.53 | C.6 |
| 1.1260 | B.54 | C.6 |
| 1.1261 | B.55 | C.6 |
| 1.1262 | B.56 | C.6 |
| 1.1263 | B.57 | C.6 |
| 1.1264 | B.58. | C.6 |
| 1.1265 | B.59 | C.6 |
| 1.1266 | B.60 | C.6 |
| 1.1267 | B.61 | C.6 |
| 1.1268 | B.62 | C.6 |
| 1.1269 | B.63 | C.6 |
| 1.1270 | B.64 | C.6 |
| 1.1271 | B.65 | C.6 |
| 1.1272 | B.66 | C.6 |
| 1.1273 | B.67 | C.6 |
| 1.1274 | B.68 | C.6 |
| 1.1275 | B.69 | C.6 |
| 1.1276 | B.70 | C.6 |
| 1.1277 | B.71 | C.6 |
| 1.1278 | B.72 | C.6 |
| 1.1279 | B.73 | C.6 |
| 1.1280 | B.74 | C.6 |
| 1.1281 | B.75 | C.6 |
| 1.1282 | B.76 | C.6 |
| 1.1283 | B.77 | C.6 |
| 1.1284 | B.78 | C.6 |
| 1.1285 | B.79 | C.6 |
| 1.1286 | B.80 | C.6 |
| 1.1287 | B.81 | C.6 |
| 1.1288 | B.82 | C.6 |
| 1.1289 | B.83 | C.6 |
| 1.1290 | B.84 | C.6 |

TABLE 1-continued compositions 1.1 to 1.3635

| comp. no. | herbicide B | safener C |
|---|---|---|
| 1.1291 | B.85 | C.6 |
| 1.1292 | B.86 | C.6 |
| 1.1293 | B.87 | C.6 |
| 1.1294 | B.88 | C.6 |
| 1.1295 | B.89 | C.6 |
| 1.1296 | B.90 | C.6 |
| 1.1297 | B.91 | C.6 |
| 1.1298 | B.92 | C.6 |
| 1.1299 | B.93 | C.6 |
| 1.1300 | B.94 | C.6 |
| 1.1301 | B.95 | C.6 |
| 1.1302 | B.96 | C.6 |
| 1.1303 | B.97 | C.6 |
| 1.1304 | B.98 | C.6 |
| 1.1305 | B.99 | C.6 |
| 1.1306 | B.100 | C.6 |
| 1.1307 | B.101 | C.6 |
| 1.1308 | B.102 | C.6 |
| 1.1309 | B.103 | C.6 |
| 1.1310 | B.104 | C.6 |
| 1.1311 | B.105 | C.6 |
| 1.1312 | B.106 | C.6 |
| 1.1313 | B.107 | C.6 |
| 1.1314 | B.108 | C.6 |
| 1.1315 | B.109 | C.6 |
| 1.1316 | B.110 | C.6 |
| 1.1317 | B.111 | C.6 |
| 1.1318 | B.112 | C.6 |
| 1.1319 | B.113 | C.6 |
| 1.1320 | B.114 | C.6 |
| 1.1321 | B.115 | C.6 |
| 1.1322 | B.116 | C.6 |
| 1.1323 | B.117 | C.6 |
| 1.1324 | B.118 | C.6 |
| 1.1325 | B.119 | C.6 |
| 1.1326 | B.120 | C.6 |
| 1.1327 | B.121 | C.6 |
| 1.1328 | B.122 | C.6 |
| 1.1329 | B.123 | C.6 |
| 1.1330 | B.124 | C.6 |
| 1.1331 | B.125 | C.6 |
| 1.1332 | B.126 | C.6 |
| 1.1333 | B.127 | C.6 |
| 1.1334 | B.128 | C.6 |
| 1.1335 | B.129 | C.6 |
| 1.1336 | B.130 | C.6 |
| 1.1337 | B.131 | C.6 |
| 1.1338 | B.132 | C.6 |
| 1.1339 | B.133 | C.6 |
| 1.1340 | B.134 | C.6 |
| 1.1341 | B.135 | C.6 |
| 1.1342 | B.136 | C.6 |
| 1.1343 | B.137 | C.6 |
| 1.1344 | B.138 | C.6 |
| 1.1345 | B.139 | C.6 |
| 1.1346 | B.140 | C.6 |
| 1.1347 | B.141 | C.6 |
| 1.1348 | B.142 | C.6 |
| 1.1349 | B.143 | C.6 |
| 1.1350 | B.144 | C.6 |
| 1.1351 | B.145 | C.6 |
| 1.1352 | B.146 | C.6 |
| 1.1353 | B.147 | C.6 |
| 1.1354 | B.148 | C.6 |
| 1.1355 | B.149 | C.6 |
| 1.1356 | B.150 | C.6 |
| 1.1357 | B.151 | C.6 |
| 1.1358 | B.152 | C.6 |
| 1.1359 | B.153 | C.6 |
| 1.1360 | B.154 | C.6 |
| 1.1361 | B.155 | C.6 |
| 1.1362 | B.156 | C.6 |
| 1.1363 | B.157 | C.6 |
| 1.1364 | B.158 | C.6 |
| 1.1365 | B.159 | C.6 |
| 1.1366 | B.160 | C.6 |
| 1.1367 | B.161 | C.6 |
| 1.1368 | B.162 | C.6 |
| 1.1369 | B.163 | C.6 |
| 1.1370 | B.164 | C.6 |
| 1.1371 | B.165 | C.6 |
| 1.1372 | B.166 | C.6 |
| 1.1373 | B.167 | C.6 |
| 1.1374 | B.168 | C.6 |
| 1.1375 | B.169 | C.6 |
| 1.1376 | B.170 | C.6 |
| 1.1377 | B.171 | C.6 |
| 1.1378 | B.172 | C.6 |
| 1.1379 | B.173 | C.6 |
| 1.1380 | B.174 | C.6 |
| 1.1381 | B.175 | C.6 |
| 1.1382 | B.176 | C.6 |
| 1.1383 | B.177 | C.6 |
| 1.1384 | B.178 | C.6 |
| 1.1385 | B.179 | C.6 |
| 1.1386 | B.180 | C.6 |
| 1.1387 | B.181 | C.6 |
| 1.1388 | B.182 | C.6 |
| 1.1389 | B.183 | C.6 |
| 1.1390 | B.184 | C.6 |
| 1.1391 | B.185 | C.6 |
| 1.1392 | B.186 | C.6 |
| 1.1393 | B.187 | C.6 |
| 1.1394 | B.188 | C.6 |
| 1.1395 | B.189 | C.6 |
| 1.1396 | B.190 | C.6 |
| 1.1397 | B.191 | C.6 |
| 1.1398 | B.192 | C.6 |
| 1.1399 | B.193 | C.6 |
| 1.1400 | B.194 | C.6 |
| 1.1401 | B.195 | C.6 |
| 1.1402 | B.196 | C.6 |
| 1.1403 | B.197 | C.6 |
| 1.1404 | B.198 | C.6 |
| 1.1405 | B.199 | C.6 |
| 1.1406 | B.200 | C.6 |
| 1.1407 | B.201 | C.6 |
| 1.1408 | B.1 | C.7 |
| 1.1409 | B.2 | C.7 |
| 1.1410 | B.3 | C.7 |
| 1.1411 | B.4 | C.7 |
| 1.1412 | B.5 | C.7 |
| 1.1413 | B.6 | C.7 |
| 1.1414 | B.7 | C.7 |
| 1.1415 | B.8 | C.7 |
| 1.1416 | B.9 | C.7 |
| 1.1417 | B.10 | C.7 |
| 1.1418 | B.11 | C.7 |
| 1.1419 | B.12 | C.7 |
| 1.1420 | B.13 | C.7 |
| 1.1421 | B.14 | C.7 |
| 1.1422 | B.15 | C.7 |
| 1.1423 | B.16 | C.7 |
| 1.1424 | B.17 | C.7 |
| 1.1425 | B.18 | C.7 |
| 1.1426 | B.19 | C.7 |
| 1.1427 | B.20 | C.7 |
| 1.1428 | B.21 | C.7 |
| 1.1429 | B.22 | C.7 |
| 1.1430 | B.23 | C.7 |
| 1.1431 | B.24 | C.7 |
| 1.1432 | B.25 | C.7 |
| 1.1433 | B.26 | C.7 |
| 1.1434 | B.27 | C.7 |
| 1.1435 | B.28 | C.7 |
| 1.1436 | B.29 | C.7 |
| 1.1437 | B.30 | C.7 |
| 1.1438 | B.31 | C.7 |
| 1.1439 | B.32 | C.7 |
| 1.1440 | B.33 | C.7 |

TABLE 1-continued compositions 1.1 to 1.3635

| comp. no. | herbicide B | safener C |
|---|---|---|
| 1.1441 | B.34 | C.7 |
| 1.1442 | B.35 | C.7 |
| 1.1443 | B.36 | C.7 |
| 1.1444 | B.37 | C.7 |
| 1.1445 | B.38 | C.7 |
| 1.1446 | B.39 | C.7 |
| 1.1447 | B.40 | C.7 |
| 1.1448 | B.41 | C.7 |
| 1.1449 | B.42 | C.7 |
| 1.1450 | B.43 | C.7 |
| 1.1451 | B.44 | C.7 |
| 1.1452 | B.45 | C.7 |
| 1.1453 | B.46 | C.7 |
| 1.1454 | B.47 | C.7 |
| 1.1455 | B.48 | C.7 |
| 1.1456 | B.49 | C.7 |
| 1.1457 | B.50 | C.7 |
| 1.1458 | B.51 | C.7 |
| 1.1459 | B.52 | C.7 |
| 1.1460 | B.53 | C.7 |
| 1.1461 | B.54 | C.7 |
| 1.1462 | B.55 | C.7 |
| 1.1463 | B.56 | C.7 |
| 1.1464 | B.57 | C.7 |
| 1.1465 | B.58. | C.7 |
| 1.1466 | B.59 | C.7 |
| 1.1467 | B.60 | C.7 |
| 1.1468 | B.61 | C.7 |
| 1.1469 | B.62 | C.7 |
| 1.1470 | B.63 | C.7 |
| 1.1471 | B.64 | C.7 |
| 1.1472 | B.65 | C.7 |
| 1.1473 | B.66 | C.7 |
| 1.1474 | B.67 | C.7 |
| 1.1475 | B.68 | C.7 |
| 1.1476 | B.69 | C.7 |
| 1.1477 | B.70 | C.7 |
| 1.1478 | B.71 | C.7 |
| 1.1479 | B.72 | C.7 |
| 1.1480 | B.73 | C.7 |
| 1.1481 | B.74 | C.7 |
| 1.1482 | B.75 | C.7 |
| 1.1483 | B.76 | C.7 |
| 1.1484 | B.77 | C.7 |
| 1.1485 | B.78 | C.7 |
| 1.1486 | B.79 | C.7 |
| 1.1487 | B.80 | C.7 |
| 1.1488 | B.81 | C.7 |
| 1.1489 | B.82 | C.7 |
| 1.1490 | B.83 | C.7 |
| 1.1491 | B.84 | C.7 |
| 1.1492 | B.85 | C.7 |
| 1.1493 | B.86 | C.7 |
| 1.1494 | B.87 | C.7 |
| 1.1495 | B.88 | C.7 |
| 1.1496 | B.89 | C.7 |
| 1.1497 | B.90 | C.7 |
| 1.1498 | B.91 | C.7 |
| 1.1499 | B.92 | C.7 |
| 1.1500 | B.93 | C.7 |
| 1.1501 | B.94 | C.7 |
| 1.1502 | B.95 | C.7 |
| 1.1503 | B.96 | C.7 |
| 1.1504 | B.97 | C.7 |
| 1.1505 | B.98 | C.7 |
| 1.1506 | B.99 | C.7 |
| 1.1507 | B.100 | C.7 |
| 1.1508 | B.101 | C.7 |
| 1.1509 | B.102 | C.7 |
| 1.1510 | B.103 | C.7 |
| 1.1511 | B.104 | C.7 |
| 1.1512 | B.105 | C.7 |
| 1.1513 | B.106 | C.7 |
| 1.1514 | B.107 | C.7 |
| 1.1515 | B.108 | C.7 |
| 1.1516 | B.109 | C.7 |
| 1.1517 | B.110 | C.7 |
| 1.1518 | B.111 | C.7 |
| 1.1519 | B.112 | C.7 |
| 1.1520 | B.113 | C.7 |
| 1.1521 | B.114 | C.7 |
| 1.1522 | B.115 | C.7 |
| 1.1523 | B.116 | C.7 |
| 1.1524 | B.117 | C.7 |
| 1.1525 | B.118 | C.7 |
| 1.1526 | B.119 | C.7 |
| 1.1527 | B.120 | C.7 |
| 1.1528 | B.121 | C.7 |
| 1.1529 | B.122 | C.7 |
| 1.1530 | B.123 | C.7 |
| 1.1531 | B.124 | C.7 |
| 1.1532 | B.125 | C.7 |
| 1.1533 | B.126 | C.7 |
| 1.1534 | B.127 | C.7 |
| 1.1535 | B.128 | C.7 |
| 1.1536 | B.129 | C.7 |
| 1.1537 | B.130 | C.7 |
| 1.1538 | B.131 | C.7 |
| 1.1539 | B.132 | C.7 |
| 1.1540 | B.133 | C.7 |
| 1.1541 | B.134 | C.7 |
| 1.1542 | B.135 | C.7 |
| 1.1543 | B.136 | C.7 |
| 1.1544 | B.137 | C.7 |
| 1.1545 | B.138 | C.7 |
| 1.1546 | B.139 | C.7 |
| 1.1547 | B.140 | C.7 |
| 1.1548 | B.141 | C.7 |
| 1.1549 | B.142 | C.7 |
| 1.1550 | B.143 | C.7 |
| 1.1551 | B.144 | C.7 |
| 1.1552 | B.145 | C.7 |
| 1.1553 | B.146 | C.7 |
| 1.1554 | B.147 | C.7 |
| 1.1555 | B.148 | C.7 |
| 1.1556 | B.149 | C.7 |
| 1.1557 | B.150 | C.7 |
| 1.1558 | B.151 | C.7 |
| 1.1559 | B.152 | C.7 |
| 1.1560 | B.153 | C.7 |
| 1.1561 | B.154 | C.7 |
| 1.1562 | B.155 | C.7 |
| 1.1563 | B.156 | C.7 |
| 1.1564 | B.157 | C.7 |
| 1.1565 | B.158 | C.7 |
| 1.1566 | B.159 | C.7 |
| 1.1567 | B.160 | C.7 |
| 1.1568 | B.161 | C.7 |
| 1.1569 | B.162 | C.7 |
| 1.1570 | B.163 | C.7 |
| 1.1571 | B.164 | C.7 |
| 1.1572 | B.165 | C.7 |
| 1.1573 | B.166 | C.7 |
| 1.1574 | B.167 | C.7 |
| 1.1575 | B.168 | C.7 |
| 1.1576 | B.169 | C.7 |
| 1.1577 | B.170 | C.7 |
| 1.1578 | B.171 | C.7 |
| 1.1579 | B.172 | C.7 |
| 1.1580 | B.173 | C.7 |
| 1.1581 | B.174 | C.7 |
| 1.1582 | B.175 | C.7 |
| 1.1583 | B.176 | C.7 |
| 1.1584 | B.177 | C.7 |
| 1.1585 | B.178 | C.7 |
| 1.1586 | B.179 | C.7 |
| 1.1587 | B.180 | C.7 |
| 1.1588 | B.181 | C.7 |
| 1.1589 | B.182 | C.7 |
| 1.1590 | B.183 | C.7 |

TABLE 1-continued compositions 1.1 to 1.3635

| comp. no. | herbicide B | safener C |
|---|---|---|
| 1.1591 | B.184 | C.7 |
| 1.1592 | B.185 | C.7 |
| 1.1593 | B.186 | C.7 |
| 1.1594 | B.187 | C.7 |
| 1.1595 | B.188 | C.7 |
| 1.1596 | B.189 | C.7 |
| 1.1597 | B.190 | C.7 |
| 1.1598 | B.191 | C.7 |
| 1.1599 | B.192 | C.7 |
| 1.1600 | B.193 | C.7 |
| 1.1601 | B.194 | C.7 |
| 1.1602 | B.195 | C.7 |
| 1.1603 | B.196 | C.7 |
| 1.1604 | B.197 | C.7 |
| 1.1605 | B.198 | C.7 |
| 1.1606 | B.199 | C.7 |
| 1.1607 | B.200 | C.7 |
| 1.1608 | B.201 | C.7 |
| 1.1609 | B.1 | C.8 |
| 1.1610 | B.2 | C.8 |
| 1.1611 | B.3 | C.8 |
| 1.1612 | B.4 | C.8 |
| 1.1613 | B.5 | C.8 |
| 1.1614 | B.6 | C.8 |
| 1.1615 | B.7 | C.8 |
| 1.1616 | B.8 | C.8 |
| 1.1617 | B.9 | C.8 |
| 1.1618 | B.10 | C.8 |
| 1.1619 | B.11 | C.8 |
| 1.1620 | B.12 | C.8 |
| 1.1621 | B.13 | C.8 |
| 1.1622 | B.14 | C.8 |
| 1.1623 | B.15 | C.8 |
| 1.1624 | B.16 | C.8 |
| 1.1625 | B.17 | C.8 |
| 1.1626 | B.18 | C.8 |
| 1.1627 | B.19 | C.8 |
| 1.1628 | B.20 | C.8 |
| 1.1629 | B.21 | C.8 |
| 1.1630 | B.22 | C.8 |
| 1.1631 | B.23 | C.8 |
| 1.1632 | B.24 | C.8 |
| 1.1633 | B.25 | C.8 |
| 1.1634 | B.26 | C.8 |
| 1.1635 | B.27 | C.8 |
| 1.1636 | B.28 | C.8 |
| 1.1637 | B.29 | C.8 |
| 1.1638 | B.30 | C.8 |
| 1.1639 | B.31 | C.8 |
| 1.1640 | B.32 | C.8 |
| 1.1641 | B.33 | C.8 |
| 1.1642 | B.34 | C.8 |
| 1.1643 | B.35 | C.8 |
| 1.1644 | B.36 | C.8 |
| 1.1645 | B.37 | C.8 |
| 1.1646 | B.38 | C.8 |
| 1.1647 | B.39 | C.8 |
| 1.1648 | B.40 | C.8 |
| 1.1649 | B.41 | C.8 |
| 1.1650 | B.42 | C.8 |
| 1.1651 | B.43 | C.8 |
| 1.1652 | B.44 | C.8 |
| 1.1653 | B.45 | C.8 |
| 1.1654 | B.46 | C.8 |
| 1.1655 | B.47 | C.8 |
| 1.1656 | B.48 | C.8 |
| 1.1657 | B.49 | C.8 |
| 1.1658 | B.50 | C.8 |
| 1.1659 | B.51 | C.8 |
| 1.1660 | B.52 | C.8 |
| 1.1661 | B.53 | C.8 |
| 1.1662 | B.54 | C.8 |
| 1.1663 | B.55 | C.8 |
| 1.1664 | B.56 | C.8 |
| 1.1665 | B.57 | C.8 |
| 1.1666 | B.58. | C.8 |
| 1.1667 | B.59 | C.8 |
| 1.1668 | B.60 | C.8 |
| 1.1669 | B.61 | C.8 |
| 1.1670 | B.62 | C.8 |
| 1.1671 | B.63 | C.8 |
| 1.1672 | B.64 | C.8 |
| 1.1673 | B.65 | C.8 |
| 1.1674 | B.66 | C.8 |
| 1.1675 | B.67 | C.8 |
| 1.1676 | B.68 | C.8 |
| 1.1677 | B.69 | C.8 |
| 1.1678 | B.70 | C.8 |
| 1.1679 | B.71 | C.8 |
| 1.1680 | B.72 | C.8 |
| 1.1681 | B.73 | C.8 |
| 1.1682 | B.74 | C.8 |
| 1.1683 | B.75 | C.8 |
| 1.1684 | B.76 | C.8 |
| 1.1685 | B.77 | C.8 |
| 1.1686 | B.78 | C.8 |
| 1.1687 | B.79 | C.8 |
| 1.1688 | B.80 | C.8 |
| 1.1689 | B.81 | C.8 |
| 1.1690 | B.82 | C.8 |
| 1.1691 | B.83 | C.8 |
| 1.1692 | B.84 | C.8 |
| 1.1693 | B.85 | C.8 |
| 1.1694 | B.86 | C.8 |
| 1.1695 | B.87 | C.8 |
| 1.1696 | B.88 | C.8 |
| 1.1697 | B.89 | C.8 |
| 1.1698 | B.90 | C.8 |
| 1.1699 | B.91 | C.8 |
| 1.1700 | B.92 | C.8 |
| 1.1701 | B.93 | C.8 |
| 1.1702 | B.94 | C.8 |
| 1.1703 | B.95 | C.8 |
| 1.1704 | B.96 | C.8 |
| 1.1705 | B.97 | C.8 |
| 1.1706 | B.98 | C.8 |
| 1.1707 | B.99 | C.8 |
| 1.1708 | B.100 | C.8 |
| 1.1709 | B.101 | C.8 |
| 1.1710 | B.102 | C.8 |
| 1.1711 | B.103 | C.8 |
| 1.1712 | B.104 | C.8 |
| 1.1713 | B.105 | C.8 |
| 1.1714 | B.106 | C.8 |
| 1.1715 | B.107 | C.8 |
| 1.1716 | B.108 | C.8 |
| 1.1717 | B.109 | C.8 |
| 1.1718 | B.110 | C.8 |
| 1.1719 | B.111 | C.8 |
| 1.1720 | B.112 | C.8 |
| 1.1721 | B.113 | C.8 |
| 1.1722 | B.114 | C.8 |
| 1.1723 | B.115 | C.8 |
| 1.1724 | B.116 | C.8 |
| 1.1725 | B.117 | C.8 |
| 1.1726 | B.118 | C.8 |
| 1.1727 | B.119 | C.8 |
| 1.1728 | B.120 | C.8 |
| 1.1729 | B.121 | C.8 |
| 1.1730 | B.122 | C.8 |
| 1.1731 | B.123 | C.8 |
| 1.1732 | B.124 | C.8 |
| 1.1733 | B.125 | C.8 |
| 1.1734 | B.126 | C.8 |
| 1.1735 | B.127 | C.8 |
| 1.1736 | B.128 | C.8 |
| 1.1737 | B.129 | C.8 |
| 1.1738 | B.130 | C.8 |
| 1.1739 | B.131 | C.8 |
| 1.1740 | B.132 | C.8 |

TABLE 1-continued compositions 1.1 to 1.3635

| comp. no. | herbicide B | safener C |
|---|---|---|
| 1.1741 | B.133 | C.8 |
| 1.1742 | B.134 | C.8 |
| 1.1743 | B.135 | C.8 |
| 1.1744 | B.136 | C.8 |
| 1.1745 | B.137 | C.8 |
| 1.1746 | B.138 | C.8 |
| 1.1747 | B.139 | C.8 |
| 1.1748 | B.140 | C.8 |
| 1.1749 | B.141 | C.8 |
| 1.1750 | B.142 | C.8 |
| 1.1751 | B.143 | C.8 |
| 1.1752 | B.144 | C.8 |
| 1.1753 | B.145 | C.8 |
| 1.1754 | B.146 | C.8 |
| 1.1755 | B.147 | C.8 |
| 1.1756 | B.148 | C.8 |
| 1.1757 | B.149 | C.8 |
| 1.1758 | B.150 | C.8 |
| 1.1759 | B.151 | C.8 |
| 1.1760 | B.152 | C.8 |
| 1.1761 | B.153 | C.8 |
| 1.1762 | B.154 | C.8 |
| 1.1763 | B.155 | C.8 |
| 1.1764 | B.156 | C.8 |
| 1.1765 | B.157 | C.8 |
| 1.1766 | B.158 | C.8 |
| 1.1767 | B.159 | C.8 |
| 1.1768 | B.160 | C.8 |
| 1.1769 | B.161 | C.8 |
| 1.1770 | B.162 | C.8 |
| 1.1771 | B.163 | C.8 |
| 1.1772 | B.164 | C.8 |
| 1.1773 | B.165 | C.8 |
| 1.1774 | B.166 | C.8 |
| 1.1775 | B.167 | C.8 |
| 1.1776 | B.168 | C.8 |
| 1.1777 | B.169 | C.8 |
| 1.1778 | B.170 | C.8 |
| 1.1779 | B.171 | C.8 |
| 1.1780 | B.172 | C.8 |
| 1.1781 | B.173 | C.8 |
| 1.1782 | B.174 | C.8 |
| 1.1783 | B.175 | C.8 |
| 1.1784 | B.176 | C.8 |
| 1.1785 | B.177 | C.8 |
| 1.1786 | B.178 | C.8 |
| 1.1787 | B.179 | C.8 |
| 1.1788 | B.180 | C.8 |
| 1.1789 | B.181 | C.8 |
| 1.1790 | B.182 | C.8 |
| 1.1791 | B.183 | C.8 |
| 1.1792 | B.184 | C.8 |
| 1.1793 | B.185 | C.8 |
| 1.1794 | B.186 | C.8 |
| 1.1795 | B.187 | C.8 |
| 1.1796 | B.188 | C.8 |
| 1.1797 | B.189 | C.8 |
| 1.1798 | B.190 | C.8 |
| 1.1799 | B.191 | C.8 |
| 1.1800 | B.192 | C.8 |
| 1.1801 | B.193 | C.8 |
| 1.1802 | B.194 | C.8 |
| 1.1803 | B.195 | C.8 |
| 1.1804 | B.196 | C.8 |
| 1.1805 | B.197 | C.8 |
| 1.1806 | B.198 | C.8 |
| 1.1807 | B.199 | C.8 |
| 1.1808 | B.200 | C.8 |
| 1.1809 | B.201 | C.8 |
| 1.1810 | B.1 | C.9 |
| 1.1811 | B.2 | C.9 |
| 1.1812 | B.3 | C.9 |
| 1.1813 | B.4 | C.9 |
| 1.1814 | B.5 | C.9 |
| 1.1815 | B.6 | C.9 |
| 1.1816 | B.7 | C.9 |
| 1.1817 | B.8 | C.9 |
| 1.1818 | B.9 | C.9 |
| 1.1819 | B.10 | C.9 |
| 1.1820 | B.11 | C.9 |
| 1.1821 | B.12 | C.9 |
| 1.1822 | B.13 | C.9 |
| 1.1823 | B.14 | C.9 |
| 1.1824 | B.15 | C.9 |
| 1.1825 | B.16 | C.9 |
| 1.1826 | B.17 | C.9 |
| 1.1827 | B.18 | C.9 |
| 1.1828 | B.19 | C.9 |
| 1.1829 | B.20 | C.9 |
| 1.1830 | B.21 | C.9 |
| 1.1831 | B.22 | C.9 |
| 1.1832 | B.23 | C.9 |
| 1.1833 | B.24 | C.9 |
| 1.1834 | B.25 | C.9 |
| 1.1835 | B.26 | C.9 |
| 1.1836 | B.27 | C.9 |
| 1.1837 | B.28 | C.9 |
| 1.1838 | B.29 | C.9 |
| 1.1839 | B.30 | C.9 |
| 1.1840 | B.31 | C.9 |
| 1.1841 | B.32 | C.9 |
| 1.1842 | B.33 | C.9 |
| 1.1843 | B.34 | C.9 |
| 1.1844 | B.35 | C.9 |
| 1.1845 | B.36 | C.9 |
| 1.1846 | B.37 | C.9 |
| 1.1847 | B.38 | C.9 |
| 1.1848 | B.39 | C.9 |
| 1.1849 | B.40 | C.9 |
| 1.1850 | B.41 | C.9 |
| 1.1851 | B.42 | C.9 |
| 1.1852 | B.43 | C.9 |
| 1.1853 | B.44 | C.9 |
| 1.1854 | B.45 | C.9 |
| 1.1855 | B.46 | C.9 |
| 1.1856 | B.47 | C.9 |
| 1.1857 | B.48 | C.9 |
| 1.1858 | B.49 | C.9 |
| 1.1859 | B.50 | C.9 |
| 1.1860 | B.51 | C.9 |
| 1.1861 | B.52 | C.9 |
| 1.1862 | B.53 | C.9 |
| 1.1863 | B.54 | C.9 |
| 1.1864 | B.55 | C.9 |
| 1.1865 | B.56 | C.9 |
| 1.1866 | B.57 | C.9 |
| 1.1867 | B.58. | C.9 |
| 1.1868 | B.59 | C.9 |
| 1.1869 | B.60 | C.9 |
| 1.1870 | B.61 | C.9 |
| 1.1871 | B.62 | C.9 |
| 1.1872 | B.63 | C.9 |
| 1.1873 | B.64 | C.9 |
| 1.1874 | B.65 | C.9 |
| 1.1875 | B.66 | C.9 |
| 1.1876 | B.67 | C.9 |
| 1.1877 | B.68 | C.9 |
| 1.1878 | B.69 | C.9 |
| 1.1879 | B.70 | C.9 |
| 1.1880 | B.71 | C.9 |
| 1.1881 | B.72 | C.9 |
| 1.1882 | B.73 | C.9 |
| 1.1883 | B.74 | C.9 |
| 1.1884 | B.75 | C.9 |
| 1.1885 | B.76 | C.9 |
| 1.1886 | B.77 | C.9 |
| 1.1887 | B.78 | C.9 |
| 1.1888 | B.79 | C.9 |
| 1.1889 | B.80 | C.9 |
| 1.1890 | B.81 | C.9 |

TABLE 1-continued compositions 1.1 to 1.3635

| comp. no. | herbicide B | safener C |
|---|---|---|
| 1.1891 | B.82 | C.9 |
| 1.1892 | B.83 | C.9 |
| 1.1893 | B.84 | C.9 |
| 1.1894 | B.85 | C.9 |
| 1.1895 | B.86 | C.9 |
| 1.1896 | B.87 | C.9 |
| 1.1897 | B.88 | C.9 |
| 1.1898 | B.89 | C.9 |
| 1.1899 | B.90 | C.9 |
| 1.1900 | B.91 | C.9 |
| 1.1901 | B.92 | C.9 |
| 1.1902 | B.93 | C.9 |
| 1.1903 | B.94 | C.9 |
| 1.1904 | B.95 | C.9 |
| 1.1905 | B.96 | C.9 |
| 1.1906 | B.97 | C.9 |
| 1.1907 | B.98 | C.9 |
| 1.1908 | B.99 | C.9 |
| 1.1909 | B.100 | C.9 |
| 1.1910 | B.101 | C.9 |
| 1.1911 | B.102 | C.9 |
| 1.1912 | B.103 | C.9 |
| 1.1913 | B.104 | C.9 |
| 1.1914 | B.105 | C.9 |
| 1.1915 | B.106 | C.9 |
| 1.1916 | B.107 | C.9 |
| 1.1917 | B.108 | C.9 |
| 1.1918 | B.109 | C.9 |
| 1.1919 | B.110 | C.9 |
| 1.1920 | B.111 | C.9 |
| 1.1921 | B.112 | C.9 |
| 1.1922 | B.113 | C.9 |
| 1.1923 | B.114 | C.9 |
| 1.1924 | B.115 | C.9 |
| 1.1925 | B.116 | C.9 |
| 1.1926 | B.117 | C.9 |
| 1.1927 | B.118 | C.9 |
| 1.1928 | B.119 | C.9 |
| 1.1929 | B.120 | C.9 |
| 1.1930 | B.121 | C.9 |
| 1.1931 | B.122 | C.9 |
| 1.1932 | B.123 | C.9 |
| 1.1933 | B.124 | C.9 |
| 1.1934 | B.125 | C.9 |
| 1.1935 | B.126 | C.9 |
| 1.1936 | B.127 | C.9 |
| 1.1937 | B.128 | C.9 |
| 1.1938 | B.129 | C.9 |
| 1.1939 | B.130 | C.9 |
| 1.1940 | B.131 | C.9 |
| 1.1941 | B.132 | C.9 |
| 1.1942 | B.133 | C.9 |
| 1.1943 | B.134 | C.9 |
| 1.1944 | B.135 | C.9 |
| 1.1945 | B.136 | C.9 |
| 1.1946 | B.137 | C.9 |
| 1.1947 | B.138 | C.9 |
| 1.1948 | B.139 | C.9 |
| 1.1949 | B.140 | C.9 |
| 1.1950 | B.141 | C.9 |
| 1.1951 | B.142 | C.9 |
| 1.1952 | B.143 | C.9 |
| 1.1953 | B.144 | C.9 |
| 1.1954 | B.145 | C.9 |
| 1.1955 | B.146 | C.9 |
| 1.1956 | B.147 | C.9 |
| 1.1957 | B.148 | C.9 |
| 1.1958 | B.149 | C.9 |
| 1.1959 | B.150 | C.9 |
| 1.1960 | B.151 | C.9 |
| 1.1961 | B.152 | C.9 |
| 1.1962 | B.153 | C.9 |
| 1.1963 | B.154 | C.9 |
| 1.1964 | B.155 | C.9 |
| 1.1965 | B.156 | C.9 |
| 1.1966 | B.157 | C.9 |
| 1.1967 | B.158 | C.9 |
| 1.1968 | B.159 | C.9 |
| 1.1969 | B.160 | C.9 |
| 1.1970 | B.161 | C.9 |
| 1.1971 | B.162 | C.9 |
| 1.1972 | B.163 | C.9 |
| 1.1973 | B.164 | C.9 |
| 1.1974 | B.165 | C.9 |
| 1.1975 | B.166 | C.9 |
| 1.1976 | B.167 | C.9 |
| 1.1977 | B.168 | C.9 |
| 1.1978 | B.169 | C.9 |
| 1.1979 | B.170 | C.9 |
| 1.1980 | B.171 | C.9 |
| 1.1981 | B.172 | C.9 |
| 1.1982 | B.173 | C.9 |
| 1.1983 | B.174 | C.9 |
| 1.1984 | B.175 | C.9 |
| 1.1985 | B.176 | C.9 |
| 1.1986 | B.177 | C.9 |
| 1.1987 | B.178 | C.9 |
| 1.1988 | B.179 | C.9 |
| 1.1989 | B.180 | C.9 |
| 1.1990 | B.181 | C.9 |
| 1.1991 | B.182 | C.9 |
| 1.1992 | B.183 | C.9 |
| 1.1993 | B.184 | C.9 |
| 1.1994 | B.185 | C.9 |
| 1.1995 | B.186 | C.9 |
| 1.1996 | B.187 | C.9 |
| 1.1997 | B.188 | C.9 |
| 1.1998 | B.189 | C.9 |
| 1.1999 | B.190 | C.9 |
| 1.2000 | B.191 | C.9 |
| 1.2001 | B.192 | C.9 |
| 1.2002 | B.193 | C.9 |
| 1.2003 | B.194 | C.9 |
| 1.2004 | B.195 | C.9 |
| 1.2005 | B.196 | C.9 |
| 1.2006 | B.197 | C.9 |
| 1.2007 | B.198 | C.9 |
| 1.2008 | B.199 | C.9 |
| 1.2009 | B.200 | C.9 |
| 1.2010 | B.201 | C.9 |
| 1.2011 | B.1 | C.10 |
| 1.2012 | B.2 | C.10 |
| 1.2013 | B.3 | C.10 |
| 1.2014 | B.4 | C.10 |
| 1.2015 | B.5 | C.10 |
| 1.2016 | B.6 | C.10 |
| 1.2017 | B.7 | C.10 |
| 1.2018 | B.8 | C.10 |
| 1.2019 | B.9 | C.10 |
| 1.2020 | B.10 | C.10 |
| 1.2021 | B.11 | C.10 |
| 1.2022 | B.12 | C.10 |
| 1.2023 | B.13 | C.10 |
| 1.2024 | B.14 | C.10 |
| 1.2025 | B.15 | C.10 |
| 1.2026 | B.16 | C.10 |
| 1.2027 | B.17 | C.10 |
| 1.2028 | B.18 | C.10 |
| 1.2029 | B.19 | C.10 |
| 1.2030 | B.20 | C.10 |
| 1.2031 | B.21 | C.10 |
| 1.2032 | B.22 | C.10 |
| 1.2033 | B.23 | C.10 |
| 1.2034 | B.24 | C.10 |
| 1.2035 | B.25 | C.10 |
| 1.2036 | B.26 | C.10 |
| 1.2037 | B.27 | C.10 |
| 1.2038 | B.28 | C.10 |
| 1.2039 | B.29 | C.10 |
| 1.2040 | B.30 | C.10 |

TABLE 1-continued compositions 1.1 to 1.3635

| comp. no. | herbicide B | safener C |
|---|---|---|
| 1.2041 | B.31 | C.10 |
| 1.2042 | B.32 | C.10 |
| 1.2043 | B.33 | C.10 |
| 1.2044 | B.34 | C.10 |
| 1.2045 | B.35 | C.10 |
| 1.2046 | B.36 | C.10 |
| 1.2047 | B.37 | C.10 |
| 1.2048 | B.38 | C.10 |
| 1.2049 | B.39 | C.10 |
| 1.2050 | B.40 | C.10 |
| 1.2051 | B.41 | C.10 |
| 1.2052 | B.42 | C.10 |
| 1.2053 | B.43 | C.10 |
| 1.2054 | B.44 | C.10 |
| 1.2055 | B.45 | C.10 |
| 1.2056 | B.46 | C.10 |
| 1.2057 | B.47 | C.10 |
| 1.2058 | B.48 | C.10 |
| 1.2059 | B.49 | C.10 |
| 1.2060 | B.50 | C.10 |
| 1.2061 | B.51 | C.10 |
| 1.2062 | B.52 | C.10 |
| 1.2063 | B.53 | C.10 |
| 1.2064 | B.54 | C.10 |
| 1.2065 | B.55 | C.10 |
| 1.2066 | B.56 | C.10 |
| 1.2067 | B.57 | C.10 |
| 1.2068 | B.58. | C.10 |
| 1.2069 | B.59 | C.10 |
| 1.2070 | B.60 | C.10 |
| 1.2071 | B.61 | C.10 |
| 1.2072 | B.62 | C.10 |
| 1.2073 | B.63 | C.10 |
| 1.2074 | B.64 | C.10 |
| 1.2075 | B.65 | C.10 |
| 1.2076 | B.66 | C.10 |
| 1.2077 | B.67 | C.10 |
| 1.2078 | B.68 | C.10 |
| 1.2079 | B.69 | C.10 |
| 1.2080 | B.70 | C.10 |
| 1.2081 | B.71 | C.10 |
| 1.2082 | B.72 | C.10 |
| 1.2083 | B.73 | C.10 |
| 1.2084 | B.74 | C.10 |
| 1.2085 | B.75 | C.10 |
| 1.2086 | B.76 | C.10 |
| 1.2087 | B.77 | C.10 |
| 1.2088 | B.78 | C.10 |
| 1.2089 | B.79 | C.10 |
| 1.2090 | B.80 | C.10 |
| 1.2091 | B.81 | C.10 |
| 1.2092 | B.82 | C.10 |
| 1.2093 | B.83 | C.10 |
| 1.2094 | B.84 | C.10 |
| 1.2095 | B.85 | C.10 |
| 1.2096 | B.86 | C.10 |
| 1.2097 | B.87 | C.10 |
| 1.2098 | B.88 | C.10 |
| 1.2099 | B.89 | C.10 |
| 1.2100 | B.90 | C.10 |
| 1.2101 | B.91 | C.10 |
| 1.2102 | B.92 | C.10 |
| 1.2103 | B.93 | C.10 |
| 1.2104 | B.94 | C.10 |
| 1.2105 | B.95 | C.10 |
| 1.2106 | B.96 | C.10 |
| 1.2107 | B.97 | C.10 |
| 1.2108 | B.98 | C.10 |
| 1.2109 | B.99 | C.10 |
| 1.2110 | B.100 | C.10 |
| 1.2111 | B.101 | C.10 |
| 1.2112 | B.102 | C.10 |
| 1.2113 | B.103 | C.10 |
| 1.2114 | B.104 | C.10 |
| 1.2115 | B.105 | C.10 |
| 1.2116 | B.106 | C.10 |
| 1.2117 | B.107 | C.10 |
| 1.2118 | B.108 | C.10 |
| 1.2119 | B.109 | C.10 |
| 1.2120 | B.110 | C.10 |
| 1.2121 | B.111 | C.10 |
| 1.2122 | B.112 | C.10 |
| 1.2123 | B.113 | C.10 |
| 1.2124 | B.114 | C.10 |
| 1.2125 | B.115 | C.10 |
| 1.2126 | B.116 | C.10 |
| 1.2127 | B.117 | C.10 |
| 1.2128 | B.118 | C.10 |
| 1.2129 | B.119 | C.10 |
| 1.2130 | B.120 | C.10 |
| 1.2131 | B.121 | C.10 |
| 1.2132 | B.122 | C.10 |
| 1.2133 | B.123 | C.10 |
| 1.2134 | B.124 | C.10 |
| 1.2135 | B.125 | C.10 |
| 1.2136 | B.126 | C.10 |
| 1.2137 | B.127 | C.10 |
| 1.2138 | B.128 | C.10 |
| 1.2139 | B.129 | C.10 |
| 1.2140 | B.130 | C.10 |
| 1.2141 | B.131 | C.10 |
| 1.2142 | B.132 | C.10 |
| 1.2143 | B.133 | C.10 |
| 1.2144 | B.134 | C.10 |
| 1.2145 | B.135 | C.10 |
| 1.2146 | B.136 | C.10 |
| 1.2147 | B.137 | C.10 |
| 1.2148 | B.138 | C.10 |
| 1.2149 | B.139 | C.10 |
| 1.2150 | B.140 | C.10 |
| 1.2151 | B.141 | C.10 |
| 1.2152 | B.142 | C.10 |
| 1.2153 | B.143 | C.10 |
| 1.2154 | B.144 | C.10 |
| 1.2155 | B.145 | C.10 |
| 1.2156 | B.146 | C.10 |
| 1.2157 | B.147 | C.10 |
| 1.2158 | B.148 | C.10 |
| 1.2159 | B.149 | C.10 |
| 1.2160 | B.150 | C.10 |
| 1.2161 | B.151 | C.10 |
| 1.2162 | B.152 | C.10 |
| 1.2163 | B.153 | C.10 |
| 1.2164 | B.154 | C.10 |
| 1.2165 | B.155 | C.10 |
| 1.2166 | B.156 | C.10 |
| 1.2167 | B.157 | C.10 |
| 1.2168 | B.158 | C.10 |
| 1.2169 | B.159 | C.10 |
| 1.2170 | B.160 | C.10 |
| 1.2171 | B.161 | C.10 |
| 1.2172 | B.162 | C.10 |
| 1.2173 | B.163 | C.10 |
| 1.2174 | B.164 | C.10 |
| 1.2175 | B.165 | C.10 |
| 1.2176 | B.166 | C.10 |
| 1.2177 | B.167 | C.10 |
| 1.2178 | B.168 | C.10 |
| 1.2179 | B.169 | C.10 |
| 1.2180 | B.170 | C.10 |
| 1.2181 | B.171 | C.10 |
| 1.2182 | B.172 | C.10 |
| 1.2183 | B.173 | C.10 |
| 1.2184 | B.174 | C.10 |
| 1.2185 | B.175 | C.10 |
| 1.2186 | B.176 | C.10 |
| 1.2187 | B.177 | C.10 |
| 1.2188 | B.178 | C.10 |
| 1.2189 | B.179 | C.10 |
| 1.2190 | B.180 | C.10 |

TABLE 1-continued compositions 1.1 to 1.3635

| comp. no. | herbicide B | safener C |
|---|---|---|
| 1.2191 | B.181 | C.10 |
| 1.2192 | B.182 | C.10 |
| 1.2193 | B.183 | C.10 |
| 1.2194 | B.184 | C.10 |
| 1.2195 | B.185 | C.10 |
| 1.2196 | B.186 | C.10 |
| 1.2197 | B.187 | C.10 |
| 1.2198 | B.188 | C.10 |
| 1.2199 | B.189 | C.10 |
| 1.2200 | B.190 | C.10 |
| 1.2201 | B.191 | C.10 |
| 1.2202 | B.192 | C.10 |
| 1.2203 | B.193 | C.10 |
| 1.2204 | B.194 | C.10 |
| 1.2205 | B.195 | C.10 |
| 1.2206 | B.196 | C.10 |
| 1.2207 | B.197 | C.10 |
| 1.2208 | B.198 | C.10 |
| 1.2209 | B.199 | C.10 |
| 1.2210 | B.200 | C.10 |
| 1.2211 | B.201 | C.10 |
| 1.2212 | B.1 | C.11 |
| 1.2213 | B.2 | C.11 |
| 1.2214 | B.3 | C.11 |
| 1.2215 | B.4 | C.11 |
| 1.2216 | B.5 | C.11 |
| 1.2217 | B.6 | C.11 |
| 1.2218 | B.7 | C.11 |
| 1.2219 | B.8 | C.11 |
| 1.2220 | B.9 | C.11 |
| 1.2221 | B.10 | C.11 |
| 1.2222 | B.11 | C.11 |
| 1.2223 | B.12 | C.11 |
| 1.2224 | B.13 | C.11 |
| 1.2225 | B.14 | C.11 |
| 1.2226 | B.15 | C.11 |
| 1.2227 | B.16 | C.11 |
| 1.2228 | B.17 | C.11 |
| 1.2229 | B.18 | C.11 |
| 1.2230 | B.19 | C.11 |
| 1.2231 | B.20 | C.11 |
| 1.2232 | B.21 | C.11 |
| 1.2233 | B.22 | C.11 |
| 1.2234 | B.23 | C.11 |
| 1.2235 | B.24 | C.11 |
| 1.2236 | B.25 | C.11 |
| 1.2237 | B.26 | C.11 |
| 1.2238 | B.27 | C.11 |
| 1.2239 | B.28 | C.11 |
| 1.2240 | B.29 | C.11 |
| 1.2241 | B.30 | C.11 |
| 1.2242 | B.31 | C.11 |
| 1.2243 | B.32 | C.11 |
| 1.2244 | B.33 | C.11 |
| 1.2245 | B.34 | C.11 |
| 1.2246 | B.35 | C.11 |
| 1.2247 | B.36 | C.11 |
| 1.2248 | B.37 | C.11 |
| 1.2249 | B.38 | C.11 |
| 1.2250 | B.39 | C.11 |
| 1.2251 | B.40 | C.11 |
| 1.2252 | B.41 | C.11 |
| 1.2253 | B.42 | C.11 |
| 1.2254 | B.43 | C.11 |
| 1.2255 | B.44 | C.11 |
| 1.2256 | B.45 | C.11 |
| 1.2257 | B.46 | C.11 |
| 1.2258 | B.47 | C.11 |
| 1.2259 | B.48 | C.11 |
| 1.2260 | B.49 | C.11 |
| 1.2261 | B.50 | C.11 |
| 1.2262 | B.51 | C.11 |
| 1.2263 | B.52 | C.11 |
| 1.2264 | B.53 | C.11 |
| 1.2265 | B.54 | C.11 |
| 1.2266 | B.55 | C.11 |
| 1.2267 | B.56 | C.11 |
| 1.2268 | B.57 | C.11 |
| 1.2269 | B.58. | C.11 |
| 1.2270 | B.59 | C.11 |
| 1.2271 | B.60 | C.11 |
| 1.2272 | B.61 | C.11 |
| 1.2273 | B.62 | C.11 |
| 1.2274 | B.63 | C.11 |
| 1.2275 | B.64 | C.11 |
| 1.2276 | B.65 | C.11 |
| 1.2277 | B.66 | C.11 |
| 1.2278 | B.67 | C.11 |
| 1.2279 | B.68 | C.11 |
| 1.2280 | B.69 | C.11 |
| 1.2281 | B.70 | C.11 |
| 1.2282 | B.71 | C.11 |
| 1.2283 | B.72 | C.11 |
| 1.2284 | B.73 | C.11 |
| 1.2285 | B.74 | C.11 |
| 1.2286 | B.75 | C.11 |
| 1.2287 | B.76 | C.11 |
| 1.2288 | B.77 | C.11 |
| 1.2289 | B.78 | C.11 |
| 1.2290 | B.79 | C.11 |
| 1.2291 | B.80 | C.11 |
| 1.2292 | B.81 | C.11 |
| 1.2293 | B.82 | C.11 |
| 1.2294 | B.83 | C.11 |
| 1.2295 | B.84 | C.11 |
| 1.2296 | B.85 | C.11 |
| 1.2297 | B.86 | C.11 |
| 1.2298 | B.87 | C.11 |
| 1.2299 | B.88 | C.11 |
| 1.2300 | B.89 | C.11 |
| 1.2301 | B.90 | C.11 |
| 1.2302 | B.91 | C.11 |
| 1.2303 | B.92 | C.11 |
| 1.2304 | B.93 | C.11 |
| 1.2305 | B.94 | C.11 |
| 1.2306 | B.95 | C.11 |
| 1.2307 | B.96 | C.11 |
| 1.2308 | B.97 | C.11 |
| 1.2309 | B.98 | C.11 |
| 1.2310 | B.99 | C.11 |
| 1.2311 | B.100 | C.11 |
| 1.2312 | B.101 | C.11 |
| 1.2313 | B.102 | C.11 |
| 1.2314 | B.103 | C.11 |
| 1.2315 | B.104 | C.11 |
| 1.2316 | B.105 | C.11 |
| 1.2317 | B.106 | C.11 |
| 1.2318 | B.107 | C.11 |
| 1.2319 | B.108 | C.11 |
| 1.2320 | B.109 | C.11 |
| 1.2321 | B.110 | C.11 |
| 1.2322 | B.111 | C.11 |
| 1.2323 | B.112 | C.11 |
| 1.2324 | B.113 | C.11 |
| 1.2325 | B.114 | C.11 |
| 1.2326 | B.115 | C.11 |
| 1.2327 | B.116 | C.11 |
| 1.2328 | B.117 | C.11 |
| 1.2329 | B.118 | C.11 |
| 1.2330 | B.119 | C.11 |
| 1.2331 | B.120 | C.11 |
| 1.2332 | B.121 | C.11 |
| 1.2333 | B.122 | C.11 |
| 1.2334 | B.123 | C.11 |
| 1.2335 | B.124 | C.11 |
| 1.2336 | B.125 | C.11 |
| 1.2337 | B.126 | C.11 |
| 1.2338 | B.127 | C.11 |
| 1.2339 | B.128 | C.11 |
| 1.2340 | B.129 | C.11 |

TABLE 1-continued compositions 1.1 to 1.3635

| comp. no. | herbicide B | safener C |
|---|---|---|
| 1.2341 | B.130 | C.11 |
| 1.2342 | B.131 | C.11 |
| 1.2343 | B.132 | C.11 |
| 1.2344 | B.133 | C.11 |
| 1.2345 | B.134 | C.11 |
| 1.2346 | B.135 | C.11 |
| 1.2347 | B.136 | C.11 |
| 1.2348 | B.137 | C.11 |
| 1.2349 | B.138 | C.11 |
| 1.2350 | B.139 | C.11 |
| 1.2351 | B.140 | C.11 |
| 1.2352 | B.141 | C.11 |
| 1.2353 | B.142 | C.11 |
| 1.2354 | B.143 | C.11 |
| 1.2355 | B.144 | C.11 |
| 1.2356 | B.145 | C.11 |
| 1.2357 | B.146 | C.11 |
| 1.2358 | B.147 | C.11 |
| 1.2359 | B.148 | C.11 |
| 1.2360 | B.149 | C.11 |
| 1.2361 | B.150 | C.11 |
| 1.2362 | B.151 | C.11 |
| 1.2363 | B.152 | C.11 |
| 1.2364 | B.153 | C.11 |
| 1.2365 | B.154 | C.11 |
| 1.2366 | B.155 | C.11 |
| 1.2367 | B.156 | C.11 |
| 1.2368 | B.157 | C.11 |
| 1.2369 | B.158 | C.11 |
| 1.2370 | B.159 | C.11 |
| 1.2371 | B.160 | C.11 |
| 1.2372 | B.161 | C.11 |
| 1.2373 | B.162 | C.11 |
| 1.2374 | B.163 | C.11 |
| 1.2375 | B.164 | C.11 |
| 1.2376 | B.165 | C.11 |
| 1.2377 | B.166 | C.11 |
| 1.2378 | B.167 | C.11 |
| 1.2379 | B.168 | C.11 |
| 1.2380 | B.169 | C.11 |
| 1.2381 | B.170 | C.11 |
| 1.2382 | B.171 | C.11 |
| 1.2383 | B.172 | C.11 |
| 1.2384 | B.173 | C.11 |
| 1.2385 | B.174 | C.11 |
| 1.2386 | B.175 | C.11 |
| 1.2387 | B.176 | C.11 |
| 1.2388 | B.177 | C.11 |
| 1.2389 | B.178 | C.11 |
| 1.2390 | B.179 | C.11 |
| 1.2391 | B.180 | C.11 |
| 1.2392 | B.181 | C.11 |
| 1.2393 | B.182 | C.11 |
| 1.2394 | B.183 | C.11 |
| 1.2395 | B.184 | C.11 |
| 1.2396 | B.185 | C.11 |
| 1.2397 | B.186 | C.11 |
| 1.2398 | B.187 | C.11 |
| 1.2399 | B.188 | C.11 |
| 1.2400 | B.189 | C.11 |
| 1.2401 | B.190 | C.11 |
| 1.2402 | B.191 | C.11 |
| 1.2403 | B.192 | C.11 |
| 1.2404 | B.193 | C.11 |
| 1.2405 | B.194 | C.11 |
| 1.2406 | B.195 | C.11 |
| 1.2407 | B.196 | C.11 |
| 1.2408 | B.197 | C.11 |
| 1.2409 | B.198 | C.11 |
| 1.2410 | B.199 | C.11 |
| 1.2411 | B.200 | C.11 |
| 1.2412 | B.201 | C.11 |
| 1.2413 | B.1 | C.12 |
| 1.2414 | B.2 | C.12 |
| 1.2415 | B.3 | C.12 |
| 1.2416 | B.4 | C.12 |
| 1.2417 | B.5 | C.12 |
| 1.2418 | B.6 | C.12 |
| 1.2419 | B.7 | C.12 |
| 1.2420 | B.8 | C.12 |
| 1.2421 | B.9 | C.12 |
| 1.2422 | B.10 | C.12 |
| 1.2423 | B.11 | C.12 |
| 1.2424 | B.12 | C.12 |
| 1.2425 | B.13 | C.12 |
| 1.2426 | B.14 | C.12 |
| 1.2427 | B.15 | C.12 |
| 1.2428 | B.16 | C.12 |
| 1.2429 | B.17 | C.12 |
| 1.2430 | B.18 | C.12 |
| 1.2431 | B.19 | C.12 |
| 1.2432 | B.20 | C.12 |
| 1.2433 | B.21 | C.12 |
| 1.2434 | B.22 | C.12 |
| 1.2435 | B.23 | C.12 |
| 1.2436 | B.24 | C.12 |
| 1.2437 | B.25 | C.12 |
| 1.2438 | B.26 | C.12 |
| 1.2439 | B.27 | C.12 |
| 1.2440 | B.28 | C.12 |
| 1.2441 | B.29 | C.12 |
| 1.2442 | B.30 | C.12 |
| 1.2443 | B.31 | C.12 |
| 1.2444 | B.32 | C.12 |
| 1.2445 | B.33 | C.12 |
| 1.2446 | B.34 | C.12 |
| 1.2447 | B.35 | C.12 |
| 1.2448 | B.36 | C.12 |
| 1.2449 | B.37 | C.12 |
| 1.2450 | B.38 | C.12 |
| 1.2451 | B.39 | C.12 |
| 1.2452 | B.40 | C.12 |
| 1.2453 | B.41 | C.12 |
| 1.2454 | B.42 | C.12 |
| 1.2455 | B.43 | C.12 |
| 1.2456 | B.44 | C.12 |
| 1.2457 | B.45 | C.12 |
| 1.2458 | B.46 | C.12 |
| 1.2459 | B.47 | C.12 |
| 1.2460 | B.48 | C.12 |
| 1.2461 | B.49 | C.12 |
| 1.2462 | B.50 | C.12 |
| 1.2463 | B.51 | C.12 |
| 1.2464 | B.52 | C.12 |
| 1.2465 | B.53 | C.12 |
| 1.2466 | B.54 | C.12 |
| 1.2467 | B.55 | C.12 |
| 1.2468 | B.56 | C.12 |
| 1.2469 | B.57 | C.12 |
| 1.2470 | B.58. | C.12 |
| 1.2471 | B.59 | C.12 |
| 1.2472 | B.60 | C.12 |
| 1.2473 | B.61 | C.12 |
| 1.2474 | B.62 | C.12 |
| 1.2475 | B.63 | C.12 |
| 1.2476 | B.64 | C.12 |
| 1.2477 | B.65 | C.12 |
| 1.2478 | B.66 | C.12 |
| 1.2479 | B.67 | C.12 |
| 1.2480 | B.68 | C.12 |
| 1.2481 | B.69 | C.12 |
| 1.2482 | B.70 | C.12 |
| 1.2483 | B.71 | C.12 |
| 1.2484 | B.72 | C.12 |
| 1.2485 | B.73 | C.12 |
| 1.2486 | B.74 | C.12 |
| 1.2487 | B.75 | C.12 |
| 1.2488 | B.76 | C.12 |
| 1.2489 | B.77 | C.12 |
| 1.2490 | B.78 | C.12 |

TABLE 1-continued compositions 1.1 to 1.3635

| comp. no. | herbicide B | safener C |
|---|---|---|
| 1.2491 | B.79 | C.12 |
| 1.2492 | B.80 | C.12 |
| 1.2493 | B.81 | C.12 |
| 1.2494 | B.82 | C.12 |
| 1.2495 | B.83 | C.12 |
| 1.2496 | B.84 | C.12 |
| 1.2497 | B.85 | C.12 |
| 1.2498 | B.86 | C.12 |
| 1.2499 | B.87 | C.12 |
| 1.2500 | B.88 | C.12 |
| 1.2501 | B.89 | C.12 |
| 1.2502 | B.90 | C.12 |
| 1.2503 | B.91 | C.12 |
| 1.2504 | B.92 | C.12 |
| 1.2505 | B.93 | C.12 |
| 1.2506 | B.94 | C.12 |
| 1.2507 | B.95 | C.12 |
| 1.2508 | B.96 | C.12 |
| 1.2509 | B.97 | C.12 |
| 1.2510 | B.98 | C.12 |
| 1.2511 | B.99 | C.12 |
| 1.2512 | B.100 | C.12 |
| 1.2513 | B.101 | C.12 |
| 1.2514 | B.102 | C.12 |
| 1.2515 | B.103 | C.12 |
| 1.2516 | B.104 | C.12 |
| 1.2517 | B.105 | C.12 |
| 1.2518 | B.106 | C.12 |
| 1.2519 | B.107 | C.12 |
| 1.2520 | B.108 | C.12 |
| 1.2521 | B.109 | C.12 |
| 1.2522 | B.110 | C.12 |
| 1.2523 | B.111 | C.12 |
| 1.2524 | B.112 | C.12 |
| 1.2525 | B.113 | C.12 |
| 1.2526 | B.114 | C.12 |
| 1.2527 | B.115 | C.12 |
| 1.2528 | B.116 | C.12 |
| 1.2529 | B.117 | C.12 |
| 1.2530 | B.118 | C.12 |
| 1.2531 | B.119 | C.12 |
| 1.2532 | B.120 | C.12 |
| 1.2533 | B.121 | C.12 |
| 1.2534 | B.122 | C.12 |
| 1.2535 | B.123 | C.12 |
| 1.2536 | B.124 | C.12 |
| 1.2537 | B.125 | C.12 |
| 1.2538 | B.126 | C.12 |
| 1.2539 | B.127 | C.12 |
| 1.2540 | B.128 | C.12 |
| 1.2541 | B.129 | C.12 |
| 1.2542 | B.130 | C.12 |
| 1.2543 | B.131 | C.12 |
| 1.2544 | B.132 | C.12 |
| 1.2545 | B.133 | C.12 |
| 1.2546 | B.134 | C.12 |
| 1.2547 | B.135 | C.12 |
| 1.2548 | B.136 | C.12 |
| 1.2549 | B.137 | C.12 |
| 1.2550 | B.138 | C.12 |
| 1.2551 | B.139 | C.12 |
| 1.2552 | B.140 | C.12 |
| 1.2553 | B.141 | C.12 |
| 1.2554 | B.142 | C.12 |
| 1.2555 | B.143 | C.12 |
| 1.2556 | B.144 | C.12 |
| 1.2557 | B.145 | C.12 |
| 1.2558 | B.146 | C.12 |
| 1.2559 | B.147 | C.12 |
| 1.2560 | B.148 | C.12 |
| 1.2561 | B.149 | C.12 |
| 1.2562 | B.150 | C.12 |
| 1.2563 | B.151 | C.12 |
| 1.2564 | B.152 | C.12 |
| 1.2565 | B.153 | C.12 |
| 1.2566 | B.154 | C.12 |
| 1.2567 | B.155 | C.12 |
| 1.2568 | B.156 | C.12 |
| 1.2569 | B.157 | C.12 |
| 1.2570 | B.158 | C.12 |
| 1.2571 | B.159 | C.12 |
| 1.2572 | B.160 | C.12 |
| 1.2573 | B.161 | C.12 |
| 1.2574 | B.162 | C.12 |
| 1.2575 | B.163 | C.12 |
| 1.2576 | B.164 | C.12 |
| 1.2577 | B.165 | C.12 |
| 1.2578 | B.166 | C.12 |
| 1.2579 | B.167 | C.12 |
| 1.2580 | B.168 | C.12 |
| 1.2581 | B.169 | C.12 |
| 1.2582 | B.170 | C.12 |
| 1.2583 | B.171 | C.12 |
| 1.2584 | B.172 | C.12 |
| 1.2585 | B.173 | C.12 |
| 1.2586 | B.174 | C.12 |
| 1.2587 | B.175 | C.12 |
| 1.2588 | B.176 | C.12 |
| 1.2589 | B.177 | C.12 |
| 1.2590 | B.178 | C.12 |
| 1.2591 | B.179 | C.12 |
| 1.2592 | B.180 | C.12 |
| 1.2593 | B.181 | C.12 |
| 1.2594 | B.182 | C.12 |
| 1.2595 | B.183 | C.12 |
| 1.2596 | B.184 | C.12 |
| 1.2597 | B.185 | C.12 |
| 1.2598 | B.186 | C.12 |
| 1.2599 | B.187 | C.12 |
| 1.2600 | B.188 | C.12 |
| 1.2601 | B.189 | C.12 |
| 1.2602 | B.190 | C.12 |
| 1.2603 | B.191 | C.12 |
| 1.2604 | B.192 | C.12 |
| 1.2605 | B.193 | C.12 |
| 1.2606 | B.194 | C.12 |
| 1.2607 | B.195 | C.12 |
| 1.2608 | B.196 | C.12 |
| 1.2609 | B.197 | C.12 |
| 1.2610 | B.198 | C.12 |
| 1.2611 | B.199 | C.12 |
| 1.2612 | B.200 | C.12 |
| 1.2613 | B.201 | C.12 |
| 1.2614 | B.1 | C.13 |
| 1.2615 | B.2 | C.13 |
| 1.2616 | B.3 | C.13 |
| 1.2617 | B.4 | C.13 |
| 1.2618 | B.5 | C.13 |
| 1.2619 | B.6 | C.13 |
| 1.2620 | B.7 | C.13 |
| 1.2621 | B.8 | C.13 |
| 1.2622 | B.9 | C.13 |
| 1.2623 | B.10 | C.13 |
| 1.2624 | B.11 | C.13 |
| 1.2625 | B.12 | C.13 |
| 1.2626 | B.13 | C.13 |
| 1.2627 | B.14 | C.13 |
| 1.2628 | B.15 | C.13 |
| 1.2629 | B.16 | C.13 |
| 1.2630 | B.17 | C.13 |
| 1.2631 | B.18 | C.13 |
| 1.2632 | B.19 | C.13 |
| 1.2633 | B.20 | C.13 |
| 1.2634 | B.21 | C.13 |
| 1.2635 | B.22 | C.13 |
| 1.2636 | B.23 | C.13 |
| 1.2637 | B.24 | C.13 |
| 1.2638 | B.25 | C.13 |
| 1.2639 | B.26 | C.13 |
| 1.2640 | B.27 | C.13 |

TABLE 1-continued compositions 1.1 to 1.3635

| comp. no. | herbicide B | safener C |
|---|---|---|
| 1.2641 | B.28 | C.13 |
| 1.2642 | B.29 | C.13 |
| 1.2643 | B.30 | C.13 |
| 1.2644 | B.31 | C.13 |
| 1.2645 | B.32 | C.13 |
| 1.2646 | B.33 | C.13 |
| 1.2647 | B.34 | C.13 |
| 1.2648 | B.35 | C.13 |
| 1.2649 | B.36 | C.13 |
| 1.2650 | B.37 | C.13 |
| 1.2651 | B.38 | C.13 |
| 1.2652 | B.39 | C.13 |
| 1.2653 | B.40 | C.13 |
| 1.2654 | B.41 | C.13 |
| 1.2655 | B.42 | C.13 |
| 1.2656 | B.43 | C.13 |
| 1.2657 | B.44 | C.13 |
| 1.2658 | B.45 | C.13 |
| 1.2659 | B.46 | C.13 |
| 1.2660 | B.47 | C.13 |
| 1.2661 | B.48 | C.13 |
| 1.2662 | B.49 | C.13 |
| 1.2663 | B.50 | C.13 |
| 1.2664 | B.51 | C.13 |
| 1.2665 | B.52 | C.13 |
| 1.2666 | B.53 | C.13 |
| 1.2667 | B.54 | C.13 |
| 1.2668 | B.55 | C.13 |
| 1.2669 | B.56 | C.13 |
| 1.2670 | B.57 | C.13 |
| 1.2671 | B.58. | C.13 |
| 1.2672 | B.59 | C.13 |
| 1.2673 | B.60 | C.13 |
| 1.2674 | B.61 | C.13 |
| 1.2675 | B.62 | C.13 |
| 1.2676 | B.63 | C.13 |
| 1.2677 | B.64 | C.13 |
| 1.2678 | B.65 | C.13 |
| 1.2679 | B.66 | C.13 |
| 1.2680 | B.67 | C.13 |
| 1.2681 | B.68 | C.13 |
| 1.2682 | B.69 | C.13 |
| 1.2683 | B.70 | C.13 |
| 1.2684 | B.71 | C.13 |
| 1.2685 | B.72 | C.13 |
| 1.2686 | B.73 | C.13 |
| 1.2687 | B.74 | C.13 |
| 1.2688 | B.75 | C.13 |
| 1.2689 | B.76 | C.13 |
| 1.2690 | B.77 | C.13 |
| 1.2691 | B.78 | C.13 |
| 1.2692 | B.79 | C.13 |
| 1.2693 | B.80 | C.13 |
| 1.2694 | B.81 | C.13 |
| 1.2695 | B.82 | C.13 |
| 1.2696 | B.83 | C.13 |
| 1.2697 | B.84 | C.13 |
| 1.2698 | B.85 | C.13 |
| 1.2699 | B.86 | C.13 |
| 1.2700 | B.87 | C.13 |
| 1.2701 | B.88 | C.13 |
| 1.2702 | B.89 | C.13 |
| 1.2703 | B.90 | C.13 |
| 1.2704 | B.91 | C.13 |
| 1.2705 | B.92 | C.13 |
| 1.2706 | B.93 | C.13 |
| 1.2707 | B.94 | C.13 |
| 1.2708 | B.95 | C.13 |
| 1.2709 | B.96 | C.13 |
| 1.2710 | B.97 | C.13 |
| 1.2711 | B.98 | C.13 |
| 1.2712 | B.99 | C.13 |
| 1.2713 | B.100 | C.13 |
| 1.2714 | B.101 | C.13 |
| 1.2715 | B.102 | C.13 |
| 1.2716 | B.103 | C.13 |
| 1.2717 | B.104 | C.13 |
| 1.2718 | B.105 | C.13 |
| 1.2719 | B.106 | C.13 |
| 1.2720 | B.107 | C.13 |
| 1.2721 | B.108 | C.13 |
| 1.2722 | B.109 | C.13 |
| 1.2723 | B.110 | C.13 |
| 1.2724 | B.111 | C.13 |
| 1.2725 | B.112 | C.13 |
| 1.2726 | B.113 | C.13 |
| 1.2727 | B.114 | C.13 |
| 1.2728 | B.115 | C.13 |
| 1.2729 | B.116 | C.13 |
| 1.2730 | B.117 | C.13 |
| 1.2731 | B.118 | C.13 |
| 1.2732 | B.119 | C.13 |
| 1.2733 | B.120 | C.13 |
| 1.2734 | B.121 | C.13 |
| 1.2735 | B.122 | C.13 |
| 1.2736 | B.123 | C.13 |
| 1.2737 | B.124 | C.13 |
| 1.2738 | B.125 | C.13 |
| 1.2739 | B.126 | C.13 |
| 1.2740 | B.127 | C.13 |
| 1.2741 | B.128 | C.13 |
| 1.2742 | B.129 | C.13 |
| 1.2743 | B.130 | C.13 |
| 1.2744 | B.131 | C.13 |
| 1.2745 | B.132 | C.13 |
| 1.2746 | B.133 | C.13 |
| 1.2747 | B.134 | C.13 |
| 1.2748 | B.135 | C.13 |
| 1.2749 | B.136 | C.13 |
| 1.2750 | B.137 | C.13 |
| 1.2751 | B.138 | C.13 |
| 1.2752 | B.139 | C.13 |
| 1.2753 | B.140 | C.13 |
| 1.2754 | B.141 | C.13 |
| 1.2755 | B.142 | C.13 |
| 1.2756 | B.143 | C.13 |
| 1.2757 | B.144 | C.13 |
| 1.2758 | B.145 | C.13 |
| 1.2759 | B.146 | C.13 |
| 1.2760 | B.147 | C.13 |
| 1.2761 | B.148 | C.13 |
| 1.2762 | B.149 | C.13 |
| 1.2763 | B.150 | C.13 |
| 1.2764 | B.151 | C.13 |
| 1.2765 | B.152 | C.13 |
| 1.2766 | B.153 | C.13 |
| 1.2767 | B.154 | C.13 |
| 1.2768 | B.155 | C.13 |
| 1.2769 | B.156 | C.13 |
| 1.2770 | B.157 | C.13 |
| 1.2771 | B.158 | C.13 |
| 1.2772 | B.159 | C.13 |
| 1.2773 | B.160 | C.13 |
| 1.2774 | B.161 | C.13 |
| 1.2775 | B.162 | C.13 |
| 1.2776 | B.163 | C.13 |
| 1.2777 | B.164 | C.13 |
| 1.2778 | B.165 | C.13 |
| 1.2779 | B.166 | C.13 |
| 1.2780 | B.167 | C.13 |
| 1.2781 | B.168 | C.13 |
| 1.2782 | B.169 | C.13 |
| 1.2783 | B.170 | C.13 |
| 1.2784 | B.171 | C.13 |
| 1.2785 | B.172 | C.13 |
| 1.2786 | B.173 | C.13 |
| 1.2787 | B.174 | C.13 |
| 1.2788 | B.175 | C.13 |
| 1.2789 | B.176 | C.13 |
| 1.2790 | B.177 | C.13 |

TABLE 1-continued compositions 1.1 to 1.3635

| comp. no. | herbicide B | safener C |
|---|---|---|
| 1.2791 | B.178 | C.13 |
| 1.2792 | B.179 | C.13 |
| 1.2793 | B.180 | C.13 |
| 1.2794 | B.181 | C.13 |
| 1.2795 | B.182 | C.13 |
| 1.2796 | B.183 | C.13 |
| 1.2797 | B.184 | C.13 |
| 1.2798 | B.185 | C.13 |
| 1.2799 | B.186 | C.13 |
| 1.2800 | B.187 | C.13 |
| 1.2801 | B.188 | C.13 |
| 1.2802 | B.189 | C.13 |
| 1.2803 | B.190 | C.13 |
| 1.2804 | B.191 | C.13 |
| 1.2805 | B.192 | C.13 |
| 1.2806 | B.193 | C.13 |
| 1.2807 | B.194 | C.13 |
| 1.2808 | B.195 | C.13 |
| 1.2809 | B.196 | C.13 |
| 1.2810 | B.197 | C.13 |
| 1.2811 | B.198 | C.13 |
| 1.2812 | B.199 | C.13 |
| 1.2813 | B.200 | C.13 |
| 1.2814 | B.201 | C.13 |
| 1.2815 | B.1 | C.14 |
| 1.2816 | B.2 | C.14 |
| 1.2817 | B.3 | C.14 |
| 1.2818 | B.4 | C.14 |
| 1.2819 | B.5 | C.14 |
| 1.2820 | B.6 | C.14 |
| 1.2821 | B.7 | C.14 |
| 1.2822 | B.8 | C.14 |
| 1.2823 | B.9 | C.14 |
| 1.2824 | B.10 | C.14 |
| 1.2825 | B.11 | C.14 |
| 1.2826 | B.12 | C.14 |
| 1.2827 | B.13 | C.14 |
| 1.2828 | B.14 | C.14 |
| 1.2829 | B.15 | C.14 |
| 1.2830 | B.16 | C.14 |
| 1.2831 | B.17 | C.14 |
| 1.2832 | B.18 | C.14 |
| 1.2833 | B.19 | C.14 |
| 1.2834 | B.20 | C.14 |
| 1.2835 | B.21 | C.14 |
| 1.2836 | B.22 | C.14 |
| 1.2837 | B.23 | C.14 |
| 1.2838 | B.24 | C.14 |
| 1.2839 | B.25 | C.14 |
| 1.2840 | B.26 | C.14 |
| 1.2841 | B.27 | C.14 |
| 1.2842 | B.28 | C.14 |
| 1.2843 | B.29 | C.14 |
| 1.2844 | B.30 | C.14 |
| 1.2845 | B.31 | C.14 |
| 1.2846 | B.32 | C.14 |
| 1.2847 | B.33 | C.14 |
| 1.2848 | B.34 | C.14 |
| 1.2849 | B.35 | C.14 |
| 1.2850 | B.36 | C.14 |
| 1.2851 | B.37 | C.14 |
| 1.2852 | B.38 | C.14 |
| 1.2853 | B.39 | C.14 |
| 1.2854 | B.40 | C.14 |
| 1.2855 | B.41 | C.14 |
| 1.2856 | B.42 | C.14 |
| 1.2857 | B.43 | C.14 |
| 1.2858 | B.44 | C.14 |
| 1.2859 | B.45 | C.14 |
| 1.2860 | B.46 | C.14 |
| 1.2861 | B.47 | C.14 |
| 1.2862 | B.48 | C.14 |
| 1.2863 | B.49 | C.14 |
| 1.2864 | B.50 | C.14 |
| 1.2865 | B.51 | C.14 |
| 1.2866 | B.52 | C.14 |
| 1.2867 | B.53 | C.14 |
| 1.2868 | B.54 | C.14 |
| 1.2869 | B.55 | C.14 |
| 1.2870 | B.56 | C.14 |
| 1.2871 | B.57 | C.14 |
| 1.2872 | B.58. | C.14 |
| 1.2873 | B.59 | C.14 |
| 1.2874 | B.60 | C.14 |
| 1.2875 | B.61 | C.14 |
| 1.2876 | B.62 | C.14 |
| 1.2877 | B.63 | C.14 |
| 1.2878 | B.64 | C.14 |
| 1.2879 | B.65 | C.14 |
| 1.2880 | B.66 | C.14 |
| 1.2881 | B.67 | C.14 |
| 1.2882 | B.68 | C.14 |
| 1.2883 | B.69 | C.14 |
| 1.2884 | B.70 | C.14 |
| 1.2885 | B.71 | C.14 |
| 1.2886 | B.72 | C.14 |
| 1.2887 | B.73 | C.14 |
| 1.2888 | B.74 | C.14 |
| 1.2889 | B.75 | C.14 |
| 1.2890 | B.76 | C.14 |
| 1.2891 | B.77 | C.14 |
| 1.2892 | B.78 | C.14 |
| 1.2893 | B.79 | C.14 |
| 1.2894 | B.80 | C.14 |
| 1.2895 | B.81 | C.14 |
| 1.2896 | B.82 | C.14 |
| 1.2897 | B.83 | C.14 |
| 1.2898 | B.84 | C.14 |
| 1.2899 | B.85 | C.14 |
| 1.2900 | B.86 | C.14 |
| 1.2901 | B.87 | C.14 |
| 1.2902 | B.88 | C.14 |
| 1.2903 | B.89 | C.14 |
| 1.2904 | B.90 | C.14 |
| 1.2905 | B.91 | C.14 |
| 1.2906 | B.92 | C.14 |
| 1.2907 | B.93 | C.14 |
| 1.2908 | B.94 | C.14 |
| 1.2909 | B.95 | C.14 |
| 1.2910 | B.96 | C.14 |
| 1.2911 | B.97 | C.14 |
| 1.2912 | B.98 | C.14 |
| 1.2913 | B.99 | C.14 |
| 1.2914 | B.100 | C.14 |
| 1.2915 | B.101 | C.14 |
| 1.2916 | B.102 | C.14 |
| 1.2917 | B.103 | C.14 |
| 1.2918 | B.104 | C.14 |
| 1.2919 | B.105 | C.14 |
| 1.2920 | B.106 | C.14 |
| 1.2921 | B.107 | C.14 |
| 1.2922 | B.108 | C.14 |
| 1.2923 | B.109 | C.14 |
| 1.2924 | B.110 | C.14 |
| 1.2925 | B.111 | C.14 |
| 1.2926 | B.112 | C.14 |
| 1.2927 | B.113 | C.14 |
| 1.2928 | B.114 | C.14 |
| 1.2929 | B.115 | C.14 |
| 1.2930 | B.116 | C.14 |
| 1.2931 | B.117 | C.14 |
| 1.2932 | B.118 | C.14 |
| 1.2933 | B.119 | C.14 |
| 1.2934 | B.120 | C.14 |
| 1.2935 | B.121 | C.14 |
| 1.2936 | B.122 | C.14 |
| 1.2937 | B.123 | C.14 |
| 1.2938 | B.124 | C.14 |
| 1.2939 | B.125 | C.14 |
| 1.2940 | B.126 | C.14 |

TABLE 1-continued compositions 1.1 to 1.3635

| comp. no. | herbicide B | safener C |
|---|---|---|
| 1.2941 | B.127 | C.14 |
| 1.2942 | B.128 | C.14 |
| 1.2943 | B.129 | C.14 |
| 1.2944 | B.130 | C.14 |
| 1.2945 | B.131 | C.14 |
| 1.2946 | B.132 | C.14 |
| 1.2947 | B.133 | C.14 |
| 1.2948 | B.134 | C.14 |
| 1.2949 | B.135 | C.14 |
| 1.2950 | B.136 | C.14 |
| 1.2951 | B.137 | C.14 |
| 1.2952 | B.138 | C.14 |
| 1.2953 | B.139 | C.14 |
| 1.2954 | B.140 | C.14 |
| 1.2955 | B.141 | C.14 |
| 1.2956 | B.142 | C.14 |
| 1.2957 | B.143 | C.14 |
| 1.2958 | B.144 | C.14 |
| 1.2959 | B.145 | C.14 |
| 1.2960 | B.146 | C.14 |
| 1.2961 | B.147 | C.14 |
| 1.2962 | B.148 | C.14 |
| 1.2963 | B.149 | C.14 |
| 1.2964 | B.150 | C.14 |
| 1.2965 | B.151 | C.14 |
| 1.2966 | B.152 | C.14 |
| 1.2967 | B.153 | C.14 |
| 1.2968 | B.154 | C.14 |
| 1.2969 | B.155 | C.14 |
| 1.2970 | B.156 | C.14 |
| 1.2971 | B.157 | C.14 |
| 1.2972 | B.158 | C.14 |
| 1.2973 | B.159 | C.14 |
| 1.2974 | B.160 | C.14 |
| 1.2975 | B.161 | C.14 |
| 1.2976 | B.162 | C.14 |
| 1.2977 | B.163 | C.14 |
| 1.2978 | B.164 | C.14 |
| 1.2979 | B.165 | C.14 |
| 1.2980 | B.166 | C.14 |
| 1.2981 | B.167 | C.14 |
| 1.2982 | B.168 | C.14 |
| 1.2983 | B.169 | C.14 |
| 1.2984 | B.170 | C.14 |
| 1.2985 | B.171 | C.14 |
| 1.2986 | B.172 | C.14 |
| 1.2987 | B.173 | C.14 |
| 1.2988 | B.174 | C.14 |
| 1.2989 | B.175 | C.14 |
| 1.2990 | B.176 | C.14 |
| 1.2991 | B.177 | C.14 |
| 1.2992 | B.178 | C.14 |
| 1.2993 | B.179 | C.14 |
| 1.2994 | B.180 | C.14 |
| 1.2995 | B.181 | C.14 |
| 1.2996 | B.182 | C.14 |
| 1.2997 | B.183 | C.14 |
| 1.2998 | B.184 | C.14 |
| 1.2999 | B.185 | C.14 |
| 1.3000 | B.186 | C.14 |
| 1.3001 | B.187 | C.14 |
| 1.3002 | B.188 | C.14 |
| 1.3003 | B.189 | C.14 |
| 1.3004 | B.190 | C.14 |
| 1.3005 | B.191 | C.14 |
| 1.3006 | B.192 | C.14 |
| 1.3007 | B.193 | C.14 |
| 1.3008 | B.194 | C.14 |
| 1.3009 | B.195 | C.14 |
| 1.3010 | B.196 | C.14 |
| 1.3011 | B.197 | C.14 |
| 1.3012 | B.198 | C.14 |
| 1.3013 | B.199 | C.14 |
| 1.3014 | B.200 | C.14 |
| 1.3015 | B.201 | C.14 |
| 1.3016 | B.1 | C.15 |
| 1.3017 | B.2 | C.15 |
| 1.3018 | B.3 | C.15 |
| 1.3019 | B.4 | C.15 |
| 1.3020 | B.5 | C.15 |
| 1.3021 | B.6 | C.15 |
| 1.3022 | B.7 | C.15 |
| 1.3023 | B.8 | C.15 |
| 1.3024 | B.9 | C.15 |
| 1.3025 | B.10 | C.15 |
| 1.3026 | B.11 | C.15 |
| 1.3027 | B.12 | C.15 |
| 1.3028 | B.13 | C.15 |
| 1.3029 | B.14 | C.15 |
| 1.3030 | B.15 | C.15 |
| 1.3031 | B.16 | C.15 |
| 1.3032 | B.17 | C.15 |
| 1.3033 | B.18 | C.15 |
| 1.3034 | B.19 | C.15 |
| 1.3035 | B.20 | C.15 |
| 1.3036 | B.21 | C.15 |
| 1.3037 | B.22 | C.15 |
| 1.3038 | B.23 | C.15 |
| 1.3039 | B.24 | C.15 |
| 1.3040 | B.25 | C.15 |
| 1.3041 | B.26 | C.15 |
| 1.3042 | B.27 | C.15 |
| 1.3043 | B.28 | C.15 |
| 1.3044 | B.29 | C.15 |
| 1.3045 | B.30 | C.15 |
| 1.3046 | B.31 | C.15 |
| 1.3047 | B.32 | C.15 |
| 1.3048 | B.33 | C.15 |
| 1.3049 | B.34 | C.15 |
| 1.3050 | B.35 | C.15 |
| 1.3051 | B.36 | C.15 |
| 1.3052 | B.37 | C.15 |
| 1.3053 | B.38 | C.15 |
| 1.3054 | B.39 | C.15 |
| 1.3055 | B.40 | C.15 |
| 1.3056 | B.41 | C.15 |
| 1.3057 | B.42 | C.15 |
| 1.3058 | B.43 | C.15 |
| 1.3059 | B.44 | C.15 |
| 1.3060 | B.45 | C.15 |
| 1.3061 | B.46 | C.15 |
| 1.3062 | B.47 | C.15 |
| 1.3063 | B.48 | C.15 |
| 1.3064 | B.49 | C.15 |
| 1.3065 | B.50 | C.15 |
| 1.3066 | B.51 | C.15 |
| 1.3067 | B.52 | C.15 |
| 1.3068 | B.53 | C.15 |
| 1.3069 | B.54 | C.15 |
| 1.3070 | B.55 | C.15 |
| 1.3071 | B.56 | C.15 |
| 1.3072 | B.57 | C.15 |
| 1.3073 | B.58. | C.15 |
| 1.3074 | B.59 | C.15 |
| 1.3075 | B.60 | C.15 |
| 1.3076 | B.61 | C.15 |
| 1.3077 | B.62 | C.15 |
| 1.3078 | B.63 | C.15 |
| 1.3079 | B.64 | C.15 |
| 1.3080 | B.65 | C.15 |
| 1.3081 | B.66 | C.15 |
| 1.3082 | B.67 | C.15 |
| 1.3083 | B.68 | C.15 |
| 1.3084 | B.69 | C.15 |
| 1.3085 | B.70 | C.15 |
| 1.3086 | B.71 | C.15 |
| 1.3087 | B.72 | C.15 |
| 1.3088 | B.73 | C.15 |
| 1.3089 | B.74 | C.15 |
| 1.3090 | B.75 | C.15 |

TABLE 1-continued compositions 1.1 to 1.3635

| comp. no. | herbicide B | safener C |
|---|---|---|
| 1.3091 | B.76 | C.15 |
| 1.3092 | B.77 | C.15 |
| 1.3093 | B.78 | C.15 |
| 1.3094 | B.79 | C.15 |
| 1.3095 | B.80 | C.15 |
| 1.3096 | B.81 | C.15 |
| 1.3097 | B.82 | C.15 |
| 1.3098 | B.83 | C.15 |
| 1.3099 | B.84 | C.15 |
| 1.3100 | B.85 | C.15 |
| 1.3101 | B.86 | C.15 |
| 1.3102 | B.87 | C.15 |
| 1.3103 | B.88 | C.15 |
| 1.3104 | B.89 | C.15 |
| 1.3105 | B.90 | C.15 |
| 1.3106 | B.91 | C.15 |
| 1.3107 | B.92 | C.15 |
| 1.3108 | B.93 | C.15 |
| 1.3109 | B.94 | C.15 |
| 1.3110 | B.95 | C.15 |
| 1.3111 | B.96 | C.15 |
| 1.3112 | B.97 | C.15 |
| 1.3113 | B.98 | C.15 |
| 1.3114 | B.99 | C.15 |
| 1.3115 | B.100 | C.15 |
| 1.3116 | B.101 | C.15 |
| 1.3117 | B.102 | C.15 |
| 1.3118 | B.103 | C.15 |
| 1.3119 | B.104 | C.15 |
| 1.3120 | B.105 | C.15 |
| 1.3121 | B.106 | C.15 |
| 1.3122 | B.107 | C.15 |
| 1.3123 | B.108 | C.15 |
| 1.3124 | B.109 | C.15 |
| 1.3125 | B.110 | C.15 |
| 1.3126 | B.111 | C.15 |
| 1.3127 | B.112 | C.15 |
| 1.3128 | B.113 | C.15 |
| 1.3129 | B.114 | C.15 |
| 1.3130 | B.115 | C.15 |
| 1.3131 | B.116 | C.15 |
| 1.3132 | B.117 | C.15 |
| 1.3133 | B.118 | C.15 |
| 1.3134 | B.119 | C.15 |
| 1.3135 | B.120 | C.15 |
| 1.3136 | B.121 | C.15 |
| 1.3137 | B.122 | C.15 |
| 1.3138 | B.123 | C.15 |
| 1.3139 | B.124 | C.15 |
| 1.3140 | B.125 | C.15 |
| 1.3141 | B.126 | C.15 |
| 1.3142 | B.127 | C.15 |
| 1.3143 | B.128 | C.15 |
| 1.3144 | B.129 | C.15 |
| 1.3145 | B.130 | C.15 |
| 1.3146 | B.131 | C.15 |
| 1.3147 | B.132 | C.15 |
| 1.3148 | B.133 | C.15 |
| 1.3149 | B.134 | C.15 |
| 1.3150 | B.135 | C.15 |
| 1.3151 | B.136 | C.15 |
| 1.3152 | B.137 | C.15 |
| 1.3153 | B.138 | C.15 |
| 1.3154 | B.139 | C.15 |
| 1.3155 | B.140 | C.15 |
| 1.3156 | B.141 | C.15 |
| 1.3157 | B.142 | C.15 |
| 1.3158 | B.143 | C.15 |
| 1.3159 | B.144 | C.15 |
| 1.3160 | B.145 | C.15 |
| 1.3161 | B.146 | C.15 |
| 1.3162 | B.147 | C.15 |
| 1.3163 | B.148 | C.15 |
| 1.3164 | B.149 | C.15 |
| 1.3165 | B.150 | C.15 |
| 1.3166 | B.151 | C.15 |
| 1.3167 | B.152 | C.15 |
| 1.3168 | B.153 | C.15 |
| 1.3169 | B.154 | C.15 |
| 1.3170 | B.155 | C.15 |
| 1.3171 | B.156 | C.15 |
| 1.3172 | B.157 | C.15 |
| 1.3173 | B.158 | C.15 |
| 1.3174 | B.159 | C.15 |
| 1.3175 | B.160 | C.15 |
| 1.3176 | B.161 | C.15 |
| 1.3177 | B.162 | C.15 |
| 1.3178 | B.163 | C.15 |
| 1.3179 | B.164 | C.15 |
| 1.3180 | B.165 | C.15 |
| 1.3181 | B.166 | C.15 |
| 1.3182 | B.167 | C.15 |
| 1.3183 | B.168 | C.15 |
| 1.3184 | B.169 | C.15 |
| 1.3185 | B.170 | C.15 |
| 1.3186 | B.171 | C.15 |
| 1.3187 | B.172 | C.15 |
| 1.3188 | B.173 | C.15 |
| 1.3189 | B.174 | C.15 |
| 1.3190 | B.175 | C.15 |
| 1.3191 | B.176 | C.15 |
| 1.3192 | B.177 | C.15 |
| 1.3193 | B.178 | C.15 |
| 1.3194 | B.179 | C.15 |
| 1.3195 | B.180 | C.15 |
| 1.3196 | B.181 | C.15 |
| 1.3197 | B.182 | C.15 |
| 1.3198 | B.183 | C.15 |
| 1.3199 | B.184 | C.15 |
| 1.3200 | B.185 | C.15 |
| 1.3201 | B.186 | C.15 |
| 1.3202 | B.187 | C.15 |
| 1.3203 | B.188 | C.15 |
| 1.3204 | B.189 | C.15 |
| 1.3205 | B.190 | C.15 |
| 1.3206 | B.191 | C.15 |
| 1.3207 | B.192 | C.15 |
| 1.3208 | B.193 | C.15 |
| 1.3209 | B.194 | C.15 |
| 1.3210 | B.195 | C.15 |
| 1.3211 | B.196 | C.15 |
| 1.3212 | B.197 | C.15 |
| 1.3213 | B.198 | C.15 |
| 1.3214 | B.199 | C.15 |
| 1.3215 | B.200 | C.15 |
| 1.3216 | B.201 | C.15 |
| 1.3217 | B.1 | C.16 |
| 1.3218 | B.2 | C.16 |
| 1.3219 | B.3 | C.16 |
| 1.3220 | B.4 | C.16 |
| 1.3221 | B.5 | C.16 |
| 1.3222 | B.6 | C.16 |
| 1.3223 | B.7 | C.16 |
| 1.3224 | B.8 | C.16 |
| 1.3225 | B.9 | C.16 |
| 1.3226 | B.10 | C.16 |
| 1.3227 | B.11 | C.16 |
| 1.3228 | B.12 | C.16 |
| 1.3229 | B.13 | C.16 |
| 1.3230 | B.14 | C.16 |
| 1.3231 | B.15 | C.16 |
| 1.3232 | B.16 | C.16 |
| 1.3233 | B.17 | C.16 |
| 1.3234 | B.18 | C.16 |
| 1.3235 | B.19 | C.16 |
| 1.3236 | B.20 | C.16 |
| 1.3237 | B.21 | C.16 |
| 1.3238 | B.22 | C.16 |
| 1.3239 | B.23 | C.16 |
| 1.3240 | B.24 | C.16 |

TABLE 1-continued compositions 1.1 to 1.3635

| comp. no. | herbicide B | safener C |
|---|---|---|
| 1.3241 | B.25 | C.16 |
| 1.3242 | B.26 | C.16 |
| 1.3243 | B.27 | C.16 |
| 1.3244 | B.28 | C.16 |
| 1.3245 | B.29 | C.16 |
| 1.3246 | B.30 | C.16 |
| 1.3247 | B.31 | C.16 |
| 1.3248 | B.32 | C.16 |
| 1.3249 | B.33 | C.16 |
| 1.3250 | B.34 | C.16 |
| 1.3251 | B.35 | C.16 |
| 1.3252 | B.36 | C.16 |
| 1.3253 | B.37 | C.16 |
| 1.3254 | B.38 | C.16 |
| 1.3255 | B.39 | C.16 |
| 1.3256 | B.40 | C.16 |
| 1.3257 | B.41 | C.16 |
| 1.3258 | B.42 | C.16 |
| 1.3259 | B.43 | C.16 |
| 1.3260 | B.44 | C.16 |
| 1.3261 | B.45 | C.16 |
| 1.3262 | B.46 | C.16 |
| 1.3263 | B.47 | C.16 |
| 1.3264 | B.48 | C.16 |
| 1.3265 | B.49 | C.16 |
| 1.3266 | B.50 | C.16 |
| 1.3267 | B.51 | C.16 |
| 1.3268 | B.52 | C.16 |
| 1.3269 | B.53 | C.16 |
| 1.3270 | B.54 | C.16 |
| 1.3271 | B.55 | C.16 |
| 1.3272 | B.56 | C.16 |
| 1.3273 | B.57 | C.16 |
| 1.3274 | B.58. | C.16 |
| 1.3275 | B.59 | C.16 |
| 1.3276 | B.60 | C.16 |
| 1.3277 | B.61 | C.16 |
| 1.3278 | B.62 | C.16 |
| 1.3279 | B.63 | C.16 |
| 1.3280 | B.64 | C.16 |
| 1.3281 | B.65 | C.16 |
| 1.3282 | B.66 | C.16 |
| 1.3283 | B.67 | C.16 |
| 1.3284 | B.68 | C.16 |
| 1.3285 | B.69 | C.16 |
| 1.3286 | B.70 | C.16 |
| 1.3287 | B.71 | C.16 |
| 1.3288 | B.72 | C.16 |
| 1.3289 | B.73 | C.16 |
| 1.3290 | B.74 | C.16 |
| 1.3291 | B.75 | C.16 |
| 1.3292 | B.76 | C.16 |
| 1.3293 | B.77 | C.16 |
| 1.3294 | B.78 | C.16 |
| 1.3295 | B.79 | C.16 |
| 1.3296 | B.80 | C.16 |
| 1.3297 | B.81 | C.16 |
| 1.3298 | B.82 | C.16 |
| 1.3299 | B.83 | C.16 |
| 1.3300 | B.84 | C.16 |
| 1.3301 | B.85 | C.16 |
| 1.3302 | B.86 | C.16 |
| 1.3303 | B.87 | C.16 |
| 1.3304 | B.88 | C.16 |
| 1.3305 | B.89 | C.16 |
| 1.3306 | B.90 | C.16 |
| 1.3307 | B.91 | C.16 |
| 1.3308 | B.92 | C.16 |
| 1.3309 | B.93 | C.16 |
| 1.3310 | B.94 | C.16 |
| 1.3311 | B.95 | C.16 |
| 1.3312 | B.96 | C.16 |
| 1.3313 | B.97 | C.16 |
| 1.3314 | B.98 | C.16 |
| 1.3315 | B.99 | C.16 |
| 1.3316 | B.100 | C.16 |
| 1.3317 | B.101 | C.16 |
| 1.3318 | B.102 | C.16 |
| 1.3319 | B.103 | C.16 |
| 1.3320 | B.104 | C.16 |
| 1.3321 | B.105 | C.16 |
| 1.3322 | B.106 | C.16 |
| 1.3323 | B.107 | C.16 |
| 1.3324 | B.108 | C.16 |
| 1.3325 | B.109 | C.16 |
| 1.3326 | B.110 | C.16 |
| 1.3327 | B.111 | C.16 |
| 1.3328 | B.112 | C.16 |
| 1.3329 | B.113 | C.16 |
| 1.3330 | B.114 | C.16 |
| 1.3331 | B.115 | C.16 |
| 1.3332 | B.116 | C.16 |
| 1.3333 | B.117 | C.16 |
| 1.3334 | B.118 | C.16 |
| 1.3335 | B.119 | C.16 |
| 1.3336 | B.120 | C.16 |
| 1.3337 | B.121 | C.16 |
| 1.3338 | B.122 | C.16 |
| 1.3339 | B.123 | C.16 |
| 1.3340 | B.124 | C.16 |
| 1.3341 | B.125 | C.16 |
| 1.3342 | B.126 | C.16 |
| 1.3343 | B.127 | C.16 |
| 1.3344 | B.128 | C.16 |
| 1.3345 | B.129 | C.16 |
| 1.3346 | B.130 | C.16 |
| 1.3347 | B.131 | C.16 |
| 1.3348 | B.132 | C.16 |
| 1.3349 | B.133 | C.16 |
| 1.3350 | B.134 | C.16 |
| 1.3351 | B.135 | C.16 |
| 1.3352 | B.136 | C.16 |
| 1.3353 | B.137 | C.16 |
| 1.3354 | B.138 | C.16 |
| 1.3355 | B.139 | C.16 |
| 1.3356 | B.140 | C.16 |
| 1.3357 | B.141 | C.16 |
| 1.3358 | B.142 | C.16 |
| 1.3359 | B.143 | C.16 |
| 1.3360 | B.144 | C.16 |
| 1.3361 | B.145 | C.16 |
| 1.3362 | B.146 | C.16 |
| 1.3363 | B.147 | C.16 |
| 1.3364 | B.148 | C.16 |
| 1.3365 | B.149 | C.16 |
| 1.3366 | B.150 | C.16 |
| 1.3367 | B.151 | C.16 |
| 1.3368 | B.152 | C.16 |
| 1.3369 | B.153 | C.16 |
| 1.3370 | B.154 | C.16 |
| 1.3371 | B.155 | C.16 |
| 1.3372 | B.156 | C.16 |
| 1.3373 | B.157 | C.16 |
| 1.3374 | B.158 | C.16 |
| 1.3375 | B.159 | C.16 |
| 1.3376 | B.160 | C.16 |
| 1.3377 | B.161 | C.16 |
| 1.3378 | B.162 | C.16 |
| 1.3379 | B.163 | C.16 |
| 1.3380 | B.164 | C.16 |
| 1.3381 | B.165 | C.16 |
| 1.3382 | B.166 | C.16 |
| 1.3383 | B.167 | C.16 |
| 1.3384 | B.168 | C.16 |
| 1.3385 | B.169 | C.16 |
| 1.3386 | B.170 | C.16 |
| 1.3387 | B.171 | C.16 |
| 1.3388 | B.172 | C.16 |
| 1.3389 | B.173 | C.16 |
| 1.3390 | B.174 | C.16 |

TABLE 1-continued compositions 1.1 to 1.3635

| comp. no. | herbicide B | safener C |
|---|---|---|
| 1.3391 | B.175 | C.16 |
| 1.3392 | B.176 | C.16 |
| 1.3393 | B.177 | C.16 |
| 1.3394 | B.178 | C.16 |
| 1.3395 | B.179 | C.16 |
| 1.3396 | B.180 | C.16 |
| 1.3397 | B.181 | C.16 |
| 1.3398 | B.182 | C.16 |
| 1.3399 | B.183 | C.16 |
| 1.3400 | B.184 | C.16 |
| 1.3401 | B.185 | C.16 |
| 1.3402 | B.186 | C.16 |
| 1.3403 | B.187 | C.16 |
| 1.3404 | B.188 | C.16 |
| 1.3405 | B.189 | C.16 |
| 1.3406 | B.190 | C.16 |
| 1.3407 | B.191 | C.16 |
| 1.3408 | B.192 | C.16 |
| 1.3409 | B.193 | C.16 |
| 1.3410 | B.194 | C.16 |
| 1.3411 | B.195 | C.16 |
| 1.3412 | B.196 | C.16 |
| 1.3413 | B.197 | C.16 |
| 1.3414 | B.198 | C.16 |
| 1.3415 | B.199 | C.16 |
| 1.3416 | B.200 | C.16 |
| 1.3417 | B.201 | C.16 |
| 1.3418 | B.1 | C.17 |
| 1.3419 | B.2 | C.17 |
| 1.3420 | B.3 | C.17 |
| 1.3421 | B.4 | C.17 |
| 1.3422 | B.5 | C.17 |
| 1.3423 | B.6 | C.17 |
| 1.3424 | B.7 | C.17 |
| 1.3425 | B.8 | C.17 |
| 1.3426 | B.9 | C.17 |
| 1.3427 | B.10 | C.17 |
| 1.3428 | B.11 | C.17 |
| 1.3429 | B.12 | C.17 |
| 1.3430 | B.13 | C.17 |
| 1.3431 | B.14 | C.17 |
| 1.3432 | B.15 | C.17 |
| 1.3433 | B.16 | C.17 |
| 1.3434 | B.17 | C.17 |
| 1.3435 | B.18 | C.17 |
| 1.3436 | B.19 | C.17 |
| 1.3437 | B.20 | C.17 |
| 1.3438 | B.21 | C.17 |
| 1.3439 | B.22 | C.17 |
| 1.3440 | B.23 | C.17 |
| 1.3441 | B.24 | C.17 |
| 1.3442 | B.25 | C.17 |
| 1.3443 | B.26 | C.17 |
| 1.3444 | B.27 | C.17 |
| 1.3445 | B.28 | C.17 |
| 1.3446 | B.29 | C.17 |
| 1.3447 | B.30 | C.17 |
| 1.3448 | B.31 | C.17 |
| 1.3449 | B.32 | C.17 |
| 1.3450 | B.33 | C.17 |
| 1.3451 | B.34 | C.17 |
| 1.3452 | B.35 | C.17 |
| 1.3453 | B.36 | C.17 |
| 1.3454 | B.37 | C.17 |
| 1.3455 | B.38 | C.17 |
| 1.3456 | B.39 | C.17 |
| 1.3457 | B.40 | C.17 |
| 1.3458 | B.41 | C.17 |
| 1.3459 | B.42 | C.17 |
| 1.3460 | B.43 | C.17 |
| 1.3461 | B.44 | C.17 |
| 1.3462 | B.45 | C.17 |
| 1.3463 | B.46 | C.17 |
| 1.3464 | B.47 | C.17 |
| 1.3465 | B.48 | C.17 |
| 1.3466 | B.49 | C.17 |
| 1.3467 | B.50 | C.17 |
| 1.3468 | B.51 | C.17 |
| 1.3469 | B.52 | C.17 |
| 1.3470 | B.53 | C.17 |
| 1.3471 | B.54 | C.17 |
| 1.3472 | B.55 | C.17 |
| 1.3473 | B.56 | C.17 |
| 1.3474 | B.57 | C.17 |
| 1.3475 | B.58. | C.17 |
| 1.3476 | B.59 | C.17 |
| 1.3477 | B.60 | C.17 |
| 1.3478 | B.61 | C.17 |
| 1.3479 | B.62 | C.17 |
| 1.3480 | B.63 | C.17 |
| 1.3481 | B.64 | C.17 |
| 1.3482 | B.65 | C.17 |
| 1.3483 | B.66 | C.17 |
| 1.3484 | B.67 | C.17 |
| 1.3485 | B.68 | C.17 |
| 1.3486 | B.69 | C.17 |
| 1.3487 | B.70 | C.17 |
| 1.3488 | B.71 | C.17 |
| 1.3489 | B.72 | C.17 |
| 1.3490 | B.73 | C.17 |
| 1.3491 | B.74 | C.17 |
| 1.3492 | B.75 | C.17 |
| 1.3493 | B.76 | C.17 |
| 1.3494 | B.77 | C.17 |
| 1.3495 | B.78 | C.17 |
| 1.3496 | B.79 | C.17 |
| 1.3497 | B.80 | C.17 |
| 1.3498 | B.81 | C.17 |
| 1.3499 | B.82 | C.17 |
| 1.3500 | B.83 | C.17 |
| 1.3501 | B.84 | C.17 |
| 1.3502 | B.85 | C.17 |
| 1.3503 | B.86 | C.17 |
| 1.3504 | B.87 | C.17 |
| 1.3505 | B.88 | C.17 |
| 1.3506 | B.89 | C.17 |
| 1.3507 | B.90 | C.17 |
| 1.3508 | B.91 | C.17 |
| 1.3509 | B.92 | C.17 |
| 1.3510 | B.93 | C.17 |
| 1.3511 | B.94 | C.17 |
| 1.3512 | B.95 | C.17 |
| 1.3513 | B.96 | C.17 |
| 1.3514 | B.97 | C.17 |
| 1.3515 | B.98 | C.17 |
| 1.3516 | B.99 | C.17 |
| 1.3517 | B.100 | C.17 |
| 1.3518 | B.101 | C.17 |
| 1.3519 | B.102 | C.17 |
| 1.3520 | B.103 | C.17 |
| 1.3521 | B.104 | C.17 |
| 1.3522 | B.105 | C.17 |
| 1.3523 | B.106 | C.17 |
| 1.3524 | B.107 | C.17 |
| 1.3525 | B.108 | C.17 |
| 1.3526 | B.109 | C.17 |
| 1.3527 | B.110 | C.17 |
| 1.3528 | B.111 | C.17 |
| 1.3529 | B.112 | C.17 |
| 1.3530 | B.113 | C.17 |
| 1.3531 | B.114 | C.17 |
| 1.3532 | B.115 | C.17 |
| 1.3533 | B.116 | C.17 |
| 1.3534 | B.117 | C.17 |
| 1.3535 | B.118 | C.17 |
| 1.3536 | B.119 | C.17 |
| 1.3537 | B.120 | C.17 |
| 1.3538 | B.121 | C.17 |
| 1.3539 | B.122 | C.17 |
| 1.3540 | B.123 | C.17 |

TABLE 1-continued compositions 1.1 to 1.3635

| comp. no. | herbicide B | safener C |
|---|---|---|
| 1.3541 | B.124 | C.17 |
| 1.3542 | B.125 | C.17 |
| 1.3543 | B.126 | C.17 |
| 1.3544 | B.127 | C.17 |
| 1.3545 | B.128 | C.17 |
| 1.3546 | B.129 | C.17 |
| 1.3547 | B.130 | C.17 |
| 1.3548 | B.131 | C.17 |
| 1.3549 | B.132 | C.17 |
| 1.3550 | B.133 | C.17 |
| 1.3551 | B.134 | C.17 |
| 1.3552 | B.135 | C.17 |
| 1.3553 | B.136 | C.17 |
| 1.3554 | B.137 | C.17 |
| 1.3555 | B.138 | C.17 |
| 1.3556 | B.139 | C.17 |
| 1.3557 | B.140 | C.17 |
| 1.3558 | B.141 | C.17 |
| 1.3559 | B.142 | C.17 |
| 1.3560 | B.143 | C.17 |
| 1.3561 | B.144 | C.17 |
| 1.3562 | B.145 | C.17 |
| 1.3563 | B.146 | C.17 |
| 1.3564 | B.147 | C.17 |
| 1.3565 | B.148 | C.17 |
| 1.3566 | B.149 | C.17 |
| 1.3567 | B.150 | C.17 |
| 1.3568 | B.151 | C.17 |
| 1.3569 | B.152 | C.17 |
| 1.3570 | B.153 | C.17 |
| 1.3571 | B.154 | C.17 |
| 1.3572 | B.155 | C.17 |
| 1.3573 | B.156 | C.17 |
| 1.3574 | B.157 | C.17 |
| 1.3575 | B.158 | C.17 |
| 1.3576 | B.159 | C.17 |
| 1.3577 | B.160 | C.17 |
| 1.3578 | B.161 | C.17 |
| 1.3579 | B.162 | C.17 |
| 1.3580 | B.163 | C.17 |
| 1.3581 | B.164 | C.17 |
| 1.3582 | B.165 | C.17 |
| 1.3583 | B.166 | C.17 |
| 1.3584 | B.167 | C.17 |
| 1.3585 | B.168 | C.17 |
| 1.3586 | B.169 | C.17 |
| 1.3587 | B.170 | C.17 |
| 1.3588 | B.171 | C.17 |
| 1.3589 | B.172 | C.17 |
| 1.3590 | B.173 | C.17 |
| 1.3591 | B.174 | C.17 |
| 1.3592 | B.175 | C.17 |
| 1.3593 | B.176 | C.17 |
| 1.3594 | B.177 | C.17 |
| 1.3595 | B.178 | C.17 |
| 1.3596 | B.179 | C.17 |
| 1.3597 | B.180 | C.17 |
| 1.3598 | B.181 | C.17 |
| 1.3599 | B.182 | C.17 |
| 1.3600 | B.183 | C.17 |
| 1.3601 | B.184 | C.17 |
| 1.3602 | B.185 | C.17 |
| 1.3603 | B.186 | C.17 |
| 1.3604 | B.187 | C.17 |
| 1.3605 | B.188 | C.17 |
| 1.3606 | B.189 | C.17 |
| 1.3607 | B.190 | C.17 |
| 1.3608 | B.191 | C.17 |
| 1.3609 | B.192 | C.17 |
| 1.3610 | B.193 | C.17 |
| 1.3611 | B.194 | C.17 |
| 1.3612 | B.195 | C.17 |
| 1.3613 | B.196 | C.17 |
| 1.3614 | B.197 | C.17 |
| 1.3615 | B.198 | C.17 |
| 1.3616 | B.199 | C.17 |
| 1.3617 | B.200 | C.17 |
| 1.3618 | B.201 | C.17 |
| 1.3619 | — | C.1 |
| 1.3620 | — | C.2 |
| 1.3621 | — | C.3 |
| 1.3622 | — | C.4 |
| 1.3623 | — | C.5 |
| 1.3624 | — | C.6 |
| 1.3625 | — | C.7 |
| 1.3626 | — | C.8 |
| 1.3627 | — | C.9 |
| 1.3628 | — | C.10 |
| 1.3629 | — | C.11 |
| 1.3630 | — | C.12 |
| 1.3631 | — | C.13 |
| 1.3632 | — | C.14 |
| 1.3633 | — | C.15 |
| 1.3634 | — | C.16 |
| 1.3635 | — | C.17 |
| 1.3636 | B.202 | — |
| 1.3637 | B.202 | C.1 |
| 1.3638 | B.202 | C.2 |
| 1.3639 | B.202 | C.3 |
| 1.3640 | B.202 | C.4 |
| 1.3641 | B.202 | C.5 |
| 1.3642 | B.202 | C.6 |
| 1.3643 | B.202 | C.7 |
| 1.3644 | B.202 | C.8 |
| 1.3645 | B.202 | C.9 |
| 1.3646 | B.202 | C.10 |
| 1.3647 | B.202 | C.11 |
| 1.3648 | B.202 | C.12 |
| 1.3649 | B.202 | C.13 |
| 1.3650 | B.202 | C.14 |
| 1.3651 | B.202 | C.15 |
| 1.3652 | B.202 | C.16 |
| 1.3653 | B.202 | C.17 |

The specific number for each single composition is deductible as follows:

Composition 1.200 for example comprises the uracilpyridine I.a.339 and cinmethylin (B.200) (see table 1, entry 1.200; as well as table B, entry B.200).

Composition 2.200 for example comprises the uracilpyridine I.a.109 (see the definition for compositions 2.1 to 2.3653, preferably 2.1 to 2.3635, below) and cinmethylin (B.200) (see table 1, entry 1.200; as well as table B, entry B.200).

Composition 7.200 for example comprises imazapyr (B.35) (see the definition for compositions 7.1 to 7.3653, preferably 7.1 to 7.3635, below), the uracilpyridine I.a.339 and cinmethylin (B.200) (see table 1, entry 1.200; as well as table B, entry B.200).

Also especially preferred are compositions 2.1 to 2.3653, more preferred 2.1. to 2.3635, which differ from the corresponding compositions 1.1 to 1.3653, more preferred 1.1 to 1.3635, only in that they comprise as the active compound A the uracilpyridine of formula (I.a.109).

Also especially preferred are compositions 3.1 to 3.3653, more preferred 3.1. to 3.3635, which differ from the corresponding compositions 1.1 to 1.3653, more preferred 1.1 to 1.3635, only in that they additionally comprise B.2 as further herbicide B.

Also especially preferred are compositions 4.1 to 4.3653, more preferred 4.1. to 4.3635, which differ from the corresponding compositions 1.1 to 1.3653, more preferred 1.1 to 1.3635, only in that they additionally comprise B.8 as further herbicide B.

Also especially preferred are compositions 5.1 to 5.3653, more preferred 5.1. to 5.3635, which differ from the corresponding compositions 1.1 to 1.3653, more preferred 1.1 to 1.3635, only in that they additionally comprise B.30 as further herbicide B.

Also especially preferred are compositions 6.1 to 6.3653, more preferred 6.1. to 6.3635, which differ from the corresponding compositions 1.1 to 1.3653, more preferred 1.1 to 1.3635, only in that they additionally comprise B.32 as further herbicide B.

Also especially preferred are compositions 7.1 to 7.3653, more preferred 7.1. to 7.3635, which differ from the corresponding compositions 1.1 to 1.3653, more preferred 1.1 to 1.3635, only in that they additionally comprise B.35 as further herbicide B.

Also especially preferred are compositions 8.1 to 8.3653, more preferred 8.1. to 8.3635, which differ from the corresponding compositions 1.1 to 1.3653, more preferred 1.1 to 1.3635, only in that they additionally comprise B.38 as further herbicide B.

Also especially preferred are compositions 9.1 to 9.3653, more preferred 9.1. to 9.3635, which differ from the corresponding compositions 1.1 to 1.3653, more preferred 1.1 to 1.3635, only in that they additionally comprise B.40 as further herbicide B.

Also especially preferred are compositions 10.1 to 10.3653, more preferred 10.1. to 10.3635, which differ from the corresponding compositions 1.1 to 1.3653, more preferred 1.1 to 1.3635, only in that they additionally comprise B.51 as further herbicide B.

Also especially preferred are compositions 11.1 to 11.3653, more preferred 11.1. to 11.3635, which differ from the corresponding compositions 1.1 to 1.3653, more preferred 1.1 to 1.3635, only in that they additionally comprise B.55 as further herbicide B.

Also especially preferred are compositions 12.1 to 12.3653, more preferred 12.1. to 12.3635, which differ from the corresponding compositions 1.1 to 1.3653, more preferred 1.1 to 1.3635, only in that they additionally comprise B.56 as further herbicide B.

Also especially preferred are compositions 13.1 to 13.3653, more preferred 13.1. to 13.3635, which differ from the corresponding compositions 1.1 to 1.3653, more preferred 1.1 to 1.3635, only in that they additionally comprise B.64 as further herbicide B.

Also especially preferred are compositions 14.1 to 14.3653, more preferred 14.1. to 14.3635, which differ from the corresponding compositions 1.1 to 1.3653, more preferred 1.1 to 1.3635, only in that they additionally comprise B.66 as further herbicide B.

Also especially preferred are compositions 15.1 to 15.3653, more preferred 15.1. to 15.3635, which differ from the corresponding compositions 1.1 to 1.3653, more preferred 1.1 to 1.3635, only in that they additionally comprise B.67 as further herbicide B.

Also especially preferred are compositions 16.1 to 16.3653, more preferred 16.1. to 16.3635, which differ from the corresponding compositions 1.1 to 1.3653, more preferred 1.1 to 1.3635, only in that they additionally comprise B.68 as further herbicide B.

Also especially preferred are compositions 17.1 to 17.3653, more preferred 17.1. to 17.3635, which differ from the corresponding compositions 1.1 to 1.3653, more preferred 1.1 to 1.3635, only in that they additionally comprise B.69 as further herbicide B.

Also especially preferred are compositions 18.1 to 18.3653, more preferred 18.1. to 18.3635, which differ from the corresponding compositions 1.1 to 1.3653, more preferred 1.1 to 1.3635, only in that they additionally comprise B.73 as further herbicide B.

Also especially preferred are compositions 19.1 to 19.3653, more preferred 19.1. to 19.3635, which differ from the corresponding compositions 1.1 to 1.3653, more preferred 1.1 to 1.3635, only in that they additionally comprise B.76 as further herbicide B.

Also especially preferred are compositions 20.1 to 20.3653, more preferred 20.1. to 20.3635, which differ from the corresponding compositions 1.1 to 1.3653, more preferred 1.1 to 1.3635, only in that they additionally comprise B.81 as further herbicide B.

Also especially preferred are compositions 21.1 to 21.3653, more preferred 21.1. to 21.3635, which differ from the corresponding compositions 1.1 to 1.3653, more preferred 1.1 to 1.3635, only in that they additionally comprise B.82 as further herbicide B.

Also especially preferred are compositions 22.1 to 22.3653, more preferred 22.1. to 22.3635, which differ from the corresponding compositions 1.1 to 1.3653, more preferred 1.1 to 1.3635, only in that they additionally comprise B.85 as further herbicide B.

Also especially preferred are compositions 23.1 to 23.3653, more preferred 23.1. to 23.3635, which differ from the corresponding compositions 1.1 to 1.3653, more preferred 1.1 to 1.3635, only in that they additionally comprise B.88 as further herbicide B.

Also especially preferred are compositions 24.1 to 24.3653, more preferred 24.1. to 24.3635, which differ from the corresponding compositions 1.1 to 1.3653, more preferred 1.1 to 1.3635, only in that they additionally comprise B.89 as further herbicide B.

Also especially preferred are compositions 25.1 to 25.3653, more preferred 25.1. to 25.3635, which differ from the corresponding compositions 1.1 to 1.3653, more preferred 1.1 to 1.3635, only in that they additionally comprise B.94 as further herbicide B.

Also especially preferred are compositions 26.1 to 26.3653, more preferred 26.1. to 26.3635, which differ from the corresponding compositions 1.1 to 1.3653, more preferred 1.1 to 1.3635, only in that they additionally comprise B.95 as further herbicide B.

Also especially preferred are compositions 27.1 to 27.3653, more preferred 27.1. to 27.3635, which differ from the corresponding compositions 1.1 to 1.3653, more preferred 1.1 to 1.3635, only in that they additionally comprise B.98 as further herbicide B.

Also especially preferred are compositions 28.1 to 28.3653, more preferred 28.1. to 28.3635, which differ from the corresponding compositions 1.1 to 1.3653, more preferred 1.1 to 1.3635, only in that they additionally comprise B.100 as further herbicide B.

Also especially preferred are compositions 29.1 to 29.3653, more preferred 29.1. to 29.3635, which differ from the corresponding compositions 1.1 to 1.3653, more preferred 1.1 to 1.3635, only in that they additionally comprise B.103 as further herbicide B.

Also especially preferred are compositions 30.1 to 30.3653, more preferred 30.1. to 30.3635, which differ from the corresponding compositions 1.1 to 1.3653, more preferred 1.1 to 1.3635, only in that they additionally comprise B.103 and B.67 as further herbicides B.

Also especially preferred are compositions 31.1 to 31.3653, more preferred 31.1. to 31.3635, which differ from the corresponding compositions 1.1 to 1.3653, more preferred 1.1 to 1.3635, only in that they additionally comprise B.103 and B.76 as further herbicides B.

Also especially preferred are compositions 32.1 to 32.3653, more preferred 32.1. to 32.3635, which differ from the corresponding compositions 1.1 to 1.3653, more preferred 1.1 to 1.3635, only in that they additionally comprise B.103 and B.82 as further herbicides B.

Also especially preferred are compositions 33.1 to 33.3653, more preferred 33.1. to 33.3635, which differ from the corresponding compositions 1.1 to 1.3653, more preferred 1.1 to 1.3635, only in that they additionally comprise B.104 as further herbicide B.

Also especially preferred are compositions 34.1 to 34.3653, more preferred 34.1. to 34.3635, which differ from the corresponding compositions 1.1 to 1.3653, more preferred 1.1 to 1.3635, only in that they additionally comprise B.104 and B.67 as further herbicides B.

Also especially preferred are compositions 35.1 to 35.3653, more preferred 35.1. to 35.3635, which differ from the corresponding compositions 1.1 to 1.3653, more preferred 1.1 to 1.3635, only in that they additionally comprise B.104 and B.76 as further herbicides B.

Also especially preferred are compositions 36.1 to 36.3653, more preferred 36.1. to 36.3635, which differ from the corresponding compositions 1.1 to 1.3653, more preferred 1.1 to 1.3635, only in that they additionally comprise B.104 and B.82 as further herbicides B.

Also especially preferred are compositions 37.1 to 37.3653, more preferred 37.1. to 37.3635, which differ from the corresponding compositions 1.1 to 1.3653, more preferred 1.1 to 1.3635, only in that they additionally comprise B.106 as further herbicide B.

Also especially preferred are compositions 38.1 to 38.3653, more preferred 38.1. to 38.3635, which differ from the corresponding compositions 1.1 to 1.3653, more preferred 1.1 to 1.3635, only in that they additionally comprise B.107 as further herbicide B.

Also especially preferred are compositions 39.1 to 39.3653, more preferred 39.1. to 39.3635, which differ from the corresponding compositions 1.1 to 1.3653, more preferred 1.1 to 1.3635, only in that they additionally comprise B. 107 and B.67 as further herbicides B.

Also especially preferred are compositions 40.1 to 40.3653, more preferred 40.1. to 40.3635, which differ from the corresponding compositions 1.1 to 1.3653, more preferred 1.1 to 1.3635, only in that they additionally comprise B. 107 and B.76 as further herbicides B.

Also especially preferred are compositions 41.1 to 41.3653, more preferred 41.1. to 41.3635, which differ from the corresponding compositions 1.1 to 1.3653, more preferred 1.1 to 1.3635, only in that they additionally comprise B. 107 and B.82 as further herbicides B.

Also especially preferred are compositions 42.1 to 42.3653, more preferred 42.1. to 42.3635, which differ from the corresponding compositions 1.1 to 1.3653, more preferred 1.1 to 1.3635, only in that they additionally comprise B.109 as further herbicide B.

Also especially preferred are compositions 43.1 to 43.3653, more preferred 43.1. to 43.3635, which differ from the corresponding compositions 1.1 to 1.3653, more preferred 1.1 to 1.3635, only in that they additionally comprise B.111 as further herbicide B.

Also especially preferred are compositions 44.1 to 44.3653, more preferred 44.1. to 44.3635, which differ from the corresponding compositions 1.1 to 1.3653, more preferred 1.1 to 1.3635, only in that they additionally comprise B.111 and B.67 as further herbicides B.

Also especially preferred are compositions 45.1 to 45.3653, more preferred 45.1. to 45.3635, which differ from the corresponding compositions 1.1 to 1.3653, more preferred 1.1 to 1.3635, only in that they additionally comprise B.111 and B.76 as further herbicides B.

Also especially preferred are compositions 46.1 to 46.3653, more preferred 46.1. to 46.3635, which differ from the corresponding compositions 1.1 to 1.3653, more preferred 1.1 to 1.3635, only in that they additionally comprise B.111 and B.82 as further herbicides B.

Also especially preferred are compositions 47.1 to 47.3653, more preferred 47.1. to 47.3635, which differ from the corresponding compositions 1.1 to 1.3653, more preferred 1.1 to 1.3635, only in that they additionally comprise B. 116 as further herbicide B.

Also especially preferred are compositions 48.1 to 48.3653, more preferred 48.1. to 48.3635, which differ from the corresponding compositions 1.1 to 1.3653, more preferred 1.1 to 1.3635, only in that they additionally comprise B.116 and B.67 as further herbicides B.

Also especially preferred are compositions 49.1 to 49.3653, more preferred 49.1. to 49.3635, which differ from the corresponding compositions 1.1 to 1.3653, more preferred 1.1 to 1.3635, only in that they additionally comprise B.116 and B.94 as further herbicides B.

Also especially preferred are compositions 50.1 to 50.3653, more preferred 50.1. to 50.3635, which differ from the corresponding compositions 1.1 to 1.3653, more preferred 1.1 to 1.3635, only in that they additionally comprise B.116 and B.103 as further herbicides B.

Also especially preferred are compositions 51.1 to 51.3653, more preferred 51.1. to 51.3635, which differ from the corresponding compositions 1.1 to 1.3653, more preferred 1.1 to 1.3635, only in that they additionally comprise B.116 and B.128 as further herbicides B.

Also especially preferred are compositions 52.1 to 52.3653, more preferred 52.1. to 52.3635, which differ from the corresponding compositions 1.1 to 1.3653, more preferred 1.1 to 1.3635, only in that they additionally comprise B.116 and B.104 as further herbicides B.

Also especially preferred are compositions 53.1 to 53.3653, more preferred 53.1. to 53.3635, which differ from the corresponding compositions 1.1 to 1.3653, more preferred 1.1 to 1.3635, only in that they additionally comprise B.116 and B.107 as further herbicides B.

Also especially preferred are compositions 54.1 to 54.3653, more preferred 54.1. to 54.3635, which differ from the corresponding compositions 1.1 to 1.3653, more preferred 1.1 to 1.3635, only in that they additionally comprise B.116 and B.111 as further herbicides B.

Also especially preferred are compositions 55.1 to 55.3653, more preferred 55.1. to 55.3635, which differ from the corresponding compositions 1.1 to 1.3653, more preferred 1.1 to 1.3635, only in that they additionally comprise B.122 as further herbicide B.

Also especially preferred are compositions 56.1 to 56.3653, more preferred 56.1. to 56.3635, which differ from the corresponding compositions 1.1 to 1.3653, more preferred 1.1 to 1.3635, only in that they additionally comprise B.126 as further herbicide B.

Also especially preferred are compositions 57.1 to 57.3653, more preferred 57.1. to 57.3635, which differ from the corresponding compositions 1.1 to 1.3653, more preferred 1.1 to 1.3635, only in that they additionally comprise B.128 as further herbicide B.

Also especially preferred are compositions 58.1 to 58.3653, more preferred 58.1. to 58.3635, which differ from the corresponding compositions 1.1 to 1.3653, more preferred 1.1 to 1.3635, only in that they additionally comprise B.131 as further herbicide B.

Also especially preferred are compositions 59.1 to 59.3653, more preferred 59.1. to 59.3635, which differ from the corresponding compositions 1.1 to 1.3653, more preferred 1.1 to 1.3635, only in that they additionally comprise B.132 as further herbicide B.

Also especially preferred are compositions 60.1 to 60.3653, more preferred 60.1. to 60.3635, which differ from the corresponding compositions 1.1 to 1.3653, more preferred 1.1 to 1.3635, only in that they additionally comprise B.133 as further herbicide B.

Also especially preferred are compositions 61.1 to 61.3653, more preferred 61.1. to 61.3635, which differ from the corresponding compositions 1.1 to 1.3653, more preferred 1.1 to 1.3635, only in that they additionally comprise B.135 as further herbicide B.

Also especially preferred are compositions 62.1 to 62.3653, more preferred 62.1. to 62.3635, which differ from the corresponding compositions 1.1 to 1.3653, more preferred 1.1 to 1.3635, only in that they additionally comprise B.137 as further herbicide B.

Also especially preferred are compositions 63.1 to 63.3653, more preferred 63.1. to 63.3635, which differ from the corresponding compositions 1.1 to 1.3653, more preferred 11.1 to 1.3635, only in that they additionally comprise B.138 as further herbicide B.

Also especially preferred are compositions 64.1 to 64.3653, more preferred 64.1. to 64.3635, which differ from the corresponding compositions 1.1 to 1.3653, more preferred 1.1 to 1.3635, only in that they additionally comprise B.140 as further herbicide B.

Also especially preferred are compositions 65.1 to 65.3653, more preferred 65.1. to 65.3635, which differ from the corresponding compositions 1.1 to 1.3653, more preferred 1.1 to 1.3635, only in that they additionally comprise B.145 as further herbicide B.

Also especially preferred are compositions 66.1 to 66.3653, more preferred 66.1. to 66.3635, which differ from the corresponding compositions 1.1 to 1.3653, more preferred 1.1 to 1.3635, only in that they additionally comprise B.153 as further herbicide B.

Also especially preferred are compositions 67.1 to 67.3653, more preferred 67.1. to 67.3635, which differ from the corresponding compositions 1.1 to 1.3653, more preferred 1.1 to 1.3635, only in that they additionally comprise B.156 as further herbicide B.

Also especially preferred are compositions 68.1 to 68.3653, more preferred 68.1. to 68.3635, which differ from the corresponding compositions 1.1 to 1.3653, more preferred 1.1 to 1.3635, only in that they additionally comprise B.171 as further herbicide B.

Also especially preferred are compositions 69.1 to 69.3653, more preferred 69.1. to 69.3635, which differ from the corresponding compositions 1.1 to 1.3653, more preferred 1.1 to 1.3635, only in that they additionally comprise B.174 as further herbicide B.

Also especially preferred are compositions 70.1 to 70.3653, more preferred 70.1. to 70.3635, which differ from the corresponding compositions 1.1 to 1.3653, more preferred 1.1 to 1.3635, only in that they comprise as the active compound A the uracilpyridine of formula (I.a.115).

Also especially preferred are compositions 71.1 to 71.3653, more preferred 71.1. to 71.3635, which differ from the corresponding compositions 1.1 to 1.3653, more preferred 1.1 to 1.3635, only in that they comprise as the active compound A the uracilpyridine of formula (I.a.255).

Also especially preferred are compositions 72.1 to 72.3653, more preferred 72.1. to 72.3635, which differ from the corresponding compositions 1.1 to 1.3653, more preferred 1.1 to 1.3635, only in that they comprise as the active compound A the uracilpyridine of formula (I.a.277).

Also especially preferred are compositions 73.1 to 73.3653, more preferred 73.1. to 73.3635, which differ from the corresponding compositions 1.1 to 1.3653, more preferred 1.1 to 1.3635, only in that they comprise as the active compound A the uracilpyridine of formula (I.a.283).

Also especially preferred are compositions 74.1 to 74.3653, more preferred 74.1. to 74.3635, which differ from the corresponding compositions 1.1 to 1.3653, more preferred 1.1 to 1.3635, only in that they comprise as the active compound A the uracilpyridine of formula (I.a.87).

Also especially preferred are compositions 75.1 to 75.3653, more preferred 75.1. to 75.3635, which differ from the corresponding compositions 1.1 to 1.3653, more preferred 1.1 to 1.3635, only in that they comprise as the active compound A the uracilpyridine of formula (I.a.361).

Also especially preferred are compositions 76.1 to 76.3653, more preferred 76.1. to 76.3635, which differ from the corresponding compositions 1.1 to 1.3653, more preferred 1.1 to 1.3635, only in that they comprise as the active compound A the uracilpyridine of formula (I.a.367).

Also especially preferred are compositions 77.1 to 77.3653, more preferred 77.1. to 77.3635, which differ from the corresponding compositions 1.1 to 1.3653, more preferred 1.1 to 1.3635, only in that they comprise as the active compound A the uracilpyridine of formula (I.h.87).

Also especially preferred are compositions 78.1 to 78.3653, more preferred 78.1. to 78.3635, which differ from the corresponding compositions 1.1 to 1.3653, more preferred 1.1 to 1.3635, only in that they comprise as the active compound A the uracilpyridine of formula (I.h.109).

Also especially preferred are compositions 79.1 to 79.3653, more preferred 79.1. to 79.3635, which differ from the corresponding compositions 1.1 to 1.3653, more preferred 1.1 to 1.3635, only in that they comprise as the active compound A the uracilpyridine of formula (I.h.115).

Also especially preferred are compositions 80.1 to 80.3653, more preferred 80.1. to 80.3635, which differ from the corresponding compositions 1.1 to 1.3653, more preferred 1.1 to 1.3635, only in that they comprise as the active compound A the uracilpyridine of formula (I.h.255).

Also especially preferred are compositions 81.1 to 81.3653, more preferred 81.1. to 81.3635, which differ from the corresponding compositions 1.1 to 1.3653, more preferred 1.1 to 1.3635, only in that they comprise as the active compound A the uracilpyridine of formula (I.h.277).

Also especially preferred are compositions 82.1 to 82.3653, more preferred 82.1. to 82.3635, which differ from the corresponding compositions 1.1 to 1.3653, more preferred 1.1 to 1.3635, only in that they comprise as the active compound A the uracilpyridine of formula (I.h.283).

Also especially preferred are compositions 83.1 to 83.3653, more preferred 83.1. to 83.3635, which differ from the corresponding compositions 1.1 to 1.3653, more preferred 1.1 to 1.3635, only in that they comprise as the active compound A the uracilpyridine of formula (I.h.339).

Also especially preferred are compositions 84.1 to 84.3653, more preferred 84.1. to 84.3635, which differ from the corresponding compositions 1.1 to 1.3653, more preferred 1.1 to 1.3635, only in that they comprise as the active compound A the uracilpyridine of formula (I.h.361).

Also especially preferred are compositions 85.1 to 85.3653, more preferred 85.1. to 85.3635, which differ from the corresponding compositions 1.1 to 1.3653, more preferred 1.1 to 1.3635, only in that they comprise as the active compound A the uracilpyridine of formula (I.h.367).

Also especially preferred are compositions 86.1 to 86.3653, more preferred 86.1. to 86.3635, which differ from the corresponding compositions 1.1 to 1.3653, more preferred 1.1 to 1.3635, only in they comprise as the active compound A the uracilpyridine of formula (I.h.339) and additionally comprise B.2 as further herbicide B.

Also especially preferred are compositions 87.1 to 87.3653, more preferred 87.1. to 87.3635, which differ from the corresponding compositions 1.1 to 1.3653, more preferred 1.1 to 1.3635, only in that they comprise as the active compound A the uracilpyridine of formula (I.h.339) and additionally comprise B.8 as further herbicide B.

Also especially preferred are compositions 88.1 to 88.3653, more preferred 88.1. to 88.3635, which differ from the corresponding compositions 1.1 to 1.3653, more preferred 1.1 to 1.3635, only in that they comprise as the active compound A the uracilpyridine of formula (I.h.339) and additionally comprise B.30 as further herbicide B.

Also especially preferred are compositions 89.1 to 89.3653, more preferred 89.1. to 89.3635, which differ from the corresponding compositions 1.1 to 1.3653, more preferred 1.1 to 1.3635, only in that they comprise as the active compound A the uracilpyridine of formula (I.h.339) and additionally comprise B.32 as further herbicide B.

Also especially preferred are compositions 90.1 to 90.3653, more preferred 90.1. to 90.3635, which differ from the corresponding compositions 1.1 to 1.3653, more preferred 1.1 to 1.3635, only in that they comprise as the active compound A the uracilpyridine of formula (I.h.339) and additionally comprise B.35 as further herbicide B.

Also especially preferred are compositions 91.1 to 91.3653, more preferred 91.1. to 91.3635, which differ from the corresponding compositions 1.1 to 1.3653, more preferred 1.1 to 1.3635, only in that they comprise as the active compound A the uracilpyridine of formula (I.h.339) and additionally comprise B.38 as further herbicide B.

Also especially preferred are compositions 92.1 to 92.3653, more preferred 92.1. to 92.3635, which differ from the corresponding compositions 1.1 to 1.3653, more preferred 1.1 to 1.3635, only in that they comprise as the active compound A the uracilpyridine of formula (I.h.339) and additionally comprise B.40 as further herbicide B.

Also especially preferred are compositions 93.1 to 93.3653, more preferred 93.1. to 93.3635, which differ from the corresponding compositions 1.1 to 1.3653, more preferred 1.1 to 1.3635, only in that they comprise as the active compound A the uracilpyridine of formula (I.h.339) and additionally comprise B.51 as further herbicide B.

Also especially preferred are compositions 94.1 to 94.3653, more preferred 94.1. to 94.3635, which differ from the corresponding compositions 1.1 to 1.3653, more preferred 1.1 to 1.3635, only in that they comprise as the active compound A the uracilpyridine of formula (I.h.339) and additionally comprise B.55 as further herbicide B.

Also especially preferred are compositions 95.1 to 95.3653, more preferred 95.1. to 95.3635, which differ from the corresponding compositions 1.1 to 1.3653, more preferred 1.1 to 1.3635, only in that they comprise as the active compound A the uracilpyridine of formula (I.h.339) and additionally comprise B.56 as further herbicide B.

Also especially preferred are compositions 96.1 to 96.3653, more preferred 96.1. to 96.3635, which differ from the corresponding compositions 1.1 to 1.3653, more preferred 1.1 to 1.3635, only in that they comprise as the active compound A the uracilpyridine of formula (I.h.339) and additionally comprise B.64 as further herbicide B.

Also especially preferred are compositions 97.1 to 97.3653, more preferred 97.1. to 97.3635, which differ from the corresponding compositions 1.1 to 1.3653, more preferred 1.1 to 1.3635, only in that they comprise as the active compound A the uracilpyridine of formula (I.h.339) and additionally comprise B.66 as further herbicide B.

Also especially preferred are compositions 98.1 to 98.3653, more preferred 98.1. to 98.3635, which differ from the corresponding compositions 1.1 to 1.3653, more preferred 1.1 to 1.3635, only in that they comprise as the active compound A the uracilpyridine of formula (I.h.339) and additionally comprise B.67 as further herbicide B.

Also especially preferred are compositions 99.1 to 99.3653, more preferred 99.1. to 99.3635, which differ from the corresponding compositions 1.1 to 1.3653, more preferred 1.1 to 1.3635, only in that they comprise as the active compound A the uracilpyridine of formula (I.h.339) and additionally comprise B.68 as further herbicide B.

Also especially preferred are compositions 100.1 to 100.3653, more preferred 100.1. to 100.3635, which differ from the corresponding compositions 1.1 to 1.3653, more preferred 1.1 to 1.3635, only in that they comprise as the active compound A the uracilpyridine of formula (I.h.339) and additionally comprise B.69 as further herbicide B.

Also especially preferred are compositions 101.1 to 101.3653, more preferred 101.1. to 101.3635, which differ from the corresponding compositions 1.1 to 1.3653, more preferred 1.1 to 1.3635, only in that they comprise as the active compound A the uracilpyridine of formula (I.h.339) and additionally comprise B.73 as further herbicide B.

Also especially preferred are compositions 102.1 to 102.3653, more preferred 102.1. to 102.3635, which differ from the corresponding compositions 1.1 to 1.3653, more preferred 1.1 to 1.3635 only in that they comprise as the active compound A the uracilpyridine of formula (I.h.339) and additionally comprise B.76 as further herbicide B.

Also especially preferred are compositions 103.1 to 103.3653, more preferred 103.1. to 103.3635, which differ from the corresponding compositions 1.1 to 1.3653, more preferred 1.1 to 1.3635, only in that they comprise as the active compound A the uracilpyridine of formula (I.h.339) and additionally comprise B.81 as further herbicide B.

Also especially preferred are compositions 104.1 to 104.3653, more preferred 104.1. to 104.3635, which differ from the corresponding compositions 1.1 to 1.3653, more preferred 1.1 to 1.3635, only in that they comprise as the active compound A the uracilpyridine of formula (I.h.339) and additionally comprise B.82 as further herbicide B.

Also especially preferred are compositions 105.1 to 105.3653, more preferred 105.1. to 105.3635, which differ from the corresponding compositions 1.1 to 1.3653, more preferred 1.1 to 1.3635, only in that they comprise as the active compound A the uracilpyridine of formula (I.h.339) and additionally comprise B.85 as further herbicide B.

Also especially preferred are compositions 106.1 to 106.3653, more preferred 106.1. to 106.3635, which differ from the corresponding compositions 1.1 to 1.3653, more preferred 1.1 to 1.3635, only in that they comprise as the active compound A the uracilpyridine of formula (I.h.339) and additionally comprise B.88 as further herbicide B.

Also especially preferred are compositions 107.1 to 107.3653, more preferred 107.1. to 107.3635, which differ from the corresponding compositions 1.1 to 1.3653, more preferred 1.1 to 1.3635, only in that they comprise as the active compound A the uracilpyridine of formula (I.h.339) and additionally comprise B.89 as further herbicide B.

Also especially preferred are compositions 108.1 to 108.3653, more preferred 108.1. to 108.3635, which differ from the corresponding compositions 1.1 to 1.3653, more preferred 1.1 to 1.3635, only in that they comprise as the active compound A the uracilpyridine of formula (I.h.339) and additionally comprise B.94 as further herbicide B.

Also especially preferred are compositions 191.1 to 109.3653, more preferred 109.1. to 109.3635, which differ from the corresponding compositions 1.1 to 1.3653, more preferred 1.1 to 1.3635, only in that they comprise as the active compound A the uracilpyridine of formula (I.h.339) and additionally comprise B.95 as further herbicide B.

Also especially preferred are compositions 110.1 to 110.3653, more preferred 110.1. to 110.3635, which differ from the corresponding compositions 1.1 to 1.3653, more preferred 1.1 to 1.3635, only in that they comprise as the active compound A the uracilpyridine of formula (I.h.339) and additionally comprise B.98 as further herbicide B.

Also especially preferred are compositions 111.1 to 111.3653, more preferred 111.1. to 111.3635, which differ from the corresponding compositions 1.1 to 1.3653, more preferred 1.1 to 1.3635, only in that they comprise as the active compound A the uracilpyridine of formula (I.h.339) and additionally comprise B.100 as further herbicide B.

Also especially preferred are compositions 112.1 to 112.3653, more preferred 112.1. to 112.3635, which differ from the corresponding compositions 1.1 to 1.3653, more preferred 1.1 to 1.3635, only in that they comprise as the active compound A the uracilpyridine of formula (I.h.339) and additionally comprise B.103 as further herbicide B.

Also especially preferred are compositions 113.1 to 113.3653, more preferred 113.1. to 113.3635, which differ from the corresponding compositions 1.1 to 1.3653, more preferred 1.1 to 1.3635, only in that they comprise as the active compound A the uracilpyridine of formula (I.h.339) and additionally comprise B.103 and B.67 as further herbicides B.

Also especially preferred are compositions 114.1 to 114.3653, more preferred 114.1. to 114.3635, which differ from the corresponding compositions 1.1 to 1.3653, more preferred 1.1 to 1.3635, only in that they comprise as the active compound A the uracilpyridine of formula (I.h.339) and additionally comprise B.103 and B.76 as further herbicides B.

Also especially preferred are compositions 115.1 to 115.3653, more preferred 115.1. to 115.3635, which differ from the corresponding compositions 1.1 to 1.3653, more preferred 1.1 to 1.3635, only in that they comprise as the active compound A the uracilpyridine of formula (I.h.339) and additionally comprise B.103 and B.82 as further herbicides B.

Also especially preferred are compositions 116.1 to 116.3653, more preferred 116.1. to 116.3635, which differ from the corresponding compositions 1.1 to 1.3653, more preferred 1.1 to 1.3635, only in that they comprise as the active compound A the uracilpyridine of formula (I.h.339) and additionally comprise B.104 as further herbicide B.

Also especially preferred are compositions 117.1 to 117.3653, more preferred 117.1. to 117.3635, which differ from the corresponding compositions 1.1 to 1.3653, more preferred 1.1 to 1.3635, only in that they comprise as the active compound A the uracilpyridine of formula (I.h.339) and additionally comprise B.104 and B.67 as further herbicides B.

Also especially preferred are compositions 118.1 to 118.3653, more preferred 118.1. to 118.3635, which differ from the corresponding compositions 1.1 to 1.3653, more preferred 1.1 to 1.3635, only in that they comprise as the active compound A the uracilpyridine of formula (I.h.339) and additionally comprise B.104 and B.76 as further herbicides B.

Also especially preferred are compositions 119.1 to 119.3653, more preferred 119.1. to 119.3635, which differ from the corresponding compositions 1.1 to 1.3653, more preferred 1.1 to 1.3635, only in that they comprise as the active compound A the uracilpyridine of formula (I.h.339) and additionally comprise B.104 and B.82 as further herbicides B.

Also especially preferred are compositions 120.1 to 120.3653, more preferred 120.1. to 120.3635, which differ from the corresponding compositions 1.1 to 1.3653, more preferred 1.1 to 1.3635, only in that they comprise as the active compound A the uracilpyridine of formula (I.h.339) and additionally comprise B.106 as further herbicide B.

Also especially preferred are compositions 121.1 to 121.3653, more preferred 121.1. to 121.3635, which differ from the corresponding compositions 1.1 to 1.3653, more preferred 1.1 to 1.3635, only in that they comprise as the active compound A the uracilpyridine of formula (I.h.339) and additionally comprise B.107 as further herbicide B.

Also especially preferred are compositions 122.1 to 122.3653, more preferred 122.1. to 122.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.67 as further herbicides B.

Also especially preferred are compositions 123.1 to 123.3653, more preferred 123.1. to 123.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.76 as further herbicides B.

Also especially preferred are compositions 124.1 to 124.3653, more preferred 124.1. to 124.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.82 as further herbicides B.

Also especially preferred are compositions 125.1 to 125.3653, more preferred 125.1. to 125.3635, which differ from the corresponding compositions 1.1 to 1.3653, more preferred 1.1 to 1.3635, only in that they comprise as the active compound A the uracilpyridine of formula (I.h.339) and additionally comprise B.109 as further herbicide B.

Also especially preferred are compositions 126.1 to 126.3653, more preferred 126.1. to 126.3635, which differ from the corresponding compositions 1.1 to 1.3653, more preferred 1.1 to 1.3635, only in that they comprise as the active compound A the uracilpyridine of formula (I.h.339) and additionally comprise B.111 as further herbicide B.

Also especially preferred are compositions 127.1 to 127.3653, more preferred 127.1. to 127.3635, which differ from the corresponding compositions 1.1 to 1.3653, more preferred 1.1 to 1.3635, only in that they comprise as the active compound A the uracilpyridine of formula (I.h.339) and additionally comprise B.111 and B.67 as further herbicides B.

Also especially preferred are compositions 128.1 to 128.3653, more preferred 128.1. to 128.3635, which differ from the corresponding compositions 1.1 to 1.3653, more preferred 1.1 to 1.3635, only in that they comprise as the active compound A the uracilpyridine of formula (I.h.339) and additionally comprise B.111 and B.76 as further herbicides B.

Also especially preferred are compositions 129.1 to 129.3653, more preferred 129.1. to 129.3635, which differ from the corresponding compositions 1.1 to 1.3653, more preferred 1.1 to 1.3635, only in that they comprise as the active compound A the uracilpyridine of formula (I.h.339) and additionally comprise B.111 and B.82 as further herbicides B.

Also especially preferred are compositions 130.1 to 130.3653, more preferred 130.1. to 130.3635, which differ from the corresponding compositions 1.1 to 1.3653, more preferred 1.1 to 1.3635, only in that they comprise as the active compound A the uracilpyridine of formula (I.h.339) and additionally comprise B.116 as further herbicide B.

Also especially preferred are compositions 131.1 to 131.3653, more preferred 131.1. to 131.3635, which differ from the corresponding compositions 1.1 to 1.3653, more preferred 1.1 to 1.3635, only in that they comprise as the active compound A the uracilpyridine of formula (I.h.339) and additionally comprise B.116 and B.67 as further herbicides B.

Also especially preferred are compositions 132.1 to 132.3653, more preferred 132.1. to 132.3635, which differ from the corresponding compositions 1.1 to 1.3653, more preferred 1.1 to 1.3635, only in that they comprise as the active compound A the uracilpyridine of formula (I.h.339) and additionally comprise B.116 and B.94 as further herbicides B.

Also especially preferred are compositions 133.1 to 133.3653, more preferred 133.1. to 133.3635, which differ from the corresponding compositions 1.1 to 1.3653, more preferred 1.1 to 1.3635, only in that they comprise as the active compound A the uracilpyridine of formula (I.h.339) and additionally comprise B.116 and B.103 as further herbicides B.

Also especially preferred are compositions 134.1 to 134.3653, more preferred 134.1. to 134.3635, which differ from the corresponding compositions 1.1 to 1.3653, more preferred 1.1 to 1.3635, only in that they comprise as the active compound A the uracilpyridine of formula (I.h.339) and additionally comprise B.116 and B.128 as further herbicides B.

Also especially preferred are compositions 135.1 to 135.3653, more preferred 135.1. to 135.3635, which differ from the corresponding compositions 1.1 to 1.3653, more preferred 1.1 to 1.3635, only in that they comprise as the active compound A the uracilpyridine of formula (I.h.339) and additionally comprise B.116 and B.104 as further herbicides B.

Also especially preferred are compositions 136.1 to 136.3653, more preferred 136.1. to 136.3635, which differ from the corresponding compositions 1.1 to 1.3653, more preferred 1.1 to 1.3635, only in that they comprise as the active compound A the uracilpyridine of formula (I.h.339) and additionally comprise B.116 and B.107 as further herbicides B.

Also especially preferred are compositions 137.1 to 137.3653, more preferred 137.1. to 137.3635, which differ from the corresponding compositions 1.1 to 1.3653, more preferred 1.1 to 1.3635, only in that they comprise as the active compound A the uracilpyridine of formula (I.h.339) and additionally comprise B.116 and B.111 as further herbicides B.

Also especially preferred are compositions 138.1 to 138.3653, more preferred 138.1. to 138.3635, which differ from the corresponding compositions 1.1 to 1.3653, more preferred 1.1 to 1.3635, only in that they comprise as the active compound A the uracilpyridine of formula (I.h.339) and additionally comprise B.122 as further herbicide B.

Also especially preferred are compositions 139.1 to 139.3653, more preferred 139.1. to 139.3635, which differ from the corresponding compositions 1.1 to 1.3653, more preferred 1.1 to 1.3635, only in that they comprise as the active compound A the uracilpyridine of formula (I.h.339) and additionally comprise B.126 as further herbicide B.

Also especially preferred are compositions 140.1 to 140.3653, more preferred 140.1. to 140.3635, which differ from the corresponding compositions 1.1 to 1.3653, more preferred 1.1 to 1.3635, only in that they comprise as the active compound A the uracilpyridine of formula (I.h.339) and additionally comprise B.128 as further herbicide B.

Also especially preferred are compositions 141.1 to 141.3653, more preferred 141.1. to 141.3635, which differ from the corresponding compositions 1.1 to 1.3653, more preferred 1.1 to 1.3635, only in that they comprise as the active compound A the uracilpyridine of formula (I.h.339) and additionally comprise B.131 as further herbicide B.

Also especially preferred are compositions 142.1 to 142.3653, more preferred 142.1. to 142.3635, which differ from the corresponding compositions 1.1 to 1.3653, more preferred 1.1 to 1.3635, only in that they comprise as the active compound A the uracilpyridine of formula (I.h.339) and additionally comprise B.132 as further herbicide B.

Also especially preferred are compositions 143.1 to 143.3653, more preferred 143.1. to 143.3635, which differ from the corresponding compositions 1.1 to 1.3653, more preferred 1.1 to 1.3635, only in that they comprise as the active compound A the uracilpyridine of formula (I.h.339) and additionally comprise B.133 as further herbicide B.

Also especially preferred are compositions 144.1 to 144.3653, more preferred 144.1. to 144.3635, which differ from the corresponding compositions 1.1 to 1.3653, more preferred 1.1 to 1.3635, only in that they comprise as the active compound A the uracilpyridine of formula (I.h.339) and additionally comprise B.135 as further herbicide B.

Also especially preferred are compositions 145.1 to 145.3653, more preferred 145.1. to 145.3635, which differ from the corresponding compositions 1.1 to 1.3653, more preferred 1.1 to 1.3635, only in that they comprise as the active compound A the uracilpyridine of formula (I.h.339) and additionally comprise B.137 as further herbicide B.

Also especially preferred are compositions 146.1 to 146.3653, more preferred 146.1. to 146.3635, which differ from the corresponding compositions 1.1 to 1.3653, more preferred 1.1 to 1.3635, only in that they comprise as the active compound A the uracilpyridine of formula (I.h.339) and additionally comprise B.138 as further herbicide B.

Also especially preferred are compositions 147.1 to 147.3653, more preferred 147.1. to 147.3635, which differ from the corresponding compositions 1.1 to 1.3653, more preferred 1.1 to 1.3635, only in that they comprise as the active compound A the uracilpyridine of formula (I.h.339) and additionally comprise B.140 as further herbicide B.

Also especially preferred are compositions 148.1 to 148.3653, more preferred 148.1. to 148.3635, which differ from the corresponding compositions 1.1 to 1.3653, more preferred 1.1 to 1.3635, only in that they comprise as the active compound A the uracilpyridine of formula (I.h.339) and additionally comprise B.145 as further herbicide B.

Also especially preferred are compositions 149.1 to 149.3653, more preferred 149.1. to 149.3635, which differ from the corresponding compositions 1.1 to 1.3653, more preferred 1.1 to 1.3635, only in that they comprise as the active compound A the uracilpyridine of formula (I.h.339) and additionally comprise B.153 as further herbicide B.

Also especially preferred are compositions 150.1 to 150.3653, more preferred 150.1. to 150.3635, which differ from the corresponding compositions 1.1 to 1.3653, more preferred 1.1 to 1.3635, only in that they comprise as the active compound A the uracilpyridine of formula (I.h.339) and additionally comprise B.156 as further herbicide B.

Also especially preferred are compositions 151.1 to 151.3653, more preferred 151.1. to 151.3635, which differ from the corresponding compositions 1.1 to 1.3653, more preferred 1.1 to 1.3635, only in that they comprise as the active compound A the uracilpyridine of formula (I.h.339) and additionally comprise B.171 as further herbicide B.

Also especially preferred are compositions 152.1 to 152.3653, more preferred 152.1. to 152.3635, which differ from the corresponding compositions 1.1 to 1.3653, more preferred 1.1 to 1.3635, only in that they comprise as the active compound A the uracilpyridine of formula (I.h.339) and additionally comprise B.174 as further herbicide B.

The invention also relates to agrochemical compositions comprising at least an auxiliary and at least one uracilpyridine of formula (I) according to the invention.

An agrochemical composition comprises a pesticidally effective amount of an uracilpyridine of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific uracilpyridine of formula (I) used.

The uracilpyridines of formula (I), their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6th Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the uracilpyridines of formula (I) on the target. Examples are surfactants, mineral or vegetable oils, and other auxiliaries. Further examples are listed by Knowles, Adjuvants and additives, Agrow Reports DS256, T & F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble concentrates (SL, LS)

10-60 wt % of an uracilpyridine of formula (I) or a herbicidal composition comprising at least one uracilpyridine of formula (I) (component A) and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of an uracilpyridine of formula (I) or a herbicidal composition comprising at least one uracilpyridine of formula (I) (component A) and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of an uracilpyridine of formula (I) or a herbicidal composition comprising at least one uracilpyridine of formula (I) (component A) and at least one further compound selected from the herbicidal compounds B (component B) and safeners C (component C) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an uracilpyridine of formula (I) or a herbicidal composition comprising at least one uracilpyridine of formula (I) (component A) and at least one further compound selected from the herbicidal compounds B (component B) and safeners C (component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an uracilpyridine of formula (I) or a herbicidal composition comprising at least one uracilpyridine of formula (I) (component A) and at least one further compound selected from the herbicidal compounds B (component B) and safeners C (component C)according to the invention are comminuted with addition of 2-10 wt % dispersants and wetting agents (e.g. sodium lignosulfonate and alcohol ethoxylate), 0,1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of an uracilpyridine of formula (I) or a herbicidal composition comprising at least one uracilpyridine of formula (I) (component A) and at least one further compound selected from the herbicidal compounds B (component B) and safeners C (component C)according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of an uracilpyridine of formula (I) or a herbicidal composition comprising at least one uracilpyridine of formula (I) (component A) and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an uracilpyridine of formula (I) or a herbicidal composition comprising at least one uracilpyridine of formula (I) (component A) and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an uracilpyridine of formula (I) or a herbicidal composition comprising at least one uracilpyridine of formula (I) (component A) and at least one further compound selected from the herbicidal compounds B (component B) and safeners C (component C) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an uracilpyridine of formula (I) or a herbicidal composition comprising at least one uracilpyridine of formula (I) (component A) and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an uracilpyridine of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of an uracilpyridine of formula (I) or a herbicidal composition comprising at least one uracilpyridine of formula (I) (component A) and at least one further compound selected from the herbicidal compounds B (component B) and safeners C (component C) according to the invention are ground finely and mixed intimately with solid carrier (e.g. finely divided kaolin) ad 100 wt %.

x) Granules (GR, FG)

0.5-30 wt % of an uracilpyridine of formula (I) or a herbicidal composition comprising at least one uracilpyridine of formula (I) (component A) and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of an uracilpyridine of formula (I) or a herbicidal composition comprising at least one uracilpyridine of formula (I) (component A) and at least one further compound selected from the herbicidal compounds B (component B) and safeners C (component C) according to the invention are dissolved in organic solvent (e.g. aromatic hydrocarbon) ad 100 wt %.

The agrochemical compositions types i) to xi) may optionally comprise further auxiliaries, such as 0,1-1 wt % bactericides, 5-15 wt % anti-freezing agents, 0,1-1 wt % anti-foaming agents, and 0,1-1 wt % colorants.

The agrochemical compositions and/or herbicidal compositions comprising generally comprise between 0.01 and 95%, preferably between 0.1 and 90%, and in particular between 0.5 and 75%, by weight of the uracilpyridines of formula (I). The uracilpyridines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying uracilpyridines of formula (I), agrochemical compositions and/or herbicidal compositions thereof, on to plant propagation material, especially seeds, include dressing, coating, pelleting, dusting, soaking and in-furrow application methods of the propagation material. Preferably, uracilpyridines of formula (I), agrochemical compositions and/or herbicidal compositions thereof thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the uracilpyridines of formula (I), the agrochemical compositions and/or the herbicidal compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the uracilpyridines of formula (I) according to the invention, the agrochemical compositions and/or the herbicidal compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising uracilpyridines of formula (I) and optionally active substances from the groups B and/or C), may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising uracilpyridines of formula (I) and optionally active substances from the groups B and/or C), can be applied jointly (e.g. after tank mix) or consecutively.

The uracilpyridines of formula (I) are suitable as herbicides. They are suitable as such, as an appropriately formulated composition (agrochemical composition) or as an herbicidal composition in combination with at least one further compound selected from the herbicidal active compounds B (component B) and safeners C (component C).

The uracilpyridines of formula (I), or the agrochemical compositions and/or herbicidal compositions comprising the uracilpyridines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The uracilpyridines of formula (I), or the agrochemical compositions and/or the herbicidal compositions comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The uracilpyridines of formula (I), or the agrochemical compositions and/or the herbicidal compositions comprising them, may also be applied by the low-volume or the ultra-low-volume method, or in the form of microgranules.

Application of the uracilpyridines of formula (I), or the agrochemical compositions and/or the herbicidal compositions comprising them, can be done before, during and/or after, preferably during and/or after, the emergence of the undesirable plants.

The uracilpyridines of formula (I), or the agrochemical compositions and/or the herbicidal compositions comprising them, can be applied pre-, post-emergence or pre-plant, or together with the seed of a crop plant. It is also possible to apply the uracilpyridines of formula (I), or the agrochemical compositions and/or the herbicidal compositions comprising them, by applying seed, pretreated with the uracilpyridines of formula (I), or the agrochemical compositions and/or the herbicidal compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the uracilpyridines of formula (I), or the agrochemical compositions and/or the herbicidal compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the uracilpyridines of formula (I), or the agrochemical compositions and/or the herbicidal compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the uracilpyridines of formula (I), component B and, if appropriate, component C without formulation auxiliaries, are, depending on the kind of effect desired, from 0.001 to 2 kg per ha, preferably from 0.005 to 2 kg per ha, more preferably from 0.05 to 1.5 kg per ha and in particular from 0.1 to 1 kg per ha.

In another embodiment of the invention, the application rate of the uracilpyridines of formula (I), component B and, if appropriate, component C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the uracilpyridines of formula (I) according to the present invention (total amount of uracilpyridines of formula (I)) are from 0.1 g/ha to 3000 g/ha, preferably 1 g/ha to 1000 g/ha, depending on the control target, the season, the target plants and the growth stage.

In another preferred embodiment of the invention, the application rates of the uracilpyridines of formula (I) are in the range from 0.1 g/ha to 5000 g/ha and preferably in the range from 0.5 g/ha to 2500 g/ha or from 2.5 g/ha to 2000 g/ha.

In another preferred embodiment of the invention, the application rate of the uracilpyridines of formula (I) is 0.1 to 1000 g/ha, preferably 0.5 to 750 g/ha, more preferably 2.5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the uracilpyridines of formula (I), component B and, if appropriate, component C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In case of herbicidal compositions according to the present invention it is immaterial whether the uracilpyridines of formula (I), and the further component B and/or the component C are formulated and applied jointly or separately.

In the case of separate application it is of minor importance, in which order the application takes place. It is only necessary, that the uracilpyridines of formula (I), and the further component B and/or the component C are applied in a time frame that allows simultaneous action of the active ingredients on the plants, preferably within a time-frame of at most 14 days, in particular at most 7 days.

Depending on the application method in question, the uracilpyridines of formula (I), or the agrochemical compositions and/or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium*

*herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum*, (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*S. vulgare*), *Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

The uracilpyridines of formula (I) according to the invention, or the agrochemical compositions and/or herbicidal compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or H MG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the CryIAb toxin), YieldGard® Plus (corn cultivars producing CryIAb and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the CryIAc toxin), Bollgard® I (cotton cultivars producing the CryIAc toxin), Bollgard® II (cotton cultivars producing CryIAc and Cry2Ab2 toxins); VIPCOT® (cotton cultivars producing a VIPtoxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the CryIAb toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the CryIAc toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the uracilpyridines of formula (I) according to the invention, or the agrochemical compositions and/or herbicidal compositions comprising them, are also suitable for the defoliation and/or desiccation of plant parts, for which crop plants such as cotton, potato, oilseed rape, sunflower, soybean, field beans, cereals (e.g. wheat, barley, sorghum, millet, oats, rye and triticale), corn and lentils; preferably cotton, potato, oilseed rape, sunflower, soybean or field beans, in particular cotton, are suitable. In this regard, agrochemical compositions and/or herbicidal compositions for the desiccation and/or defoliation of plants, processes for preparing these agrochemical compositions and/or herbicidal compositions and methods for desiccating and/or defoliating plants using the uracilpyridines of formula (I) have been found.

As desiccants, the uracilpyridines of formula (I) are particularly suitable for desiccating the above-ground parts of crop plants such as potato, oilseed rape, sunflower and soybean, but also cereals (e.g. wheat, barley, sorghum, millet, oats, rye and triticale), corn and lentils. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

Moreover, it has been found, that the uracilpyridines of formula (I), or the agrochemical compositions and/or herbicidal compositions comprising the uracilpyridines of formula (I), very efficiently also control PPO resistant weeds.

Accordingly, the present invention also provides a method for controlling the growth of PPO resistant weeds, which comprises contacting such weeds, parts of it, its propagation material or its habitat with uracilpyridines of formula (I), wherein the PPO resistant weeds are weeds, that are resistant to PPO-inhibiting herbicides except the uracilpyridines of formula (I).

The invention particularly relates to a method for controlling PPO resistant weeds in crops which comprises applying uracilpyridines of formula (I) to crops, where said PPO herbicide resistant weeds occur or might occur.

As used herein, the terms "PPO inhibitor", "PPO inhibitor herbicide", "PPO-inhibiting herbicide", "protoporphyrinogen IX oxidase inhibitor herbicide", "protoporphyrinogen IX oxidase-inhibiting herbicide", "protoporphyrinogen oxidase inhibitor herbicide" and "protoporphyrinogen oxidase-inhibiting herbicide" are synonyms and refer to a herbicide that inhibits the enzyme protoporphyrinogen oxidase of a plant.

As used herein, the terms "PPO inhibitor herbicide resistant weed", "PPO-inhibiting herbicide resistant weed","PPO inhibitor resistant weed", "PPO resistant weed", "protoporphyrinogen IX oxidase inhibitor herbicide resistant weed", "protoporphyrinogen IX oxidase inhibiting herbicide resistant weed", "protoporphyrinogen oxidase inhibitor herbicide resistant weed", and "protoporphyrinogen oxidase inhibiting herbicide resistant weed" are synonyms and refer to a plant that, in relation to a treatment with an appropriate or over-appropriate rate of PPO-inhibiting herbicide application, has inherited, developed or acquired an ability (1) to survive that treatment, if it is one that is lethal to (i.e. eradicates) the wild type weed; or (2) to exhibit significant vegetative growth or thrive after that treatment, if it is one that suppresses groth of the wild-type weed.

Effective weed control is defined as at least 70% weed suppresison or eradication from the crop, or as at least 70% weed plant phototixicty, as determined 2 weeks after treatment.

Thus, PPO resistant weeds are weeds, which are not controlled by the application of PPO inhibitors except the uracilpyridines of formula (I), whereas the respective sensitive biotype is controlled at that use rate.

Here, "not controlled" means that in a visual rating the weed control (herbicidal effect) is <70% of weed suppression or eradication as determined 2 weeks after treatment; and "controlled" means that in a visual rating the weed control is >90% of weed suppression or eradication as determined 2 weeks after treatment.

Preferably, PPO resistant weeds are weeds, which are not controlled (i.e. in a visual rating the weed control is <70% of weed suppression or eradication as determined 2 weeks after treatment) by the application of PPO-inhibiting herbicides except the uracilpyridines of formula (I).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin, fomesafen and lactofen.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from fomesafen and lactofen.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides except the uracilpyridines of formula (I), whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from azafenidin, fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably PPO-resistant weeds are those classified as being "PPO resistant" and thus listed according to Anonymous: List of herbicide resistant weeds by herbicide mode of action—weeds resistant to PPO-inhibitors (URL: http://www.weedscience.org/summary/MOA.aspx).

Particularly preferred the PPO resistant weeds are selected from the group consisting of *Acalypha* ssp., *Amaranthus* ssp., *Ambrosia* ssp., *Avena* ssp., *Conyza* ssp., *Descurainia* ssp., *Euphorbia* ssp. and *Senecio* ssp.;
especially preferred *Amaranthus* ssp., *Ambrosia* ssp. and *Euphorbia* ssp.;
more preferred *Amaranthus* ssp. and *Ambrosia* ssp.

Also particularly preferred the PPO resistant weeds are selected from the group consisting of Asian copperleaf (*Acalypha australis*), smooth pigweed (*Amaranthus hybridus*), Palmer amaranth (*Amaranthus Palmeri*), redroot pigweed (*Amaranthus retroflexus*), tall/common waterhemp (*Amaranthus tuberculatus, Amaranthus rudis*, or *Amaranthus tamariscinus*), common ragweed (*Ambrosia artemisiifolia*), wild oat (*Avena fatua*), fleabane (*Conyza ambigua*), marestail (*Conyza Canadensis*), flixweed (*Descurainia Sophia*), wild poinsettia (*Euphorbia heterophylla*) and eastern groundsel (*Senecio vernalis*);

especially preferred smooth pigweed (*Amaranthus hybridus*), Palmer amaranth (*Amaranthus Palmeri*), redroot pigweed (*Amaranthus retroflexus*), tall/common waterhemp (*Amaranthus tuberculatus* or *Amaranthus rudis*), common ragweed (*Ambrosia artemisiifolia*) and wild poinsettia (*Euphorbia heterophylla*);

more preferred tall/common waterhemp (*Amaranthus tuberculatus, Amaranthus rudis* or *Amaranthus tamariscinus*) and common ragweed (*Ambrosia artemisiifolia*).

Most PPO resistant weeds, in particular the biotypes of *Amaranthus tuberculatus*, are resistant due to a codon deletion on the nuclear-encoded gene PPX2L that codes for the PPO enzyme which is dual-targeted to the mitochondria and the chloroplasts. This results in a loss of the glycine amino acid in position 210 (see e.g. B. G. Young et al, Characterization of PPO-Inhibitor-Resistant Waterhemp (*Amaranthus tuberculatus*) Response to Soil-Applied PPO-Inhibiting Herbicides, Weed Science 2015, 63, 511-521).

A second type of mutation, in particular in a resistant biotype of *Ambrosia artemisiifolia*, was identified as a mutation that expressed a R98L change of the PPX2 enzyme (S. L. Rousonelos, R. M. Lee, M. S. Moreira, M. J. Van-Gessel, P. J. Tranel, Characterization of a Common Ragweed (*Ambrosia artemisiifolia*) Population Resistant to ALS- and PPO-Inhibiting Herbicides, Weed Science 60, 2012, 335-344.).

Accordingly, preferably PPO-resistant weeds are weeds whose Protox enzyme is resistant to the application of PPO inhibitors due to a mutation that is expressed as a ΔG210 or R98L change of said Protox enzyme or equivalents to the PPX2L or PPX2 respectively, in particular that is expressed as a ΔG210 or R98L change of said Protox enzyme.

The preparation of the phenyluracils of formula (I) is illustrated by examples; however, the subject matter of the present invention is not limited to the examples given.

A Preparation Examples

Example 1

Ethyl 2-[2-[[3-chloro-5-fluoro-6-[3-methyl-2,6-dioxo-4-(trifluoromethyl)pyrimidin-1-yl]-2-pyridyl]oxy]phenoxy]acetate

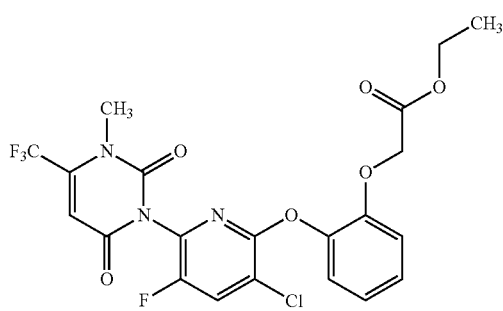 [SMILES: CCOC(=O)COc1ccccc1Oc1nc(-n2c(=O)cc(C(F)(F)F)n(C)c2=O)c(F)cc1Cl]

Example 1.1: 2-Azido-6-(2-benzyloxyphenoxy)-5-chloro-3-fluoro-pyridine

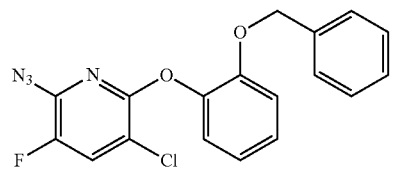 [SMILES: [N-]=[N+]=Nc1nc(Oc2ccccc2OCc2ccccc2)c(Cl)cc1F]

To a solution of 5.0 g (29 mmol) 3-chloro-2,5,6-trifluoropyridine (CAS 2879-42-7) in 50 mL DMSO was added 2.1 g (33 mmol) NaN$_3$ and the solution was stirred at room temperature for 3 hours. Then 19.5 g (60 mmol) Cs$_2$CO$_3$ was added followed by a solution of 6.2 g (31 mmol) 2-(Benzyloxy)phenol in 40 mL DMSO. The mixture was stirred at room temperature for 16 hours, water was added and the mixture was extracted with ethyl acetate. The organic layer was separated, washed with brine, dried over anhydrous Na$_2$SO$_4$, filtered and the solvent was removed under reduced pressure. The crude material (15 g) was used without further purification in the next step.

[M+H]=371.0; Rt=1.368 min

Example 1.2: 2-Amino-6-(2-benzyloxyphenoxy)-5-chloro-3-fluoro-pyridine

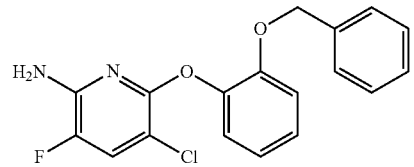 [SMILES: Nc1nc(Oc2ccccc2OCc2ccccc2)c(Cl)cc1F]

To a solution of 15 g of compound 1.1 in THF was added 9.7 g (150 mmol) zinc and 100 mL semi-saturated aq. NH$_4$Cl dropwise at 0° C. The mixture was stirred for 16 hours at room temperature, filtered and the filter cake was washed with ethyl acetate. The filtrate was extracted with ethyl acetate, the combined organic layer was dried over anhydrous Na$_2$SO$_4$, filtered and the solvent was removed under reduced pressure. The crude material was purified by silica gel column (petrol ether/ethyl acetate) to give 8.8 g (25.6 mmol, 88% over 2 steps from 3-chloro-2,5,6-trifluoropyridine) of the desired product 1.2.

[M+H]=345.0; Rt=1.232 min

Example 1.3: Ethyl N-[6-(2-benzyloxyphenoxy)-5-chloro-3-fluoro-2-pyridyl]carbamate

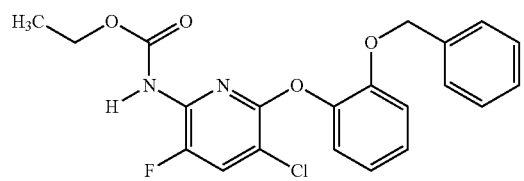 [SMILES: CCOC(=O)Nc1nc(Oc2ccccc2OCc2ccccc2)c(Cl)cc1F]

To a solution of 8.8 g (25.6 mmol) of compound 1.2 in 80 ml dichloromethane was added 3 g (38 mmol) pyridine followed by 4 g (37.5 mmol) ethyl chloroformate. The mixture was stirred at 25° C. for 20 hours, diluted with water and extracted with dichloromethane. The combined organic layer was washed with brine, dried over anhydrous Na$_2$SO$_4$ and concentrated to give 14.4 g of a mixture of carbamate 1.3 and the di-substituted derivative. The crude mixture (12.4 g) was dissolved in 200 mL ethanol and aqueous NaOH (1M) was added dropwise at 0° C. with stirring. The mixture was stirred at 15° C. for 6 hours, diluted with brine and extracted with ethyl acetate. The combined organic layer was dried over anhydrous Na$_2$SO$_4$, filtered and the solvent was removed under reduced pressure. The crude product was purified by column chromatography on silica (petrol ether/ethyl acetate) to give 6.6 g (15.9 mmol, 62%) of the desired compound 1.3.

[M+H]=417.1; Rt=1.293 min

Example 1.4: 3-[6-(2-benzyloxyphenoxy)-5-chloro-3-fluoro-2-pyridyl]-6-(trifluoromethyl)-1H-pyrimidine-2,4-dione

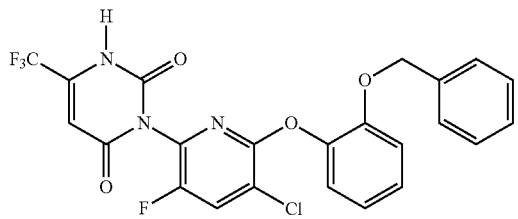 [SMILES: O=c1cc(C(F)(F)F)[nH]c(=O)n1-c1nc(Oc2ccccc2OCc2ccccc2)c(Cl)cc1F]

To a solution of 1.7 g (43 mmol) NaH in NMP (N-Methyl-2-pyrrolidone) (60 mL) at 0° C. was added 6 g (14 mmol) of compound 1.3 and the mixture was stirred for 30 minutes at 35° C. Then 3.9 g (21 mmol) of ethyl (E)-3-amino-4,4,4-trifluoro-but-2-enoate (CAS: 372-29-2) was added and the reaction mixture was stirred at 100° C. for 3 days. The resulting mixture was quenched with ice water, acidified to pH=2 by using 6N HCl and extracted with ethyl acetate. The combined organic layer was washed with brine, dried over anhydrous Na$_2$SO$_4$, concentrated and directly used in the next step.

[M+H]=508.0; Rt=1.240 min

Example 1.5: 3-[6-(2-benzyloxyphenoxy)-5-chloro-3-fluoro-2-pyridyl]-1-methyl-6-(trifluoromethyl)-pyrimidine-2,4-dione

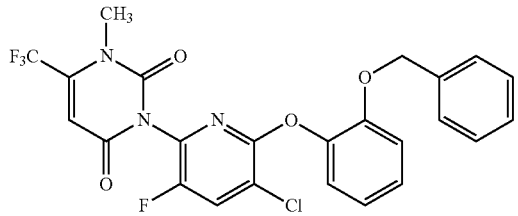 [SMILES: Cn1c(C(F)(F)F)cc(=O)n(-c2nc(Oc3ccccc3OCc3ccccc3)c(Cl)cc2F)c1=O]

To a solution of 6.5 g (12.8 mmol) of compound 1.4 in 65 mL acetonitrile was added 5.3 g (38 mmol) K$_2$CO$_3$ followed by 7.3 g (51 mmol) methy iodide at 0° C. with stirring. The mixture was stirred at 15° C. for 16 hours, then water (80 mL) was added and the pH was adjusted to pH=5 by using 2N HCl. The mixture was extracted with ethyl acetate, the combined organic layer was washed with brine and dried over anhydrous Na$_2$SO$_4$, filtered and the solvent was removed under reduced pressure yielding 7 g of the crude product 1.5, which was used without further purification.

$^1$H-NMR (CDCl$_3$, ppm): 7.63 (d, J=7.28 Hz, 1H); 7.21-7.25 (m, 4H); 7.12-7.17 (m, 2H); 6.98 (t, J=7.03 Hz, 3H); 6.26 (s, 1H); 4.99 (s, 2H); 3.47 (s, 3H). [M+H]=522.0; Rt=1.323 min Example 1.6: 3-[5-Chloro-3-fluoro-6-(2-hydroxyphenoxy)-2-pyridyl]-1-methyl-6-(trifluoromethyl) pyrimidine-2,4-dione

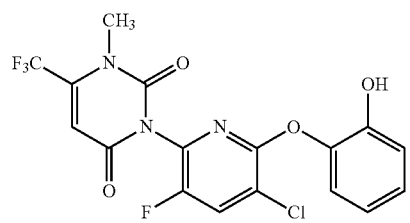 [SMILES: Cn1c(C(F)(F)F)cc(=O)n(-c2nc(Oc3ccccc3O)c(Cl)cc2F)c1=O]

To a solution of 7 g (13.4 mmol) of compound 1.5 in 70 mL xylene was added 3.6 g (26 mmol) solid AlCl$_3$ at 15° C. with stirring. The mixture was stirred at 130° C. for 16 hours and after cooling to 15° C., ice-water was added to the mixture. After separation of the xylene layer, the water phase was extracted with ethyl acetate, the combined organic layer was dried over anhydrous Na$_2$SO$_4$, filtered and the solvent was removed under reduced pressure. The crude product was purified by column chromatography on silica gel (petrol ether/ethyl acetate) to give 3.2 g (7.4 mmol, 55%) of the desired product 1.6.

$^1$H-NMR (CDCl$_3$, ppm): 7.80 (d, J=7.26 Hz, 1H); 7.03-7.19 (m, 3H); 6.93 (dt, J=7.68 Hz, J=1.7 Hz, 1H); 6.3 (s, 1H); 5.6 (s, 1H); 3.5 (s, 3H).

[M+H]=431.9; Rt=1.077 min

Example 1.7: Ethyl 2-[2-[[3-chloro-5-fluoro-6-[3-methyl-2,6-dioxo-4-(trifluoromethyl)pyrimidin-1-yl]-2-pyridyl]oxy]phenoxy]acetate (=Example 1)

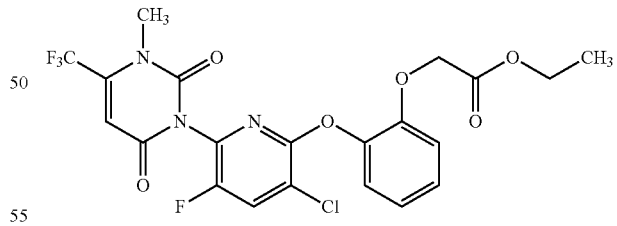

To a solution of 0.2 g (0.46 mmol) of compound 1.6 in 10 mL dry acetonitrile was added 0.19 g (1.3 mmol) K$_2$CO$_3$ at 0° C. followed by dropwise addition of 0.15 g (0.92 mmol) ethyl bromoacetate. The mixture was stirred at 15° C. for 16 hours, diluted with 15 ml water and extracted with ethyl acetate. The combined organic layer was washed with brine, dried over anhydrous Na$_2$SO$_4$, filtered and the solvent was removed under reduced pressure. The crude product was purified by reversed phase preparative HPLC (acetonitrile/water containing trifluoroacetic acid) to give 0.16 g (0.31 mmol, 67%) of the desired title compound.

¹H-NMR (CDCl₃, ppm): 7.76 (d, J=7.28 Hz, 1H); 7.22 (d, J=7.72 Hz, 1H); 7.17 (t, J=7.83 Hz, 1H); 6.99-7.06 (m, 1H); 6.88 (d, J=7.94 Hz, 1H); 6.25 (s, 1H); 4.49 (s, 2H); 4.19 (q, J=7.20 Hz, 2H); 3.47 (s, 3H); 1.25 (t, J=7.17 Hz, 3H).

[M+H]=518.0; Rt=1.217 min

Recrystallization from ethanol provides the title compound in a crystalline form A.

The crystalline form A of example 1 displays a thermogram with a characteristic melting peak in the range from 96 to 108° C. The melting point, determined as the onset of the melting peak, typically lies in the range from about 100 to 106° C. The values quoted here relate to values determined by differential calorimetry (differential scanning calorimetry, DSC). The melting points were determined using DSC with a Mettler Toledo DSC 823e/700/229 module. The samples were placed in glass standard pans. The sample size in each case was 1 to 20 mg. The heating rate was 2.50 K/min. The samples were purged with a stream of nitrogen during the experiment. The melting point was determined as the extrapolated peak onset temperature (also called onset temperature) defined by the point of intersection of the tangent at the half height of the melting peak, on the principal side of the peak with the linelarily extrapolated initial base line.

The form A was investigated by powder X-ray diffraction (PXRD). PXRD was carried out with a Panalytical X'Pert Pro X-ray diffractometer using CuK$_\alpha$ radiation in reflection geometry (Bragg-Brentano). The powder is placed in a silicon single crystal sample holder of 0.2 mm depth and gently and precisely flattened. The tube voltage is 45 kV and current is 40 mA. The PXRD data are collected at room temperature in the range from 2θ=3.0°-40.0° with increments of e.g. 0.017° and measurement time of 19.7 s/step.

The PXRD pattern is displayed in FIG. 1. Characteristic peak positions are listed in table 2:

TABLE 2

Peak positions observed in the PXRD pattern of example 1 in its form A:

| °θ, Cu Kα radiation | d [Å] |
|---|---|
| 5.5 ± 0.2 | 16.2 ± 0.6 |
| 7.4 ± 0.2 | 12.0 ± 0.3 |
| 7.8 ± 0.2 | 11.4 ± 0.3 |
| 10.0 ± 0.2 | 8.9 ± 0.2 |
| 10.3 ± 0.2 | 8.6 ± 0.2 |
| 11.2 ± 0.2 | 7.9 ± 0.1 |
| 11.8 ± 0.2 | 7.5 ± 0.1 |
| 17.1 ± 0.2 | 5.19 ± 0.06 |
| 18.0 ± 0.2 | 4.92 ± 0.06 |
| 18.8 ± 0.2 | 4.73 ± 0.05 |
| 19.3 ± 0.2 | 4.59 ± 0.05 |
| 20.9 ± 0.2 | 4.24 ± 0.04 |
| 21.5 ± 0.2 | 4.13 ± 0.04 |
| 21.9 ± 0.2 | 4.06 ± 0.04 |
| 23.0 ± 0.2 | 3.87 ± 0.04 |
| 26.3 ± 0.2 | 3.39 ± 0.03 |

Most prominent peaks are 5.5±0.2, 7.4±0.2, 7.8±0.2, 10.0±0.2, 11.2±0.2, 17.1±0.2, 18.0±0.2, 21.5±0.2, 21.9±0.2 and 26.3±0.2° 2θ.

Studies on single crystals of form A demonstrate that the underlying crystal structure is triclinic. The unit cell has the space group P$\bar{1}$. The characteristic data of the crystal structure (determined at 100 K) are compiled in the following table 3:

TABLE 3

| Parameter | Example 1 form A |
|---|---|
| class | triclinic |
| space group | P$\bar{1}$ |
| a | 11.1534(8) Å |
| b | 12.4573(9) Å |
| c | 16.8546(12) Å |
| α | 72.960(3)° |
| β | 82.651(3)° |
| γ | 83.283(3)° |
| volume | 2212.8(3) Å³ |
| Z | 4 |
| density (calculated) | 1.554 g/cm³ |
| wavelength | 1.54178 Å |
| largest diff peak and hole | 0.716/−0.362 eÅ⁻³ | a, b, c = unit cell length
α, β, γ = unit cell angle
Z = number of molecules in the unit cell Example 2

Methyl 2-[2-[[3-chloro-5-fluoro-6-[3-methyl-2,6-dioxo-4-(trifluoromethyl)pyrimidin-1-yl]-2-pyridyl]oxy]phenoxy]-2-methoxy-acetate

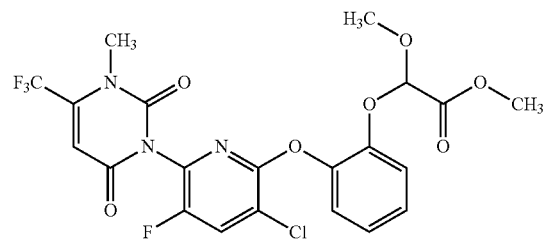 [SMILES: COC(=O)C(OC)Oc1ccccc1Oc1nc(-n2c(=O)cc(C(F)(F)F)n(C)c2=O)c(F)cc1Cl]

To a solution of 2.5 g (5.8 mmol) of compound 1.6 in 20 mL dry acetonitrile was added 2.2 g (16 mmol) K₂CO₃ over 10 minutes at 0° C. under N₂ with stirring. Then 1.4 g (7.5 mmol) of methyl 2-bromo-2-methoxy-acetate (CAS: 5193-96-4) was added dropwise to the mixture, which was stirred at 15° C. for 16 hours. The reaction mixture was filtered and the filter cake was washed with ethyl acetate. The filtrate was concentrated and the crude product was purified by reversed phase preparative HPLC (acetonitrile/water containing trifluoroacetic acid) to give 0.97 g (1.8 mmol, 31%) of the desired compound 2.

¹H-NMR (CDCl₃, ppm): 7.77 (d, J=7.03 Hz, 1H); 7.15-7.27 (m, 3H); 7.07-7.13 (m, 1H); 6.24 (s, 1H); 5.40 (d, J=8.53 Hz, 1H); 3.70 (s, 3H); 3.46 (br. s., 3H); 3.39 (s, 3H).

[M+H]=534.1; Rt=1.233 min

Example 3

2-[2-[[3-chloro-5-fluoro-6-[3-methyl-2,6-dioxo-4-(trifluoromethyl)pyrimidin-1-yl]-2-pyridyl]oxy]phenoxy]acetic acid

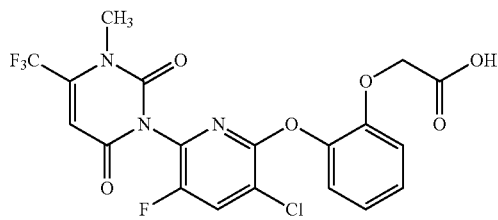 [SMILES: Cn1c(C(F)(F)F)cc(=O)n(-c2nc(Oc3ccccc3OCC(=O)O)c(Cl)cc2F)c1=O]

A solution of 3.5 g (6.8 mmol) of ethyl 2-[2-[[3-chloro-5-fluoro-6-[3-methyl-2,6-dioxo-4-(trifluoromethyl)pyrimidin-1-yl]-2-pyridyl]oxy]phenoxy]acetate (example 1) in 20 ml aqueous conc. HCl and 20 mL of glacial acetic acid was stirred at 60° C. for 3 hours. Water was added and the mixture was extracted with ethyl acetate. The combined organic layer was washed with water and brine, dried over anhydrous Na$_2$SO$_4$, filtered and the solvent was removed under reduced pressure to give 2.3 g (4.7 mmol, 69%) of 2-[2-[[3-chloro-5-fluoro-6-[3-methyl-2,6-dioxo-4-(trifluoromethyl)pyrimidin-1-yl]-2-pyridyl]oxy]phenoxy]acetic acid.

$^1$H-NMR (CDCl$_3$, ppm): 7.77 (d, J=7.21 Hz, 1H); 7.15-7.25 (m, 2H); 7.06 (dt, J=7.74 Hz, J=1.46 Hz, 1H); 6.91 (dd, J=8.15 Hz, J=1.44 Hz, 1H); 6.25 (s, 1H); 4.55 (s, 2H), 3.45 (s, 3H).

[M+H]=490.0; Rt=1.189 min

Example 4

2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide

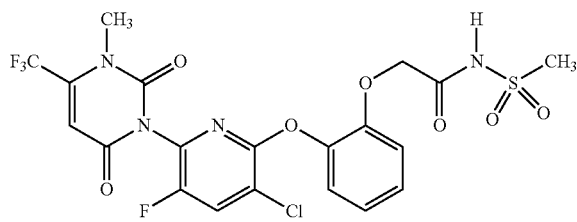 [SMILES: Cn1c(C(F)(F)F)cc(=O)n(-c2nc(Oc3ccccc3OCC(=O)NS(C)(=O)=O)c(Cl)cc2F)c1=O]

To a solution of 0.7 g (1.5 mmol) 2-[2-[[3-chloro-5-fluoro-6-[3-methyl-2,6-dioxo-4-(trifluoromethyl)pyrimidin-1-yl]-2-pyridyl]oxy]phenoxy]acetic acid in 20 mL dry THF under an Argon atmosphere was added 1.0 g (7.4 mmol) diisopropylethyl amine followed by 0.8 g (3.0 mmol) 2-chloro-1-methyl-pyridinium chloride (CAS: 112277-86-8) and 0.2 g (2.2 mmol) methansulfonamide (CAS: 3144-09-0). The suspension was stirred at room temperature for 16 hours. Then water was added, the mixture was extracted with ethyl acetate, the combined organic layer was washed with water and brine, dried over anhydrous Na$_2$SO$_4$, filtered and the solvent was removed under reduced pressure. The crude product was purified by column chromatography on silica (cyclohexane/ethyl acetate) to give 0.1 g (0.24 mmol, 16%) of the desired product.

$^1$H-NMR (CDCl$_3$, ppm): 8.6 (s, 1H); 7.8 (d, 1H); 7.2-7.3 (m, 2H); 7.1 (m, 1H); 6.9 (d, 1H); 6.3 (s, 1H); 4.5 (s, 2H); 3.5 (s, 3H); 3.1 (s, 3H).

[M+H]=567.1; Rt=1.123 min

Example 5 ethyl 2-[2-[[3,5-difluoro-6-[3-methyl-2,6-dioxo-4-(trifluoromethyl)pyrimidin-1-yl]-2-pyridyl]oxy]phenoxy]acetate

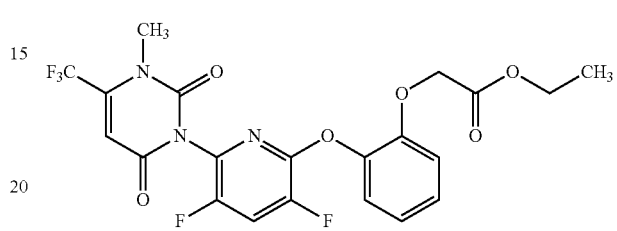

Example 5.1: Ethyl (Z)-3-(dimethylcarbamoylamino)-4,4,4-trifluoro-but-2-enoate

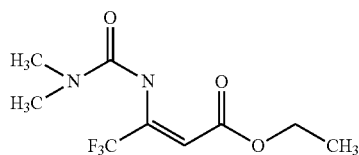

To a solution of 104 g (2.73 mol) NaH in 600 mL dry DMF under a N$_2$-atmosphere was added 233 g (2.18 mol) N,N-dimethylcarbamoyl chloride (CAS: 79-44-7) dissolved in 200 mL dry DMF dropwise over 1 hour at 0-5° C. with stirring. Then 200 g (1.09 mol) ethyl (Z)-3-amino-4,4,4-trifluoro-but-2-enoate (CAS: 372-29-2) dissolved in 200 mL dry DMF was added dropwise at a temperature of 0-5° C. over 1 hour with stirring. The mixture was stirred at room temperature for another 2 hours and then poured into ice-water. The mixture was extracted with ethyl acetate, the combined organic layer was washed with brine, dried over anhydrous Na$_2$SO$_4$, filtered and the solvent was removed under reduced pressure. The crude product was purified by column chromatography on silica (petrol ether/ethyl acetate) to give 170 g (0.67 mol, 64%) of the desired product 5.1.

Example 5.2: 2-(dimethylamino)-4-(trifluoromethyl)-1,3-oxazin-6-one

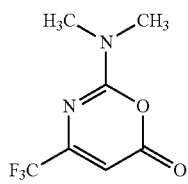

To a solution of 170 g (0.67 mol) of compound 5.1 in 102 mL POCl$_3$ was added 139 g (0.67 mol) PCl$_5$ at 0° C. in three portions with 15 minutes stirring in between and the mixture was stirred another hour at 0° C. The mixture was then stirred at room temperature for another 3 hours. The reaction mixture was poured into 250 mL ice water and the precipitate was collected via filtration and dried to give 84 g (0.40 mol, 60%) of the desired product 5.2.

¹H-NMR (CDCl₃, ppm): 5.9 (s, 1H); 3.2 (d, J=19.58 Hz, 6H).

[M+H]=209.1; Rt=0.980 min

Example 5.3: 6-(trifluoromethyl)-3-(3,5,6-trifluoro-2-pyridyl)-1H-pyrimidine-2,4-dione

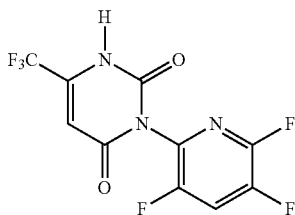 [SMILES: O=c1cc(C(F)(F)F)[nH]c(=O)n1-c1nc(F)c(F)cc1F]

A solution of 1.5 g (15.2 mmol) 2-amino-3,5,6-trifluoropyridine (CAS 3534-50-7) and 3.1 g (15.2 mmol) of compound 5.2 in 15 mL glacial acetic acid was stirred at 95° C. for 16 hours. Then water was added and the mixture was extracted with ethyl acetate. The combined organic layer was washed with water and brine, dried over anhydrous Na₂SO₄, filtered and the solvent was removed under reduced pressure to give 3.9 g (12.5 mmol, 82%) of the desired product 5.3.

¹H-NMR (CDCl₃, ppm): 7.6 (m, 1H); 6.25 (s, 1H).

[M+H]=312.0; Rt=0.873 min

Example 5.4: 1-methyl-6-(trifluoromethyl)-3-(3,5,6-trifluoro-2-pyridyl)pyrimidine-2,4-dione

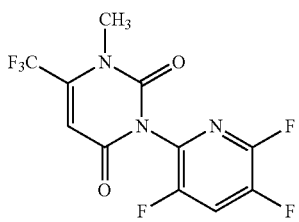 [SMILES: Cn1c(C(F)(F)F)cc(=O)n(-c2nc(F)c(F)cc2F)c1=O]

To a solution of 35 g (0.11 mol) of compound 5.3 in 400 mL DMF was added 31 g (0.23 mol) K₂CO₃ followed by 32 g (0.23 mol) methyl iodide at 0° C. and the mixture was stirred at room temperature for 16 hours. Then water was added, the mixture was extracted with ethyl acetate, the combined organic layer was washed with water and brine, then dried over anhydrous Na₂SO₄, filtered and the solvent was removed under reduced pressure. The crude product was purified by column chromatography on silica (petrol ether/ethyl acetate) to give 15 g (46 mmol, 42%) of the desired product 5.4.

¹H-NMR (CDCl₃, ppm): 7.6 (q, J=7.06 Hz, 1H); 6.4 (s, 1H); 3.6 (s, 3H).

[M+H]=325.9; Rt=1.058 min

Example 5.5: 3-[3,5-Difluoro-6-(2-methoxyphenoxy)-2-pyridyl]-1-methyl-6-(trifluoromethyl)pyrimidine-2,4-dione

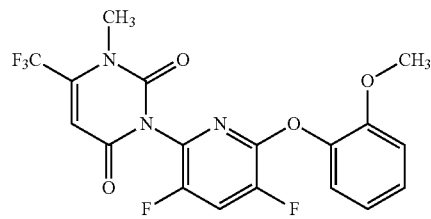 [SMILES: COc1ccccc1Oc1nc(-n2c(=O)cc(C(F)(F)F)n(C)c2=O)c(F)cc1F]

To a solution of 5 g (0.04 mol) of 2-methoxyphenol (CAS: 90-05-1) in 400 mL THF was added 6.9 g (0.06 mol) KO^tBu at 0° C. over 5 minutes with stirring. Then 10 g (31 mmol) of compound 5.4 was added, the mixture was heated to 80° C. for 2 hours and then poured into ice water. The mixture was extracted with ethyl acetate, the combined organic layer was washed with brine, dried over anhydrous Na₂SO₄, filtered and the solvent was removed under reduced pressure. The crude product was purified by column chromatography on silica (petrol ether/ethyl acetate) to give 9.3 g (22 mmol, 71%) of the desired product 5.5.

¹H-NMR (CDCl₃, ppm): 7.5 (t, J=7.78 Hz, 1H); 7.2-7.3 (m, 2H); 6.9-7.0 (m, 2H); 6.3 (s, 1H); 3.7 (s, 3H).

[M+H]=430.0; Rt=1.197 min

Example 5.6: 3-[3,5-Difluoro-6-(2-hydroxyphenoxy)-2-pyridyl]-1-methyl-6-(trifluoromethyl)pyrimidine-2,4-dione

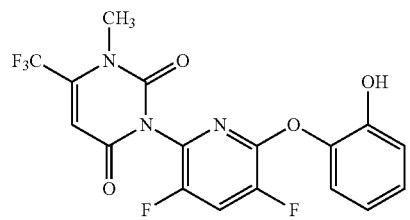 [SMILES: Cn1c(C(F)(F)F)cc(=O)n(-c2nc(Oc3ccccc3O)c(F)cc2F)c1=O]

To a solution of 9 g (20 mmol) of compound 5.5 in 200 mL dichloromethane cooled to −78° C. was added 7.9 g (30 mmol) BBr₃ in 50 mL dichloromethane. The mixture was warmed to room temperature over 5 hours, poured into ice water and extracted with dichloromethane. The combined organic layer was washed with brine, dried over anhydrous Na₂SO₄, filtered and the solvent was removed under reduced pressure to give the desired product 5.6 which was used without further purification in the next step.

¹H-NMR (CDCl₃, ppm): 7.54 (m, 1H); 7.09-7.18 (m, 2H); 7.00-7.08 (m, 1H); 6.87-6.96 (m, 1H); 6.3 (s, 1H); 5.7 (br. s., 1H); 3.5 (s, 3H).

[M+H]=416.0; Rt=1.117 min

Example 5.7: Ethyl 2-[2-[[3,5-difluoro-6-[3-methyl-2,6-dioxo-4-(trifluoromethyl)pyrimidin-1-yl]-2-pyridyl]oxy]phenoxy]acetate

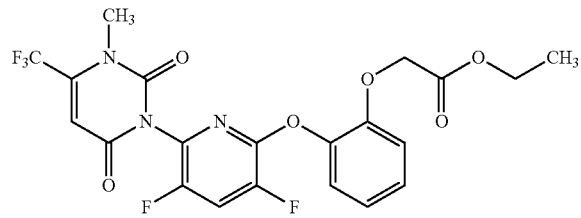 [SMILES: CCOC(=O)COc1ccccc1Oc1nc(-n2c(=O)cc(C(F)(F)F)n(C)c2=O)c(F)cc1F]

To a solution of 9.5 g (22.8 mmol) of compound 5.6 in 300 mL acetonitrile was added 6.3 g (45.7 mmol) $K_2CO_3$ at 0° C. with stirring. Then 7.6 g (45.7 mmol) ethyl bromoacetate (CAS: 105-36-2) was added and the mixture was stirred at 80° C. for 16 hours. Water was added, the mixture was extracted with ethyl acetate, the combined organic layer was dried over anhydrous $Na_2SO_4$, filtered and the solvent was removed under reduced pressure. The crude product was purified by column chromatography on silica (petrol ether/ethyl acetate) and recrystallized from methyl tert-butyl ether and n-hexanes to give 3.9 g (7.8 mmol, 34%) of the desired product 5.7.

$^1$H-NMR (CDCl$_3$, ppm): 7.5 (t, J=7.83 Hz, 1H); 7.2 (d, J=7.50 Hz, 1H); 7.1-7.2 (m, 1H); 7.0 (t, J=7.72 Hz, 1H); 6.9 (d, J=8.16 Hz, 1H); 6.3 (s, 1H); 4.5 (s, 1H); 4.2 (q, J=7.13 Hz, 2H); 3.5 (s, 3H); 1.3 (t, J=7.17 Hz, 3H).

[M+H]=502.2; Rt=1.221 min

Example 6

Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]propanoate

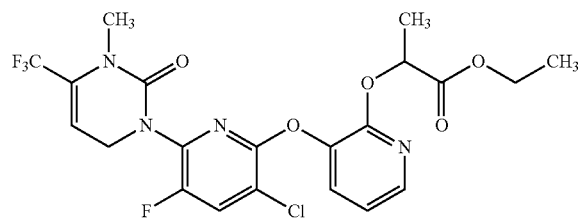 [SMILES: CCOC(=O)C(C)Oc1ncccc1Oc1nc(N2CC=C(C(F)(F)F)N(C)C2=O)c(F)cc1Cl]

To a solution of 0.22 g (1.1 mmol) of ethyl 2-[(3-hydroxy-2-pyridyl)oxy]propanoate (CAS: 353292-83-8) in 4 mL DMSO was added 0.042 g (1.1 mmol) NaH at 15° C. The suspension was stirred for 10 minutes at this temperature before 0.3 g (0.88 mmol) 3-(5-chloro-3,6-difluoro-2-pyridyl)-1-methyl-6-(trifluoromethyl)pyrimidine-2,4-dione was added to the mixture at 15° C. The resulting mixture was stirred at 90-100° C. for 2 hours, poured into water and extracted with ethyl acetate. The combined organic layer was dried over anhydrous $Na_2SO_4$, filtered and the solvent was removed under reduced pressure. The crude product was purified by reversed phase preparative HPLC (acetonitrile/water containing trifluoroacetic acid) to give 0.17 g (0.32 mmol, 36%) of the desired product.

$^1$H-NMR (CDCl$_3$, ppm): 7.9 (d, J=4.52 Hz, 1H); 7.8 (d, J=7.28 Hz, 1H); 7.5 (d, J=7.53 Hz, 1H); 6.9 (t, J=5.52 Hz, 1H); 6.3 (d, J=3.26 Hz, 1H); 5.0-5.1 (m, 1H); 4.2 (q, J=7.11 Hz, 2H); 3.5 (d, J=4.27 Hz, 3H); 1.4 (d, J=7.03 Hz, 3H); 1.2 (t, J=7.15 Hz, 3H).

Example 7

Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate

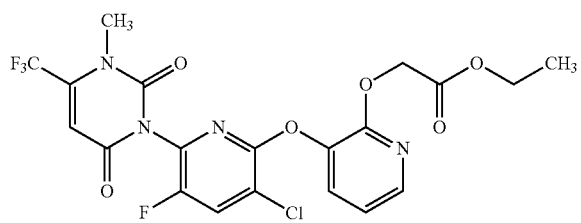

Example 7.1: Ethyl 2-[[3-[(6-azido-3-chloro-5-fluoro-2-pyridyl)oxy]-2-pyridyl]oxy]acetate

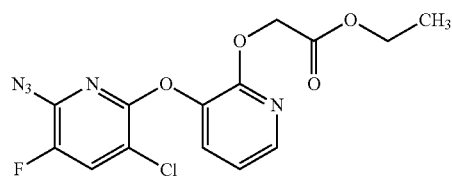 [SMILES: CCOC(=O)COc1ncccc1Oc1nc(N=[N+]=[N-])c(F)cc1Cl]

To a solution of 1.8 g (10.78 mmol) 3-chloro-2,5,6-trifluoropyridine (CAS 2879-42-7) in 20 mL DMSO at room temperature was added 0.77 g (11.8 mmol) sodium azide and the mixture was stirred 3 hours at room temperature. Then a suspension of 2.2 g (11.3 mmol) ethyl 2-[(3-hydroxy-2-pyridyl)oxy]acetate (CAS: 353292-81-6) and 7 g (21.5 mmol) $Cs_2CO_3$ in 10 mL DMSO was added to the above mixture in portions. The resulting mixture was stirred at room temperature for 15 hours, diluted with water and extracted with ethyl acetate. The combined organic layer was washed with brine, dried over anhydrous $Na_2SO_4$, filtered and the solvent was removed under reduced pressure. The crude product 7.1 was used without further purification in the next step.

Example 7.2: Ethyl 2-[[3-[(6-amino-3-chloro-5-fluoro-2-pyridyl)oxy]-2-pyridyl]oxy]acetate

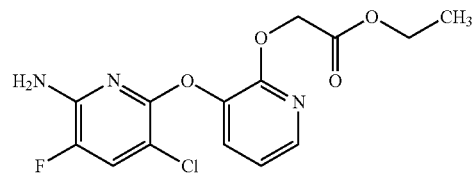 [SMILES: CCOC(=O)COc1ncccc1Oc1nc(N)c(F)cc1Cl]

To a suspension of 4.8 g (13 mmol) of compound 7.1 and 4.3 g (66 mmol) zinc in 100 mL THF was added dropwise 50 mL semi-saturated aqueous NH$_4$Cl solution at 0° C. The mixture was stirred at room temperature for 5 hours, filtered and the filter cake was washed with ethyl acetate. To the filtrate was added 200 mL water, the mixture was extracted with ethyl acetate, the organic layer was dried over anhydrous Na$_2$SO$_4$, filtered and the solvent was removed under reduced pressure. The crude product was purified by column chromatography on silica (petrol ether/ethyl acetate) to give 2.7 g (8 mmol, 61%) of the desired product 7.2.

$^1$H-NMR (CDCl$_3$, ppm): 7.9 (dd, J=4.89 Hz, J=1.51 Hz, 1H); 7.4 (d, J=7.39 Hz, 1H); 7.3 (d, J=9.06 Hz, 1H); 6.9 (dd, J=7.65 Hz, J=4.89 Hz, 1H); 4.9 (s, 2H); 4.5 (s, 2H); 4.2 (q, J=7.15 Hz, 2H); 1.25 (t, J=7.15 Hz, 3H).
[M+H]=428.1; Rt=1.332 min Example 7.3: Ethyl 2-[[3-[[3-chloro-6-[2,4-dioxo-6-(trifluoromethyl)-1H-pyrimidin-3-yl]-5-fluoro-2-pyridyl]oxy]-2-pyridyl]oxy]acetate

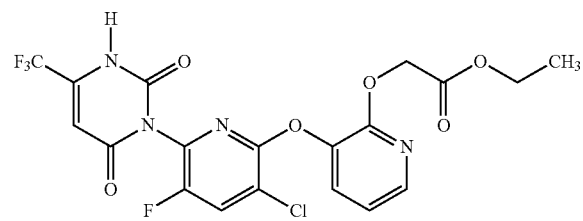 [SMILES: CCOC(=O)COc1ncccc1Oc1nc(-n2c(=O)cc(C(F)(F)F)[nH]c2=O)c(F)cc1Cl]

A solution of 16 g (47 mmol) of compound 7.2 and 9.8 g (47 mmol) of compound 5.2 in 430 mL glacial acetic acid was stirred at 80° C. for 16 hours. Then 9.8 g (47 mmol) of compound 5.2 was added and the mixture stirred at 80° C. for 16 hours. Again 2.9 g (14 mmol) of compound 5.2 was added and the mixture stirred at 80° C. for 16 hours. Again 9.8 g (47 mmol) of compound 5.2 was added and the mixture stirred at 80° C. for 16 hours. Then water was added, the mixture was extracted with ethyl acetate, the combined organic layer was washed with water and brine, dried over anhydrous Na$_2$SO$_4$, filtered and the solvent was removed under reduced pressure. The crude product 7.3 (23 g, 46 mmol, 97%) was used in the next step without further purification.

Example 7.4: Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate

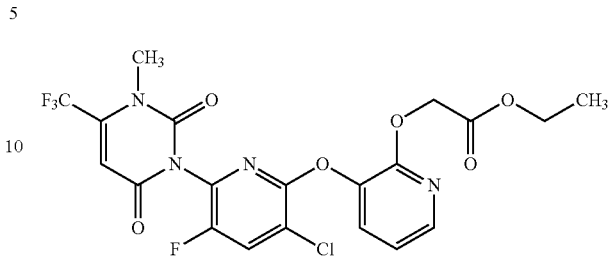

To a solution of 23 g (46 mmol) of the crude compound 7.3 in 500 mL DMF was added 38 g (275 mmol) K$_2$CO$_3$ followed by 26.6 g (187 mmol) methyl iodide at 0° C. The reaction mixture was stirred at room temperature for 16 hours, then 38 g (275 mmol) K$_2$CO$_3$ was added again followed by 26.6 g (187 mmol) methyl iodide and the mixture was again stirred at room temperature for 48 hours. The mixture was poured into water, extracted with ethyl acetate, the combined organic layer was washed with water and brine, dried over anhydrous Na$_2$SO$_4$, filtered and the solvent was removed under reduced pressure. The crude product was purified by reversed phase preparative HPLC (acetonitrile/water containing trifluoroacetic acid) to give 10.3 g (19.9 mmol, 43%) of the desired product ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate.

$^1$H-NMR (CDCl$_3$, ppm): 7.96 (d, J=3.97 Hz, 1H); 7.76 (d, J=7.50 Hz, 1H); 7.49 (d, J=7.06 Hz, 1H); 6.95 (dd, J=7.50 Hz, J=5.29 Hz, 1H); 6.26 (s, 1H) 4.79 (s, 2H); 4.19 (q, J=7.06 Hz, 2H); 3.48 (s, 3H); 1.24 (t, J=7.06 Hz, 3H).
[M+H]=519.0; Rt=1.183 min The compounds listed below in tables 4 to 9 can be prepared similarly to the examples mentioned above.

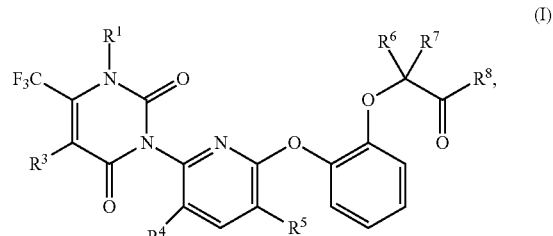

(I)

wherein R$^2$ is CF$_3$, n is 1,
Q, W, X and Y are O, and
Z is Z$^1$, wherein R$^a$, R$^b$, R$^c$ and R$^d$ are H

TABLE 4

| no | R$^1$ | R$^3$ | R$^4$ | R$^5$ | R$^6$ | R$^7$ | R$^8$ | m/z [M + H] | R$_t$ [min] |
|---|---|---|---|---|---|---|---|---|---|
| 8 | CH$_3$ | H | H | Cl | H | H | OH | 472 | 1.015 |
| 9 | CH$_3$ | H | H | Cl | H | H | OCH$_3$ | 486 | 1.11 |
| 10 | CH$_3$ | H | H | Cl | H | H | OCH$_2$CH$_3$ | 500 | 1.197 |
| 11 | CH$_3$ | H | F | F | H | H | OH | 474 | 1.004 |
| 12 | CH$_3$ | H | F | F | H | H | OCH$_3$ | 488 | 1.167 |
| 13 | CH$_3$ | H | F | Cl | H | H | NHCH$_2$(CO)OCH$_3$ | 561 | 1.086 |
| 14 | CH$_3$ | H | F | Cl | H | H | NHCH$_2$CH$_2$(CO)OCH$_3$ | 575 | 1.094 |
| 15 | CH$_3$ | H | F | Cl | CH$_3$ (S) | H | OCH$_2$CH$_3$ | 532 | 1.306 |
| 16 | CH$_3$ | H | F | Cl | CH$_3$ (R) | H | OCH$_2$CH$_3$ | 532 | 1.306 |

TABLE 4-continued

| no | R¹ | R³ | R⁴ | R⁵ | R⁶ | R⁷ | R⁸ | m/z [M + H] | R_t [min] |
|---|---|---|---|---|---|---|---|---|---|
| 17 | CH₃ | H | F | CN | H | H | OCH₂CH₃ | 509 | 1.212 |
| 18 | CH₃ | H | H | Cl | OCH₃ | H | OCH₃ | 516 | 1.155 |
| 19 | CH₃ | H | H | Cl | CH₃ (S) | H | OCH₂CH₃ | 514 | 1.241 |
| 20 | CH₃ | H | H | Cl | CH₃ (R) | H | OCH₂CH₃ | 514 | 1.241 |
| 21 | CH₃ | H | F | F | OCH₃ | H | OCH₂CH₃ | 532 | 1.214 |
| 22 | CH₃ | H | F | F | CH₃ (S) | H | OCH₂CH₃ | 516 | 1.241 |
| 23 | CH₃ | H | F | F | CH₃ (R) | H | OCH₂CH₃ | | |
| 24 | CH₃ | H | F | Cl | CH₃ | CH₃ | OCH₃ | 532 | 1.266 |
| 25 | CH₃ | H | F | Cl | F | H | OCH₂CH₃ | 536 | 1.287 |
| 26 | CH₃ | H | F | Cl | F | CH₃ | OCH₃ | 536 | 1.242 |
| 27 | CH₃ | H | F | Cl | F | F | OCH₂CH₃ | 554 | 1.239 |
| 28 | CH₃ | H | F | Cl | SCH₃ | H | OCH₃ | | |
| 29 | CH₃ | H | F | Cl | SCH₃ | H | OCH₂CH₃ | 550 | 1.248 |
| 30 | CH₃ | H | F | Cl | CH₂OCH₃ | H | OCH₃ | 548 | 1.195 |
| 31 | CH₃ | H | F | Cl | CO₂CH₂CH₃ | H | OCH₂CH₃ | 590 | 1.324 |
| 32 | CH₃ | H | Cl | Cl | H | H | OCH₃ | | |
| 33 | CH₃ | H | Cl | Cl | H | H | OCH₂CH₃ | 534 | 1.270 |
| 34 | CH₃ | H | H | Br | H | H | OCH₂CH₃ | 544 | 1.199 |
| 35 | CH₃ | H | F | Br | H | H | OCH₂CH₃ | 564 | 1.247 |
| 36 | CH₃ | H | H | CF3 | H | H | OCH₂CH₃ | 534 | 1.300 |
| 37 | CH₃ | H | F | CF3 | H | H | OCH₂CH₃ | | |
| 38 | CH₃ | H | H | NO₂ | H | H | OCH₂CH₃ | 511 | 1.165 |
| 39 | CH₃ | H | F | NO₂ | H | H | OCH₂CH₃ | | |
| 40 | CH₃ | H | H | NH₂ | H | H | OCH₂CH₃ | 481 | 1.068 |
| 41 | NH₂ | H | F | Cl | H | H | OCH₃ | | |
| 42 | NH₂ | H | F | Cl | H | H | OCH₂CH₃ | 519 | 1.172 |
| 43 | CD₃ | H | F | Cl | H | H | OCH₂CH₃ | 521 | 1.229 |
| 44 | H | H | F | Cl | H | H | OCH₂CH₃ | 504 | 1.180 |
| 45 | CH₃ | CH₃ | F | Cl | H | H | OCH₃ | | |
| 46 | CH₃ | CH₃ | F | Cl | H | H | OCH₂CH₃ | 532 | 1.294 |
| 47 | CH₃ | H | F | Cl | H | H | OCH₃ | 504 | 1.186 |
| 48 | CH₃ | H | F | Cl | H | H | SCH₃ | 520 | 1.278 |
| 49 | CH₃ | H | F | Cl | H | H | OCH₂C≡CH | 528 | 1.209 |
| 50 | CH₃ | H | F | Cl | H | H | OCH₂CH=CH₂ | 530 | 1.251 |
| 51 | CH₃ | H | F | Cl | H | H | OCH₂C≡CCH₃ | 542 | 1.288 |
| 52 | CH₃ | H | F | Cl | H | H | OCH₂C(CH₃)=CH₂ | 544 | 1.334 |
| 53 | CH₃ | H | F | Cl | H | H | OCH₂CH₂CH₃ | 532 | 1.319 |
| 54 | CH₃ | H | F | Cl | H | H | OCH(CH₃)₂ | 532 | 1.312 |
| 55 | CH₃ | H | F | Cl | H | H | OC(CH₃)₃ | | |
| 56 | CH₃ | H | F | Cl | H | H | OCH₂CH(CH₃)₂ | 546 | 1.368 |
| 57 | CH₃ | H | F | Cl | H | H | OCH₂CH₂Cl | 552 | 1.242 |
| 58 | CH₃ | H | F | Cl | H | H | OCH₂CCl₂H | 588 | 1.326 |
| 59 | CH₃ | H | F | Cl | H | H | OCH₂CF₂H | 554 | 1.226 |
| 60 | CH₃ | H | F | Cl | H | H | O-c-C₃H₅ | | |
| 61 | CH₃ | H | F | Cl | H | H | O-c-C₄H₇ | 544 | 1.335 |
| 62 | CH₃ | H | F | Cl | H | H | O-c-C₅H₉ | 558 | 1.370 |
| 63 | CH₃ | H | F | Cl | H | H | O-c-C₆H₁₁ | 572 | 1.418 |
| 64 | CH₃ | H | F | Cl | H | H | O-phenyl | 566 | 1.339 |
| 65 | CH₃ | H | F | Cl | H | H | O(oxetan-3-yl) | 546 | 1.179 |
| 66 | CH₃ | H | F | Cl | H | H | O(tetrahydropyran-4-yl) | 574 | 1.234 |
| 67 | CH₃ | H | F | Cl | H | H | OCH₂-c-C₃H₅ | 544 | 1.283 |
| 68 | CH₃ | H | F | Cl | H | H | OCH₂-c-C₄H₇ | 558 | 1.349 |
| 69 | CH₃ | H | F | Cl | H | H | OCH₂(phenyl) | 580 | 1.322 |
| 70 | CH₃ | H | F | Cl | H | H | OCH₂(furan-2-yl) | 570 | 1.290 |
| 71 | CH₃ | H | F | Cl | H | H | OCH₂CH₂OCH₃ | 548 | 1.187 |
| 72 | CH₃ | H | F | Cl | H | H | OCH₂CH₂OCH₂CH₃ | 562 | 1.234 |
| 73 | CH₃ | H | F | Cl | H | H | OCH₂CH₂OCH(CH₃)₂ | 576 | 1.277 |
| 74 | CH₃ | H | F | Cl | H | H | OCH₂CH₂CH₂OCH₃ | 562 | 1.253 |
| 75 | CH₃ | H | F | Cl | H | H | OCH₂CH(OCH₃)₂ | 600* | 1.216 |
| 76 | CH₃ | H | F | Cl | H | H | OCH₂CH(OCH₂CH₃)₂ | 628* | 1.302 |
| 77 | CH₃ | H | F | Cl | H | H | OCH₂CO₂CH₃ | 562 | 1.182 |
| 78 | CH₃ | H | F | Cl | H | H | OCH(CH₃)CO₂CH₃ | 576 | 1.257 |
| 79 | CH₃ | H | F | Cl | H | H | OCH₂CO₂CH₂CH₃ | 576 | 1.228 |
| 80 | CH₃ | H | F | Cl | H | H | OCH₂CO₂CH(CH₃)₂ | 590 | 1.272 |
| 81 | CH₃ | H | F | Cl | H | H | NHCH₃ | 503 | 1.125 |
| 82 | CH₃ | H | F | Cl | H | H | N(CH₃)₂ | 517 | 1.135 |
| 83 | CH₃ | H | F | Cl | H | H | NHOH | 505 | 0.996 |
| 84 | CH₃ | H | F | Cl | H | H | NHOCH₃ | 519 | 1.096 |
| 85 | CH₃ | H | F | Cl | H | H | N(CH₃)OCH₃ | 533 | 1.162 |
| 86 | CH₃ | H | F | Cl | H | H | NHCH₂C≡CH | 527 | 1.153 |
| 87 | CH₃ | H | F | Cl | H | H | NHCH₂CH₂CH₂CO₂CH₃ | 589 | 1.159 |
| 88 | CH₃ | H | F | Cl | H | H | NHSO₂CH(CH₃)₂ | | |
| 89 | CH₃ | H | F | Cl | H | H | NHSO₂N(CH₃)₂ | 596 | 1.165 |
| 90 | CH₃ | H | F | Cl | H | H | NHSO₂N(CH₃)CH(CH₃)₂ | | |

*[M + Na]

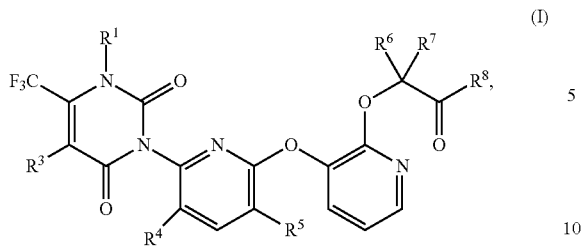

wherein R² is CF₃, n is 1,
Q, W, X and Y are O, and
Z is Z⁷, wherein R$^a$, R$^b$, and R$^c$ are H

TABLE 5

| no | R¹ | R³ | R⁴ | R⁵ | R⁶ | R⁷ | R⁸ | m/z [M + H] | R$_t$ [min] |
|---|---|---|---|---|---|---|---|---|---|
| 91 | CH₃ | H | F | Cl | H | | OH | 491 | 1.052 |
| 92 | NH₂ | H | F | Cl | H | H | OCH₃ | | |
| 93 | NH₂ | H | F | Cl | H | H | OCH₂CH₃ | 520 | 1.156 |
| 94 | CD₃ | H | F | Cl | H | H | OCH₂CH₃ | 522 | 1.215 |
| 95 | CH₂C≡CH | H | F | Cl | H | H | OCH₂CH₃ | 543 | 1.215 |
| 96 | CH₃ | CH₃ | F | Cl | H | H | OCH₃ | | |
| 97 | CH₃ | CH₃ | F | Cl | H | H | OCH₂CH₃ | 533 | 1.269 |
| 98 | CH₃ | H | F | Cl | H | H | NHCH₂(CO)OCH₃ | | |
| 99 | CH₃ | H | F | Cl | H | H | NHCH₂CH₂(CO)OCH₃ | | |
| 100 | CH₃ | H | F | Cl | CH₃ (S) | H | OCH₂CH₃ | | |
| 101 | CH₃ | H | F | Cl | CH₃ (R) | H | OCH₂CH₃ | | |
| 102 | CH₃ | H | F | CN | H | H | OCH₂CH₃ | | |
| 103 | CH₃ | H | H | Cl | CH₃ (S) | H | OCH₂CH₃ | | |
| 104 | CH₃ | H | H | Cl | CH₃ (R) | H | OCH₂CH₃ | | |
| 105 | CH₃ | H | F | F | H | H | OCH₂CH₃ | 503 | 1.171 |
| 106 | CH₃ | H | F | F | CH₃ (S) | H | OCH₂CH₃ | | |
| 107 | CH₃ | H | F | F | CH₃ (R) | H | OCH₂CH₃ | | |
| 108 | CH₃ | H | F | Cl | CH₃ | CH₃ | OCH₃ | | |
| 109 | CH₃ | H | F | Cl | F | H | OCH₂CH₃ | | |
| 110 | CH₃ | H | F | Cl | F | CH₃ | OCH₃ | | |
| 111 | CH | H | F | Cl | F | F | OCH₂CH₃ | | |
| 112 | CH₃ | H | F | Cl | SCH₃ | H | OCH₃ | | |
| 113 | CH₃ | H | F | Cl | SCH₃ | H | OCH₂CH₃ | | |
| 114 | CH₃ | H | Cl | Cl | H | H | OCH₃ | | |
| 115 | CH₃ | H | Cl | Cl | H | H | OCH₂CH₃ | | |
| 116 | CH₃ | H | H | Br | H | H | OCH₂CH₃ | | |
| 117 | CH₃ | H | F | Br | H | H | OCH₂CH₃ | | |
| 118 | CH₃ | H | H | CF₃ | H | H | OCH₂CH₃ | | |
| 119 | CH₃ | H | F | CF₃ | H | H | OCH₂CH₃ | | |
| 120 | CH₃ | H | H | NO₂ | H | H | OCH₂CH₃ | | |
| 121 | CH₃ | H | F | NO₂ | H | H | OCH₂CH₃ | | |
| 122 | CH₃ | H | H | NH₂ | H | H | OCH₂CH₃ | | |
| 123 | CH₃ | H | F | Cl | H | H | OCH₃ | 505 | 1.154 |
| 124 | CH₃ | H | F | Cl | H | H | SCH₃ | | |
| 125 | CH₃ | H | F | Cl | H | H | OCH₂C≡CH | 529 | 1.201 |
| 126 | CH₃ | H | F | Cl | H | H | OCH₂CH=CH₂ | 531 | 1.226 |
| 127 | CH₃ | H | F | Cl | H | H | OCH₂C≡CCH₃ | | |
| 128 | CH₃ | H | F | Cl | H | H | OCH₂C(CH₃)=CH₂ | 545 | 1.305 |
| 129 | CH₃ | H | F | Cl | H | H | OCH₂CH₂CH₃ | 533 | 1.290 |
| 130 | CH₃ | H | F | Cl | H | H | OCH(CH₃)₂ | 533 | 1.282 |
| 131 | CH₃ | H | F | Cl | H | H | OC(CH₃)₃ | | |
| 132 | CH₃ | H | F | Cl | H | H | OCH₂CH(CH₃)₂ | 547 | 1.335 |
| 133 | CH₃ | H | F | Cl | H | H | OCH₂CH₂Cl | | |
| 134 | CH₃ | H | F | Cl | H | H | OCH₂CCl₂H | | |
| 135 | CH₃ | H | F | Cl | H | H | OCH₂CF₂H | 555 | 1.255 |
| 136 | CH₃ | H | F | Cl | H | H | O-c-C₃H₅ | | |
| 137 | CH₃ | H | F | Cl | H | H | O-c-C₄H₇ | | |
| 138 | CH₃ | H | F | Cl | H | H | O-c-C₅H₉ | | |
| 139 | CH₃ | H | F | Cl | H | H | O-c-C₆H₁₁ | 573 | 1.395 |
| 140 | CH₃ | H | F | Cl | H | H | O-phenyl | | |
| 141 | CH₃ | H | F | Cl | H | H | O(oxetan-3-yl) | 547 | 1.143 |
| 142 | CH₃ | H | F | Cl | H | H | O(tetrahydropyran-4-yl) | | |
| 143 | CH₃ | H | F | Cl | H | H | OCH₂-c-C₃H₅ | 545 | 1.257 |
| 144 | CH₃ | H | F | Cl | H | H | OCH₂-c-C₄H₇ | 559 | 1.359 |
| 145 | CH₃ | H | F | Cl | H | H | OCH₂(phenyl) | 581 | 1.330 |
| 146 | CH₃ | H | F | Cl | H | H | OCH₂(furan-2-yl) | | |
| 147 | CH₃ | H | F | Cl | H | H | OCH₂CH₂OCH₃ | 549 | 1.174 |

TABLE 5-continued

| no | R¹ | R³ | R⁴ | R⁵ | R⁶ | R⁷ | R⁸ | m/z [M + H] | $R_t$ [min] |
|---|---|---|---|---|---|---|---|---|---|
| 148 | CH₃ | H | F | Cl | H | H | OCH₂CH₂OCH₂CH₃ | 563 | 1.228 |
| 149 | CH₃ | H | F | Cl | H | H | OCH₂CH₂OCH(CH₃)₂ | 577 | 1.272 |
| 150 | CH₃ | H | F | Cl | H | H | OCH₂CH₂CH₂OCH₃ | 563 | 1.217 |
| 151 | CH₃ | H | F | Cl | H | H | OCH₂CH(OCH₃)₂ | 579 | 1.207 |
| 152 | CH₃ | H | F | Cl | H | H | OCH₂CH(OCH₂CH₃)₂ | 629* | 1.305 |
| 153 | CH₃ | H | F | Cl | H | H | OCH₂CO₂CH₃ | | |
| 154 | CH₃ | H | F | Cl | H | H | OCH(CH₃)CO₂CH₃ | 577 | 1.223 |
| 155 | CH₃ | H | F | Cl | H | H | OCH₂CO₂CH₂CH₃ | 577 | 1.220 |
| 156 | CH₃ | H | F | Cl | H | H | OCH₂CO₂CH(CH₃)₂ | | |
| 157 | CH₃ | H | F | Cl | H | H | NHCH₃ | | |
| 158 | CH₃ | H | F | Cl | H | H | N(CH₃)₂ | | |
| 159 | CH₃ | H | F | Cl | H | H | NHOH | | |
| 160 | CH₃ | H | F | Cl | H | H | NHOCH₃ | | |
| 161 | CH₃ | H | F | Cl | H | H | N(CH₃)OCH₃ | | |
| 162 | CH₃ | H | F | Cl | H | H | NHCH₂C≡CH | | |
| 163 | CH₃ | H | F | Cl | H | H | NHCH₂CH₂CH₂CO₂CH₃ | | |
| 164 | CH₃ | H | F | Cl | H | H | NHSO₂CH₃ | 568 | 1.052 |
| 165 | CH₃ | H | F | Cl | H | H | NHSO₂CH(CH₃)₂ | 596 | 1.126 |
| 166 | CH₃ | H | F | Cl | H | H | NHSO₂N(CH₃)₂ | | |
| 167 | CH₃ | H | F | Cl | H | H | NHSO₂N(CH₃)CH(CH₃)₂ | | |

*[M + Na]

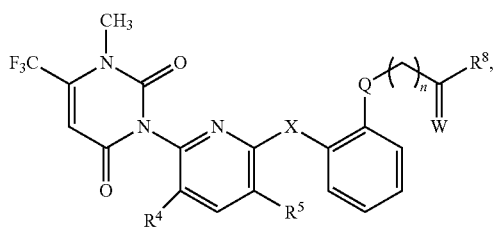

(I)

wherein R¹ is CH₃, R² is CF₃,
R³, R⁶, and R⁷ are H,
Y is O, and
Z is Z¹, wherein R$^a$, R$^b$, R$^c$ and R$^d$ are H

TABLE 6

| no | R⁴ | R⁵ | n | X | Q | W | n | R⁸ | m/z [M + H] | $R_t$ [min] |
|---|---|---|---|---|---|---|---|---|---|---|
| 168 | H | Cl | 1 | S | O | O | 1 | OCH₃ | | |
| 169 | H | Cl | 1 | S | O | O | 1 | OCH₂CH₃ | 516 | 1.222 |
| 170 | F | F | 1 | S | O | O | 1 | OCH₃ | | |
| 171 | F | F | 1 | S | O | O | 1 | OCH₂CH₃ | | |
| 172 | F | Cl | 1 | S | O | O | 1 | OCH₃ | | |
| 173 | F | Cl | 1 | S | O | O | 1 | OCH₂CH₃ | | |
| 174 | F | Cl | 1 | O | O | S | 1 | OCH₃ | | |
| 175 | F | Cl | 1 | O | O | S | 1 | OCH₂CH₃ | | |
| 176 | F | Cl | 1 | O | NH | O | 1 | OCH₃ | | |
| 177 | F | Cl | 1 | O | NH | O | 1 | OCH₂CH₃ | | |
| 178 | F | Cl | 1 | O | NCH₃ | O | 1 | OCH₃ | | |
| 179 | F | Cl | 1 | O | NCH₃ | O | 1 | OCH₂CH₃ | 531 | 1.280 |
| 180 | F | Cl | 1 | O | S | O | 1 | OCH₃ | | |
| 181 | F | Cl | 1 | O | S | O | 1 | OCH₂CH₃ | | |
| 182 | F | Cl | 1 | O | SO | O | 1 | OCH₃ | | |
| 183 | F | Cl | 1 | O | SO | O | 1 | OCH₂CH₃ | | |
| 184 | F | Cl | 1 | O | SO₂ | O | 1 | OCH₃ | | |
| 185 | F | Cl | 1 | O | SO₂ | O | 1 | OCH₂CH₃ | | |
| 186 | F | Cl | 1 | O | CH₂ | O | 1 | OCH₃ | 502 | 1.243 |
| 187 | F | Cl | 1 | O | CH₂ | O | 1 | OCH₂CH₃ | | |
| 188 | F | Cl | 2 | O | NH | O | 2 | OCH₃ | | |
| 189 | F | Cl | 2 | O | NH | O | 2 | OCH₂CH₃ | | |
| 190 | F | Cl | 2 | O | NCH₃ | O | 2 | OCH₃ | | |
| 191 | F | Cl | 2 | O | NCH₃ | O | 2 | OCH₂CH₃ | | |
| 192 | F | Cl | 2 | O | CH₂ | O | 2 | OCH₃ | | |
| 193 | F | Cl | 2 | O | CH₂ | O | 2 | OCH₂CH₃ | | |
| 194 | F | Cl | 3 | O | O | O | 3 | OCH₃ | | |
| 195 | F | Cl | 3 | O | O | O | 3 | OCH₂CH₃ | 546 | 1.300 |

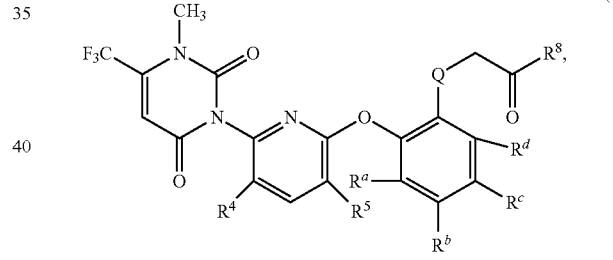

(I)

wherein R¹ is CH₃, R² is CF₃,
R³, R⁶, and R⁷ are H,
n is 1, Q, W, X and Y are O, and
Z is Z¹

TABLE 7

| no | R⁴ | R⁵ | R$^a$ | R$^b$ | R$^c$ | R$^d$ | R⁸ | m/z [M + H] | $R_t$ [min] |
|---|---|---|---|---|---|---|---|---|---|
| 196 | F | Cl | F | H | H | H | OCH₃ | | |
| 197 | F | Cl | F | H | H | H | OCH₂CH₃ | 536 | 1.230 |
| 198 | F | Cl | H | F | H | H | OCH₃ | | |
| 199 | F | Cl | H | F | H | H | OCH₂CH₃ | 536 | 1.258 |
| 200 | F | Cl | H | H | F | H | OCH₃ | | |
| 201 | F | Cl | H | H | F | H | OCH₂CH₃ | 536 | 1.258 |
| 202 | F | Cl | H | H | H | F | OCH₃ | | |
| 203 | F | Cl | H | H | H | F | OCH₂CH₃ | 536 | 1.240 |
| 204 | F | Cl | Cl | H | H | H | OCH₃ | | |
| 205 | F | Cl | Cl | H | H | H | OCH₂CH₃ | | |
| 206 | F | Cl | H | Cl | H | H | OCH₃ | | |
| 207 | F | Cl | H | Cl | H | H | OCH₂CH₃ | 552 | 1.303 |
| 208 | F | Cl | H | H | Cl | H | OCH₃ | | |
| 209 | F | Cl | H | H | Cl | H | OCH₂CH₃ | | |

TABLE 7-continued

| no | R⁴ | R⁵ | Rᵃ | Rᵇ | Rᶜ | Rᵈ | R⁸ | m/z [M + H] | R_t [min] |
|---|---|---|---|---|---|---|---|---|---|
| 210 | F | Cl | H | H | H | Cl | OCH₃ | | |
| 211 | F | Cl | H | H | H | Cl | OCH₂CH₃ | | |
| 212 | F | Cl | CH₃ | H | H | H | OCH₃ | | |
| 213 | F | Cl | CH₃ | H | H | H | OCH₂CH₃ | | |
| 214 | F | Cl | H | CH₃ | H | H | OCH₃ | | |
| 215 | F | Cl | H | CH₃ | H | H | OCH₂CH₃ | | |
| 216 | F | Cl | H | H | CH₃ | H | OCH₃ | | |
| 217 | F | Cl | H | H | CH₃ | H | OCH₂CH₃ | | |
| 218 | F | Cl | H | H | H | CH₃ | OCH₃ | | |
| 219 | F | Cl | H | H | H | CH₃ | OCH₂CH₃ | | |
| 220 | F | Cl | CF₃ | H | H | H | OCH₃ | | |
| 221 | F | Cl | CF₃ | H | H | H | OCH₂CH₃ | | |
| 222 | F | Cl | H | CF₃ | H | H | OCH₃ | | |
| 223 | F | Cl | H | CF₃ | H | H | OCH₂CH₃ | | |
| 224 | F | Cl | H | H | CF₃ | H | OCH₃ | | |
| 225 | F | Cl | H | H | CF₃ | H | OCH₂CH₃ | 586 | 1.331 |
| 226 | F | Cl | H | H | H | CF₃ | OCH₃ | | |
| 227 | F | Cl | H | H | H | CF₃ | OCH₂CH₃ | | |

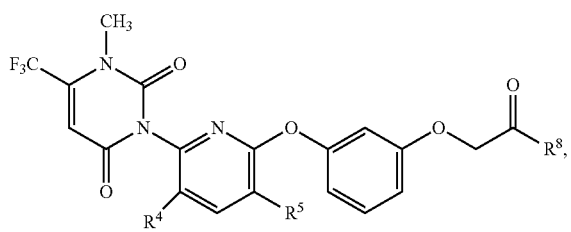

(I)

wherein R¹ is CH₃, R² is CF₃,
R³, R⁶, and R⁷ are H,
n is 1, Q, W, X and Y are O, and
Z is Z², wherein Rᵃ, Rᵇ, and Rᶜ are H

TABLE 8

| no | R⁴ | R⁵ | R⁸ | m/z [M + H] | Rt [min] |
|---|---|---|---|---|---|
| 228 | F | Cl | OCH₂CH₃ | 518 | 1.267 |

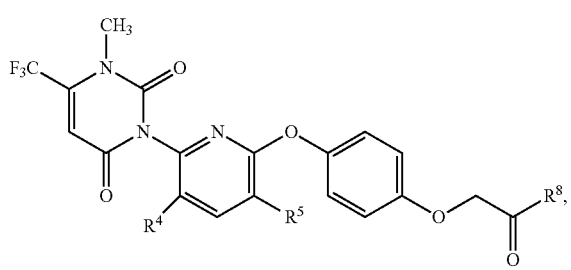

(I)

wherein R¹ is CH₃, R² is CF₃,
R³, R⁶, and R⁷ are H,
n is 1, Q, W, X and Y are O, and
Z is Z³, wherein Rᵃ, Rᵇ, and Rᶜ are H

TABLE 9

| no | R⁴ | R⁵ | R⁸ | m/z [M + N] | Rt [min] |
|---|---|---|---|---|---|
| 229 | F | Cl | OCH₂CH₃ | 518 | 1.256 |

B Use Examples

The herbicidal activity of the uracilpyridines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| ALOMY | *Alopecurus myosuroides* |
| AMARE | *Amaranthus retroflexus* |
| BRADC | *Brachiaria decumbens* |
| CHEAL | *Chenopodium album* |
| ECHCG | *Echinocloa crus-galli* |
| LOLMU | *Lolium multiflorum* |
| MATCH | *Matricaria chamomilla* |
| SETVI | *Setaria viridis* |
| ZEAMX | *Zea mays* |

At an application rate of 16 g/ha, the compounds 1, 2, 4, 5, 6, 7, 8, 9, 10, 11, 12, 13, 14, 15, 16, 17, 20, 21, 22, 24, 25, 26, 27, 33, 34, 35, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 83, 84, 85, 86, 89, 91, 97, 125, 126, 128, 129, 130, 132, 135, 143, 145, 147, 149, 150, 151, 152, 154, 165, 169, 199, 201, 207, 228 and 229 applied by the post-emergence method, showed very good herbicidal activity against AMARE, CHEAL, ECHCG and SETVI.

At an application rate of 16 g/ha, the compounds 18, 82, 87 and 155 applied by the post-emergence method, showed very good herbicidal activity against AMARE, CHEAL and SETVI.

TABLE 10

Comparison of the herbicidal activity of example 2 of the present invention and compound no. 3 known from WO 11/137088 post emergence (greenhouse)

| compound | Example 2 | Cmpd no. 3 (WO 11/137088) |
|---|---|---|
| application rate [g/ha] | 8 | 8 |
| unwanted plants | damages | |
| ALOMY | 70 | 40 |
| LOLMU | 70 | 40 |
| MATCH | 70 | 60 |
| application rate [g/ha] | 2 | 2 |
| unwanted plants | damages | |
| BRADC | 80 | 20 |
| crop plants ZEAMX | 25 | 40 |
| application rate [g/ha] | 1 | 1 |
| unwanted plants | damages | |
| CHEAL | 90 | 45 |

The data clearly demonstrate the superior herbicidal activity of the inventive compounds of formula I of the present invention over the compounds known from the prior art.

The replacement of the central phenyl ring by a pyridine ring leads not only to a much better herbicidal activity, but also to a much better crop compatability as achieved by the compound known from WO 11/137088.

The control of resistant weeds by the compounds of formula (I) was demonstrated by the following greenhouse experiment:

The culture containers used were plastic flowerpots containing loamy sand with approximately 3.0% of humus as the substrate. The seeds of the test plants were sown separately for each species and/or resistant biotype. For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. Depending on the species, the plants were kept at 10-25° C. or 20-35° C., respectively. The test period extended over 2 to 4 weeks. During this time, the plants were tended, and their response to the individual treatments was evaluated. The evaluation was carried out by using a scale from 0 to 100. 100 means no emergence of the plants or complete destruction of at least the above-ground parts, and 0 means no damage, or normal course of growth.

The plants used in the greenhouse experiments were of the following species and biotype:

| weed no. | Bayer code | Scientific name | Common name | Biotype |
|---|---|---|---|---|
| w.1 | AMATA | Amaranthus tamariscinus | Common waterhemp | Sensitive |
| w.2 | AMATA | Amaranthus tamariscinus | Common waterhemp | PPO resistant biotype 1 that was shown to contain the ΔG210 mutation |
| w.3 | AMATA | Amaranthus tamariscinus | Common waterhemp | PPO resistant biotype 2 that was shown to contain the ΔG210 mutation |

The results shown in the following table demonstrate that compound 7 and compound 1 have very good activity on both sensitive (w.1) and resistant weeds containing the ΔG210 mutation (w.2, w.3) whereas the known PPO inhibitor azafenidin shows much weaker control of resistant in comparison to sensitive biotypes.

| herbicide compound | use rate | weed control (%) | | |
|---|---|---|---|---|
| | | w.1 | w.2 | w.3 |
| 1 | 4 g/ha | 100 | 100 | 100 |
| 1 | 2 g/ha | 88 | 87 | 98 |
| 7 | 4 g/ha | 100 | 100 | 100 |

-continued

| herbicide compound | use rate | weed control (%) | | |
|---|---|---|---|---|
| | | w.1 | w.2 | w.3 |
| 7 | 2 g/ha | 93 | 100 | 100 |
| azafenidin | 4 g/ha | 100 | 78 | 77 |
| azafenidin | 2 g/ha | 88 | 62 | 77 |

The invention claimed is:

1. A compound of formula (I)

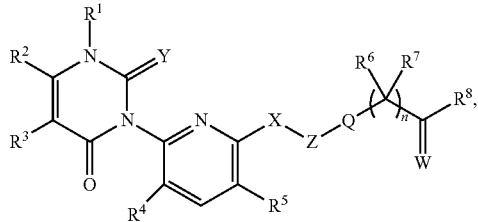

(I)

wherein the variables have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$ or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$;
wherein $R^{14}$ is halogen, $NO_2$, CN, $C_1$-$C_4$-alkyl, $C_1$-$C_4$-haloalkyl, $C_1$-$C_4$-alkoxy or $C_1$-$C_4$-alkoxy-carbonyl;
$R^{10}$, $R^{11}$ independently of one another are $R^9$, or together form a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$;
n 1 to 3;
Q $CH_2$, O, S, SO, $SO_2$, NH or ($C_1$-$C_3$-alkyl)N;
W O or S;
X NH, $NCH_3$, O or S;
Y O or S
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
or an agriculturally acceptable salt or derivative, provided the compounds of formula (I) have a carboxyl group.

2. The compound of claim 1 wherein $R^1$ is $C_1$-$C_6$-alkyl, $R^2$ is $C_1$-$C_4$-haloalkyl, $R^3$ is H and Y is O.

3. The compound of claim 1, wherein $R^4$ is H or F, and $R^5$ is F, Cl, Br or CN.

4. The compound of claim 1, wherein $R^6$ is H, $C_1$-$C_3$-alkyl or $C_1$-$C_3$-alkoxy, and $R^7$ is H.

5. The compound of claim 1 wherein $R^8$ is $OR^9$, $NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl; and
$R^{10}R^{11}$ are $C_1$-$C_6$-alkyl.

6. The compound of claim 1, wherein n is 1.

7. The compound of claim 1, wherein Q, W and X are O.

8. The compound of claim 1, wherein Z is phenyl or pyridyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy.

9. Acid halides of formula (II)

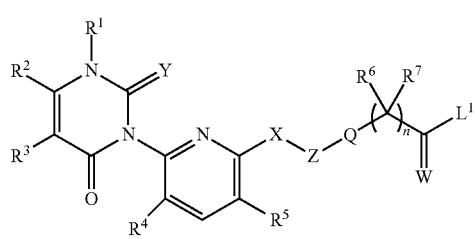

(II)

wherein $R^2$, $R^3$, $R^4$, $R^5$, $R^6$, $R^7$, n, Q, W, X, Y and Z are as defined in claim 1, and $L^1$ is halogen.

10. An intermediate of formula (int-1)

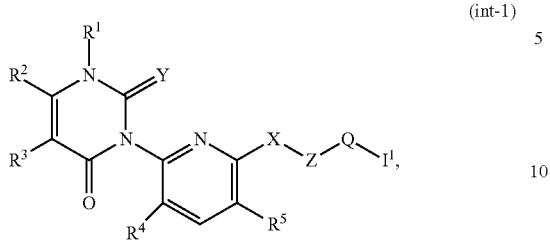

wherein $R^1$, $R^2$, $R^3$, $R^4$, $R^5$, Q, X, Y and Z are as defined in claim 1, and
$I^1$ is H or PG, wherein PG is a protecting group selected from the group consisting of
$C_1$-$C_6$-alkyl, $C_1$-$C_6$-cyanoalkyl, $C_1$-$C_6$-haloalkyl, $C_1$-$C_6$-alkylthio-$C_1$-$C_4$-alkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, (tri-$C_1$-$C_6$-alkyl)silyl-$C_1$-$C_4$-alkyl, (tri-$C_1$-$C_6$-alkyl)silyl-$C_1$-$C_4$-alkyoxy-$C_1$-$C_4$-alkyl, $C_2$-$C_6$-alkenyl, $C_3$-$C_6$-alkynyl, $C_3$-$C_6$-cycloalkyl, $C_3$-$C_6$-cylcloalkyl-$C_1$-$C_4$-alkyl, $C_5$-$C_6$-cycloalkenyl, tetrahydropyranyl, (tri-$C_1$-$C_6$-alkyl)silyl, [(diphenyl)($C_1$-$C_4$-alkyl)]silyl, formyl, $C_1$-$C_6$-alkyl-carbonyl, $C_1$-$C_6$-alkyl-O-carbonyl, $C_2$-$C_6$-alkenyl-O-carbonyl, [(diphenyl)($C_1$-$C_4$-alkyl)]silyl-$C_1$-$C_4$-alkyl, phenyl-$C_1$-$C_4$-alkyl, phenylthio-$C_1$-$C_6$-alkyl, phenylcarbonyl,
wherein each phenyl ring can be substituted by one to three substituents selected from the group consisting of halogen, CN, $NO_2$, $C_1$-$C_4$-alkyl and $C_1$-$C_4$-alkoxy;
or a salt thereof.

11. An intermediate of formula (int-2)

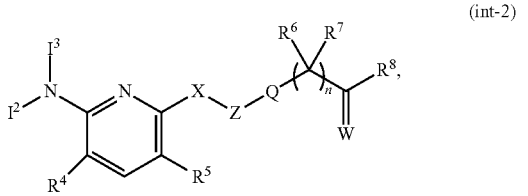

wherein $R^4$, $R^5$, $R^6$, $R^7$, $R^8$, n, Q, W, X, Y and Z are as defined in claim 1, and
$I^2$ is H; and
$I^3$ is H or C(=Y)$L^2$, wherein
Y is O or S, and
$L^2$ is $C_1$-$C_6$-alkoxy, $C_1$-$C_6$-alkylthio or aryloxy,
wherein the aryl moiety may itself be partly or fully halogenated and/or may be substituted by from one to three substituents from the group of cyano, nitro, $C_1$-$C_4$-alkyl, $C_1$-$C_4$-alkoxy and $C_1$-$C_4$-alkylthio;
or $I^2$ and $I^3$ together with the N-atom, to which they are attached, form a group "YCN",
wherein Y is O or S,
or a group "PGN", which is a protected amine substituent selected from the group consisting of $N_3$, aliphatic or aromatic carbamates, aliphatic or aromatic amides, N-$C_1$-$C_6$-alkyl-amines, N-aryl-amines or heteroarylamides,
or a salt thereof.

12. An intermediate of formula (int-3)

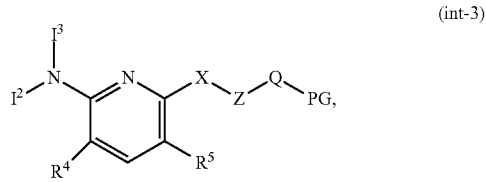

wherein $R^4$, Q, X and Z are as defined in claim 1,
$R^5$ is a halogen or CN; and
PG is a protecting group selected from the group consisting of
$C_1$-$C_6$-alkyl, $C_1$-$C_6$-cyanoalkyl, $C_1$-$C_6$-haloalkyl, $C_1$-$C_6$-alkylthio-$C_1$-$C_4$-alkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, (tri-$C_1$-$C_6$-alkyl)silyl-$C_1$-$C_4$-alkyl, (tri-$C_1$-$C_6$-alkyl)silyl-$C_1$-$C_4$-alkyoxy-$C_1$-$C_4$-alkyl, $C_2$-$C_6$-alkenyl, $C_3$-$C_6$-alkynyl, $C_3$-$C_6$-cycloalkyl, $C_3$-$C_6$-cylcloalkyl-$C_1$-$C_4$-alkyl, $C_5$-$C_6$-cycloalkenyl, tetrahydropyranyl, (tri-$C_1$-$C_6$-alkyl)silyl, [(diphenyl)($C_1$-$C_4$-alkyl)]silyl, formyl, $C_1$-$C_6$-alkyl-carbonyl, $C_1$-$C_6$-alkyl-O-carbonyl, $C_2$-$C_6$-alkenyl-O-carbonyl, [(diphenyl)($C_1$-$C_4$-alkyl)]silyl-$C_1$-$C_4$-alkyl, phenyl-$C_1$-$C_4$-alkyl, phenylthio-$C_1$-$C_6$-alkyl, phenylcarbonyl,
wherein each phenyl ring can be substituted by one to three substituents selected from the group consisting of halogen, CN, $NO_2$, $C_1$-$C_4$-alkyl and $C_1$-$C_4$-alkoxy;
$I^2$ H; and
$I^3$ H or C(=Y)$L^2$, wherein
Y is O or S, and
$L^2$ is $C_1$-$C_6$-alkoxy, $C_1$-$C_6$-alkylthio or aryloxy,
wherein the aryl moiety may itself be partly or fully halogenated and/or may be substituted by from one to three substituents from the group of cyano, nitro, $C_1$-$C_4$-alkyl, $C_1$-$C_4$-alkoxy and $C_1$-$C_4$-alkylthio;
or $I^2$ and $I^3$ together with the N-atom, to which they are attached, form a group "YCN",
wherein Y is O or S,
or a group "PGN", which is a protected amine substituent selected from the group consisting of $C_1$-$C_6$-alkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH—, N-phthalimide, phenyl-O(CO)NH—, phenyl-$C_1$-$C_4$-alkyl-O(CO)NH—, phenyl-$C_1$-$C_4$-alkyl-NH—, di(phenyl-C1-C4-alkyl)N—,
wherein each phenyl ring can be substituted by one to three $C_1$-$C_4$-alkoxy substituents,
or a salt thereof.

13. A herbicidal composition comprising an herbicidally active amount of at least one uracilpyridine of formula (I) as claimed in claim 1 and at least one inert liquid and/or solid carrier and, optionally, at least one surface-active substance.

14. A process for the preparation of herbicidal active compositions, which comprises mixing an herbicidally active amount of at least one uracilpyridine of formula (I) as claimed in claim 1 and at least one inert liquid and/or solid carrier and, optionally, at least one surface-active substance.

15. A method of controlling undesired vegetation, which comprises allowing an herbicidally active amount of at least one uracilpyridine of formula (I) as claimed in claim 1 to act on plants, their environment or on seed.

16. The method of claim 15, wherein $R^1$ is $C_1$-$C_6$-alkyl, $R^2$ is C1-C4-haloalkyl, $R^3$ is H and Y is O.

17. The method of claim 15, wherein $R^4$ is H or F, and $R^5$ is F, Cl, Br or CN.

18. The method of claim 15, wherein $R^6$ is H, $C_1$-$C_3$-alkyl or $C_1$-$C_3$-alkoxy, and $R^7$ is H.

19. The method of claim 15, wherein $R^8$ is $OR^9$, $NR^9S(O)_2R^{10}$ or $NR^9S(O)_2NR^{10}R^{11}$, wherein $R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl; and $R^{10}$, $R^{11}$ are $C_1$-$C_6$-alkyl.

20. The method of claim 15, wherein n is 1.

21. The method of claim 15, wherein Q, W and X are O.

22. The method of claim 15, wherein Z is phenyl or pyridyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy and $C_1$-$C_6$-haloalkoxy.

* * * * *